(12) United States Patent
Chatterjee et al.

(10) Patent No.: US 11,230,706 B2
(45) Date of Patent: Jan. 25, 2022

(54) METHOD OF GENERATING A SYNTHETIC ANTIBODY LIBRARY, SAID LIBRARY AND APPLICATION(S) THEREOF

(71) Applicant: ZUMUTOR BIOLOGICS, INC., Woburn, MA (US)

(72) Inventors: Sohang Chatterjee, Lexington, MA (US); Kavitha Iyer Rodrigues, Karnataka Bangalore (IN); Maloy Ghosh, Karnataka Bangalore (IN); Sunit Maity, Karnataka Bangalore (IN); Divya Unnikrishnan, Karnataka Bangalore (IN); Yogendra Manjunath Bangalore Muniraju, Karnataka Bangalore (IN); Sathyabalan Murugesan, Karnataka Bangalore (IN); Pavithra Mukunda, Karnataka Kundapur (IN); Bhargav Prasad, Tamil Nadu Chennai (IN); Veeresha Kamanagowda, Karnataka Bangalore (IN); Sanghamitra Bhattacharjee, Karnataka Bangalore (IN); Pravin Kumar Dakshinamurthy, Tamil Nadu Chennai (IN); Vivek Halan, Tamil Nadu Aravenu (IN); Sankaranarayanan Srinivasan, Karnataka Bangalore (IN); Anuradha Hora, Uttar Pradesh Sitapur (IN); Bairavabalakumar Natarajan, Tamil Nadu Chennai (IN); Karthika Nair, Karnataka Bangalore (IN); Aswini Thanigaivel, Tamil Nadu Chennai (IN); Maliwalave Amol, Karnataka Bangalore (IN); Bharath Ravindra Shenoy, Karnataka Bangalore (IN); Sahana Bhima Rao, Karnataka Bangalore (IN); Subhra Prakash Chakrabarty, Karnataka Bangalore (IN); Ashvini Kumar Dubey, Karnataka Bangalore (IN); Amir Khan, Uttar Pradesh Aligarh (IN); Ankurina Sharma, Karnataka Bangalore (IN); Rashmi Sharma, Uttarakhand Haridwar (IN); Anurag Tiwari, Uttar Pradesh Varanasi (IN); Santosh Kumar, Jharkhand Charki Giridih (IN); Shivani Patel, Madhya Pradesh Adhartal (IN); Nikitha Markanda, Karnataka Bangalore (IN)

(73) Assignee: ZUMUTOR BIOLOGICS, INC., Woburn, MA (US)

(*) Notice: Subject to any disclaimer, the term of this patent is extended or adjusted under 35 U.S.C. 154(b) by 299 days.

(21) Appl. No.: 16/071,425
(22) PCT Filed: Jan. 19, 2017
(86) PCT No.: PCT/IB2017/050280
§ 371 (c)(1),
(2) Date: Jul. 19, 2018

(87) PCT Pub. No.: WO2017/125871
PCT Pub. Date: Jul. 27, 2017

(65) Prior Publication Data
US 2020/0149032 A1    May 14, 2020

(30) Foreign Application Priority Data
Jan. 19, 2016    (IN) .............................. 201641001955

(51) Int. Cl.
*C40B 40/08* (2006.01)
*C12N 15/10* (2006.01)
(Continued)

(52) U.S. Cl.
CPC ........ *C12N 15/1037* (2013.01); *C07K 16/005* (2013.01); *C40B 40/02* (2013.01);
(Continued)

(58) Field of Classification Search
None
See application file for complete search history.

(56) References Cited

FOREIGN PATENT DOCUMENTS

| WO | 2008/053275 | 5/2008 |
| WO | 2009/036379 | 3/2009 |

OTHER PUBLICATIONS

Prassler et al., "HuCAL Platinum, a Synthetic Fab Library Optimized for Sequence Diversity and Superior Performance in Mammalian Expression Systems", Journal of Molecular Biology, vol. 413, pp. 261-278 (2011).

(Continued)

*Primary Examiner* — Christian C Boesen
(74) *Attorney, Agent, or Firm* — Hamre, Schumann, Mueller & Larson, P.C.

(57) ABSTRACT

The present disclosure relates to a method of generating an antibody library, not limiting to a synthetic antibody gene (Continued)

expression library built on pool of consensus nucleic acid sequences by using codon replacement technology. The present disclosure also relates to a synthetic antibody library generated by employing the method of the present disclosure and application(s) of said antibody library.

14 Claims, 29 Drawing Sheets

Specification includes a Sequence Listing.

(51) Int. Cl.
C07K 16/00 (2006.01)
C40B 40/02 (2006.01)
C40B 40/10 (2006.01)

(52) U.S. Cl.
CPC .............. *C40B 40/08* (2013.01); *C40B 40/10* (2013.01); *C07K 2317/21* (2013.01); *C07K 2317/565* (2013.01); *C07K 2317/567* (2013.01); *C07K 2317/60* (2013.01)

(56) References Cited

OTHER PUBLICATIONS

Zhai et al., "Synthetic Antibodies Designed on Natural Sequence Landscapes", Journal of Molecular Biology vol. 412, pp. 55-71 (2011).
International Search Report and Written Opinion, International Patent Application No. PCT/IB2017/050280, dated May 18, 2017 (12 pages).
International Preliminary Report on Patentability, International Patent Application No. PCT/IB2017/050280, dated Jul. 13, 2018 (14 pages).

| Lane 1 | Undigested Clone |
| Lane 2 to 3 | Clones digested with NcoI-HF & XbaI |
| Lane 4 | GeneRuler 1 kb DNA Ladder (Thermoscientific) |
| Lane 5 to 6 | Clones digested with NcoI-HF & XbaI |
| Lane 7 | Undigested Clone |

A.

B.

| | |
|---|---|
| Lane 1 | H1A library undigested |
| Lane 2 | H1A library digested with *BstEII* & *XbaI* |
| Lane 3 | GeneRuler 100 bp DNA Ladder (Thermoscientific) |
| Lane 4 | GeneRuler 1 kb DNA Ladder (Thermoscientific) |
| Lane 5 | H1A library undigested |
| Lane 6 | H1A library digested with *BstEII* |
| Lane 7 | H1A library digested with *XbaI* |
| Lane 8 | H1A library digested with *SfiI* |

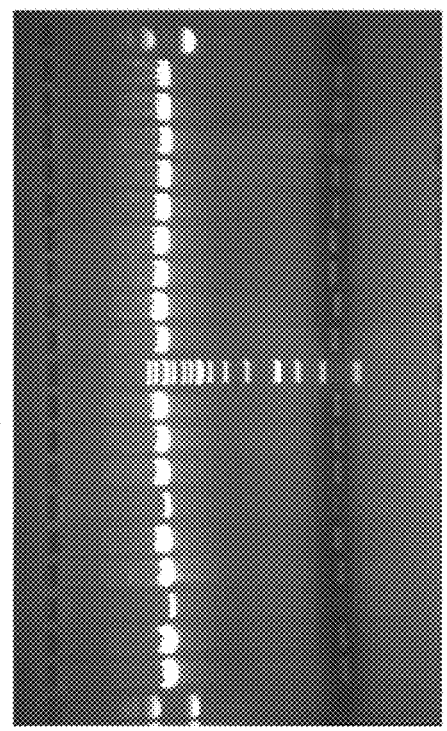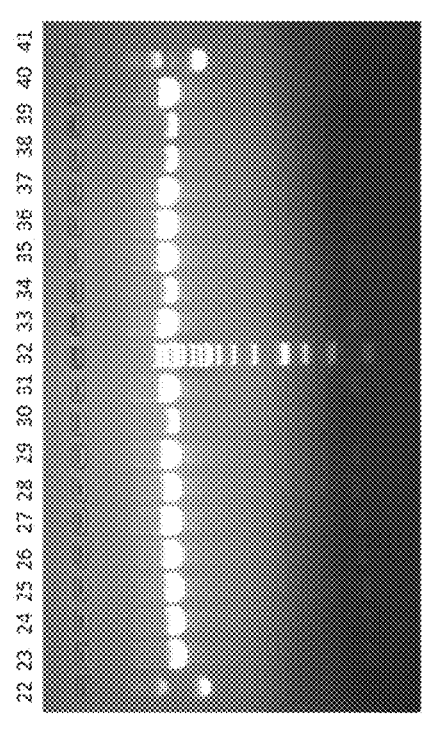
FIG. 21A
FIG. 21B

METHOD OF GENERATING A SYNTHETIC ANTIBODY LIBRARY, SAID LIBRARY AND APPLICATION(S) THEREOF

TECHNICAL FIELD

The present disclosure generally relates to the field of biotechnology, genetic engineering and immunology. Particularly, the present disclosure relates to a method of generating an antibody library, not limiting to a synthetic antibody gene expression library built on pool of consensus nucleic acid sequences by using codon replacement technology. The present disclosure also relates to a synthetic antibody library generated by employing the method of the present disclosure and application(s) of said antibody library.

BACKGROUND OF THE DISCLOSURE

Human antibody repertoires that are collections of human immunoglobulin (Ig) genes with most frequently found rearranged antibodies comprise of human variable-heavy chain (VH) segment that is well expressed and pairs with all light chains (Vk and Vλ) in a situation dependent fashion. In natural immune system, this diversity via rearrangement of genes occurs during B-lymphocyte maturation in an orderly manner. The naïve diversity that arises due to antigen independent process evolves further when a B-lymphocyte bearing surface antibody encounters an antigen with moderate affinity. Thus activation, maturation and differentiation process of virgin B-cells to mature B-cell ensue from collaboration with T-cells resulting B-cell's proliferation, secretion of antibody, production of IgG, somatic hypermutation and production of memory B-cells.

Human monoclonal antibody (mAb) and their derivatives are one of the largest and fastest growing segments of biopharmaceutical industry. Recent application of recombinant DNA technology for generating and expressing antibodies has attained a significant amount of interest among scientists from industry and academia.

Chimeric, humanized and human mAb, the prevailing formats of therapeutic mAb, share human constant domains but are discerned by the origin of their variable domains. Human mAb have a set of variable domains that are entirely stemmed from human antibody repertoires. Chimeric antibodies are artificially developed using the human codon usage which might result in anti-antibody response. This is one of the most important therapeutic limitations of early monoclonal antibody therapy. Moreover, this development of immune response can affect its efficacy and safety for example, reduced target binding, altered clearance and pharmacokinetics. Furthermore, humanized antibodies yielded from humanization process of the antibodies or grafting of CDR sequences bind antigen differently than the parent antibody. Thus, human monoclonal antibodies are generally viewed to have better pharmacokinetic and pharmacodynamic features when compared to monoclonal antibodies from nonhuman antibody repertoires. Immunogenicity of humanized mAbs is substantially less in comparison with nonhuman and chimeric monoclonal antibodies.

Approaches such as immunization and murine hybridoma technology are traditionally followed for generation of antibodies. However, limitations of immunization have been with safety and pharmacokinetic properties which directly impact utility and efficacy of drug molecule development. Limitations of hybridoma technology have been with the antigens' toxicity or non-immunogenicity in mice. Considering the high sequence homologies between the human and the respective murine antigen, generation of antibodies to self-antigens can be challenging.

More specifically, limitations associated with hybridoma technology are multifactorial. There is no control over the epitopes to which antibodies are formed. Antibodies must be screened extensively after they are created in the hope that one has been created with characteristics that are desirable to the investigator. Moreover, Sensitive antigens (e.g. membrane proteins and nucleic acids) could be destroyed in the animal while toxic antigens might kill the animal. Considering the high sequence homology between the human and the mice, respective murine antigen might give rise to non-immunogenicity in mice wherein generation of antibodies to self-antigens can be challenging. The scope of further development of antibodies in terms of rationally introducing features exhibiting higher affinity is extremely limited and difficult to do.

A synthetic diversity mimics the pattern of mutations seen in immunoglobulins after immunization and clonal selection. Therefore, synthetic libraries fundamentally differ from immune or naïve libraries in the origin of the sequences used to build and develop the library. In synthetic libraries the antibody diversity is designed in silico and synthesized in a controlled manner, while naïve libraries are amplified from a natural source and diversity is random. The ratio of naturally-derived and synthetically-designed segments varies in different libraries designating a library from semi-synthetic to fully synthetic.

To develop a wide diverse synthetic antibody library, understanding on amino acid positional and compositional biasness could be explored along with the related information on length variation. Moreover, the diversity in synthetic antibody repertoire is solely relying on rational designing guided by structure-function studies of antibody-antigen interactions. In 1992, semi-synthetic scFv-antibody phage display libraries, comprising 49 VH sequences and a single Vλ light chain sequence were developed by Hoogenboom and Winter, wherein five to eight residues in the CDR-H3 region were randomized via PCR-based approach generating libraries with a size of $1 \times 10^7$. Subsequent libraries were built with the addition of 26 kappa and 21 lambda sequences. Length variability mediated diversity was introduced in a library through randomization of 4-12 residues in CDR-H3, 1-3 residues in kappa CDR-L3 and 0-5 residues in lambda CDR-L3 resulting a library size expanded up to $6.5 \times 10^{10}$. Researchers made a surprising observation wherein post selection certain frameworks (predominantly VH1 and VH3) are over represented in phage display platform, beyond the expectation from the input library. This observation prompted to the development of single consensus acceptor sequence where the heavy and light chain sequence were identified/chosen based on the frequency of use and stability and/or expression levels.

Unlike Naïve library, selective binding can be introduced through alteration in single frame work region which hinders the ability of the antibodies of the library to bind all types of antigens. Among various formats, genes encoding single chain antibody (scFv) or Fab were made by randomly combining heavy and light chain V-genes using PCR and the combinatorial library could be cloned in phagemids or yeast for display on the surface of a phage. Alternatively libraries may be obtained through the artificial introduction of mutations into the complementarity determining regions (CDR) of the heavy chains or of the light chain domains. Heavy chain CDR3 is key contributor towards antigen binding and is the most variable among the CDRs in natural antibody.

The CDR3 of the variable heavy genes varies in size and sequence during the rearrangement of the V-D-J segments plays a dominant role in the antibody diversity. Naive libraries were constructed by the use of degenerate primers while synthetic libraries are made through randomization of the CDR3 amino acid composition. Several studies showed that medium size libraries ($5 \times 10^7$ members) with variation in the heavy chain CDR3 have provided a successful identification of novel antibody specificities. Larger libraries of more than $10^8$ molecules with heavy chain CDR3 sequence lengths of 4 to 21 residues from 50 VH and 6 to 15 residues in 49 different VH genes allowed the selection of antibody fragments with different specificities. Work done by De Kruif and collaborators had successfully used all 49 human germline VH genes and seven different light chain genes (4 from variable kappa, 3 from variable lambda) with CDR-H3 length variability ranging from 6 to 15 residues to construct a library of $3.6 \times 10^8$. The approach included the complete randomization of shorter CDR-H3s of six amino acid length while for the longer CDR-H3s the design involved a stretch of fully randomized amino acid residues flanked by regions of lower diversity resembling human natural antibody sequences. The CDRH3 strongly contributes to the overall specificity of an antibody. However, the other five CDRs may also contribute to the specificity and affinity of the antibody.

Another approach which combines all the CDRs uses a CDR-Implantation Technology or CDR grafting technology. As can be understood, the degree of functional variation arising by simultaneous and random combination of six CDRs is enormous. Usefulness of a library in terms of finding specific set of antibody fragments to both haptens and protein antigens could be selected from the smallest libraries; however, affinities is expected to be moderately low. A great extent of work done on these aspects had led to observation that there is a strong bias towards the VH3 framework. As exemplified by the use of a ten times larger library resulted in selection of scFv fragments against 18 different antigens. Another observation indicated that all VH families except VH2 were found wherein VH3 family was seen as strongly overrepresented.

Accumulating results from selections done with the early libraries confirmed that the larger libraries yield more specific antibodies with higher affinities. Another observation is that certain frameworks (predominantly VH1 and VH3) are generally over represented after phage display selection wherein, the ratio is often different than the input libraries. This has led to the development of single acceptor framework libraries wherein sequence for VH and VL frameworks were chosen based on the frequency of use and for their favorable stability. One such example Libraries that are made of a single framework combination often use the heavy chain framework VH3_23, a framework that is frequently found in human antibodies. This exclusive heavy chain pairs with most of the light chains and shows a good expression in bacteria and displays well on phages.

Pini and others have used VH3_23 heavy chain and the light chain corresponding to the Vκ3_20 germline for its expression levels and stability properties wherein designated positions were randomized in CDR-L3 and CDR-H3, resulting in a library size of $>3 \times 10^8$. 88% of the clones were shown to express a functional antibody and scFvs were selected with monovalent affinities at nano molar level. The same frame work was used by Bioinvent in combination with V_lambda (DPL3) to generate n-CoDeR® scFv library. The natural diversity was used to introduce the diversity for this library. This specific library consists of sequences encoding in vivo formed CDRs originated from rearranged immunoglobulin genes of different germline sources which were combined into one single master framework by PCR amplification of CDR sequences. As there is only one fixed framework, CDR sequences from other germlines were combined with the fixed framework. CDR sequences were amplified from various sources with an assumption that these CDR regions might contain less T-cell epitopes compared to an in silico design. This assumption was based on the existence of in vivo proofreading mechanism. Although the initial library size was of $2 \times 10^9$, which was increased by one decade of magnitude and found to be selective molecules in the sub-nanomolar range of affinities.

For another instance, Lee and coworkers had used a similar framework sequence to construct libraries with synthetic CDR sequences based on a single scaffold. The library was constructed using the framework sequence of the humanized 4D5 antibody (Herceptin®), a framework derived from VH3_23 and V_kappa). In addition, natural diversity of human repertoire was mimicked by the use of custom tailored codon choices. These libraries resulted affinities in the low nanomolar ranges. On the other hand, in parallel with ScFv and Fab formats, single domain synthetic antibodies libraries were established by Tanha and others. A human VH library was constructed based on a camelized VH sequence through complete randomization of 19 of the 23 CDR3 residues.

Another example of combining synthetic diversity in CDR-H1 and -H2 with length and sequence diversity in CDR-H3 from natural origin can be seen in literature where in Hoet and coworkers at Dyax had introduced hotspot mutations in germline sequences and strategically placed in CDRH1 and H2 regions. This resulted to a library with a size of $3.5 \times 10^{10}$ and a phage library with a size of $1.0 \times 10^{10}$ with affinities ranging in the sub-nanomolar level. Based on the similar principle, Schoonbroodt and coworkers had generated a library on anti-carbohydrate antibodies wherein the library was customized for the generation of antibodies recognizing negatively charged carbohydrates by introducing basic residues at defined positions. Sequence alignment studies done on several carbohydrate binding antibodies prompted designated positions for mutations. The library was successfully tested on two human charged carbohydrate targets, heperan sulfate and 6-sulfosialyl Lewis X core. In another instance, designed library named as HUCAL®, is based on consensus sequences representing multiple germline families rather than using a single germline sequence. This concept incorporates the different framework sequences contributing to the structural diversity of human antibodies.

Taken together, the approach describes concept of one consensus framework for each of the human VH and VL subfamilies that is frequently used during an immune response, resulting in seven master genes for VH and seven master genes for VL to obtain 49 possible combinations in Fab format. The sequencing of 257 members of the unselected libraries indicated that the frequency of correct and potentially functional sequences was not more than 61%. However, structural incompatibility between these newly introduced CDRs and the fixed framework might prevent the formation of functional antibody. Optimization of an antibody selected from a library screening involves various in vitro strategies including site specific mutagenesis based on structural information or combinatorial mutagenesis of CDR/s.

All high-affinity antibodies are generated by the immune system through a combination of steps introducing diversity (somatic hypermutation) and a subsequent selection (clonal expansion) in vivo. During antigen stimulated B-cell proliferation, the immunoglobulin locus undergoes a very high rate of somatic mutation. There are several different approaches to mimic these events in vitro to improve the affinity of antibodies obtained from combinatorial synthetic libraries. For in vitro affinity maturation, selected molecules are randomized to introduce diversity followed by selection with selective pressure to identify improved variants which in turn can differentiate between targeted and non-targeted diversification strategies.

Among various non-targeted diversification approaches, error prone PCR and the use of mutator E. coli strains are employed to introduce mutations resulting diversity. However, as sequence diversity is introduced randomly into the whole antibody sequence, therefore, this leads to the introduction of deleterious mutations in conserved framework regions and demands the screening of a large repertoire to identify potential candidates. Error prone PCR in combination with phage display was used by Hawkins and colleagues wherein a moderate 4.5-fold rise in affinity of a hapten specific antibody fragment was observed. Another group had used E. coli mutator strain mutD5 in combination with subsequent phage display. This resulted in an increased affinity of a phOx antibody fragment by a factor of 100-fold. Though not popularly used, but, chain shuffling is another method that exists for non-targeted diversification. This approach entails replacement of one of the two antibody chains by a repertoire keeping other chain constant. As exemplified by the work of Marks and colleagues, wherein, the method of chain shuffling with a ScFv that is specific for the hapten phOx, was used for subsequent screening experiments. Various groups of researchers had successfully used antibody chain shuffling for affinity maturation resulting in significant affinity improvement such as 5 to 6 fold affinity improvement of an erbB2 specific antibody fragment while a 30-fold affinity improvement was seen for a VEGF specific antibody fragment.

The designed strategy to develop synthetic library comprises of targeted schemes to introduce diversity at defined positions that are predicted to contribute to the antigen binding, primarily in the CDR regions. CDR-targeted mutagenesis is advantageous since optimization of these regions is likely to improve affinity without creating issues with protein stability or functionality. Among several adopted methodologies, CDR walking has been used with a scope of limited diversity wherein short stretches of 4 to 6 amino acids of a single CDR are targeted. There is both parallel and sequential CDR walking which can be introduced by the use of degenerated oligonucleotides. One such example is improved affinity of a gp120 (HIV antigen) specific antibody.

A series of libraries were constructed utilizing a subset of amino acids for diversification. This is in contrast to the approach of maximizing diversity within the framework sequences of the naturally occurring antibody sequence space. It has been observed from crystallographic analyses and associated findings that naturally occurring tyrosine and serine residues are favored in their antigen binding sites. Researchers at Genentech had randomized selected solvent accessible CDR positions to create a small synthetic library which was later successfully screened against VEGF giving rise to potential molecules with low nano molar affinity.

Various synthetic combinatorial antibody libraries differ in terms of their design, origin of sequence diversity and method of generation. All these aspects have multifactorial impacts on the essential features of the library: i) size and ii) functional diversity. These in turn will be reflected in the ability to screen and deliver high affinity antibodies with acceptable and improved biophysical properties.

Selection and screening studies done with the earlier libraries have confirmed the expectation that larger libraries yield more specific antibodies with higher affinities. Several display and protein interaction systems have been established as selection methods for antibody-antigen interaction while most preferred being a display of the antibody on the surface of, either phages, yeast, or on ribosomes following an in vitro transcription. In contrast, intracellular selection methods, such as yeast-two-hybrid system or protein complementation assay directly rely on intracellular expression of the target protein.

The ribosome display method is technically more challenging due to relative instability of the RNA and the ribosomal complex. Phage display is the most accepted method due to ease of cloning, allowing for large library sizes, monovalent display and easy to determine various stability parameters. However, with phage display, there are limitations on proper protein folding due to prokaryotic expression system and lack of post translational modifications of the displayed antibody fragments. To overcome these limitations, yeast display platform, a eukaryotic display system is of choice as it is compatible with fluorescence activated cell sorter (FACS)-sorting techniques, which allows antibody selection close to natural conditions in solution and in parallel, parameters like antibody expression levels, number of bound antigen, or cross-reactivity could be assessed. However, major challenge in case of yeast display would be relatively smaller library size.

The instant disclosure, is directed towards addressing such limitations of the prior art and therefore aims at designing and creating highly diverse antibody synthetic gene libraries which are capable of accommodating a large library size, which can thereby improve the potential of identifying and generating unique molecules against multitude of antigens with varied affinities and specificities.

BRIEF DESCRIPTION OF THE ACCOMPANYING FIGURES

The features of the present disclosure will become fully apparent from the following description taken in conjunction with the accompanying figures. With the understanding that the figures depict only several embodiments in accordance with the disclosure and are not to be considered limiting of its scope, the disclosure will be described further through use of the accompanying figures:

FIG. 1 illustrates analysis of CDRH3 length distribution.

FIG. 2 illustrates relative amino acid frequency distribution for heavy chain CDRH3. Data represents CDRH3 length of 14 amino acids. Kabat nomenclature has been followed.

FIG. 3 illustrates strategy to generate phagemid consensus constructs

A. generation of kappa light chains (K1 to K4) containing consensus sequences

B. generation of lambda light chains (L1 to L3) containing consensus sequences

C. schematic depiction of synthetic CDRH3 library into heavy chain variable region between framework 3 (FR3) and framework 4 (FR4).

FIG. 4 illustrates analysis of independent clones from H1A consensus constructs using NcoI-HF & XbaI enzymes.

FIG. 5 shown as FIG. 5A, FIG. 5B, FIG. 5C and FIG. 5D, illustrates analysis of representative clones from H1A consensus constructs with Kappa light chain variable region using HindIII-HF & AscI enzymes.

FIG. 5A represents K1 family; FIG. 5B represents K2 family; FIG. 5C represents K3 family and FIG. 5D represents K4 family.

FIG. 6 illustrates analysis of representative clones from H1A consensus constructs with lambda light chain variable region using HindIII-HF & AscI enzymes
  A. L1 family; B. L2 family and C. L3 family.

FIG. 7 illustrates quantification of synthesized CDRH3 library through real time PCR.

FIG. 8 illustrates NGS sequence analysis of CDRH3 synthetic library
  A. Sequence correctness of synthetic library
  B. CDRH3 length distribution of synthetic library.

FIG. 9 illustrates relative amino acid frequency distribution of synthesized CDRH3 library
  A. CDRH3 length—4 amino acids
  B. CDRH3 length—5 amino acids
  C. CDRH3 length—6 amino acids
  D. CDRH3 length—7 amino acids.

FIG. 10 illustrates relative amino acid frequency distribution of synthesized CDRH3 library
  A. CDRH3 length—8 amino acids
  B. CDRH3 length—9 amino acids
  C. CDRH3 length—10 amino acids
  D. CDRH3 length—11 amino acids.

FIG. 11 illustrates relative amino acid frequency distribution of synthesized CDRH3 library
  A. CDRH3 length—12 amino acids
  B. CDRH3 length—13 amino acids
  C. CDRH3 length—14 amino acids
  D. CDRH3 length—15 amino acids.

FIG. 12 illustrates relative amino acid frequency distribution of synthesized CDRH3 library
  A. CDRH3 length—16 amino acids
  B. CDRH3 length—17 amino acids
  C. CDRH3 length—18 amino acids
  D. CDRH3 length—19 amino acids.

FIG. 13 illustrates relative amino acid frequency distribution of synthesized CDRH3 library
  A. CDRH3 length—20 amino acids
  B. CDRH3 length—21 amino acids
  C. CDRH3 length—22 amino acids
  D. CDRH3 length—23 amino acids.

Figure 21C:
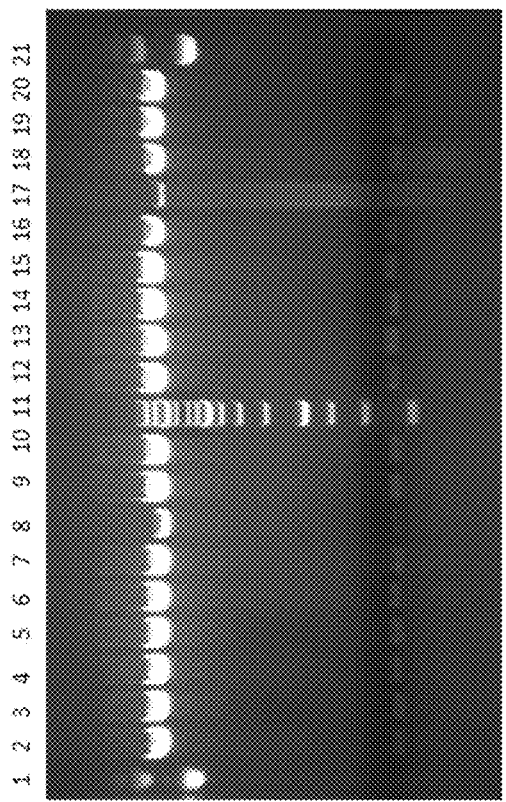

FIG. 21 shown as FIG. 21A, FIG. 21B and FIG. 21C, illustrates restriction enzyme digestion of independent clones in yeast expression vectors.

FIG. 21A represents heavy chain clones;

FIG. 21B represents kappa light chain clones; and

FIG. 21C represents lambda light chain clones.

Figure 22:
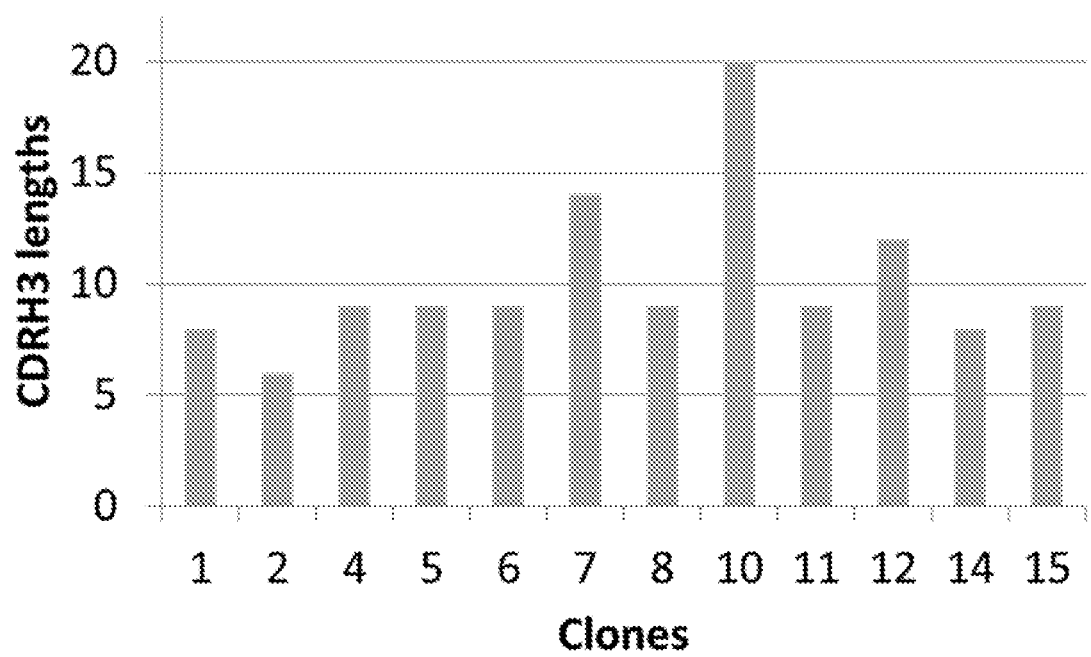

FIG. 22 illustrates sequence analysis of independent clones in yeast vectors showing CDRH3 length variation.

Figure 23:
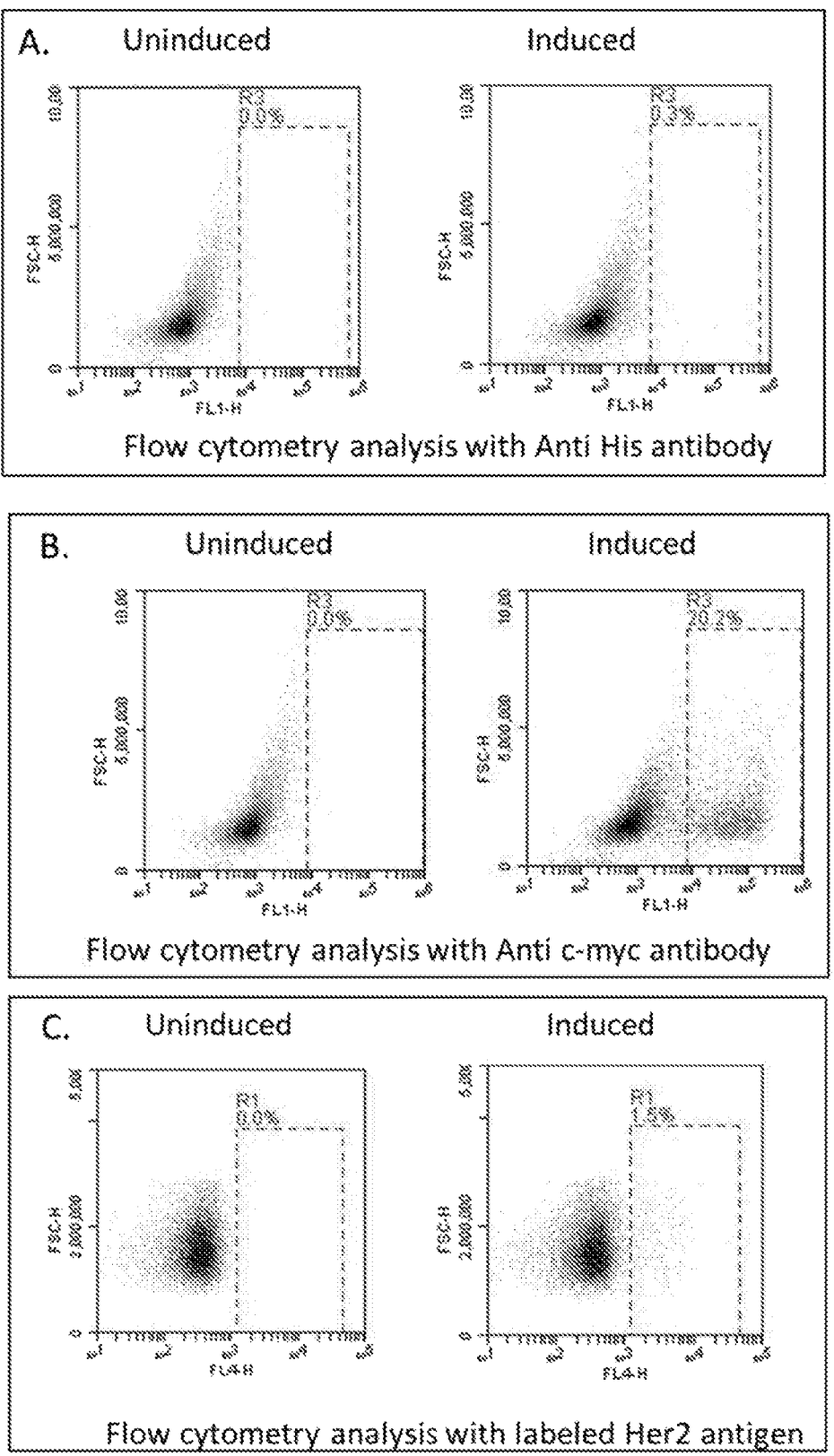

FIG. 23 illustrates flow cytometry analysis of yeast synthetic CDRH3 library with Kappa light chain against Her2 antigen
  A. Flow cytometry analysis with Anti His antibody
  B. Flow cytometry analysis with Anti c-myc antibody
  C. Flow cytometry analysis with labeled Her2 antigen.

Figure 24:
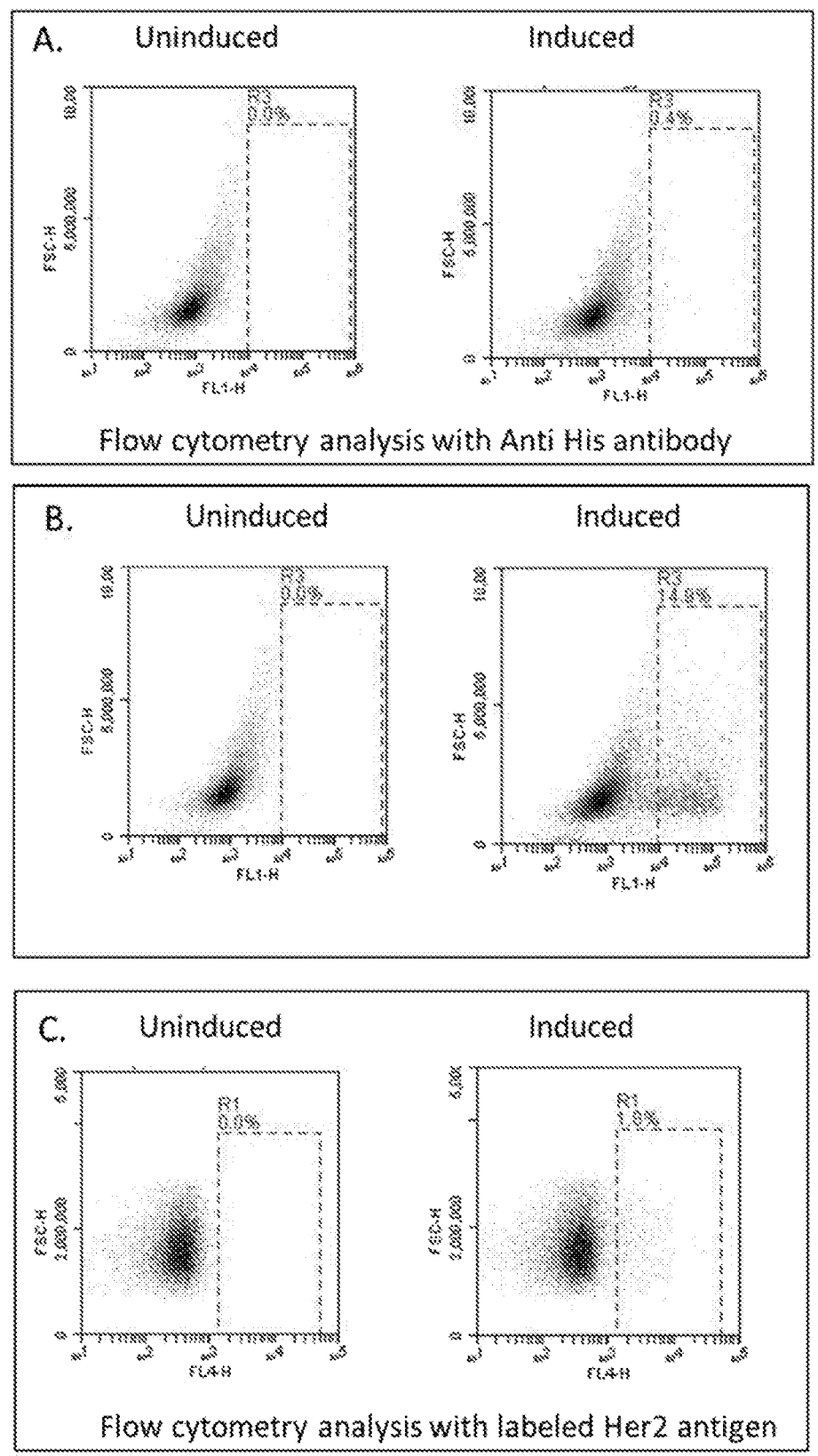

FIG. 24 illustrates flow cytometry analysis of yeast synthetic CDRH3 library with Lambda light chain against Her2 antigen.
  A. Flow cytometry analysis with Anti His antibody
  B. Flow cytometry analysis with Anti c-myc antibody
  C. Flow cytometry analysis with labeled Her2 antigen.

Figure 25:
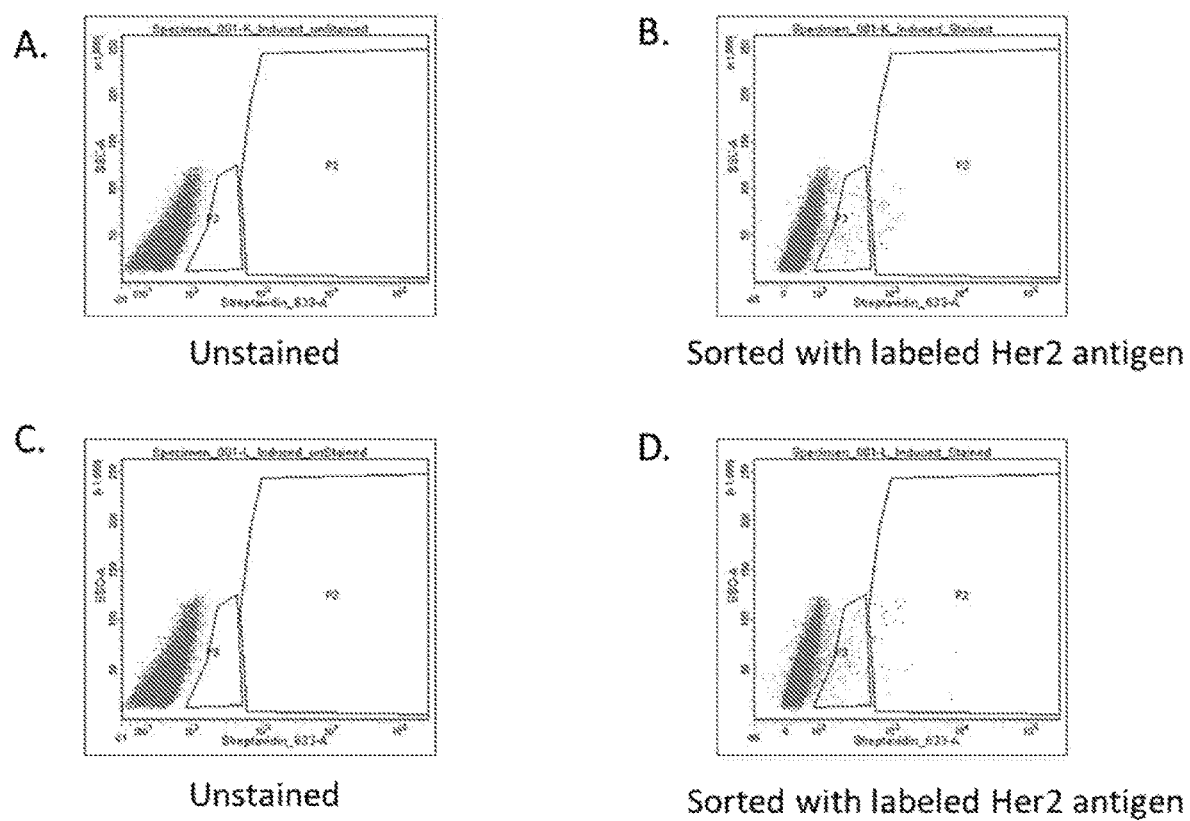
Figure 26:
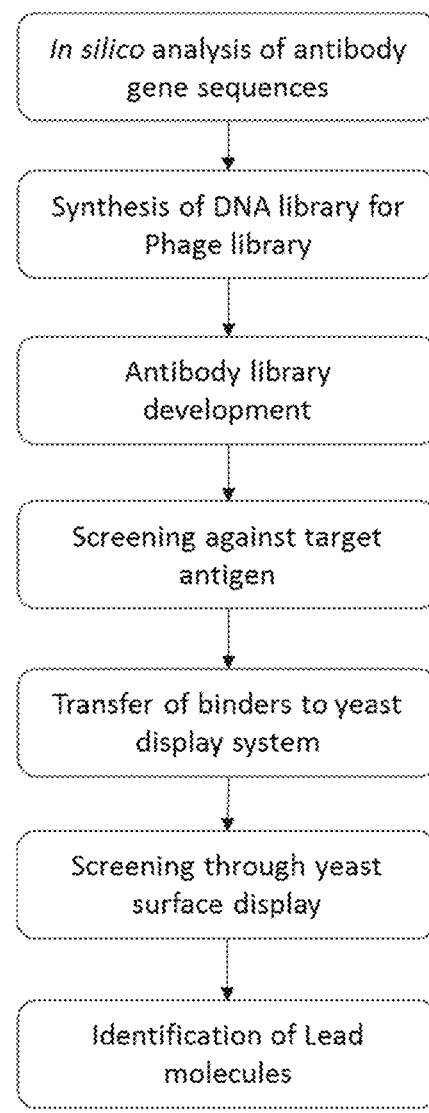

FIG. 25 illustrates flow cytometry sorting of yeast synthetic CDRH3 library with Kappa light chain (A and B) and with lambda light chain (C and D) against Her2 antigen. Yeast libraries were induced for 24 hours with galactose for surface display of Antibody
  A. Unstained yeast cells
  B. Yeast cells sorted with labeled Her2 antigen
  C. Unstained yeast cells
  D. Yeast cells sorted with labeled Her2 antigen FIG. 26 provides a flow chart illustrating the present method of generating synthetic human antibody library.

Figure 27A:
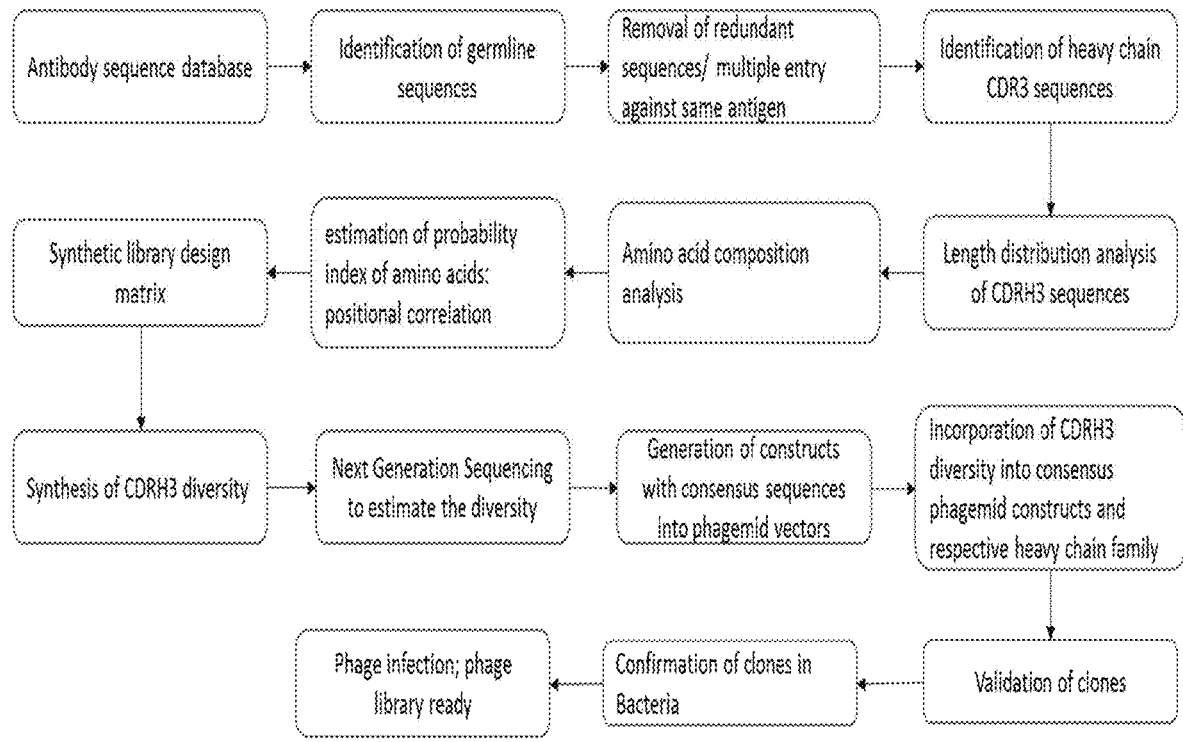

FIG. 27A provides a flow chart illustrating the process steps starting from designing of synthetic diversity to creation of synthetic antibody library in phage.

Figure 27B:
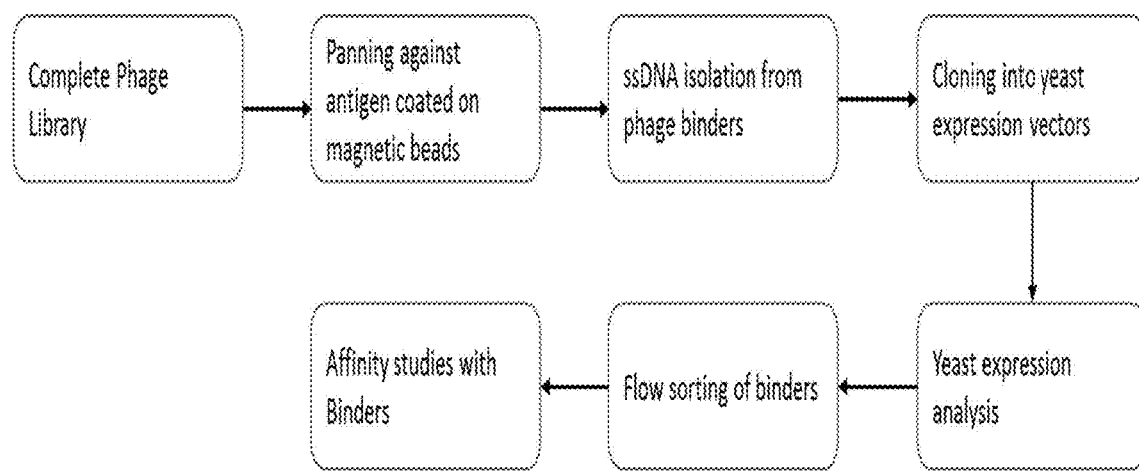

FIG. 27B provides a flow chart illustrating the process steps involving phage library screening to yeast clone development using flow sorting of independent binders.

STATEMENT OF THE DISCLOSURE

Accordingly, the present disclosure relates to a synthetic library of antibody molecule(s) comprising modified CDR of heavy chain of the antibody molecule(s) having length varying from about 4 amino acids to about 23 amino acids, wherein when the length of said CDR is 4 amino acids, frequency of amino acid Aspartic Acid at position 2 is about 20%, when the length of said CDR ranges from 5 to 17 amino acids, frequency of amino acid Aspartic Acid at second last position ranges from about 40% to about 80% or frequency of amino acid Tyrosine at last position ranges from about 40% to about 65% or when the length of said CDR ranges from 18 to 23 amino acids, frequency of amino acid Valine at last position ranges from about 20% to about 67% or frequency of amino acid Isoleucine at last position ranges from about 17% to about 24%; a method of obtaining the synthetic library as above comprising steps of screening and identifying antibody molecules having at least one predetermined characteristic(s), analysing the identified molecules on the basis of length distribution analysis of CDR3 heavy chain (CDRH3) and frequency of occurrence of amino acids within said CDRH3 to determine optimal chain length and amino acid frequency, designing altered antibody molecule(s) followed by subjecting the molecule (s) to codon replacement technology on the basis of said optimal chain length and amino acid frequency as defined above, to obtain antibody molecule(s) with modified CDRH3, and cloning said molecule(s) to form the library; an antibody molecule isolated from the synthetic library as above or as obtained by the method as above; an antibody molecule comprising a heavy chain consensus amino acid sequence selected from SEQ ID 2, 4, 6, 8, 10, 12 or 14 encoded by corresponding nucleic acid sequence selected from SEQ ID 1, 3, 5, 7, 9, 11 or 13, the light chain consensus amino acid sequence selected from SEQ ID 16, 18, 20 or 22 encoded by corresponding nucleic acid sequence selected from SEQ ID 15, 17, 19 or 21, or consensus amino acid sequence selected from SEQ ID 24, 26 or 28 encoded by corresponding nucleic acid sequence selected from SEQ ID 23, 25 or 27, framework regions encoded by consensus nucleic acid sequence selected from SEQ ID 29-49, 64-79 or 92-103 and CDR encoded by consensus nucleic acid sequence selected from SEQ ID 50-63, 80-91 or 104-112, wherein, when the length of said CDR is 4, frequency of amino acid Arginine at positions 2, 3 and 4 varies from about 18% to about 20%, when the length of said CDR is 5, frequency of amino acid Proline at position 3 is at about 20%, when the length of said CDR is 6, frequency of amino acid Phenyl alanine at position 4 is about 25%, when the length of said CDR is 7, frequency of amino acid Phenyl alanine at position 5 is about 43.63%, when the length of said CDR is 8, frequency of amino acid Phenyl alanine at position 6 is about 35.24%, when the length of said CDR is 9, frequency of amino acid Phenyl alanine at position 7 is about 44.15%, when the length of said CDR is 10, frequency of amino acid Phenyl alanine at position 8 is about 55.93%, when the length of said CDR is 11, frequency of amino acid Phenyl alanine at position 9 is about 54.27%, when the length of said CDR is 12, frequency of amino acid Phenyl alanine at position 10 is about 52.70%, when the length of said CDR is 13, frequency of amino acid Phenyl alanine at position 11 is about 54.39%, when the length of said CDR is 14, frequency of amino acid Phenyl alanine at position 12 is about 54.77%, when the length of said CDR is 15, frequency of amino acid Phenyl alanine at position 13 is about 54.81%, when the length of said CDR is 16, frequency of amino acid Phenyl alanine at position 14 is about 50.47%, when the length of said CDR is 17, frequency of amino acid Phenyl alanine at position 15 is about 37.93%, when the length of said CDR is 18, frequency of amino acid Phenyl alanine at position 16 is about 37.96%, when the length of said CDR is 19, frequency of amino acid Phenyl alanine at position 17 is about 40.09%, when the length of said CDR is 20, frequency of amino acid Glutamic acid at position 1 is about 15.56%, when the length of said CDR is 21, frequency of amino acid Phenyl alanine at position 19 is about 35.45%, when the length of said CDR is 22, frequency of amino acid Phenyl alanine at position 20 is about 36.27% and when the length of said CDR is 23, frequency of amino acid Phenyl alanine at position 21 is about 43.24%; and a synthetic antibody library of above or as obtained by method of above for use in therapeutics for treatment of diseases selected from a group comprising cancer, rheumatoid arthritis, neurological disorders, infectious diseases and metabolic disorders or any combination thereof as diagnostics, as prognostics for research purposes, target discovery, validation in functional genomics or any application where antibodies or derivatives of antibodies are employed.

DETAILED DESCRIPTION OF THE DISCLOSURE

Unless otherwise defined herein, scientific and technical terms used in connection with the present disclosure shall have the meanings that are commonly understood by those of ordinary skill in the art. Further, unless otherwise required by context, singular terms shall include the plural and plural terms shall include the singular as is considered appropriate to the context and/or application. The various singular/plural permutations may be expressly set forth herein for the sake of clarity. Generally, nomenclatures used in connection with, and techniques of biotechnology, immunology, molecular and cellular biology, recombinant DNA technology described herein are those well-known and commonly used in the art. Certain references and other documents cited herein are expressly incorporated herein by reference. In case of conflict, the present specification, including definitions, will control. The materials, methods, figures and examples are illustrative only and not intended to be limiting.

Furthermore, the methods, preparation and use of the antibody synthetic library disclosed employ, unless otherwise indicated, conventional techniques in molecular biology, biochemistry, computational chemistry, cell culture, recombinant DNA technology, Polymerase Chain Reaction (PCR) and related fields. These techniques, their principles, and requirements are explained in the literature and known to a person skilled in the art.

Before the method of generating the antibody synthetic library and the nucleic acids which make up the antibody synthetic library and other embodiments of the present disclosure are disclosed and described, it is to be understood that the terminologies used herein are for the purpose of describing particular embodiments only and are not intended to be limiting. It must be noted that, as used in the specification and the appended claims, the singular forms "a," "an" and "the" include plural referents unless the context clearly dictates otherwise.

As used herein, the terms "library" and "libraries" are used interchangeably within this disclosure which relate to the product of the disclosure. Furthermore, it refers to a collection or pool of nucleic acid sequences.

As used herein, the terms 'pooling', 'pooled', 'pool', 'pools' in the context of the instant disclosure mean combining the samples/nucleic acid sequences/nucleic acid fragments/gene clones/amplified product/antibodies obtained by employing the method of the instant disclosure.

As used herein, the term "Antigen" refers to any foreign substance which induces an immune response in the body.

As used herein, the term "antibody" refers to an immunoglobulin which may be derived from natural sources or synthetically produced, in whole or in part. The terms "antibody" and "immunoglobulin" are used synonymously throughout the specification unless indicated otherwise.

As used herein, the term "antibody" includes both polyclonal and monoclonal antibody preparations and also includes the following: Chimeric antibody molecules, F(ab')2 and F(ab) fragments, Fv molecules, single chain Fv molecules (ScFv), dimeric and trimeric antibody fragments, minibodies, humanized monoclonal antibody molecules, human antibodies, fusion proteins comprising Fc region of antibody and any functional fragments arising out of these molecules, where derivative molecules retain immunological functionality of the parent antibody molecule.

As used herein, the term "monoclonal antibody" in the present disclosure, refers to an antibody composition having a homogeneous antibody population. The antibody is not limited to the species or source of the antibody or by the manner in which it is made. The term encompasses whole immunoglobulins as well as fragments such as Fab, F(ab')2, Fv, and other fragments, as well as chimeric and humanized homogeneous antibody populations that exhibit immunological binding properties of the parent monoclonal antibody molecule.

As used herein, "antibody fragment" is a portion of a whole antibody which retains the ability to exhibit antigen binding activity. The terms Fab or ScFv are used as antibody fragments with specific mention.

As used herein, "Antibody display library" refers to a platform(s) expressing antibodies on the surface of cell or cell-free suited for a screening methodology against target antigens. Herein, phage display library and yeast display library are used with accurate specification unless indicated otherwise.

As used herein, the term "synthetic library" refers to a collection of nucleic acid sequences encoding a synthetically designed VH repertoire.

As used herein, the term "VH" refers to the single heavy chain variable domain of antibody of the type that can be found in mammals which are naturally devoid of light chains or parts of the same;

As used herein, the term "VL" refers to single light chain variable domain of the antibody; they are found in two types based on the constant domain sequence. Vk (with kappa constant region) and Vl (lambda constant region) are understood accordingly.

As used herein, the term "CDR" refers to complementary determining region of the antibody structure.

As used herein, the term "repertoire," means a collection, indicating genetic diversity.

As used herein, the term "framework region" is used herein to refer to the nucleic acid sequence regions of an antibody molecule that encode the structural elements of the molecule.

As used herein, the term "flaking region" is used to refer to nucleotide and/or amino acid sequences adjacent to the mentioned region.

As used herein, the term "randomization" is used to refer to creation of amino acid and/or nucleotide sequence diversity based on specific design.

As used herein, the term "Aga2p" refers to a yeast protein used as an anchor protein displaying antibody of interest on the yeast surface.

As used herein, the term "Immunoglobulin" refers to glycoprotein molecules acting as a critical part of the immune response by specifically recognizing and binding to particular antigens.

As used herein, the term "PCR" refers to polymerase chain reaction, a molecular biology technique that is used to amplify a segment of DNA using appropriate primers.

As used herein, the term "Primer" refers to a short fragment of DNA or RNA to initiate DNA synthesis.

As used herein "vector" refers to a DNA related to a cloning or expression system to accommodate antibody genes in specific designated restriction sites. Phagemid vectors (applicable to phage display system) or yeast vectors (applicable to yeast display system) are understood accordingly.

As used herein, the term "Phagemid" refers to a DNA expression system wherein it can be replicated as a plasmid, and also be packaged as single stranded DNA in viral particles. Phagemid is used to accommodate the whole repertoire of antibody genes wherein post infection to bacteria it requires additional proteins provided by helper phage to create phage particles that display recombinant protein.

As used herein, the term "Phage" means virus particles which infect bacteria and amplify.

As used herein, "Helper Phage" refers to a specific phage particle which supply all required proteins/materials to produce functional phage particles.

As used herein, the term "Plaque" refers to visible structure formed on lawn of bacteria due to cell destructions.

As used herein, "Phage amplification" refers to growth of phage particles.

As used herein, the term "Panning" refers to an affinity selection technique which selects for binders against a specific target/antigen.

As used herein "Salmon sperm DNA" refers to a low molecular weight deoxyribonucleic acid isolated from salmon sperm aiding phage DNA precipitation.

As used herein "ssDNA" refers to single stranded DNA.

As used herein "positional correlation index" refers to a probabilistic value that defines how an amino acid of specific frequency residing in CDR of particular length is related to a different position.

As used herein "Peer group sequencing" refers to a set of processes comprising of nucleotide sequences derived from several individual clones as a true representation of a large library.

As used herein "codon replacement technology" refers to using preassembled tri-nucleotide building blocks to complete customization of the amino acid composition at specific site of interest leading to controlled diversification.

As used herein, "consensus sequence" refers to amino acid sequence, encoding nucleic acid sequence of synthetic DNA, not limiting to human variable heavy and light chain regions of immunoglobulins, which are designed in silico.

As used herein "Shannon Entropy" refers to a parameter to deduce the true diversity.

The present disclosure relates to a synthetic library of antibody molecule(s) comprising modified CDR of heavy chain of the antibody molecule(s) having length varying from about 4 amino acids to about 23 amino acids, wherein:
when the length of said CDR is 4 amino acids, frequency of amino acid Aspartic Acid at position 2 is about 20%;
when the length of said CDR ranges from 5 to 17 amino acids, frequency of amino acid Aspartic Acid at second last position ranges from about 40% to about 80% or frequency of amino acid Tyrosine at last position ranges from about 40% to about 65%; or
when the length of said CDR ranges from 18 to 23 amino acids, frequency of amino acid Valine at last position ranges from about 20% to about 67% or frequency of amino acid Isoleucine at last position ranges from about 17% to about 24%.

In an embodiment, the synthetic library comprises the antibody molecule(s) comprising modified CDR of heavy chain of the antibody molecule(s) having length varying from about 4 amino acids to about 23 amino acids with a specific combination of amino acid frequency, wherein:
when the length of said CDR is 4 amino acids, frequency of amino acid Glycine at positions 1 and 3 ranges from about 16 to 36%;
when the length of said CDR is 5 amino acids, frequency of amino acid Glycine at first 3 positions ranges from about 20 to 38%;
when the length of said CDR is 6 amino acids, frequency of amino acid Glycine at first 4 positions ranges from about 11 to 35%;
when the length of said CDR is 7 amino acids, frequency of amino acid Glycine at first 4 positions ranges from about 12 to 38%;
when the length of said CDR is 8 amino acids, frequency of amino acid Glycine at first 5 positions ranges from about 14 to 34%;
when the length of said CDR is 9 amino acids, frequency of amino acid Glycine at first 6 positions ranges from about 12 to 43%;

when the length of said CDR is 10 amino acids, frequency of amino acid Glycine at first 7 positions ranges from about 14 to 30%;

when the length of said CDR is 11 amino acids, frequency of amino acid Glycine at first 8 positions ranges from about 14 to 28%;

when the length of said CDR is 12 amino acids, frequency of amino acid Glycine at first 9 positions ranges from about 15 to 28%;

when the length of said CDR is 13 amino acids, frequency of amino acid Glycine at first 10 positions ranges from about 13 to 26%;

when the length of said CDR is 14 amino acids, frequency of amino acid Glycine at first 11 positions ranges from about 8 to 26%;

when the length of said CDR is 15 amino acids, frequency of amino acid Glycine at first 12 positions ranges from about 8 to 30%;

when the length of said CDR is 16 amino acids, frequency of amino acid Glycine at first 13 positions ranges from about 7 to 35%;

when the length of said CDR is 17 amino acids, frequency of amino acid Glycine at first 14 positions ranges from about 7 to 36%;

when the length of said CDR is 18 amino acids, frequency of amino acid Glycine at first 15 positions ranges from about 7 to 30%;

when the length of said CDR is 19 amino acids, frequency of amino acid Glycine at first 16 positions ranges from about 7 to 45%;

when the length of said CDR is 20 amino acids, frequency of amino acid Glycine at first 17 positions ranges from about 3 to 44%;

when the length of said CDR is 21 amino acids, frequency of amino acid Glycine at first 18 positions ranges from about 2 to 44%;

when the length of said CDR is 22 amino acids, frequency of amino acid Glycine at first 19 positions ranges from about 3 to 58%; or when the length of said CDR is 23 amino acids, frequency of amino acid Glycine at first 20 positions ranges from about 0.5 to 58%.

In another embodiment, the synthetic library comprises the antibody molecule(s) comprising modified CDR of heavy chain of the antibody molecule(s) having length varying from about 4 amino acids to about 23 amino acids with a specific combination of amino acid frequency at each position, wherein:

when the length of said CDR is 4—
a. frequency of amino acid Aspartic Acid at positions 1 and 2 is about 10%, and about 20%, respectively;
b. frequency of amino acid Proline at positions 1 to 3 varies from about 0.05% to about 0.15%, and at position 4 is about 15%; and
c. frequency of amino acid Arginine at position 1 is about 5%, and at positions 2, 3 and 4 varies from about 18% to about 20%, when the length of said CDR is 5—
a. frequency of amino acid Proline at positions 1, 2, 3, 4 and 5 is about 3%, 0.05%, 20%, 0.1%, and 6%, respectively; and
b. frequency of amino acid Arginine at positions 1, 2, 3, 4 and 5 is about 6%, 18%, 0.2%, 0.1%, and 0.05%, respectively, when the length of said CDR is 6—
a. frequency of amino acid Phenylalanine at positions 1, 2, 3, 4, 5 and 6 is about 3.00%, 0.15%, 2%, 25%, 0.05% and 3.5%, respectively;
b. frequency of amino acid Asparagine at positions 1, 2, 3, 4, 5 and 6 is about 3.43%, 5.61%, 0.09%, 0.06%, 7.79% and 0.08%, respectively;
c. frequency of amino acid Proline at positions 1, 2, 3, 4, 5 and 6 is about 0.05%, 7.78%, 7.48%, 4.37%, 4.53%, and 1.77%, respectively; and
d. frequency of amino acid Serine at positions 1, 2, 3, 4, 5 and 6 is about 1.76%, 9.44%, 8.13%, 8.93%, 0.26%, and 1.43%, respectively, when the length of said CDR is 7—
a. frequency of amino acid Phenylalanine at positions 1, 2, 3, 4, 5, 6 and 7 is about 3.65%, 0.18%, 0.08%, 3.09%, 43.63%, 0.15% and 3.01%, respectively;
b. frequency of amino acid Asparagine at positions 1, 2, 3, 4, 5, 6 and 7 is about 3.33%, 7.19%, 12.74%, 1.11%, 0.21%, 0.09% and 3.34%, respectively;
c. frequency of amino acid Proline at positions 1, 2, 3, 4, 5, 6 and 7 is about 0.09%, 4.68%, 0.23%, 2.74%, 3.95%, 0.06%, and 3.53%, respectively; and
d. frequency of amino acid Arginine at positions 1, 2, 3, 4, 5, 6 and 7 is about 6.98%, 15.99%, 3.98%, 4.13%, 1.00%, 1.16% and 0.67%, respectively, when the length of said CDR is 8—
a. frequency of amino acid Phenylalanine at positions 1, 2, 3, 4, 5, 6, 7 and 8 is about 4.56%, 6.02%, 2.69%, 4.00%, 1.82%, 35.24%, 0.98% and 2.61%, respectively;
b. frequency of amino acid Asparagine at positions 1, 2, 3, 4, 5, 6, 7 and 8 is about 3.17%, 3.28%, 3.30%, 5.44%, 2.19%, 2.99%, 0.93% and 4.74%, respectively;
c. frequency of amino acid Proline at positions 1, 2, 3, 4, 5, 6, 7 and 8 is about 0.05%, 6.05%, 3.76%, 1.04%, 3.79%, 1.47%, 0.68% and 4.64%, respectively; and
d. frequency of amino acid Arginine at positions 1, 2, 3, 4, 5, 6, 7 and 8 is about 6.24%, 5.58%, 8.88%, 8.36%, 5.24%, 0.10%, 0.88% and 3.18%, respectively, when the length of said CDR is 9—
a. frequency of amino acid Phenylalanine at positions 1, 2, 3, 4, 5, 6, 7, 8 and 9 is about 0.96%, 1.92%, 2.31%, 2.13%, 2.36%, 2.05%, 44.15%, 0.86% and 2.59%, respectively;
b. frequency of amino acid Asparagine at positions 1, 2, 3, 4, 5, 6, 7, 8 and 9 is about 0.68%, 2.83%, 3.24%, 3.36%, 3.13%, 3.94%, 1.12%, 0.93% and 4.74%, respectively;
c. frequency of amino acid Proline at positions 1, 2, 3, 4, 5, 6, 7, 8 and 9 is about 0.98%, 3.49%, 3.57%, 3.96%, 3.79%, 9.19%, 3.71%, 1.06% and 5.26%, respectively; and
d. frequency of amino acid Arginine at positions 1, 2, 3, 4, 5, 6, 7, 8 and 9 is about 4.93%, 9.19%, 9.45%, 9.10%, 9.50%, 3.21%, 0.07%, 0.83% and 3.97%, respectively, when the length of said CDR is 10—
a. frequency of amino acid Phenylalanine at positions 1, 2, 3, 4, 5, 6, 7, 8, 9 and 10 is about 0.12%, 2.44%, 2.27%, 2.49%, 2.18%, 2.78%, 2.64%, 55.93%, 0.56% and 2.32%, respectively;
b. frequency of amino acid Asparagine at positions 1, 2, 3, 4, 5, 6, 7, 8, 9 and 10 is about 0.66%, 2.95%, 3.25%, 3.15%, 3.22%, 3.10%, 1.22%, 1.35%, 0.91% and 4.76%, respectively;

c. frequency of amino acid Proline at positions 1, 2, 3, 4, 5, 6, 7, 8, 9 and 10 is about 1.42%, 3.12%, 3.57%, 2.78%, 3.00%, 2.81%, 4.00%, 1.22%, 0.78% and 4.08%, respectively; and
d. frequency of amino acid Arginine at positions 1, 2, 3, 4, 5, 6, 7, 8, 9 and 10 is about 5.28%, 9.13%, 9.97%, 9.70%, 10.04%, 9.91%, 4.20%, 0.07%, 1.12% and 3.81%, respectively, when the length of said CDR is 11—
a. frequency of amino acid Phenylalanine at positions 1, 2, 3, 4, 5, 6, 7, 8, 9, 10 and 11 is about 0.10%, 2.30%, 2.51%, 2.24%, 2.47%, 2.43%, 2.24%, 2.10%, 54.27%, 0.58% and 2.76%, respectively;
b. frequency of amino acid Asparagine at positions 1, 2, 3, 4, 5, 6, 7, 8, 9, 10 and 11 is about 0.68%, 2.74%, 2.98%, 3.40%, 2.98%, 3.33%, 3.54%, 4.20%, 0.97%, 1.26% and 4.40%, respectively;
c. frequency of amino acid Proline at positions 1, 2, 3, 4, 5, 6, 7, 8, 9, 10 and 11 is about 1.61%, 3.72%, 2.90%, 3.27%, 3.07%, 2.90%, 2.98%, 5.78%, 3.05%, 0.99% and 4.22%, respectively; and
d. frequency of amino acid Arginine at positions 1, 2, 3, 4, 5, 6, 7, 8, 9, 10 and 11 is about 5.62%, 9.57%, 10.06%, 10.35%, 9.61%, 9.14%, 10.00%, 2.18%, 0.00%, 1.11% and 4.14%, respectively, when the length of said CDR is 12—
a. frequency of amino acid Phenylalanine at positions 1, 2, 3, 4, 5, 6, 7, 8, 9, 11 and 12 is about 0.06%, 2.42%, 2.08%, 2.44%, 1.88%, 2.46%, 2.59%, 2.34%, 2.17%, 52.70%, 0.65% and 2.49%, respectively;
b. frequency of amino acid Asparagine at positions 1, 2, 3, 4, 5, 6, 7, 8, 9, 11 and 12 is about 0.59%, 3.31%, 3.58%, 3.12%, 3.24%, 3.27%, 3.62%, 6.42%, 1.28%, 0.89%, 1.14%, and 4.65%, respectively;
c. frequency of amino acid Proline at positions 1, 2, 3, 4, 5, 6, 7, 8, 9, 11 and 12 is about 1.62%, 3.52%, 3.50%, 3.43%, 3.64%, 2.72%, 3.35%, 4.82%, 6.23%, 3.16%, 0.82%, and 3.96%, respectively; and
d. frequency of amino acid Arginine at positions 1, 2, 3, 4, 5, 6, 7, 8, 9, 11 and 12 is about 5.18%, 10.28%, 10.15%, 10.64%, 10.28%, 10.11%, 10.11%, 5.52%, 2.88%, 0.00%, and 0.80% and 3.50%, respectively, when the length of said CDR is 13—
a. frequency of amino acid Phenylalanine at positions 1, 2, 3, 4, 5, 6, 7, 8, 9, 11, 12 and 13 is about 0.02%, 2.09%, 2.13%, 2.28%, 2.44%, 2.32%, 2.49%, 2.40%, 4.51%, 4.85%, 54.39%, 0.86% and 2.65%, respectively;
b. frequency of amino acid Asparagine at positions 1, 2, 3, 4, 5, 6, 7, 8, 9, 11, 12 and 13 is about 0.61%, 3.28%, 3.34%, 3.07%, 3.47%, 3.22%, 3.32%, 3.34%, 9.54%, 2.13%, 0.94%, 1.11% and 4.16%, respectively;
c. frequency of amino acid Proline at positions 1, 2, 3, 4, 5, 6, 7, 8, 9, 11, 12 and 13 is about 1.86%, 3.70%, 3.49%, 3.53%, 3.07%, 3.07%, 3.24%, 3.24%, 1.98%, 4.26%, 2.61%, 0.75% and 3.38%, respectively; and
d. frequency of amino acid Arginine at positions 1, 2, 3, 4, 5, 6, 7, 8, 9, 11, 12 and 13 is about 5.85%, 9.77%, 9.46%, 9.38%, 9.86%, 9.94%, 9.90%, 9.54%, 5.14%, 1.34%, 0.00%, 0.81% and 3.13%, respectively, when the length of said CDR is 14—
a. frequency of amino acid Phenylalanine at positions 1, 2, 3, 4, 5, 6, 7, 8, 9, 11, 12 and 13 and 14 is about 0.00%, 2.48%, 2.33%, 2.42%, 2.37%, 3.01%, 2.42%, 2.22%, 2.79%, 4.02%, 4.09%, 54.77%, 0.70% and 1.96%, respectively;
b. frequency of amino acid Asparagine at positions 1, 2, 3, 4, 5, 6, 7, 8, 9, 11, 12, 13 and 14 is about 0.46%, 3.49%, 3.56%, 3.41%, 3.23%, 3.58%, 3.27%, 3.25%, 3.19%, 2.04%, 2.37%, 0.92%, 1.54%, 2.94%, respectively;
c. frequency of amino acid Proline at positions 1, 2, 3, 4, 5, 6, 7, 8, 9, 11, 12, 13 and 14 is about 1.82%, 3.58%, 3.41%, 3.10%, 2.86%, 3.45%, 2.50%, 3.05%, 2.53%, 7.32%, 5.36%, 3.05%, 0.81% and 0.26%, respectively; and
d. frequency of amino acid arginine at positions 1, 2, 3, 4, 5, 6, 7, 8, 9, 11, 12, 13 and 14 is about 5.78%, 9.69%, 8.94%, 9.53%, 10.04%, 9.89%, 9.82%, 10.26%, 10.22%, 10.26%, 1.82%, 0.00%, 0.90% and 1.14%, respectively, when the length of said CDR is 15—
a. frequency of amino acid Phenylalanine at positions 1, 2, 3, 4, 5, 6, 7, 8, 9, 11, 12, 13, 14 and 15 is about 0.07%, 2.02%, 2.25%, 2.29%, 2.82%, 2.43%, 2.38%, 2.32%, 3.74%, 3.23%, 4.03%, 4.38%, 54.81%, 0.80% and 2.29%, respectively;
b. frequency of amino acid Asparagine at positions 1, 2, 3, 4, 5, 6, 7, 8, 9, 11, 12, 13, 14 and 15 is about 0.80%, 3.32%, 2.91%, 2.98%, 3.42%, 3.46%, 2.89%, 3.44%, 1.93%, 2.34%, 2.73%, 2.77%, 0.78%, 1.33%, and 2.54%, respectively;
c. frequency of amino acid Proline at positions 1, 2, 3, 4, 5, 6, 7, 8, 9, 11, 12, 13, 14 and 15 is about 1.65%, 3.44%, 3.62%, 3.58%, 3.09%, 3.12%, 2.66%, 2.61%, 7.66%, 6.92%, 7.40%, 3.12%, 2.43%, 0.69% and 0.23%, respectively; and
d. frequency of amino acid Arginine at positions 1, 2, 3, 4, 5, 6, 7, 8, 9, 11, 12, 13, 14 and 15 is about 5.96%, 10.13%, 9.26%, 9.58%, 10.32%, 10.09%, 9.01%, 9.67%, 11.10%, 10.45%, 9.67%, 3.42%, 0.00%, 0.83%, and 0.85%, respectively, when the length of said CDR is 16—
a. frequency of amino acid Phenylalanine at positions 1, 2, 3, 4, 5, 6, 7, 8, 9, 11, 12, 13, 14, 15 and 16 is about 0.12%, 1.57%, 1.75%, 2.62%, 2.85%, 2.50%, 2.85%, 2.21%, 2.97%, 2.74%, 3.38%, 3.38%, 2.39%, 50.47%, 1.22%, and 2.91%, respectively;
b. frequency of amino acid Asparagine at positions 1, 2, 3, 4, 5, 6, 7, 8, 9, 11, 12, 13, 14, 15 and 16 is about 0.87%, 2.33%, 3.03%, 2.85%, 3.67%, 2.56%, 3.32%, 2.74%, 2.68%, 1.98%, 2.39%, 2.27%, 0.17%, 0.64%, 0.81% and 2.79%, respectively;
c. frequency of amino acid Proline at positions 1, 2, 3, 4, 5, 6, 7, 8, 9, 11, 12, 13, 14, 15 and 16 is about 2.44%, 16.94%, 3.61%, 6.00%, 3.61%, 3.61%, 3.73%, 3.38%, 7.51%, 10.30%, 11.76%, 8.21%, 4.95%, 2.56%, 0.81% and 1.34%, respectively; and
d. frequency of amino acid arginine at positions 1, 2, 3, 4, 5, 6, 7, 8, 9, 11, 12, 13, 14, 15 and 16 is about 6.40%, 9.72%, 8.91%, 9.84%, 10.01%, 9.14%, 9.66%, 9.49%, 8.21%, 9.60%, 8.15%, 8.96%, 0.58%, 0.00%, 1.34% and 0.99%, respectively, when the length of said CDR is 17—
a. frequency of amino acid Phenylalanine at positions 1, 2, 3, 4, 5, 6, 7, 8, 9, 11, 12, 13, 14, 15, 16 and 17 is about 0.06%, 1.37%, 2.47%, 2.96%, 2.91%, 2.01%, 2.85%, 2.44%, 3.05%, 2.59%, 3.31%, 3.37%, 2.59%, 0.64%, 37.93%, 0.70% and 3.31%, respectively;
b. frequency of amino acid Asparagine at positions 1, 2, 3, 4, 5, 6, 7, 8, 9, 11, 12, 13, 14, 15, 16 and 17 is about 0.64%, 4.56%, 3.14%, 2.47%, 3.69%, 3.25%, 3.11%, 3.84%, 3.55%, 2.27%, 1.95%, 1.74%, 2.35%, 1.71%, 0.00%, 1.28%, 1.39% and respectively;

c. frequency of amino acid Proline at positions 1, 2, 3, 4, 5, 6, 7, 8, 9, 11, 12, 13, 14, 15, 16 and 17 is about 2.79%, 7.29%, 3.31%, 10.52%, 2.44%, 4.50%, 3.89%, 4.53%, 3.95%, 9.79%, 9.82%, 10.20%, 10.32%, 2.32%, 1.63%, 1.25% and 7.90%, respectively; and d. frequency of amino acid arginine at positions 1, 2, 3, 4, 5, 6, 7, 8, 9, 11, 12, 13, 14, 15, 16 and 17 is about 5.81%, 14.44%, 9.97%, 8.95%, 8.78%, 9.47%, 8.37%, 9.47%, 9.33%, 9.82%, 10.29%, 9.76%, 9.85%, 1.31%, 0.00%, 1.16% and 1.02%, respectively, when the length of said CDR is 18— a. frequency of amino acid Phenylalanine at positions 1, 2, 3, 4, 5, 6, 7, 8, 9, 11, 12, 13, 14, 15, 16, 17 and 18 is about 0.05%, 1.37%, 2.07%, 2.43%, 3.39%, 2.28%, 2.73%, 3.39%, 2.83%, 2.53%, 3.59%, 3.19%, 3.14%, 3.14%, 0.56%, 37.96%, 1.11% and 3.39%, respectively;

b. frequency of amino acid Asparagine at positions 1, 2, 3, 4, 5, 6, 7, 8, 9, 11, 12, 13, 14, 15, 16, 17 and 18 is about 0.66%, 2.78%, 2.83%, 1.52%, 2.33%, 3.64%, 3.90%, 2.73%, 3.64%, 4.25%, 2.02%, 2.53%, 2.63%, 2.94%, 0.51%, 0.05%, 1.32% and 1.42%, respectively;

c. frequency of amino acid Proline at positions 1, 2, 3, 4, 5, 6, 7, 8, 9, 11, 12, 13, 14, 15, 16, 17 and 18 is about 2.02%, 4.35%, 3.64%, 11.69%, 11.03%, 3.29%, 4.61%, 3.54%, 5.31%, 4.55%, 11.39%, 8.76%, 10.17%, 8.76%, 5.11%, 2.13%, 0.91% and 9.67%, respectively; and d. frequency of amino acid arginine at positions 1, 2, 3, 4, 5, 6, 7, 8, 9, 11, 12, 13, 14, 15, 16, 17 and 18 is about 5.97%, 9.77%, 9.01%, 9.56%, 8.50%, 8.96%, 9.36%, 9.11%, 10.98%, 9.46%, 10.58%, 8.96%, 9.36%, 8.25%, 2.23%, 0.05%, 0.76% and 0.86%, respectively, when the length of said CDR is 19— a. frequency of amino acid Phenylalanine at positions 1, 2, 3, 4, 5, 6, 7, 8, 9, 11, 12, 13, 14, 15, 16, 17, 18 and 19 is about 0.17%, 0.81%, 2.20%, 3.08%, 2.84%, 3.28%, 6.30%, 8.97%, 2.40%, 3.08%, 3.39%, 3.73%, 3.45%, 1.19%, 4.20%, 0.44%, 40.09%, 1.02% and 3.49%, respectively;

b. frequency of amino acid Asparagine at positions 1, 2, 3, 4, 5, 6, 7, 8, 9, 11, 12, 13, 14, 15, 16, 17, 18 and 19 is about 0.98%, 1.69%, 2.88%, 2.84%, 2.64%, 1.76%, 4.03%, 2.57%, 4.30%, 3.12%, 2.47%, 2.10%, 2.64%, 11.45%, 7.31%, 0.03%, 0.00%, 1.46% and 1.19%, respectively;

c. frequency of amino acid Proline at positions 1, 2, 3, 4, 5, 6, 7, 8, 9, 11, 12, 13, 14, 15, 16, 17, 18 and 19 is about 2.54%, 10.26%, 3.66%, 11.62%, 9.82%, 9.92%, 0.44%, 4.03%, 4.27%5.25%, 9.85%, 9.99%, 8.84%, 2.44%, 3.05%, 2.78%, 1.42%, 0.81% and 9.72° 5 respectively; and d. frequency of amino acid arginine at positions 1, 2, 3, 4, 5, 6, 7, 8, 9, 11, 12, 13, 14, 15, 16, 17, 18 and 19 is about 5.38%, 12.09%, 7.92%, 9.04%, 9.21%, 8.53%, 0.61%, 1.76%, 9.18%, 8.91%, 10.19%, 8.77%, 9.11%, 3.93%, 0.54%, 1.08%, 0.00%, 0.95% and 1.05%, respectively, when the length of said CDR is 20— a. frequency of amino acid Glutamic acid at positions 1, 2, 3, 4, 5, 6, 7, 8, 9, 11, 12, 13, 14, 15, 16, 17, 18, 19 and 20 is about 15.56%, 4.65%, 3.96%, 7.86%, 4.75%, 2.14%, 0.82%, 3.96%, 4.59%, 399%, 5.19%, 4.71%, 5.03%, 0.31%, 399%, 0.06%, 0.06%, 0.00%, 2.39% and 0.00%, respectively;

b. frequency of amino acid Asparagine at positions 1, 2, 3, 4, 5, 6, 7, 8, 9, 11, 12, 13, 14, 15, 16, 17, 18, 19 and 20 is about 0.66%, 2.67%, 3.17%, 1.13%, 2.01%, 0.31%, 3.52%, 3.49%, 3.36%, 3.21%, 2.36%, 2.64%, 2.42%, 4.34%, 4.09%, 3.96%, 1.16%, 0.09%, 1.45% and 1.07%, respectively;

c. frequency of amino acid Proline at positions 1, 2, 3, 4, 5, 6, 7, 8, 9, 11, 12, 13, 14, 15, 16, 17, 18, 19 and 20 is about 2.39%, 3.49%, 3.61%, 3.11%, 11.44%, 1.76%, 1.38%, 4.37%, 3.71%, 5.00%, 10.09%, 9.90%, 9.90%, 6.38%, 4.87%, 6.44%, 0.31%, 1.19%, 0.91% and 9.55%, respectively; and d. frequency of amino acid arginine at positions 1, 2, 3, 4, 5, 6, 7, 8, 9, 11, 12, 13, 14, 15, 16, 17, 18, 19 and 20 is about 5.41%, 8.67%, 9.71%, 4.87%, 9.37%, 1.98%, 3.49%, 8.74%, 9.21%, 8.89%, 8.96%, 9.87%, 10.47%, 4.43%, 1.67%, 4.09%, 2.83%, 0.00%, 0.97% and 1.26%, respectively, when the length of said CDR is 21— a. frequency of amino acid Phenylalanine at positions 1, 2, 3, 4, 5, 6, 7, 8, 9, 11, 12, 13, 14, 15, 16, 17, 18, 19, 20 and 21 is about 0.00%, 2.07%, 0.28%, 2.93%, 2.31%, 5.82%, 6.92%, 7.44%, 7.10%, 7.13%, 7.20%, 11.47%, 0.59%, 0.65%, 4.34%, 6.17%, 2.20%, 0.17%, 35.45%, 2.17% and 2.58%, respectively;

b. frequency of amino acid Asparagine at positions 1, 2, 3, 4, 5, 6, 7, 8, 9, 11, 12, 13, 14, 15, 16, 17, 18, 19, 20 and 21 is about 0.65%, 0.14%, 4.17%, 2.79%, 3.44%, 1.52%, 1.31%, 0.93%, 1.17%, 1.38%, 1.76%, 2.89%, 6.48%, 0.41%, 4.20%, 0.24%, 4.51%, 0.34%, 0.00%, 1.03% and 2.17%, respectively;

c. frequency of amino acid Proline at positions 1, 2, 3, 4, 5, 6, 7, 8, 9, 11, 12, 13, 14, 15, 16, 17, 18, 19, 20 and 21 is about 2.20%, 9.06%, 4.48%, 4.24%, 4.13%, 2.86%, 2.55%, 2.24%, 3.10%, 3.38%, 3.31%, 18.05%, 6.44%, 8.54%, 2.79%, 2.89%, 8.27%, 1.10%, 1.83%, 1.55% and 8.23%, respectively; and d. frequency of amino acid arginine at positions 1, 2, 3, 4, 5, 6, 7, 8, 9, 11, 12, 13, 14, 15, 16, 17, 18, 19, 20 and 21 is about 5.99%, 3.82%, 8.96%, 9.20%, 9.20%, 4.27%, 4.13%, 4.68%, 4.99%, 4.62%, 4.00%, 10.27%, 6.30%, 9.68% 5.99%, 1.79%, 3.41%, 1.72%, 0.24%, 1.00% and 0.03%, respectively, when the length of said CDR is 22— a. frequency of amino acid Phenylalanine at positions 1, 2, 3, 4, 5, 6, 7, 8, 9, 11, 12, 13, 14, 15, 16, 17, 18, 19, 20, 21 and 22 is about 0.04%, 5.37%, 3.13%, 6.33%, 3.67%, 0.27%, 6.95%, 6.49%, 7.34%, 3.79%, 3.28%, 3.79%, 599% 7.34%, 0.19%, 0.27%, 0.19%, 0.31%, 3.24%, 36.27%, 0.85% and 9.35%, respectively;

b. frequency of amino acid Asparagine at positions 1, 2, 3, 4, 5, 6, 7, 8, 9, 11, 12, 13, 14, 15, 16, 17, 18, 19, 20, 21 and 22 is about 0.50%, 0.00%, 4.21%, 0.19%, 4.17%, 4.21%, 1.04%, 1.43%, 1.51%, 1.85%, 2.90%, 2.01%, 1.27%, 1.08%, 0.39%, 0.27%, 0.12%, 7.61%, 0.12%, 0.08%, 1.47% and 0.00%, respectively;

c. frequency of amino acid Proline at positions 1, 2, 3, 4, 5, 6, 7, 8, 9, 11, 12, 13, 14, 15, 16, 17, 18, 19, 20, 21 and 22 is about 2.74%, 7.96%, 4.75%, 18.23%, 8.50%, 3.59%, 2.47%, 2.94%, 2.74%, 10.31%, 10.35%, 9.62%, 3.13%, 3.05%, 13.90%, 0.27%, 5.37%, 0.23%, 0.31%, 1.78%, 1.39%, and 2.47%, respectively; and d. frequency of amino acid arginine at positions 1, 2, 3, 4, 5, 6, 7, 8, 9, 11, 12, 13, 14, 15, 16, 17, 18, 19, 20, 21 and 22 is about 5.83%, 17.50%, 8.42%, 5.06%, 4.52%, 4.79%, 4.91%, 4.48%, 4.60%, 9.39%, 8.42%, 8.57%, 4.36%, 4.44%, 0.58%, 3.59%, 6.06%, 0.23%, 6.30%, 0.04%, 0.77% and 0.00%, respectively, when the length of said CDR is 23—
a. frequency of amino acid Phenylalanine at positions 1, 2, 3, 4, 5, 6, 7, 8, 9, 11, 12, 13, 14, 15, 16, 17, 18, 19, 20, 21, 22 and 23 is about 0.00%, 0.29%, 0.15%, 0.49%, 8.00%, 3.07%, 3.76%, 0.59%, 9.03%, 3.90%, 4.25%, 9.42%, 0.44%, 3.90%, 0.34%, 3.32%, 3.51%, 0.10%, 3.90%, 0.39%, 43.24%, 0.83% and 4.73%, respectively;
b. frequency of amino acid Asparagine at positions 1, 2, 3, 4, 5, 6, 7, 8, 9, 11, 12, 13, 14, 15, 16, 17, 18, 19, 20, 21, 22 and 23 is about 0.24%, 0.05%, 0.15%, 0.15%, 4.69%, 5.32%, 0.10%, 0.15%, 14.84%, 0.20%, 4.49%, 4.64%, 4.25%, 5.42%, 0.10%, 8.30%, 0.05%, 0.10%, 4.69%, 0.00%, 0.00%, 1.12% and 0.00%, respectively;
c. frequency of amino acid Proline at positions 1, 2, 3, 4, 5, 6, 7, 8, 9, 11, 12, 13, 14, 15, 16, 17, 18, 19, 20, 21, 22 and 23 is about 0.24%, 9.91%, 3.71%, 3.61%, 5.32%, 2.73%, 3.61%, 3.81%, 7.42%, 2.10%, 6.69%, 4.34%, 2.93%, 8.39%, 11.27%, 3.17%, 0.20%, 0.24%, 0.34%, 4.05%, 0.88%, 1.22% and 9.22%, respectively; and
d. frequency of amino acid arginine at positions 1, 2, 3, 4, 5, 6, 7, 8, 9, 11, 12, 13, 14, 15, 16, 17, 18, 19, 20, 21, 22 and 23 is about 0.44%, 4.39%, 8.69%, 22.40%, 7.76%, 4.49%, 4.05%, 3.42%, 0.78%, 9.13%, 10.35%, 3.66%, 11.52%, 3.95%, 0.29%, 8.25%, 0.20%, 6.69%, 0.20%, 0.44%, 0.00%, 1.95% and 0.05%, respectively.

In yet another embodiment, the CDR is selected from a group comprising CDR1, CDR2 and CDR3; and wherein preferably CDR is CDR3.

In still another embodiment,
the heavy chain of the antibody molecule(s) comprises consensus amino acid sequence selected from SEQ ID 2, 4, 6, 8, 10, 12 or 14 encoded by corresponding nucleic acid sequence selected from SEQ ID 1, 3, 5, 7, 9, 11 or 13;
the light chain (kappa) of the antibody molecule(s) comprises consensus amino acid sequence selected from SEQ ID 16, 18, 20 or 22 encoded by corresponding nucleic acid sequence selected from SEQ ID 15, 17, 19 or 21; or wherein the light chain (lambda) of the antibody molecule(s) comprises consensus amino acid sequence selected from SEQ ID 24, 26 or 28 encoded by corresponding nucleic acid sequence selected from SEQ ID 23, 25 or 27;
framework regions 1, 2 and 3 of the heavy chain comprises amino acid sequence encoded by consensus nucleic acid sequence selected from SEQ ID 29-49;
CDR 1 and 2 of the heavy chain comprises amino acid sequence encoded by consensus nucleic acid sequence selected from SEQ ID 50-63;
framework regions 1, 2, 3 and 4 of the light chain (kappa) comprises amino acid sequence encoded by consensus nucleic acid sequence selected from SEQ ID 64-79;
CDR 1, 2 and 3 of the light chain (kappa) comprises amino acid sequence encoded by consensus nucleic acid sequence selected from SEQ ID 80-91;
framework regions 1, 2, 3 and 4 of the light chain (lambda) comprises amino acid sequence encoded by consensus nucleic acid sequence selected from SEQ ID 92-103; and
CDR 1, 2 and 3 of the light chain (lambda) comprises amino acid sequence encoded by consensus nucleic acid sequence selected from SEQ ID 104-112.

In still another embodiment, the library comprises about $10^{10}$ to about $10^{11}$ clones; and wherein the synthetic antibody library is a collection of the antibody molecule(s) expressed on surface of phage or yeast, or is a collection of the antibody molecule(s) isolated from the phage or the yeast or a combination thereof.

The present disclosure also relates to a method of obtaining the synthetic library as above, comprising steps of:
a) screening and identifying antibody molecules having at least one predetermined characteristic(s),
b) analysing the identified molecules on the basis of length distribution analysis of CDR3 heavy chain (CDRH3) and frequency of occurrence of amino acids within said CDRH3 to determine optimal chain length and amino acid frequency,
c) designing altered antibody molecule(s) followed by subjecting the molecule(s) to codon replacement technology on the basis of said optimal chain length and amino acid frequency as defined above, to obtain antibody molecule(s) with modified CDRH3, and
d) cloning said molecule(s) to form the library.

In an embodiment, the screening involves analysing antibody gene sequences from available online database (IMGT database) for removal of redundancy; and wherein the predetermined characteristic(s) is selected from a group comprising annotation level, species, configuration type, rearranged gene type and functionality, or any combination thereof.

In another embodiment, the designing comprises synthesizing an antibody molecule(s) comprising heavy chain amino acid sequence selected from SEQ ID 2, 4, 6, 8, 10, 12 or 14 and light chain amino acid sequence selected from SEQ ID 16, 18, 20, 22, 24, 26 or 28; and framework regions and CDRs having one or more amino acid sequence encoded by nucleic acid sequence selected from SEQ ID 29-112.

In yet another embodiment, the antibody molecule(s) with modified CDRH3 are displayed individually by phage vector or sequentially by phage vector followed by yeast vector.

In still another embodiment, the display of the antibody molecule(s) by a phage or yeast vector, involves:
cloning of corresponding antibody genes into the phage to obtain phage antibody library followed by screening of displayed molecule(s) against antigen(s) to obtain panned phage antibody library,
transferring the panned phage antibody library into yeast for display of said antibody molecule(s) on surface of the yeast followed by screening the yeast displayed antibody molecule(s) against antigen(s) to obtain yeast screened antibody library, and
selecting the phage or the yeast displayed antibody molecule(s) with desired functional properties to form the synthetic antibody library or isolating selected antibody molecule(s) with desired functional properties from the phage antibody library or the yeast antibody library to generate screened antibody synthetic library.

In still another embodiment, the antibody molecule(s) are in Fab or Scfv format for cloning into phage or yeast vector; and wherein transformation efficiency into the phage vector is in the range of about $10^9$ to about $10^{10}$; and transformation efficiency into the yeast vector is in the range of about $10^6$ to about $10^8$.

In still another embodiment, the screening to obtain phage library involves panning with antigens coated on magnetic beads to isolate antibody of interest; and wherein said phage display screening/panning is employed to remove antibody non-binders.

In still another embodiment, the screening to obtain yeast library by the surface display is carried out by employing competing antigenic epitopes, antibody paratope conformation, sequences and sequence motifs or any combination thereof to isolate Fab or ScFv molecule using protease cleavage sites selected from a group comprising Tobacco Etch Virus (TEV), Enterokinase, Thrombin, Factor X a, HRV 3C protease and similar protease cleavage proteins or any combination thereof.

In still another embodiment, the synthetic antibody library is a collection of the antibody molecule(s) expressed on surface of the phage or the yeast, or is a collection of the antibody molecule(s) isolated from the phage or the yeast or a combination thereof.

The present disclosure also relates to an antibody molecule isolated from the synthetic library as above or as obtained by the method as above.

The present disclosure also relates to an antibody molecule comprising:
- a heavy chain consensus amino acid sequence selected from SEQ ID 2, 4, 6, 8, 10, 12 or 14 encoded by corresponding nucleic acid sequence selected from SEQ ID 1, 3, 5, 7, 9, 11 or 13,
- the light chain consensus amino acid sequence selected from SEQ ID 16, 18, 20 or 22 encoded by corresponding nucleic acid sequence selected from SEQ ID 15, 17, 19 or 21; or consensus amino acid sequence selected from SEQ ID 24, 26 or 28 encoded by corresponding nucleic acid sequence selected from SEQ ID 23, 25 or 27;
- framework regions encoded by consensus nucleic acid sequence selected from SEQ ID 29-49, 64-79 or 92-103; and
- CDR encoded by consensus nucleic acid sequence selected from SEQ ID 50-63, 80-91 or 104-112.
wherein,
- when the length of said CDR is 4, frequency of amino acid Arginine at positions 2, 3 and 4 varies from about 18% to about 20%;
- when the length of said CDR is 5, frequency of amino acid Proline at position 3 is at about 20%;
- when the length of said CDR is 6, frequency of amino acid Phenyl alanine at position 4 is about 25%;
- when the length of said CDR is 7, frequency of amino acid Phenyl alanine at position 5 is about 43.63%;
- when the length of said CDR is 8, frequency of amino acid Phenyl alanine at position 6 is about 35.24%;
- when the length of said CDR is 9, frequency of amino acid Phenyl alanine at position 7 is about 44.15%;
- when the length of said CDR is 10, frequency of amino acid Phenyl alanine at position 8 is about 55.93%;
- when the length of said CDR is 11, frequency of amino acid Phenyl alanine at position 9 is about 54.27%;
- when the length of said CDR is 12, frequency of amino acid Phenyl alanine at position 10 is about 52.70%;
- when the length of said CDR is 13, frequency of amino acid Phenyl alanine at position 11 is about 54.39%;
- when the length of said CDR is 14, frequency of amino acid Phenyl alanine at position 12 is about 54.77%;
- when the length of said CDR is 15, frequency of amino acid Phenyl alanine at position 13 is about 54.81%;
- when the length of said CDR is 16, frequency of amino acid Phenyl alanine at position 14 is about 50.47%;
- when the length of said CDR is 17, frequency of amino acid Phenyl alanine at position 15 is about 37.93%;
- when the length of said CDR is 18, frequency of amino acid Phenyl alanine at position 16 is about 37.96%;
- when the length of said CDR is 19, frequency of amino acid Phenyl alanine at position 17 is about 40.09%;
- when the length of said CDR is 20, frequency of amino acid Glutamic acid at position 1 is about 15.56%;
- when the length of said CDR is 21, frequency of amino acid Phenyl alanine at position 19 is about 35.45%;
- when the length of said CDR is 22, frequency of amino acid Phenyl alanine at position 20 is about 36.27%; and
- when the length of said CDR is 23, frequency of amino acid Phenyl alanine at position 21 is about 43.24%.

The present disclosure also relates to a synthetic antibody library of above or as obtained by method of above for use in therapeutics for treatment of diseases selected from a group comprising cancer, rheumatoid arthritis, neurological disorders, infectious diseases and metabolic disorders or any combination thereof; as diagnostics; as prognostics; for research purposes; target discovery; validation in functional genomics or any application where antibodies or derivatives of antibodies are employed.

The present disclosure relates to a design or method of generating an antibody library not limiting to a synthetic antibody gene expression library. Said synthetic antibody library is constructed on a pool of consensus amino acid sequences which possess diversity not restricting to complementary determining regions (CDRs).

In a non-limiting embodiment of the present disclosure, CDR is selected from a group comprising CDR1, CDR2 and CDR3.

In another non-limiting embodiment of the present disclosure, the synthetic library is constructed by employing precisely designed oligonucleotides via replace-codon technology/codon replacement technology.

The basis of said technology stems from substituting specific amino acid residues at a particular position of antibody CDR. Due to extreme variability of amino acid sequence and length of CDR regions, each position is substituted with multiple amino acids at a predetermined frequency. Such substitutions lead to large number of independent molecules which represent antibody repertoire, a prerequisite for diverse antigen recognition. The oligonucleotides synthesized are designed with variable codons to represent amino acid diversity at each position.

In yet another non-limiting embodiment of the present disclosure, the codon replacement technology introduces amino acid compositional biasness using input obtained from in silico analysis data. For said analysis, amino acid sequences of several antibodies from publicly available antibody database are employed. Frequency of presence of specific amino acid molecule at specific position is determined in silico. The data obtained is used for synthesis of oligonucleotide sequences representing diversity of amino acid frequency.

In a preferred embodiment of the present disclosure, the consensus amino acids, encoding nucleic acid sequence includes synthetic DNA, not limiting to human variable heavy and light chain regions of immunoglobulins, which are designed in silico.

In a non-limiting embodiment of the present disclosure, the method of generating the synthetic antibody library includes screening procedure for specific antigens, by employing combinatorial tools.

In an exemplary embodiment, the combinatorial tools include phage display technology and yeast display technology. In another embodiment, the method employs screening by employing phage display technology and/or yeast display technology to create synthetic antibody gene expression library. In yet another embodiment, the method employs screening by employing phage display technology sequentially followed by yeast display technology to create synthetic antibody gene expression library.

In a non-limiting embodiment of the present disclosure, the synthetic antibody gene expression library allow isolation of unique antibody molecules with the desired functional properties for a specific therapeutic target i.e., antigen, with enhanced affinity and specificity.

In another non-limiting embodiment of the present disclosure, the desired functional properties of the antibodies are selected from a group comprising, but not limiting to affinity, specificity, manufacturability, generation of new epitopes, thermal stability, antigenicity, solubility, aggregation and catalytic activity, or any combination thereof and any other properties related to successful product commercialization.

In yet another non-limiting embodiment of the present disclosure, the method of generating the synthetic antibody gene expression library includes sequentially exploring the expression of pools of consensus amino acid sequences by utilizing two separate scanning tools, 1) a phage display technology and 2) a yeast display technology. Sequential use of these technologies allows in harnessing larger set of antibody gene diversity, a character of phage based library. The antibody clones are thereafter screened through yeast display system. Use of yeast system for antibody gene expression is advantageous because of eukaryotic protein translation, processing and proper folding of the antibody products on cell surface. Further, yeast expression allows proper interaction with antigenic targets with high specificity. Information obtained using these two complementary systems generate "lead molecules" (i.e., antibodies specific to an antigen) with higher success rate in terms of commercialization potential.

The expression profiling and screening strategies adopted in the present disclosure enables to smoothly transit between phage to yeast display platforms. The phage display accommodates the library size ($\sim 10^{11}$) for primary screening which is focused on stringency and specificity of antibody-antigen interaction in a high-throughput format while screened molecules would again go through a combinatorial or non-combinatorial process for antibody display via yeast platform. Thus, each platform contributes combinatorially to the pipeline of developing functionally specific yet structurally varied antibody moieties. The process of multiple rounds of selection on an antigen or on antigen-expressing cells or antigen coated particles via two different display systems are extremely valuable to positively or negatively select a range of desired antibody properties, such as but not limiting to affinity, specificity, manufacturability, new epitopes, thermal stability, antigenicity, solubility, aggregation of antibodies, catalytic activity etc. The present method enables to preserve diversity in the library which facilitates in identification of unique molecules against varied antigenic targets. Generation of the synthetic library of human antibodies with high diversity serves as a tremendous resource for new antibody identification and further commercial development.

In a non-limiting embodiment of the present disclosure, the methodology also involves a strategy wherein the diversity is translated between two platforms and explored as various engineered antibody formats such as, but not limiting to chimeric antibody molecules, Fab, fragments, F(ab')2 fragments, Fv molecules, ScFv, ScFab, dimeric and trimeric antibody fragments, minibodies, humanized monoclonal antibody molecules, human antibodies, fusion proteins comprising Fc region of antibody, any functional fragments arising out of these molecules where derivative molecules retain immunological functionality of the parent antibody molecule and all other antibody formats.

In another non-limiting embodiment, the method of the present disclosure also involves incorporating yeast mating type based strategies, a feature of the haploid/diploid lifecycle of yeast which allows generation of larger libraries (ScFv or Fab or full antibody) in yeast from two separate yeast vectors and is also amenable to chain randomization for affinity improvement.

In yet another non-limiting embodiment of the present disclosure, the features such as synthetic library size and diversity are suspected to be directly linked in achieving improved antibody specificity and affinity.

The present method of generating or development of the synthetic antibody library, preferably synthetic human antibody library is set forth in the flow chart illustrated in FIG. 26.

a) More specifically, the present method of generating a synthetic antibody library, preferably synthetic human antibody gene expression library, which also includes screening against antigen(s) comprises the acts/steps of: in silico analysis of antibody amino acid sequences;

b) Designing and creating heavy chain CDR3 diversity through in silico approaches; synthesis of entire diversity through codon-replacement technology.

c) Cloning of consensus antibody nucleic acid sequences into phagemid vectors; incorporation of synthetic nucleic acid repertoire into phagemid vectors to generate synthetic phage library;

d) Screening of the phage display library, against specific antigens or antigen producing cells.

e) transferring/cloning screened product of step d) into yeast vectors followed by screening said product against antigen(s); and f) Selecting antibody molecules with desired functional properties from phage libraries.

In a preferred embodiment, the libraries are further improved through adopting rational designing approach, where antibody structural information is used to positively or negatively select a range of desired antibody properties, such as but not limiting to affinity, specificity, manufacturability, new epitopes, thermal stability, antigenicity, solubility, aggregation of antibodies, catalytic activity etc.

In a preferred embodiment, the present method of generating the human synthetic antibody library comprises the following steps wherein large number of human antigen-antibody structures are analyzed in silico and based on the information obtained therefrom, synthetic DNA is created, gene alterations are carried out in the amino acid sequence coding the nucleic acid sequence of the synthetic DNA by employing codon-replacement technology. Thereafter, the altered nucleic acid sequence encoding the antibody are cloned into phage and/or yeast vectors followed by carrying out about two to about five rounds of library screening against specific antigen targets. Thereafter, screened pool of molecules are cloned into yeast vectors and about one to about three rounds of screening against specific antigen targets is done. Specific populations showing higher affinity to target antigen or other desired antibody characteristic(s) are isolated, individual clones are separated and clonal populations obtained therefrom are used for selecting specific molecule for further antibody development.

In an exemplary embodiment of the present disclosure, the method of generating the human synthetic antibody library comprises the following steps.

Step 1: Creating of altered nucleic acid sequences or synthetic DNA based on in silico analysis done on several antibody sequences downloaded from various databases. Said step includes creating a precisely controlled design enabling the use of highly optimized consensus sequences of human immunoglobulin variable heavy chains (VH) & variable light chains (VL) in specific phage expression vectors. The consensus regions are interspersed with highly variable CDR regions. The CDR regions are variable for amino acid sequence as well as length of each CDR. Information on CDR length and CDR amino acid composition are analyzed to derive frequency of amino acid variability at each position; similarly the length distribution is also determined. This composite of amino acid substitution in specific CDRs and corresponding CDR length will contribute in diverse antigen recognition. Preferably, the complete methods for the design, construction, and application of synthetic antibody libraries are built on a consensus heavy and light chain sequence with diversity not restricted to complementarity-determining regions. The diversity of the synthetic molecules is achieved through a strategic design of distribution matrix of amino acids that is derived through in silico analysis and understanding of positional diversity of amino acid frequency and various length distribution of CDR3 of variable heavy sequences. The diversity of amino acid composition thus obtained is used for generating DNA molecules using codon replacement technology. Step 2: Synthetically prepared DNA fragments are collected together/pooled and cloned in specific set of phagemid vectors. Said cloning into phagemid vectors is carried out with a notion of capturing the vast size and diversity of the library molecules. Step 3: The said vectors are used for expressing the antibody genes and are subjected to screening against specific antigen targets. Preferably, the screening of library of molecules will be done by biopanning via one round of selection against specific antigen. Specific binders are selected out from the library by washing away non-binders, selectively eluting bound clones and re-amplification of the selected clones in host, not limiting to E. coli. Step 4: Selected pool of molecules from phage display platform are transferred to yeast display platform. Preferably, selected pool of molecules screened in phage display platform are transferred with randomization or non-randomization of selected diversity i.e., combination of heavy chain and light chain to a eukaryotic system, thereby, preserving the selected pool of molecules with or without specific combination of heavy and light chains. This transfer will be specifically done to overcome issues with folding and pairing of heavy and light chains in phage display platform. The yeast display platform comprises of various set up expressing variety of antibody moieties in different formats.

Step 5: The molecules/antibody fragments displayed by using yeast platform are screened against specific antigens targets. Specific antibody populations showing higher affinity to the target antigen are separated. These selected pools are further tested for antigen specificity, if required.

Step 6: Individual clones from the screened pool of antibodies are separated and clonal populations are used for isolating nucleic acid sequences coding for the "lead molecules". Careful analyses and understanding of antibody-antigen interaction studies using several bio-informatics tools will allow in incorporating further changes in nucleic acid sequence of the lead molecules.

Sequential use of phage and yeast display platforms expressing human synthetic antibody repertoire, which are developed via combinatorial approach i.e., by employing the concept of randomly combined heavy and light chains, permit to screen a wide range of therapeutic targets and steer to identification of unique antibody molecules with enhanced affinity and specificity. In addition, another approach that is employed, preserves a particular combination of heavy and light chains obtained from phage display library screening followed by transferring from phage to yeast exploiting a flexibility of keeping a specific combination in various antibody format unchanged. Flexibility of using sequential or combinatorial yeast display system/platform and phage display system is not only for the various output formats such as Fab, ScFV, ScFab molecules or any antibody format, but it is also a convenient choice for haploid cell expression and diploid cell expression. Multiple option availability enables this combinatorial yeast display and phage display format a unique, flexible and indispensable platform to select ligand mimicking the immunoglobulin structure, a success.

Detailed understanding of antigen and antibody structure-function analysis will allow further modification of amino acid sequence motifs and thereby enhance scope of generating lead molecules with increased affinity, stability, expression, efficacy etc. Hence, the present disclosure archives not only unique monoclonal antibodies identification against targets of various diseases but also to play a vital role in target discovery and validation in the area of functional genomics.

The present disclosure also relates to an antibody gene expression library comprising a repertoire of synthetic nucleic acid sequences prepared by employing the method of the instant disclosure.

Antibody library such as synthetic library allows for isolation of novel antibody fragments or molecules with the desired functional properties for a specific therapeutic target i.e., antigen. Uniqueness of the said category of library is to have a wide variety of antibodies which are designed in a controlled manner with affinities and specificities beyond the scope of natural antibodies from immune system; which may have the potential for targeting antigen(s) with higher affinity and specificity. However, with regard to naïve antibody library, the information therein will not include amino acid variability that arises out of, for Example: somatic hypermutation or other physiological phenomena, which may be of interest. Further the naïve library affinity is expected to be moderate when compared to that of synthetic library affinity as in the instant disclosure, as the antibody repertoire in the naïve library is not shaped by antigen encounter, at least not significantly. In comparison, affinity of synthetic library towards antigen is expected to be high and specific, as in silky studies are employed to mimic pattern of mutations seen in immunoglobulins after immunization and clonal selection.

The present disclosure also relates to use of an antibody gene expression library comprising a repertoire of synthetic nucleic acid sequences prepared by the method of the present disclosure, to screen against antigen targets.

In a non-limiting embodiment, the antibody gene expression library of the instant disclosure finds application in several fields, including, but not limiting to therapeutics, diagnostics, prognostics, research purposes and virtually any application where antibodies or derivatives of antibodies are employed.

Summarizing, the aforementioned aspects, the present disclosure in particular relates to the creation of highly diverse and functional synthetic antibody repertoire which can be used to screen and generate antibodies or antibody fragments against a multitude of antigens with varied affinities and specificities. This exclusive design of present disclosure and generation of synthetic antibody libraries are deeply dependent on understanding of the existing technical field and valuable insights from studies done on existing synthetic antibody libraries and natural antibody repertoire, in addition to the knowledge obtained and analyses of antibody sequence diversity and structure-function studies of antibody-antigen interaction as carried out by the instant disclosure.

This instant disclosure describes the strategy for the design and generation of aptly designed antibody display methodologies built on pool of consensus amino acid sequences with diversity not restricted to complementarity-determining region (CDR3) by using codon-replacement technology. In addition, this disclosure also brings the specific modifications that are present on relatively conserved framework regions. Apart from sequence diversity, variation in lengths also has been considered with a focus centered on the distribution of various lengths of CDR in the data base wherein the strategy towards an equal equivalent representation of Fab antibody molecule is incorporated.

The instant disclosure will sequentially explore the expression profiles of a pool of clones by utilizing two separate scanning tools, the phage display technology and the yeast display technology. Sequential uses of these technologies will allow harnessing larger set of antibody gene diversity, a character of phage based library and the antibody clones could then be screened through yeast display system. Use of yeast display system for antibody gene expression is advantageous because of eukaryotic protein translation, processing and proper folding of the antibody products on cell surface. It is hypothesized that yeast expression will allow proper interaction with antigenic targets with high specificity. Information obtained using these two complementary systems will generate "lead molecules" with higher success rate in terms of commercialization potential. The proposed methodology also involves a strategy wherein the diversity can be translated between two platforms and explored as various engineered antibody formats as exemplified by Fab, ScFv, ScFab and other antibody formats as detailed in the aforementioned sections of the instant disclosure. The candidate antibody molecules will further be optimized through rational designing guided by structure-function studies of antibody-antigen interactions.

In a non-limiting embodiment, the candidate antibody molecules obtained by the present method are further optimized through rational designing guided by structure-function studies of antibody-antigen interactions. The process of drug development especially antibody based drugs, is challenging, time consuming, and expensive. Several multidisciplinary approaches are required to meet these challenges which collectively form the basis of rational drug designing. The prerequisite for success of manufacturability of monoclonal antibody drugs are dependent on a variety of biological and/or correlated properties such as solubility, aggregation, antigenicity, stability and so on. Many of these properties are dependent on different structural motifs of antibody; which can be predicted through in silico approaches. As exemplified, structure-based drug designing which is rational, evidence based and faster, has contributed tremendously in the field of cancer chemotherapy, drug resistant infections, neurological diseases, to mention a few. The resulting outcome of these methods is employed in the instant disclosure to improve synthetic antibody library construction and manufacturability of selected molecules.

The present disclosure generally relates to the field of biotechnology, genetic engineering and immunology. The present disclosure in particular, relates to the creation of highly diverse and functional synthetic antibody repertoire which can be used to screen and generate antibodies or antibody fragments against a multitude of antigens with varied affinities and specificities. Taken together, the interest of the present disclosure has been centralized around sequential or combinatorial library techniques along with a combinatorial approach, aiming at more efficient utilization of the synthetic antibody repertoire. Synthetic library of antibodies allows in vitro selection of human mAbs of strong specificity and greater affinity. Owing to its design, this technique permits both genetic (nucleic acid level) and functional analyses (protein level) of the selected mAb thus facilitating studies on mechanisms of the human immune system. Translational research approaches embracing such library may converge on new future therapies.

The present disclosure is further described with reference to the following examples, which are only illustrative in nature and should not be construed to limit the scope of the present disclosure in any manner.

EXAMPLES

Materials Employed:
DPBS (GIBCO, USA); FBS (Moregate Biotech, Australia); dNTPs (Ambion, USA); 1 Kb Ladder (Invitrogen, USA); Phusion enzyme (NEB, USA); Agarose (SIGMA, USA); PCR purification Kit (Qiagen, USA); Agarose (SIGMA, USA); Gel elution Kit (Qiagen, USA); Mini prep Kit (Qiagen, USA); dATP (NEB, USA); T4 DNA ligase (NEB, USA); LB-Agar (Himedia, India), Neb5alpha (NEB, USA); Ampicillin (MP Biomedicals, USA); NcoI-HF, (NEB, USA); XbaI, (NEB, USA); HindIII-HF, (NEB, USA); AscI (NEB, USA); BstEII (NEB, USA); BstBI (NEB, USA); AscI (NEB, USA); Nod (NEB, USA), TG1 cells (Lucigen, USA); PCR purification Kit (Qiagen, USA); LB-Agar (Himedia, India); Mini prep Kit (Qiagen, USA); LB-Broth (Himedia, India); Ampicillin (MP Biomedicals, USA); dam$^-$/dcm$^-$ Competent *E. coli* (NEB, USA)

Kanamycin (MP biomedicals, USA); M13KO7 helper Phage (Thermo Scientific, USA); Glycerol (Fischer Scientific, USA); PEG 8000, (SIGMA, USA); Sodium Chloride, (SIGMA, USA); PBS (SIGMA, USA); BSA (Biovision, USA); Anti-FLAG, (Sigma, USA); HRP Goat Anti-mouse (Biolegend, USA); TMB Substrate (Sunmodics, USA); Herclon® (Roche, USA); Goat-Anti human_IgGFc-HRP Conjugated (Bethyl, USA); Tween 20 (Fisher Scientific, USA); Her2 (Acrobiosystems, China).

Example 1

Generalized Procedure for Synthetic Antibody Library Generation.

The success of synthetic libraries solely depends on the unique design which has to be diverse and on final library size which should be sufficiently large. Synthetic antibody library size & diversity and antibody specificity & affinity are directly linked. To have a reasonable number of clones covering the diversity and uniqueness, large number of antibody sequences are analyzed in silico. Codon replacement technology is used to synthesize altered antibody sequences with certainty and diversity and cloned into in-house phagemid vector having accession number MTCC 25125. The cloned genes in specific vectors which represent the pool of synthetic library are panned against specific antigen solely based on stringency. Selected pool of molecules is transferred to specific yeast display vectors (Accession numbers MTCC 25126, MTCC 25127 and MTCC 25128) via combinatorial or non-combinatorial approaches. However, a randomization of heavy and light chains is allowed to compensate the differences across two display systems. The displayed fragments are screened against specific antigenic targets and the populations showing higher affinity to target antigens are separated. Selected pools are optionally tested for antigen specificity and individual clones from the pools are separated and clonal populations are used for isolating nucleic acid sequences coding for the lead molecules.

Example 2

Antibody sequences are downloaded from various websites as exemplified by NCBI, V-base, Genbank etc. Functional germline and rearranged antibody sequences are downloaded from IMGT data base. To an approximate, 4300 unique sequences are analyzed, post removal of redundant sequences. Multiple entry of antibody sequences against same antigen or targets are also not considered in the analysis. As CDR3 region of heavy chains (CDRH3) are mostly involved in antigen binding, only CDRH3 diversity is planned to be incorporated in the synthetic library.

All CDRH3 sequences are extracted and aligned for further analysis. Length distribution analysis of CDRH3 sequences indicate that the variation in length ranges from 4 to 36 amino acids. Due to less diversity and frequency distribution of amino acids observed in CDRH3 lengths more than 24 amino acids, it was decided to go ahead with lengths till 23 amino acids to introduce the diversity. Amino acid compositional distribution is estimated for each position. Based on a calculated probability index for a particular mixture of amino acids with defined percentage of frequency of appearance/occurrence, synthesis matrix is designed followed by synthesis using codon-replacement technology. Next generation sequencing is performed on synthesized CDRH3 repertoire and compared with theoretical design. Flanking regions for these diversity are compatible with all seven heavy chain sub-families i.e., H1A, H1B, H2, H3, H4, H5 and H6. These flanking regions are also attached with specific restriction enzymes which will be used as mode of entry point into consensus sequence constructs. The consensus sequences for all 7 heavy chain, 4 kappa light chain and 3 lambda chain sub-families are human codon optimized, synthesized and incorporated into in-house phagemid vectors in all 49 combinations (via sequences recited in the Sequence Listing). This is done to maintain the Fab format. However, all 49 consensus sequence constructs in Phagemid vectors are categorized into 7 pools of families based on presence of heavy chain sub-family wherein all constructs are pooled under one heavy chain in equimolar ratio. CDRH3 diversity flanking with specific heavy chain family is incorporated between specific restriction sites BstEII/BstBI and XbaI. Cloning of CDRH3 repertoire is carried out in Fab format with a transformation efficiency of >$10^9$ wherein the confirmation of presence of insert is done by restriction digestion analysis and which is not less than 90-95%. Optionally, peer group sequencing is further executed to estimate the functional diversity, which is expected to be >80%. All 7 bacterial libraries are pooled in equal cell number ranging from 2 to $5 \times 10^{10}$. Phage library generation is carefully carried out with a calculated number of phage particles which is $6 \times 10^{10} - 10^{11}$. For panning experiments against antigens, the magnetic bead based approach is adopted in order to have a better control on the binders. For the preparation of antigen coated on magnetic dynabeads the bead conjugation efficiency is set at >90%. Moreover, the panning is fixed at one round to remove only non-binders with a number not more than $10^7$ phage particles. This step is well aligned with the next step of yeast display library screening. In order to avoid any biased amplification or target unrelated population enrichment, a fixed 90 minutes of phage amplification duration is employed. To transfer the panned naïve library, ssDNA is isolated in the presence of salmon sperm DNA followed by amplification of insert i.e., heavy and light chain repertoire. Purified repertoire is digested and ligated into yeast expression vector in two different formats, Fab format and ScFv format. Multiple yeast vectors are designed to express the Antibody heavy chain and light chain from same vector either from same promoter or from two separate promoters and from two separate vectors using yeast mating type. In all cases the transformation efficiency in yeast is obtained >$10^7$. Transformed yeast cells are checked for heavy chain, light chain and Fab molecule expression which is not less than 15-50% of the whole population. For mating type, the mating efficiency is ranging from 30-50%. The expression analysis is performed with multiple tags such as FLAG, c-Myc and $(His)_6$-tag and V5-tag for heavy chains and light chains respectively. Flow based sorting for antigen binding is analysed with double positive for both antigen and either of the heavy or light chain. Sorted yeast clones are collected, grown and screened for two to three more rounds against specific antigens before they are grown individually and tested for binding studies.

Flow charts illustrated in FIG. 27A and FIG. 27B describe the important process steps of the present disclosure.

Stage 1: The flow chart under FIG. 27A illustrates the process steps starting from designing of synthetic diversity to creation of synthetic antibody library in phage.

Stage 2: The flow chart under FIG. 27B illustrates the process steps involving phage library screening to Yeast clone development using flow sorting of independent binders.

Sequence Analysis

Antibody sequences are downloaded from IMGT database (http://www.imgt.org/IMGT_jcta/jcta?livret=0), wherein the rearranged sequences are identified using the following parameters; ANNOTATION_LEVEL=fully annotated SPECIES=*Homo sapiens* (human); CONFIGURATION_TYPE=germline, rearranged GENE_TYPE=variable, diversity, joining; FUNCTIONALITY=functional, productive GROUP=IGHV. The sequences are filtered through a redundancy check and thereby total number of ~4300 sequences are reduced to ~2830 sequences. Initial sequences are also checked for any multiple entries of antibody sequences against same antigen or not. Only unique sequences are retained for subsequent analysis.

A large number of structure-function studies done on antigen-antibody interactions suggest that CDR3 of heavy chain (CDRH3) makes the maximum number of contacts with targets and contributes mostly in antigen binding. Therefore, the preferred CDR for introducing diversity through designing is CDRH3. However, the efficiency and productivity of a synthetic library depends on diversity and size of the library which solely rests on the unique design to provide diversity and supporting technology to accommodate the size. CDRH3 sequences are extracted based on relatively conserved boundaries of framework 3 and framework 4 sequences.

Figure 1:
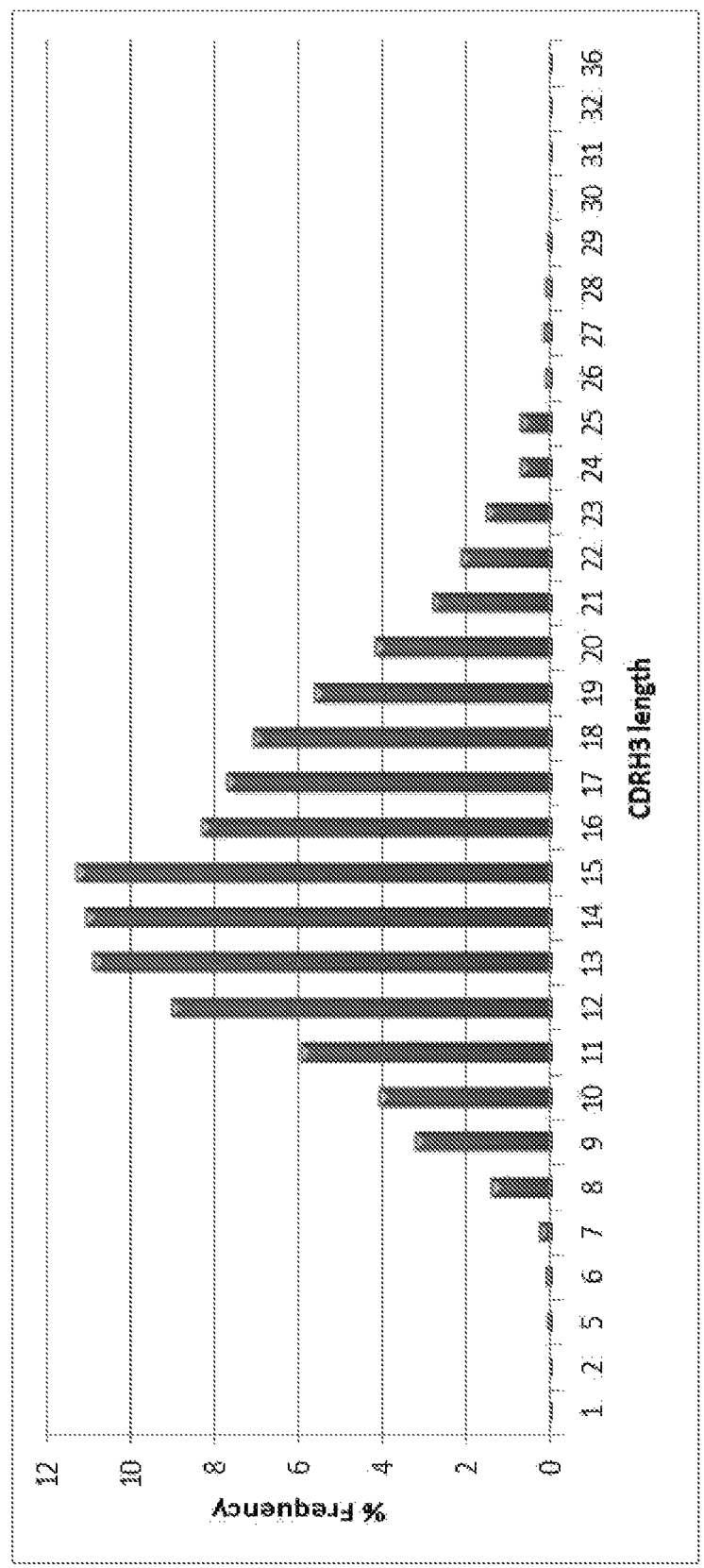
Figure 2:
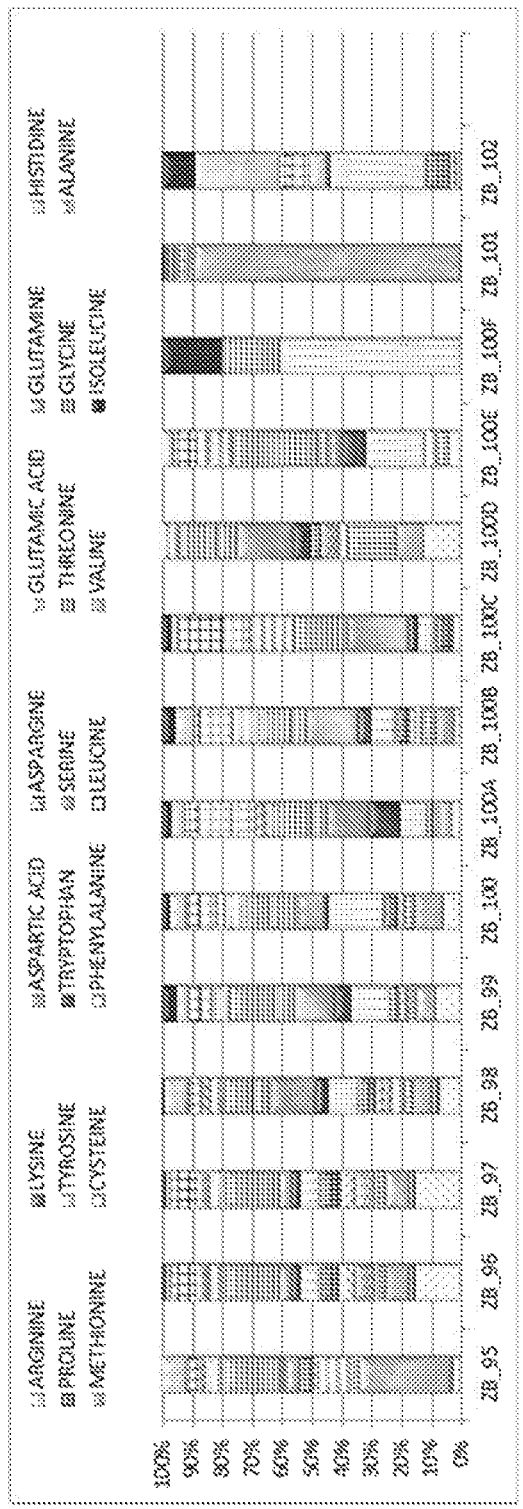

All CDRH3 sequences are categorized based on length and composition at each sequence position. The CDRH3 sequences obtained spanned different lengths ranging from 4 to 36 (FIG. 1). The Gaussian frequency distribution seen for the length variation clearly indicates a definite bias of CDRH3 lengths in nature. Noticeably, the frequency of antibody population having >24 amino acids long CDRH3, were extremely low. Therefore, it was decided to work and focus on CDRH3 lengths ranging from 4 to 23 amino acids. Post sorting of lengths, respective CDRH3 sequences are analyzed for compositional biasness wherein frequency of occurrence for each of the 20 natural amino acids for a particular position is determined. Positional preference for amino acids is determined (FIG. 2) and found to be similar to its natural existence. The bias of amino acids diversity seen in nature will be preserved in the design as well. However, a complete randomization of all the CDRH3 lengths along with all 20 amino acid replacements will give rise to an astronomical number which is $>10^{23}$. In the present disclosure, a refined method to reduce the number without compromising the diversity is developed.

Therefore, a unique concept of positional correlation in the synthetic library designing is introduced. However, there are several findings which came out of sequence analysis such as the probabilities of all 20 amino acids to occur in CDRH3 regions of lengths 4 to 10 while number of amino acids goes down with increasing length of CDRH3. A few notable features stand out even without the correlation analysis. For instance, at each length there are certain positions that are invariably occupied by one predominant amino acid, as exemplified by glycine that has a high occurrence probability in nearly all positions. Another finding is related to a strong preference for the CDRH3 region to end with a Tyrosine (Y) with occurrence ranging from 40% to 58% while a strong tendency is seen for the second last residue to be Aspartic acid (D) with probability varying from 54% to 85%. Interestingly, preference for Tyrosine as last residue is seen till CDRH3 length of 14 while CDRH3 length 15 amino acids onwards the preference for tyrosine subdues and shifts to Valine. Sequence position correlation is also taken into account. For instance, the designed sequences should have the same proportion of Tyrosine in the last position and Aspartic Acid/Valine in the second last position. The initial sequence analysis results in a total number of 270 positions that needs to be randomized in order to synthesize the library. To do further analysis, the probabilities between different positions at different CDRH3 lengths are calculated. Next, probability differences for 20 individual amino acids are added to generate one number per two positions and are compared with another pair of positions. Smaller the difference means the more similar are the positions. As exemplified, probability difference value for length 8 position 7 with length 21 position 19 is 1.98 while the probability difference value between length 12 position 10 and length 11 position 9 is 0.15, thus, indicating higher similarity in amino acid compositional frequency in later pair than the former pair. Hence in principle, the same mixture can be used for synthesis which resides within limit and thereby no compromises on the diversity. It was decided to go ahead with a probability difference number as 0.5; The output values and corresponding amino acid distribution is manually checked as well and found to be in agreement with the value. Based on prior successes seen for several groups of researchers, codon replacement technology is adopted to synthesize the repertoire. Codon replacement technology involves the use of a tri-nucleotide of choice as building blocks to diversify a specific position. This allows complete customization of amino acids compositions avoiding the occurrence of unwanted stop codons or amino acids to achieve a significantly higher quality library than by using conventional technologies such as randomization using degenerate codons. Taken together, codon replacement technology provides complete control over incorporation of desired amino acids with fewer out-of-frame, stop codon and unwanted amino acids containing sequences. Thus, the technology creates rational diversity in position/s where it is expected to have the most impact. However, without the positional correlation index there are 270 unique mixtures needed to tap the complete diversity. Introduction of the positional correlation concept to design the synthetic library has reduced amino acid mixtures from 270 to 101 unique mixtures. This concept makes the whole process extremely efficient and compatible with several technological limitations associated with synthesis and subsequent steps. The outcome of this concept is 12 unique groups of amino acids mixture wherein the representative mixture needs to be chosen. This is crucial as representative mixture should not miss out on any combination. To overcome this challenge, the concept of true diversity i.e., Shannon entropy is employed wherein this measures the unpredictability of information content. Shannon entropy measurements include two parameters such as the richness and abundance in the system. The richness indicates the variety of amino acids while the abundance includes the probability of occurrence. The calculation is performed using following equation, wherein Pi relates to probability of occurrence of amino acids.

$$H[p] = -\sum_{i=1}^{k} p_i \log p_i$$

To benchmark the program two known situations are provided wherein probability of one amino acid is 1 and other 19 amino acids being zero. For second condition, all 20 amino acids were having equal probability of occurrence indicating highest diversity. For zero diversity the value is 1 while for maximum diversity the value is 0.05. As mentioned before, synthesis of the library is done through codon-replace technology to have better control over the product. The choice of codons is restricted to human codon usage.

Generation of Consensus Constructs

Figure 3:
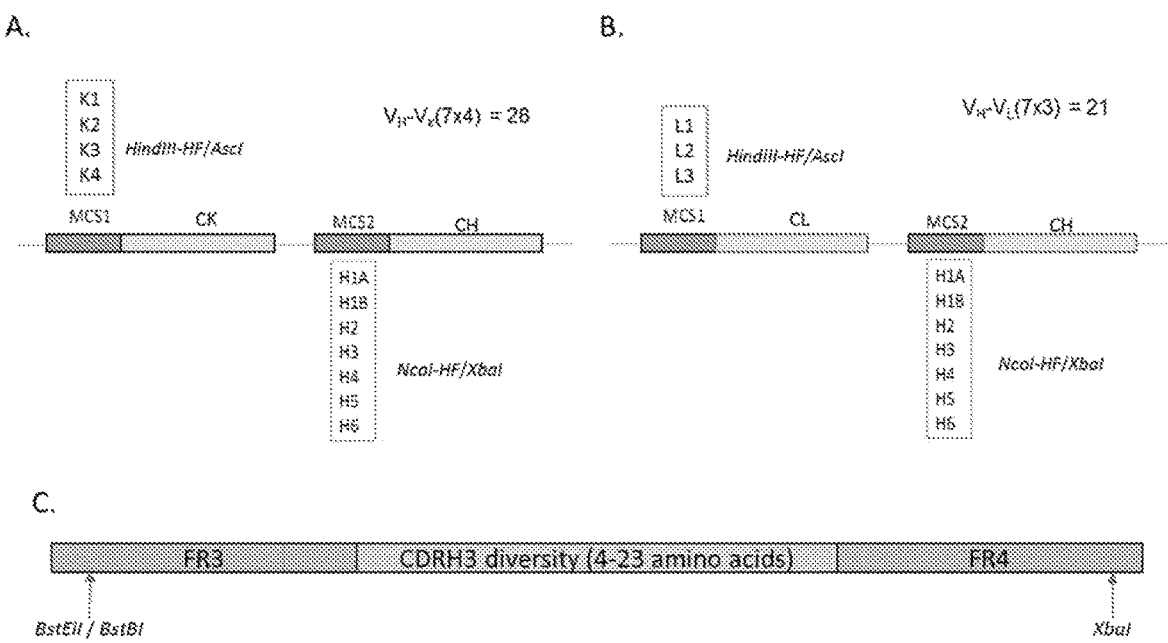

It is seen in germline families that the rearranged sequences are biased at certain positions towards amino acid residues and selection of dominating sequences are seen after screening against antigens. Therefore, in order to have a complete un-biasness regarding selection of most frequently used sequences later on, consensus sequences are synthesized and used as constant background (as per Sequence listing) on which CDRH3 diversity is introduced for generation of synthetic library. For both heavy chains and light chains CDR1 and CDR2 regions, the consensus of rearranged sequences is replaced with the amino acid sequence of one of the germline sequences of the corresponding family. Thus, this procedure removes any bias, as the CDRs of rearranged and mutated sequences are known to be mutated due to selection towards their particular antigens. 7 heavy chain and 7 light chain (4 kappa light chains & 3 lambda light chains) consensus sequences are codon optimized for human and synthesized from Geneart (Thermo Fischer, Germany). Synthesized genes are flanked by compatible restriction sites for respective entry into inhouse phagemid vectors (accession #MTCC 25125). Thus total 49 individual consensus sequences containing constructs are generated (FIGS. 3A & B). In order to incorporate the synthetic diversity of CDRH3, 5' BstEII site is chosen in FR3 region for H1A, H1B, H4 and H5 families while 5'BstBI restriction site is fixed for H2, H3 and H6 heavy chain families. XbaI is decided as 3' restriction site for all the heavy chain families (FIG. 3C). 11 μg of the heavy chain (H1A, H1B, H2, H3, H4, H5 and H6), along with corresponding phagemid vectors containing either kappa or lambda light chain constants regions are digested with NcoI-HF & XbaI at 37° C. for 3 hr in a total volume of 100 μL (Table 1). The digested samples are gel eluted wherein excised gel is dissolved by mixing 3 volumes of Buffer QX1 solution. 30 μL of QIAEX II beads are added by vortexing for 30 s followed by incubation at 50° C. for 10 minutes. Series of washes are given to beads; first with 500 μL of QX1 followed by 2 washes with 500 μL of PE buffer. DNA is eluted with 30 μL of nuclease-free water. Eluted DNA is used for ligation set up as describe in Table 2 at 4° C. for overnight.

TABLE 1

| | |
|---|---|
| DNA (vector/H1A) | 10 μg |
| NcoI-HF (20 U/μL) | 4 μL |
| XbaI (20 U/μL) | 4 μL |
| Cut smart Buffer | 10 μL |
| Water | respective volume of milli-Q water |
| Total | 100 μL |

TABLE 2

| | |
|---|---|
| DNA (Vector) | 50 ng |
| DNA (insert) | 125 ng |
| T4 DNA ligase | 1 μL |
| T4 DNA ligase buffer (10×) | 1 μL |
| Water | 2.5 μL |
| Total | 10 μL |

Figure 4:
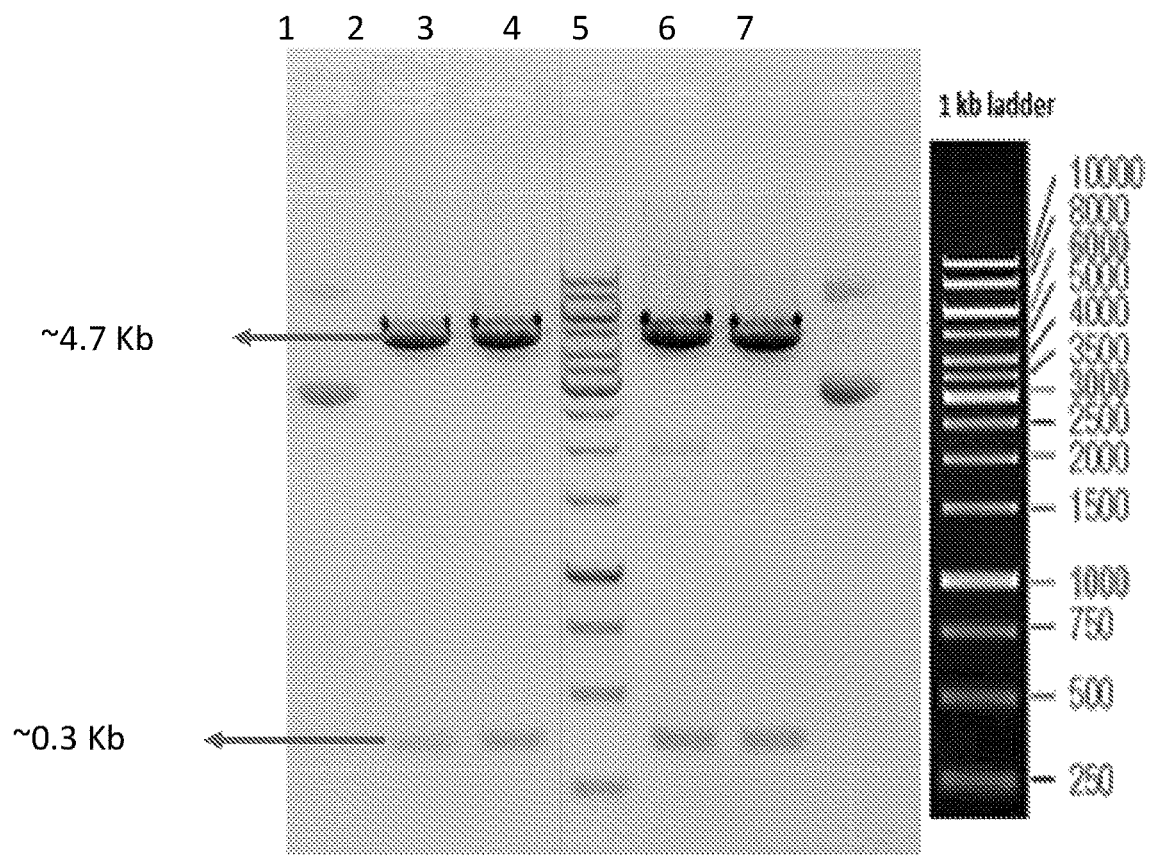
Figure 5A:
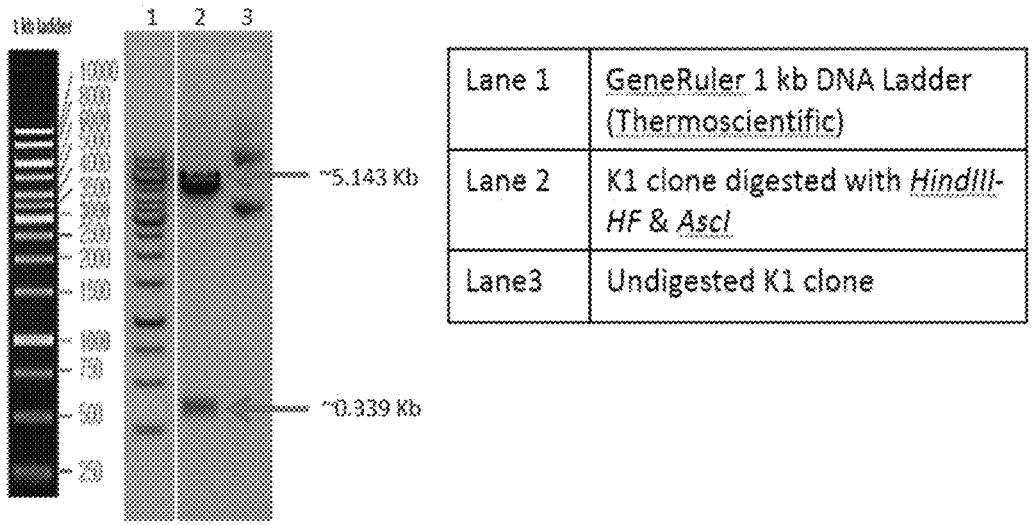
Figure 5B:
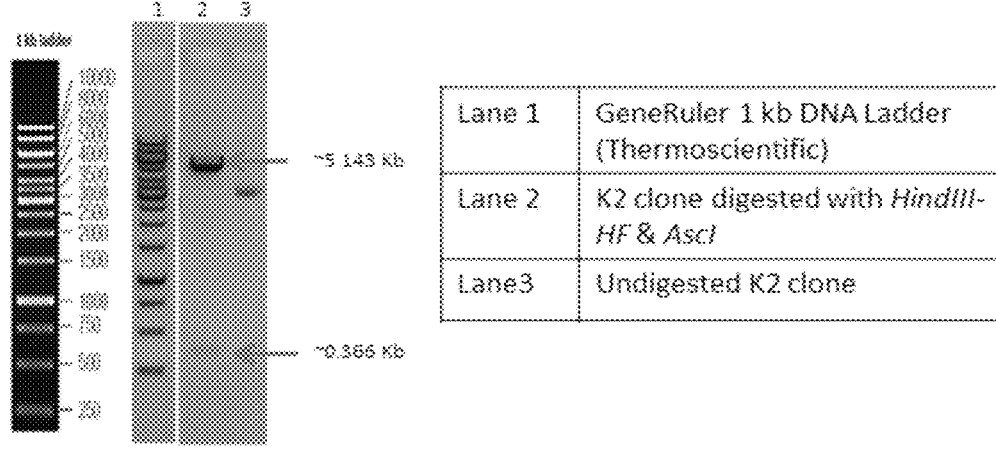
Figure 5C:
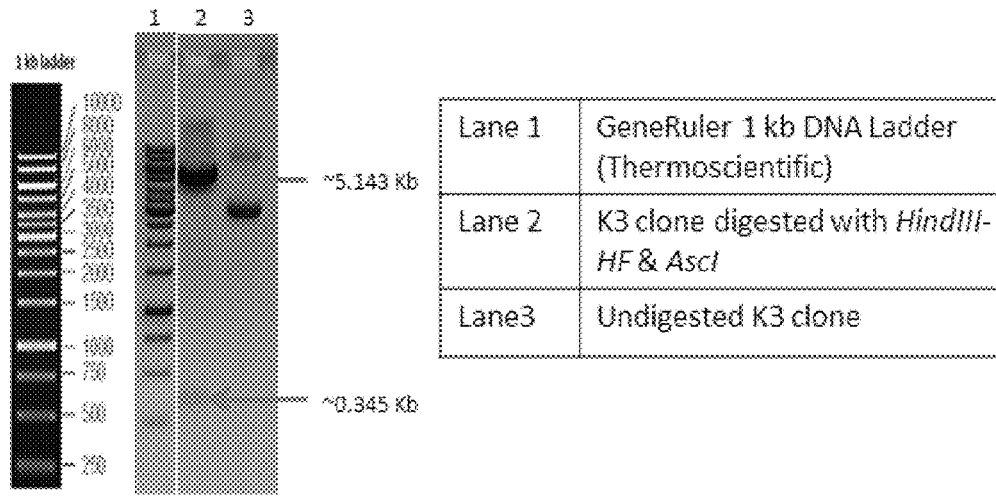
Figure 5D:
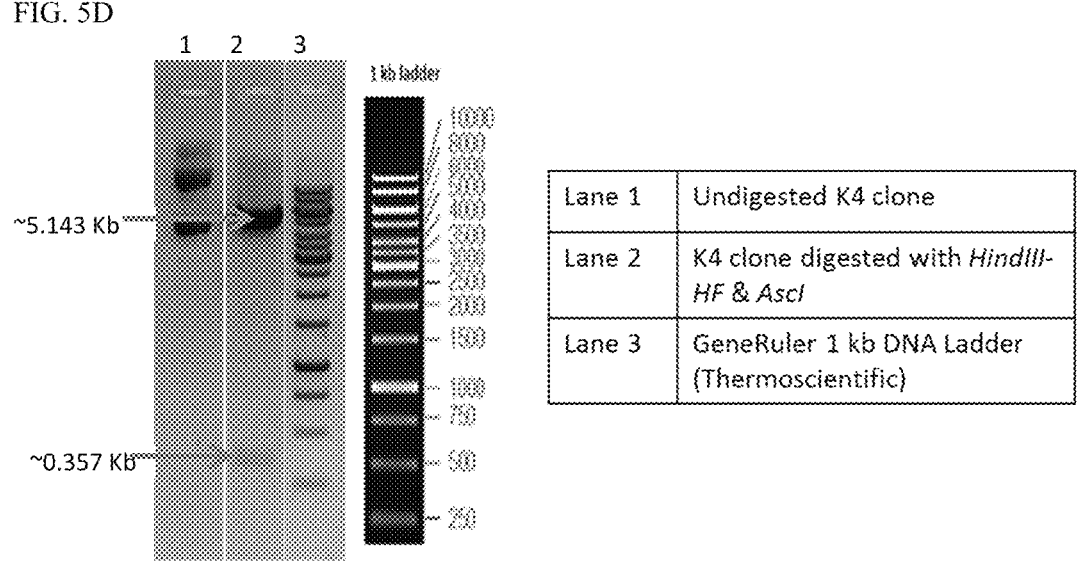
Figure 6:
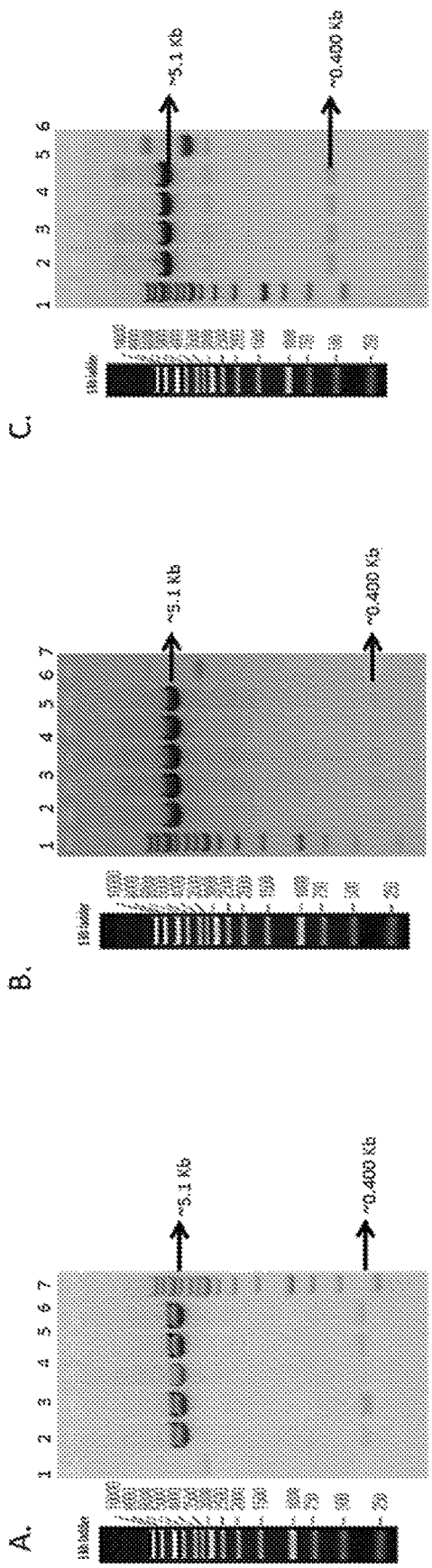

5 μL of the ligated samples is transformed into dam−/dcm− Competent *E. coli* by heat shock method followed by overnight incubation of transformed cells plated on LB-Agar-Ampicillin medium. Clones are confirmed by restriction digestion with NcoI-HF & XbaI (FIG. 4; Table 3). Similarly, heavy chain consensus constructs are generated for H1B, H2, H3, H4, H5 and H6.

TABLE 3

| Reaction mix | |
|---|---|
| DNA | 2 μg |
| Buffer | 2 μl |
| NcoI-HF (20 U/μL) | 1 μl |
| XbaI (20 U/μL) | 1 μl |
| Water | Respective volume of Mili-Q water |
| Total | 20 μl |

Further H1A consensus sequence containing Phagemid constructs (light chain kappa or light chain lambda constant regions) are isolated using midi prep kit and digested in bulk quantity along with light chain kappa (K1, K2, K3 and K4) and light chain lambda (L1, L2 and L3) consensus sequences with HindIII-HF and AscI restriction enzymes (Table 4).

TABLE 4

| | H1A consensus Phagemid | K1 to K4 insert source | L1 to L3 insert source |
|---|---|---|---|
| DNA (H1A) | 10.0 μg | 10.0 μg | 10.0 μg |
| HindIII-HF (20 U/μL) | 4 μL | 4 μL | 4 μL |
| AscI (10 U/μL) | 4 μL | 4 μL | 4 μL |
| Cut smart Buffer | 10 μL | 10 μL | 10 μL |
| Water | Respective volume of Mili-Q water | Respective volume of Mili-Q water | Respective volume of Mili-Q water |
| Total | 100 μL | 100 μL | 100 μL |

The digested samples are gel eluted as described above. Eluted DNA is used for ligation set up individually for K1 to K4 and L1 to L3 as describe in Table 5 and incubated at 4° C. for overnight.

TABLE 5

| | |
|---|---|
| DNA (Vector) | 50 ng |
| DNA (insert, K1 to K4 or L1 to L3) | 125 ng |
| T4 DNA ligase | 1 μL |
| T4 DNA ligase buffer (10×) | 1 μL |
| Water | 2.5 μL |
| Total | 10 μL |

5 μL of the ligated samples is transformed into dam−/dcm− Competent *E. coli* by heat shock method followed by overnight incubation of transformed cells plated on LB-Agar-Ampicillin medium. Clones for respective light chains are confirmed by restriction digestion with HindIII-HF & AscI (FIG. 5A, FIG. 5B, FIG. 5C, FIG. 5D and FIG. 6). Identical methodology is followed for HIB, H2, H3, H4, H5 and H6 containing Phagemid consensus constructs to generate a total number of 49 constructs.

Synthesis and Validation of Diversity

Figure 7:
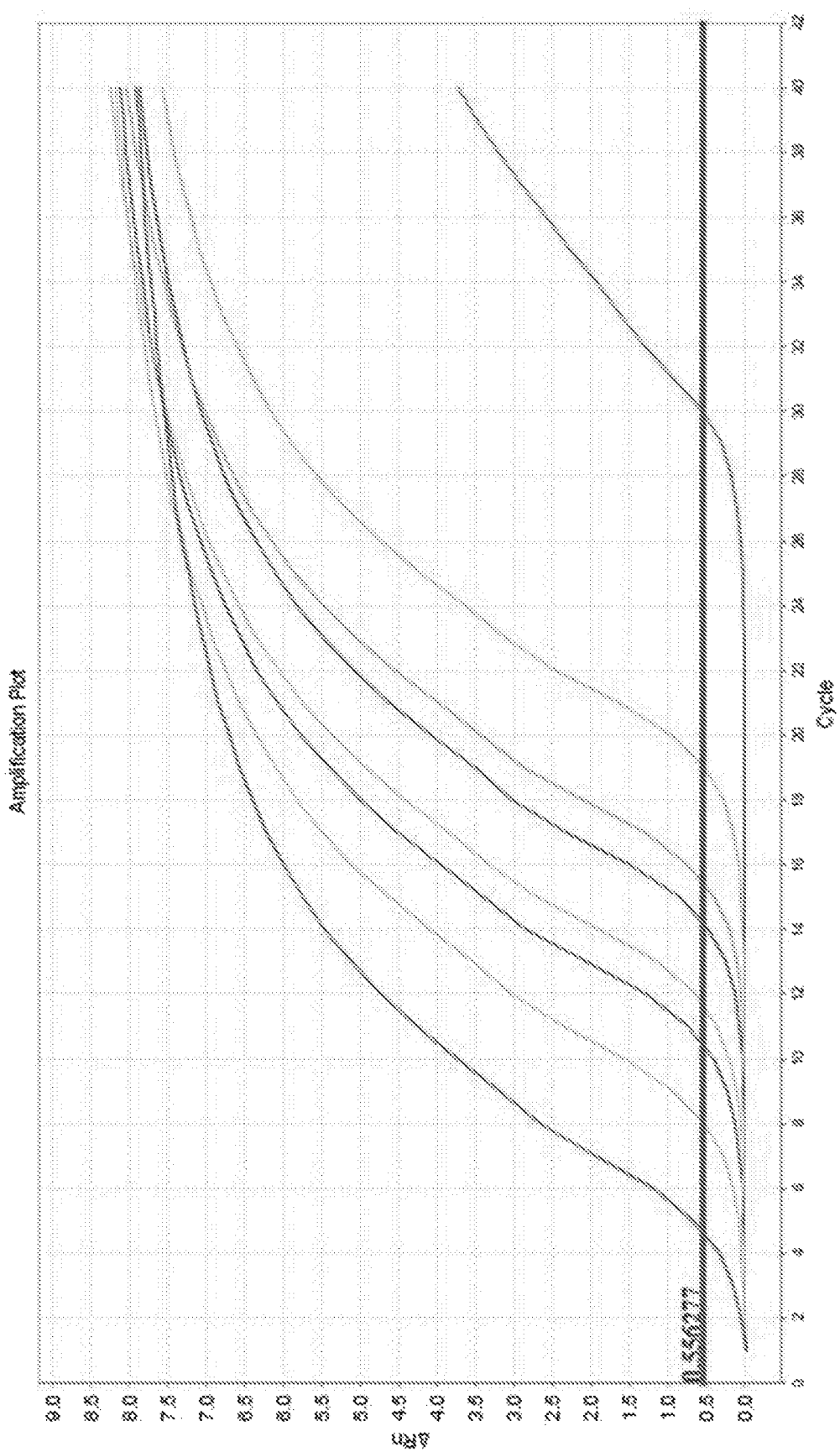
Figure 8:
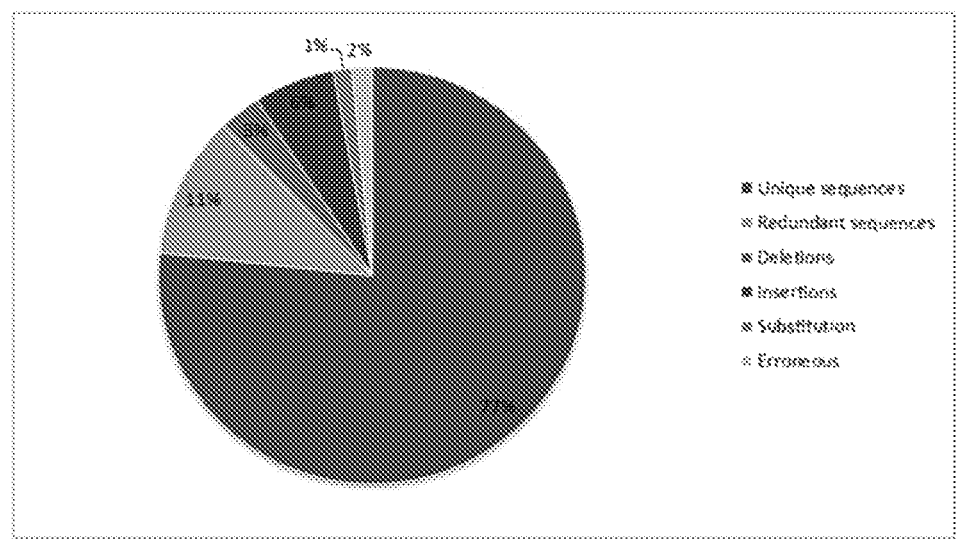
Figure 8:
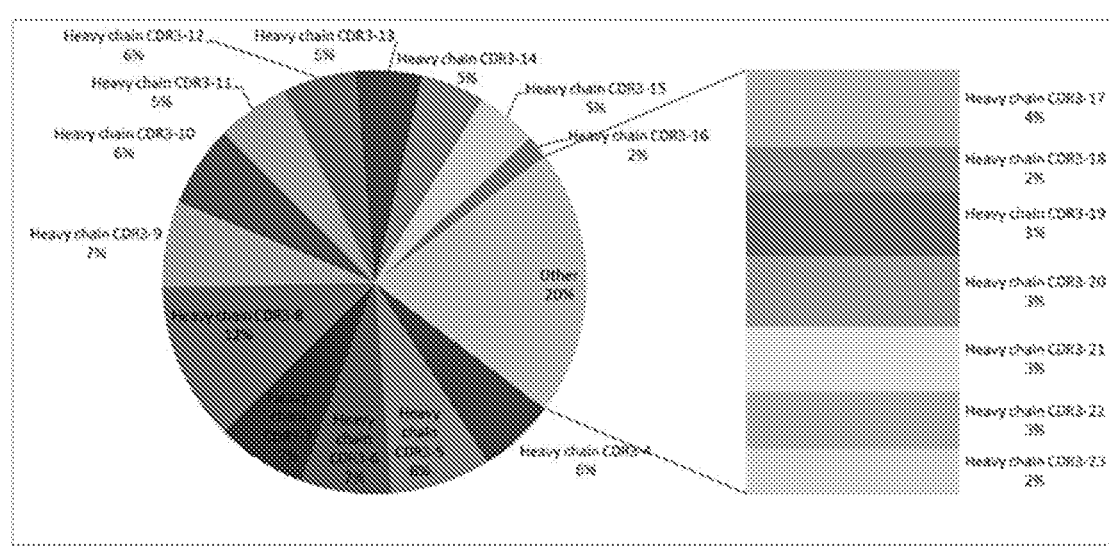
Figure 9:
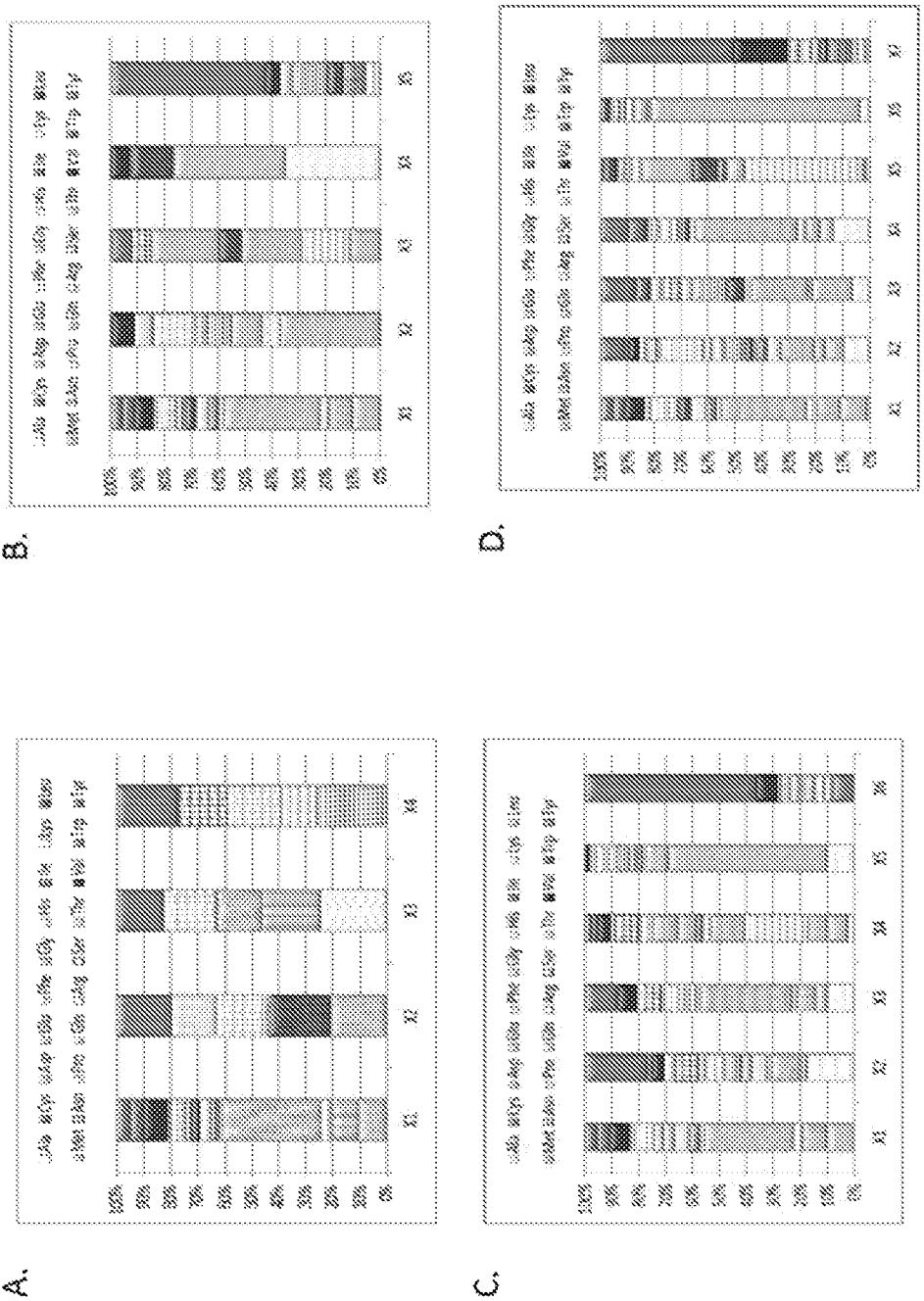
Figure 10:
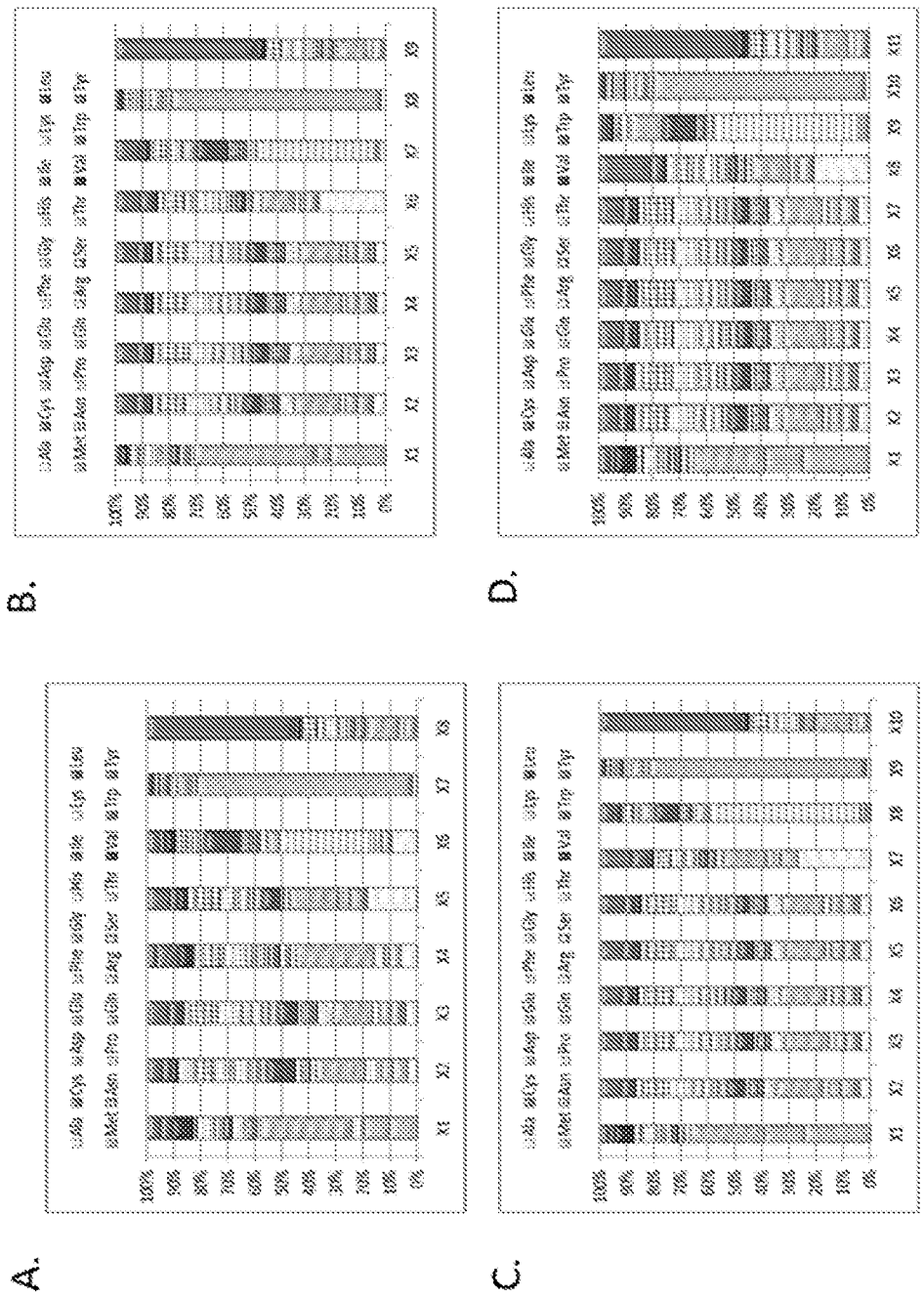
Figure 11:
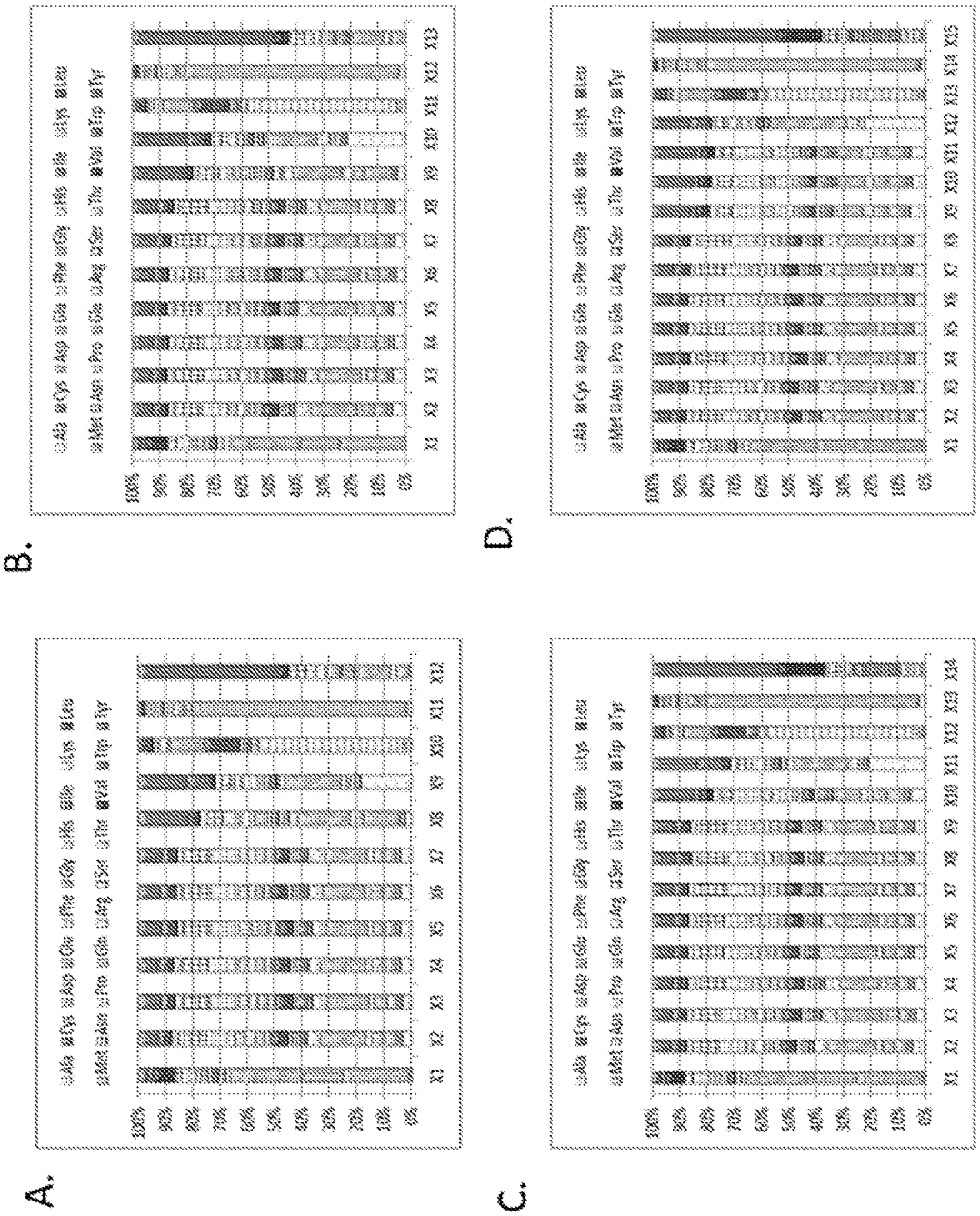
Figure 12:
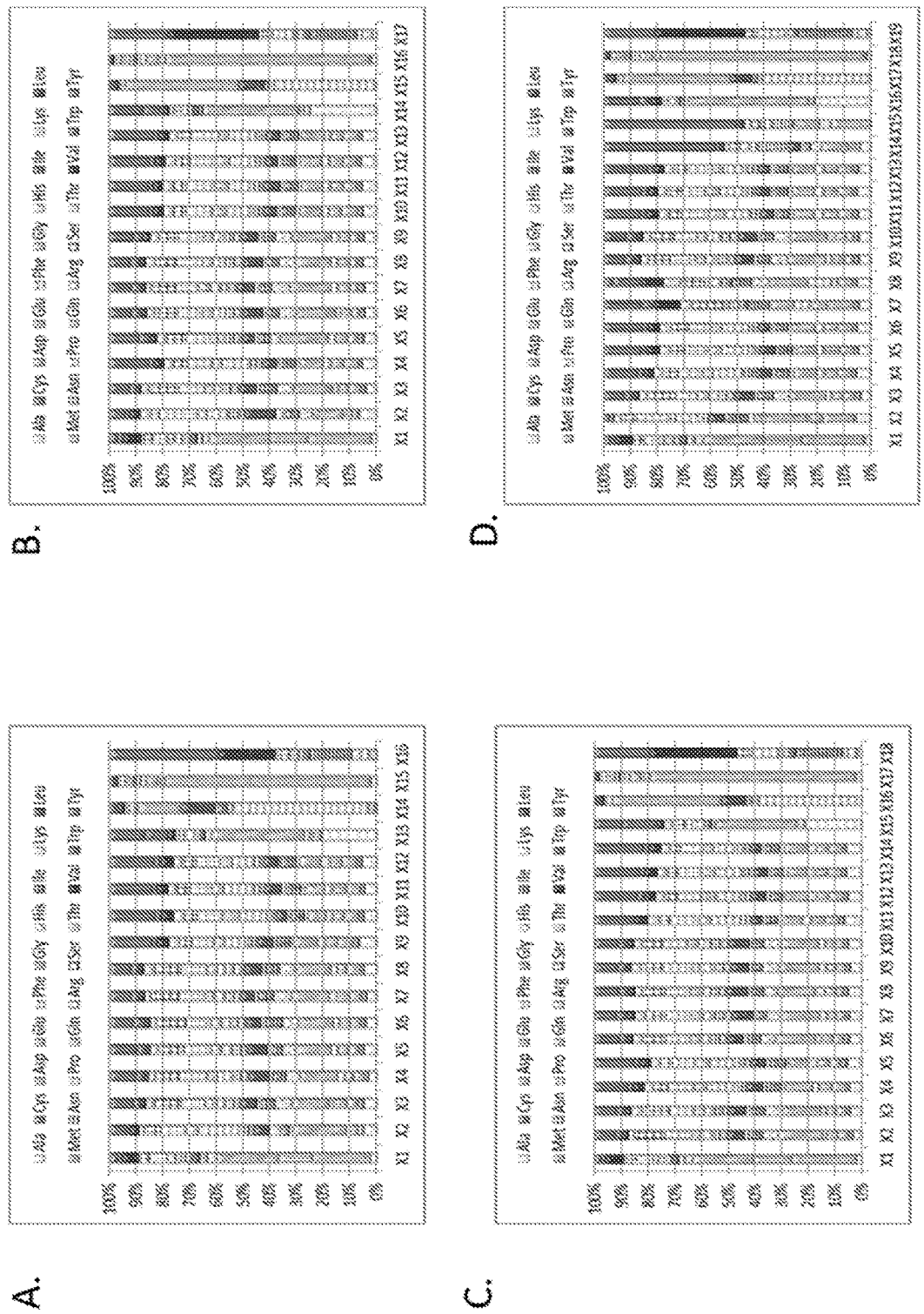
Figure 13:
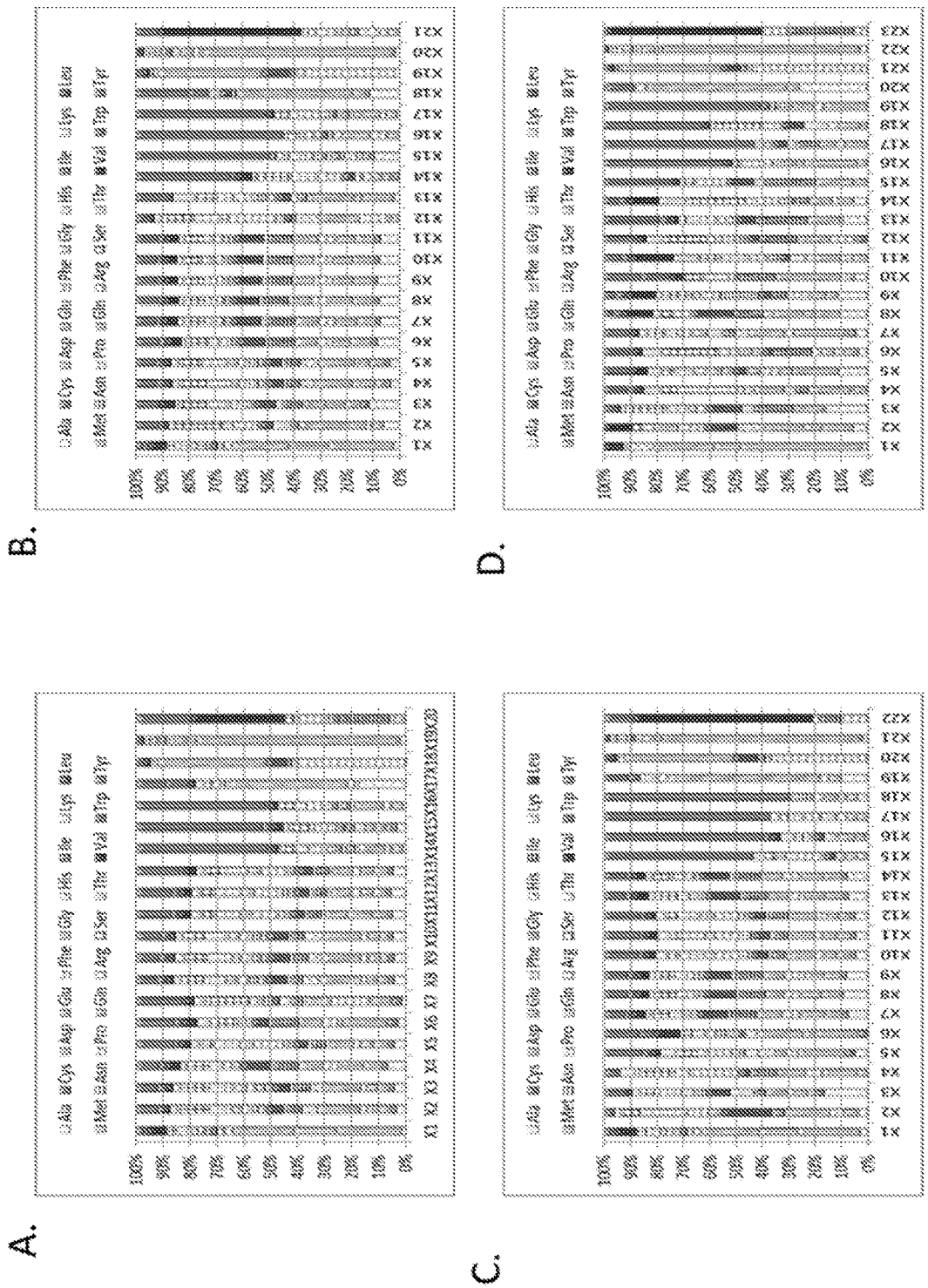

The synthesis of designed CDRH3 diversity is completed using codon replacement technology. The synthesized library is quantified by real time PCR (FIG. 7). The library is analyzed by next generation sequencing using Ion Torrent PGM, Hi-Q-View chemistry. The Average Number of Reads per Sequence is 24.4. The analysis indicates that there are 10947 of the 105174 sequences contained erroneous sequences with deletions (3409), insertions (6558) or substitutions (1525) within the reading frame (FIG. 8A). The viability of the library is found to be 91.2% while the correctness of the library is 89.6%. Number of synthesized molecules for each CDRH3 length is found to be equally abundant to an approximate (FIG. 8B). Unlike natural CDRH3 length distribution synthesized CDRH3 length distribution does not follow any Gaussian distribution (FIG. 8C). This probably implies the strength of designed library wherein unbiased presence of molecules with different lengths ranging from 4 to 23. Moreover, percentage occurrence of 4 to 10 amino acids long CDRH3, which is under represented in natural repertoire when compared to other CDRH3 lengths, has been increased; thereby increasing a potential number of diverse molecules in the synthetic pool. In addition, the dominating lot of CDRH3 with 10 to 19 long amino acids is kept at similar level with similar percentage of frequency of occurrence; thus maximum diversity in these segments is retained. There are no significant changes seen with CDRH3 lengths ranging from 20 to 23 amino acids, between natural repertoire and synthesized repertoire. Amino acid frequency distribution analysis is performed for all the synthesized CDRH3 lengths (FIGS. 9 to 13). The synthetic library is also analysed by peer group sequencing via Sanger sequencing. Total 96 individual colonies are picked and sequenced. 5 sequences out of 95 contained erroneous sequences with deletions (1), insertions (0) or substitutions (4) within the reading frame. Taken together the correctness of the library obtained from peer group sequencing is found to be 95%.

Incorporation of Diversity into Heavy Chain and Light Chain Containing Consensus Constructs In order to generate synthetic library, a fixed heavy chain containing individual constructs (with either kappa or lambda light chains) are pooled. As exemplified for H1A heavy chain family, there are 7 constructs with following combinations; H1A-K1, H1A-K2, H1A-K3, H1A-K4, H1A-L1, H1A-L2 and H1A-L3. All these constructs are pooled at equal amount of 2.9 µg each and a master pool of H1A constructs are made.

CDRH3 diversity is synthesized in accordance with the aforementioned design. The diversity is associated with respective heavy chain family i.e., H1A, H1B, H2, H3, H5 and H6. All the libraries are associated with respective BstEII/BstBI and XbaI restriction enzymes which are used aptly for the release of library followed incorporation into individual heavy chain pool of consensus constructs.

Figure 14:
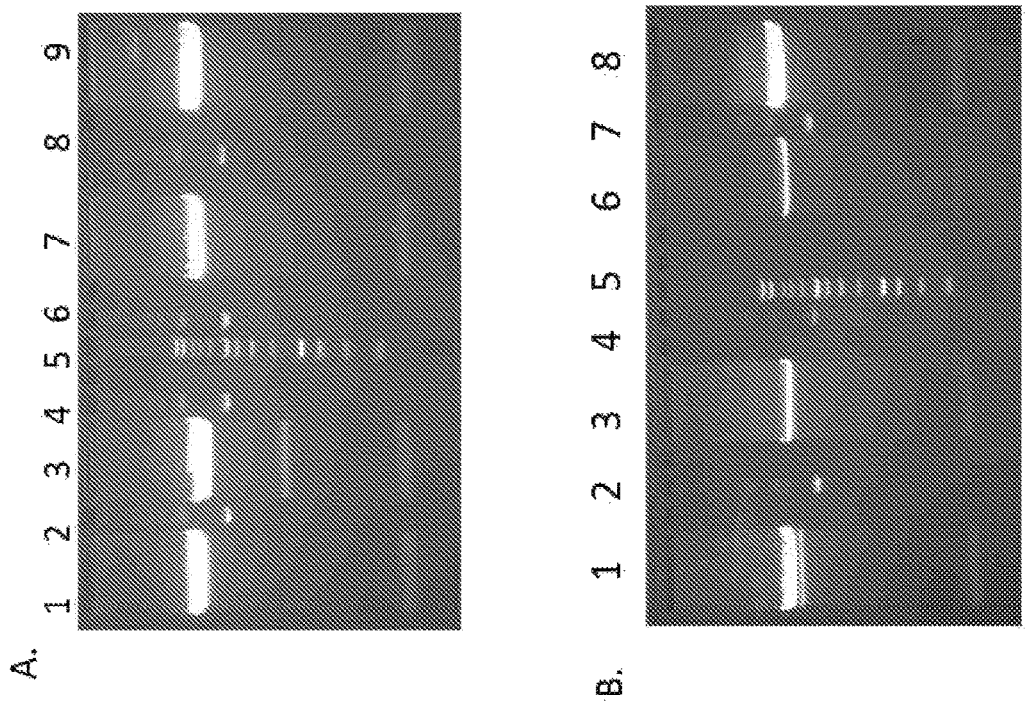
FIG. 14 illustrates restriction digestion with BstEII/BstBI and XbaI of heavy chain pool
  A. pool of consensus constructs H1A to H3 families
  B. pool of consensus constructs H4 to H6 families.
Figure 15:
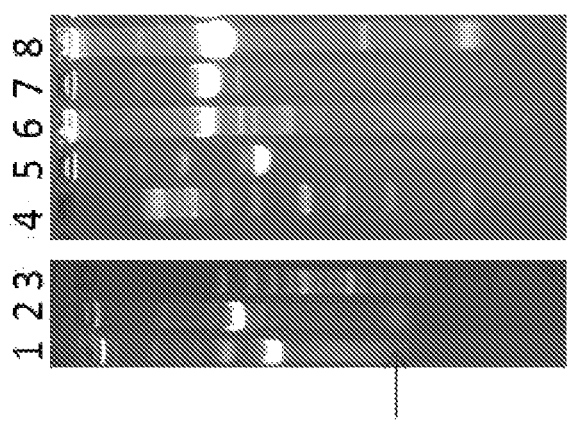
FIG. 15 illustrates restriction digestion of H1A family pool containing synthesized CDRH3 library.

For H1A pool of consensus constructs CDRH3 diversity compatible with H1A flanking region having BstEII and XbaI restriction sites are used for the generation of H1A-Synthetic library. 10 µg of H1A pool consensus constructs and 15 µg of H1A-CDRH3 diversity pool are digested sequentially with BstEII at 65° C. for 8 hr followed by XbaI at 37° C. overnight at a total volume of 100 µL (FIGS. 14 & 15; Table 6). Identical methodology is followed for H1B, H2, H3, H4, H5 and H6 constructs as well (FIG. 14). The digested samples are gel eluted wherein excised gel is dissolved by mixing 3 volumes of Buffer QX1 solution. 30 µL of QIAEX II beads is added by vortexing for 30 s followed by incubation at 50° C. for 10 minutes. Series of washes are given to beads; first with 500 µL of QX1 followed by 2 washes with 500 µL of PE buffer. DNA is eluted with 30 µL of nuclease-free water. Eluted DNA is used for ligation set up as describe in Table 7 at 4° C. for overnight.

TABLE 6

|  | Vector | Insert |
| --- | --- | --- |
| H1A pool | 10 µg | 15 µg |
| Cut smart Buffer (10×) | 10 µl | 10 µl |
| BstEII (20 U/µl) | 4 µl | 4 µl |
| XbaI (20 U/µl) | 4 µl | 4 µl |
| Water | 39 µl | 72 µl |
| Total volume | 100 µl | 100 µl |

TABLE 7

| Ligation | |
| --- | --- |
| Vector | 400 ng |
| Insert | 80 ng |
| Ligase buffer (10×) | 3 µl |
| T4 DNA ligase | 0.6 µl |
| Water | 13.8 µl |
| Total volume | 30 µl |

25-50 ng of ligation mixture is transformed into 25 µL of TG1 cells through electroporation wherein 1.0 mm cuvette is used with an optimal setting of 1800 volts, 600 ohm and 10 µF. Post recovery in recovery media, 200 µL of transformed cells are spread on 144 mm plates and incubated overnight at 37° C. In total there are 6-8 plates from which colonies are scraped on following day and stocks are made with 20% glycerol. Transformation efficiency is calculated by dilution plating and found to be in the range of $10^9$ to about $10^{10}$, preferably at $\sim 10^9$.

The total numbers of cells are determined per vial of glycerol stocks through dilution plating and found to be $10^{12}$. Colonies are inoculated in 5 mL LB-Amp and plasmid is isolated. The isolated plasmids are checked for restriction digestion analysis and confirmed for the presence of CDRH3 library in the pool.

Figure 16:
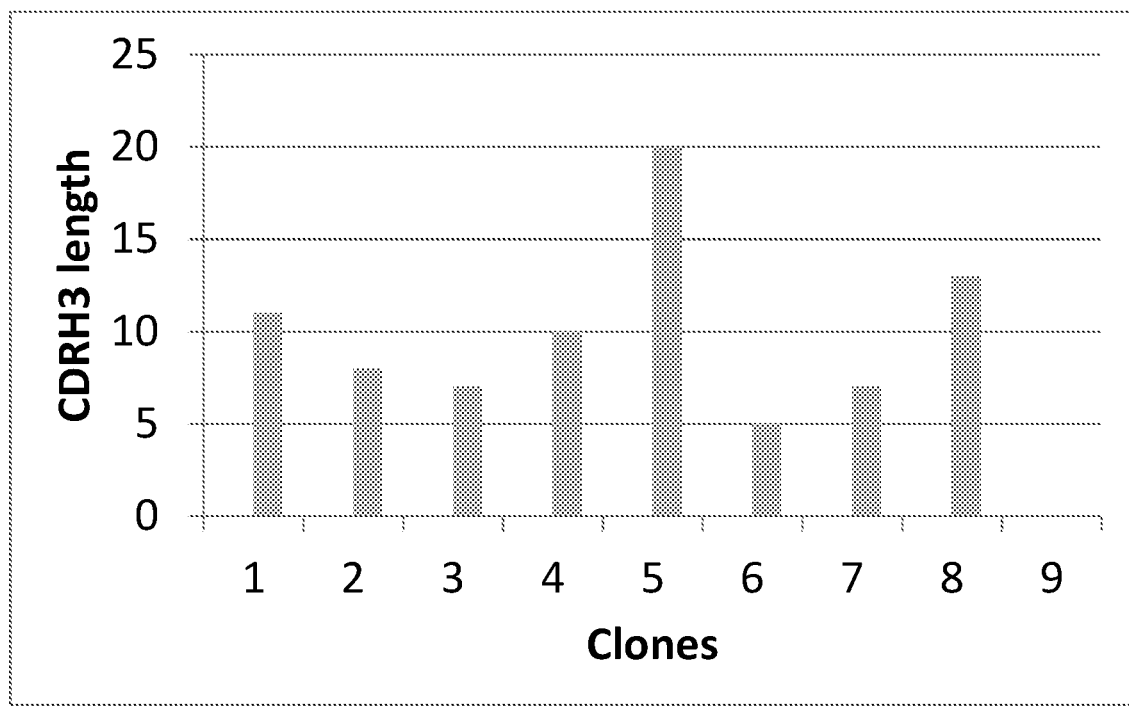
FIG. 16 illustrates sequence analysis of independent clones from H1A synthetic library showing CDRH3 length variation.

Transformation efficiency of $\sim 10^9$ indicates a high number of independent clones present in the pool thus tapping the maximum diversity. Colonies are scraped and stored as glycerol stocks for future use. The estimated number of cells per vial is $10^{12}$ representing the complete diversity. Few of the representative clones are used for plasmid isolation and optionally sent for peer group sequencing. The sequencing result indicates that almost all of the cloned molecules are functional and are having different CDRH3 sequences and lengths ranging from 4 to 22 amino acids (FIG. 16). This indicates a transfer of significant amount of diversity from synthesis to bacterial library (FIG. 16). Similar strategy is followed for other heavy chain families and bacterial stocks are generated.

Preparation of Bacterial Synthetic Library

Before proceeding with phage library generation, it is essential to generate a master stock of all heavy chain families containing CDRH3 diversity wherein the contribution in term of numbers of cells is kept same. This is done with a purpose of employing an unbiased scenario which will provide us information on preferences of heavy chain families selected after a screening against a target molecule, if any. Therefore, all heavy chain synthetic libraries are pooled at a cell number of $10^{10}$ per family. Pooled library is used in subsequent steps for phage library preparation.

Phage Library Generation 1 ml of pooled synthetic library containing bacterial master glycerol stock are grown into 200 ml LB-AMP medium at 37° C. until OD at 600 nm reaches 0.8. Further, M13K07 helper phage at multiplicity of infection (MOI) of 10 to the bacteria is added and incubated at 37° C. for another 30 minutes. Post infection, infected bacteria is centrifuged and the pellet is re-suspended into 200 ml of LB with 100 µg/ml ampicillin and 25 µg/ml kanamycin followed by growth at 30° C. for overnight at 250 rpm. Suspension is spun down at 8000 rpm for 15 min at 4° C. followed by discarding the pellet. Separated supernatant is mixed with PEG/NaCl solution in ¼ volume of supernatant and the mixture is incubated on ice for 1 h. The mixture is centrifuged at 10000 g for 15 min and the phage pellet is re-suspended into 20 ml of PBS. Glycerol is added to a final concentration of 50% to the entire phage suspension and frozen in aliquots of 1 ml at −80° C. as phage library stock.

Figure 17:
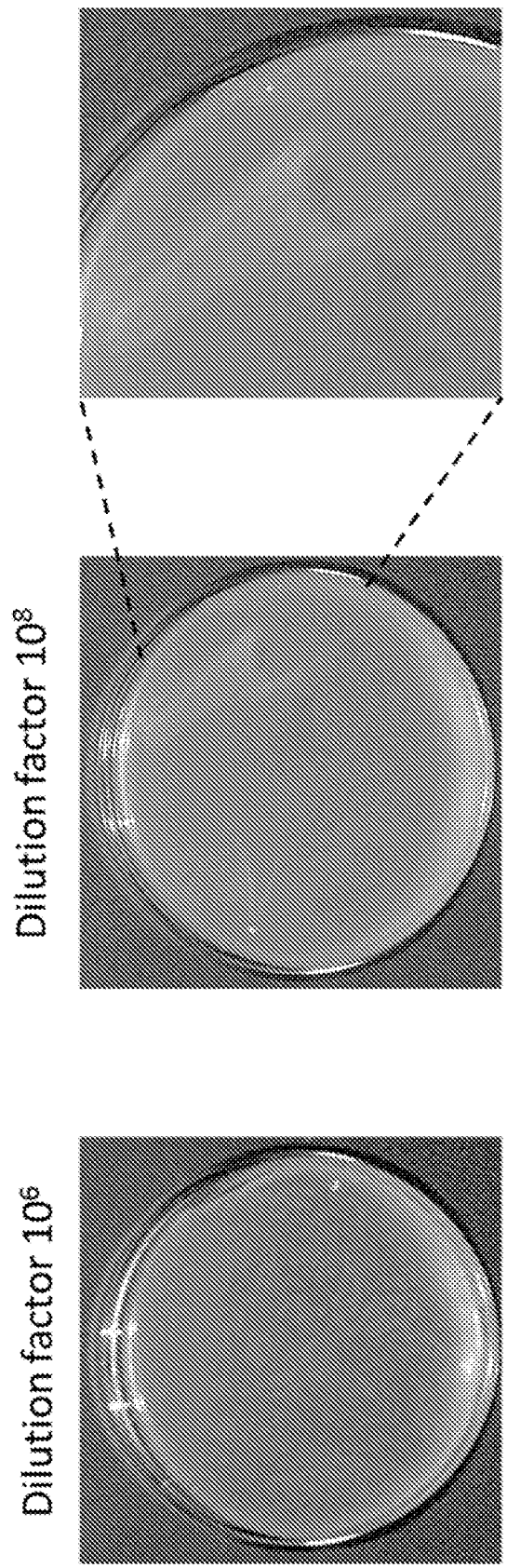
FIG. 17 illustrates plaque assay of Synthetic antibody gene library.

With addition of helper phage, the phage particles displaying the diversity are precipitated and purified, and stored as glycerol stocks for future use. The estimated number of phage library that is derived from plaque forming assay, is found to be about $10^{10}$ to about $10^{11}$, preferably $\sim 10^{11}$ pfu/mL (FIG. 17).

Screening of Library/Strategy for Panning

Screening of synthetic library is the most important step as this will produce the stream of potential binders against specific target antigen. Taking the whole process of generation and developing the binders into mind, the aim of panning is to remove the non-specific binders from the pool of naïve repertoire. Therefore, the phage screening strategy consisting of binding, amplification and restriction digestion and sequence confirmation steps needs to be carefully decided. In addition to having an efficient binding, the ratio of antigen and phage molecules is also to be decided accordingly to avoid any kind of biasness during binding.

A library of phage-displayed antibodies contains clones that bind to a target better than other clones and clones that amplify faster than other clones. These characteristics are mostly independent. This also indicates that a longer period of amplification might drive towards loss of diversity of binders. Moreover, there might be an enrichment of target unrelated antibodies.

Keeping the above mentioned criteria in practice, the ratio of antigen molecules to phage particles is kept at least 10-100 times higher. To avoid any sort of non-specific binder's enrichment, the amplification is kept for not more than 90 minutes.

Estimation of Phage Number

A single colony from the TG1 bacterial plate is inoculated in bacteria in 3 ml LB medium and grown at 37° C. until OD600≈0.9. 0.7% of agarose is prepared in Milli-Q water and stored at 50° C. in aliquots of 3 ml each in a 15 ml of falcon tubes. The phage supernatant and pellet are diluted at respective steps from $10^{-1}$ to $10^{-4}$. 100 ul of diluted phage and 100 µl TG1 cells are added in to each of agarose aliquots and mixed followed by immediately spreading on LB Agar plate. The plates are incubated in 37° C. incubator for overnight. The plaque formation is observed and counted on next day. The number of panned molecules is calculated based on number of plaques observed.

Bead Conjugation

Dyna beads are weighed at a quantity of 0.5 mg corresponding to ~$10^8$ beads and dissolved into 0.1 M sodium phosphate buffer, pH 7.4. This suspension is vortexed for 30 sec followed by incubation at room temperature for 10 min with continuous rotation. The suspension is washed twice with 0.1 M sodium phosphate buffer and resuspended again into 100 µL of 0.1 M sodium phosphate buffer. Her2, ligand solution, (~100 µL) is added the 10 µg of to the bead suspension. Further, the suspension is mixed well before adding the 100 µL of ammonium sulfate solution (3 M ammonium sulfate). The mixture is incubated for 20 hr at 37° C. with slow tilt but continuous rotation. Post incubation the tube is placed on the magnet holder for 1 min for magnetic separation. The magnet holder (with the tube in place) is carefully turned upside-down twice to ensure no beads remain in the cap. The supernatant is removed and beads are washed four times with 1 mL 1×PBS containing BSA (0.05%). Finally, the beads are re-suspended in 100 µL of 1×PBS with BSA (0.05%) and are used in panning.

Bead Conjugation Efficiency by FACS

Figure 18:
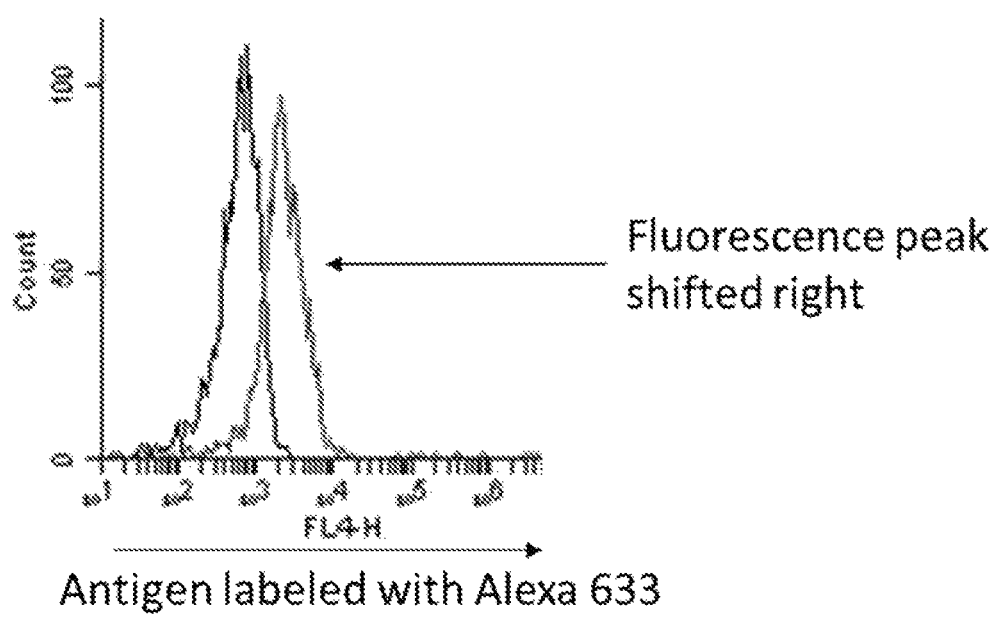
FIG. 18 illustrates estimation of magnetic bead conjugation efficiency by flow cytometry.

In order to perform magnetic separation based approach for panning, generation of antigen coated magnetic beads is done. The conjugation efficiency is determined using Flow cytometer (FIG. 18). Purified Her2 is used as the antigen. The experiments start with an incubation of ~$10^5$ beads with various combinations of antibody. Herein the antibody which binds with the ligand is labeled with biotin. N-Hydroxysuccinimide (NHS) ester-activated biotins are the most popular type of biotinylation reagent. NHS esters react efficiently with primary amino groups (—NH) in pH 7-9 buffers to form stable amide bonds. Because antibodies and other proteins generally contain multiple lysine (K) residues in addition to the N-terminus of each polypeptide, they have multiple primary amines available as targets for labeling with NHS-activated reagents. The extent of biotin labeling depends on the size and distribution of amino groups on the protein and the amount of reagent used. 10 mM Biotin solution is made by mixing 2.2 mg of Sulfo-NHS-Biotin with 500 µL of water. Trastuzumab, Anti-Her2 antibody, solution in 1×PBS is made at a concentration 2 mg/mL. 27 µL of biotin solution is added to 1 mL of trastuzumab followed by incubation for 2 hr on ice. Thermo Scientific ZebaSpin Desalting Column is used to desalt the excess and unbound biotin molecules from the solution. The protein concentration is estimated using a spectrophotometer and the concentration is found to be with insignificant change. Rituximab, a non-specific antibody is also biotinylated and the concentration estimation to post biotinylation is 2 mg/mL. Streptavidin with Alexa 633 fluorophore is used as secondary antibody to tap the extent of biotinylation. 1 µL of bead alone and bead coated with Her2 ligand are mixed with no antibody, biotinylated trastuzumab, biotinylated rituximab at a concentration of 0.05 mg/mL followed by volume make up to 100 µL with 1×PBS containing 0.5% BSA. The mixture is incubated for 2 hrs on ice followed by a washing with 1×PBS containing 0.5% BSA. Finally the beads are re-suspended in 25 µL of streptavidin-alexa633 solution in 1×PBS containing 0.5% BSA and volume is increased to 500 µL before readings are taken. All the flow experiments are done by using Accuri C6 flow cytometer while the analysis is done by using BD Accuri C6 software. Firstly forward and side scatter data is seen to fix a gate followed by fluorescence reading through FLH4 filter. At least 10000 data points are collected for each sample.

Panning

Single colony from the freshly streaked TG1 bacterial plate is inoculated into 3 ml LB medium followed by incubation at 37° C. until OD600≈0.9 and this is used for phage infection later. 100 µl 0.5% MPBS is added to the 100 µl suspension of antigen conjugated magnetic beads and incubated for 2 hr at room temperature. A phage library aliquot is thawed and the phage particles are precipitated with 250 µl (¼ of the phage suspension volume) PEG/NaCl solutions (20% PEG 8000 and 2.5 M NaCl) and incubated on ice for 30 min followed by centrifugation of the precipitated phage at 10,000 g for 10 minutes. The supernatant is discarded and the phage pellet is re-suspended in 200 µl PBS solution. Phage suspension (200 µl) is added to the conjugated bead with antigen and incubated on a rotator at room temperature for 2 h. The beads are washed at least two times with 1 ml 0.05% PBST (0.05% Tween-20 in PBS). Finally, magnetic beads bound with phage particle binders are re-suspended in 100 µl PBS. 10 µL of beads suspension is kept aside for plaques assay later on. The remaining 90 µl of the suspension is added to 2 ml of grown TG1 cells prepared earlier and the mixture is incubated at 37° C. for 1 h. Post incubation it is diluted into 10 ml LB medium containing ampicillin at a final concentration of 25 µg/ml. After two more hours of incubation at 37° C. with shaking at 250 rpm, concentration of ampicillin is increased to a final concentration of 100 µg/ml. M13K07, helper phage, is mixed into the amplified TG1 cells with an MOI of 10 and incubated at 37° C. for another 30 minutes. Helper phage-infected bacteria is spun down and the pellet is re-suspended into 10 ml of LB medium supplemented with 100 µg/ml ampicillin and 25 µg/ml kanamycin followed by incubation at 30° C. for 90 minutes for phage amplification. The bacterial culture is pelleted down by centrifugation for 10 min at 10,000 g. The pellet is discarded and supernatant is used for precipitation of amplified phage molecules by adding PEG/NaCl solution to the supernatant (¼th volume of supernatant). The mixture is incubated for 30 min on ice, followed by spinning the precipitated phage at 10,000 g for 10 minutes. Supernatant is discarded and pellet is re-suspended in 1 ml of PBS. The Plaques assay is performed from the 10 µL of amplified phage suspension to estimate the amplified phage number while the remaining of the precipitated phage are stored with 50% glycerol at −80° C. freezer for long term storage.

Figure 19:
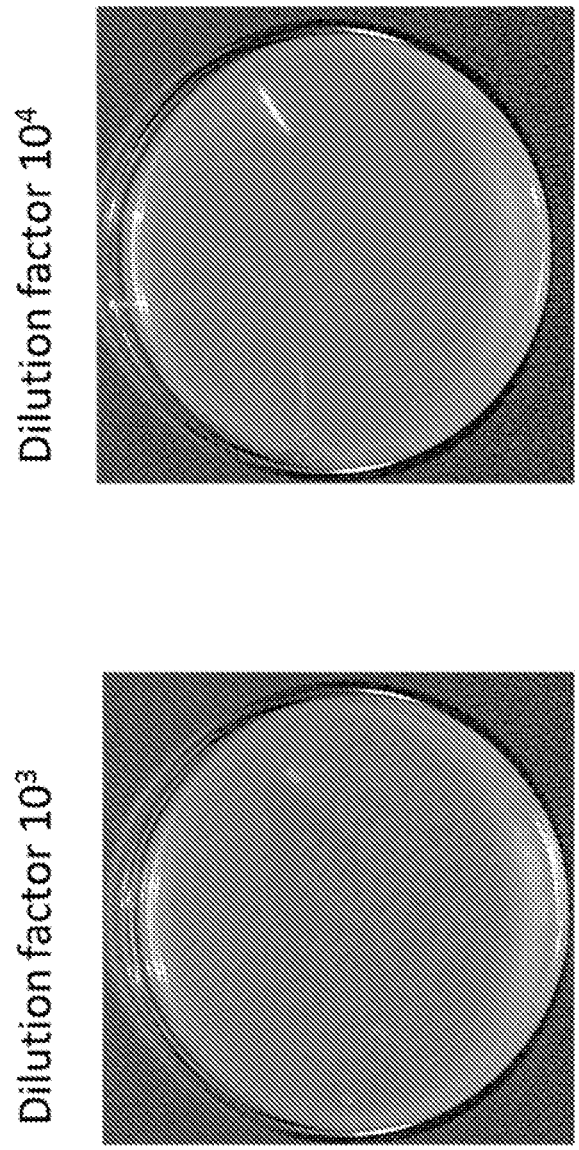
FIG. 19 illustrates plaque assay of Synthetic antibody gene library after one round of phage panning.

Plaque assay is performed at every step to ensure the numbers of phage particles. A single colony from the TG1 bacterial plate is inoculated in bacteria in 3 ml LB medium and is grown at 37° C. until OD600≈0.9. 0.7% of agarose is prepared in Milli-Q water and stored at 50° C. in aliquots of 3 ml each in a 15 ml of falcon tubes. The phage supernatant and pellet are diluted at respective steps from $10^{-1}$ to $10^{-4}$. 100 µl of diluted phage and 100 µl TG1 cells are added in to each of agarose aliquots and mixed followed by immediately spreading on LB Agar plate. The plates are incubated in 37° C. in an incubator for overnight. The plaque formation is observed and counted on next day. The number of panned molecules is calculated based on number of plaques observed (FIG. 19).

Isolation of Phage ssDNA and Amplification of Heavy and Light Chain Diversity Through PCR One vial of amplified phage is thawed and 200 µl of 20% PEG/2.5 M NaCl along with 5 µg of salmon sperm DNA is added to it by inverting the mixture several times, followed by letting it stay at 4° C. for 2 hr. (In order to transfer the panned pool to yeast display system for further selection and sorting, the ssDNA of the binders have to be isolated in enough quantity so that it represents the panned diversity. The use of sheared and boiled salmon sperm DNA specifically improves the yield of panned ssDNA.) Salmon sperm DNA is sheared and boiled before use. Salmon DNA is weighed and mixed with nuclease free water to a concentration of 5 mg/mL. The DNA is sheared with gentle mixing for 3 times with a 22 gauge needle followed by boiling for 5 minutes. Further the fragmented DNA is stored in aliquots at −20° C. for future use. The mixture, containing phage, PEG/NaCl and salmon sperm DNA, is centrifuged at 14,000×rpm for 10 minutes at 4° C. and the supernatant is discarded. Point to be noted here is that in case of no phage pellet seen, mixture is re-spun briefly at same speed. The supernatant is carefully pipetted out leaving only pellet. The pellet is re-suspended thoroughly in 100 µl of Iodide Buffer (10 mM Tris-HCl (pH 8.0), 1 mM EDTA, 4 M sodium iodide (NaI) by vortexing the tube. 250 µl of 100% ethanol is added and incubated overnight at −80° C. The preparation is centrifuged at 14,000 rpm for 30 minutes at 4° C., and supernatant is discarded. The pellet is washed twice with 0.5 ml of 70% ethanol followed by air drying the pellet. The pellet containing ssDNA is re-suspended in 20 µL of nuclease free water.

Figure 20:
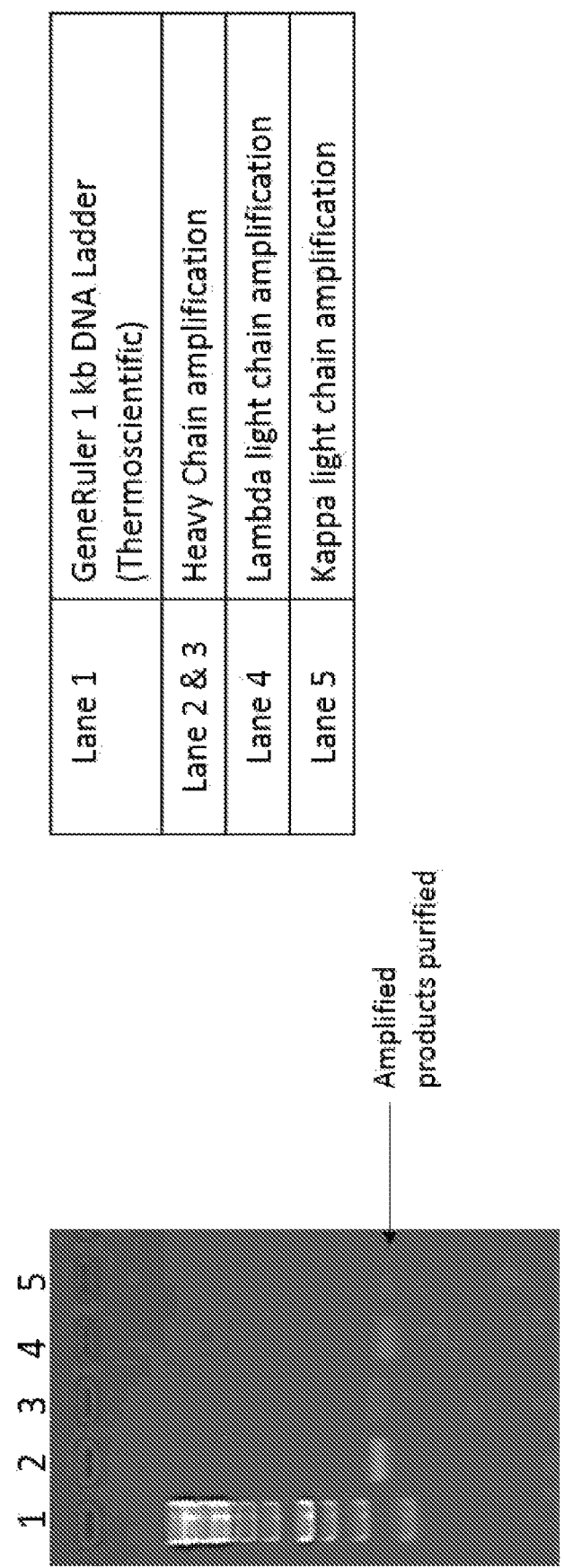
FIG. 20 illustrates PCR amplification of antibody heavy chain, antibody kappa chain and antibody lambda light chains from panned phage library.

PCR amplification is done with specific set of Vh, Vl and Vk primers and is amplified to correct size which is ~500 bp for Vh while ~600 bp for Vk and Vl. The use of PCR cycles is kept in limited number avoiding the chances of PCR mediated incorporation of mutations. The amplicons are gel eluted and digested with NcoI-HF and NotI-HF for Vh while for Vk or Vl, HindIII-HF and AscI are used (FIG. 20). The PCR set-up details are provided in Table 8.

TABLE 8

| PCR setup | 1× (µL) | 3× (µL) |
| --- | --- | --- |
| SSDNA | 1 | 3 |
| dNTPs | 1 | 3 |
| 5× GC buffer | 10 | 30 |
| Water | 23 | 69 |
| Reverse primer (H/K/L) | 2 | 6 |
| Forward primer (H/K/L) | 2 | 6 |
| Phusion enzyme (2 U/µl) | 1 | 3 |

Construction of Heavy and Light Chain Libraries in to Yeast Shuttle Vectors

The protocol involves transfer of all binders from phage to yeast expression vectors in order to do the screening and sorting in yeast system. An affinity based method is employed using a compatible method i.e., FACS to further select and rank the best binders.

As choice of antibody format, the Fab is preferred as this would prompt to develop rapid high through-put affinity-screening assays for crude antibody preparations. The Fab library is developed by exploiting the mating system wherein light chain library and heavy chain library is cloned in different yeast expression vectors (Accession #MTCC 25126, MTCC 25127 and MTCC 25128). However, the kappa and lambda light chain PCR pool of panned molecules along with the in-house yeast expression vector exclusively designed and generated for light chains are digested with HindIII-HF and AscI followed by ligation and transformation individually into TG1, highly competent cells.

Likewise, HC chain pool and the respective vector are digested with NcoI-HF and NotI-HF followed by ligation and transformation into TG1, highly competent cells. Transformation efficiency obtained for both heavy and light chain panned library are >$10^7$ cfu. In addition to these vectors, there are several expression vectors that are generated with exclusive features that are common to all vectors; on the contrary, though formats of antibody fragments displayed on yeast surface might vary but the transferred variable pool remain constant throughout.

Obtained transformed colonies for both heavy and light chain libraries are checked for insert release using NcoI-HF/NotI-HF for heavy chain (FIG. 21A) and HindIII-HF/AscI for light chain kappa (FIG. 21B) and lambda (FIG. 21C) before they are scraped for glycerol stock preparation. Insert release for both the chains confirmed the presence of panned molecules. Glycerol stocks are stored at −80° C. for future use. Tables 9, 10 and 11 provide for components applicable in constructing libraries in yeast vector.

Few of the representative clones are used for plasmid isolation and sent for peer group sequencing. The sequencing result indicates that almost all of the cloned molecules are productive and diverse with CDRH3 lengths ranging from 4 to 22 amino acids (FIG. 22).

TABLE 9

| | 1× |
| --- | --- |
| DNA | 10 µg |
| NcoI-HF (20 U/µL) | 1 µL |
| NotI-HF (20 U/µL) | 1 µL |
| Cut smart Buffer | 10 µL |
| Water | Respective volume of Mili-Q water |
| Total | 100 µL |

TABLE 10

| | 1× |
|---|---|
| DNA | 10 μg |
| HindIII-HF (20 U/μL) | 1 μL |
| AscI (10 U/μL) | 2 μL |
| Cut smart Buffer | 10 μL |
| Water | Respective volume of Mili-Q water |
| Total | 100 μL |

TABLE 11

| | |
|---|---|
| DNA (Vector) | 200 ng |
| DNA (insert) | 60 ng |
| T4 DNA ligase | 0.6 μL |
| T4 DNA ligase buffer (10×) | 2 μL |
| Water | Respective volume of Mili-Q water |
| Total | 20 μL |

Transformation of Heavy Chain and Light Chain Library in Yeast

Large amount of plasmid DNA isolation is done for both the libraries followed by restriction digestion with respective enzymes for confirmation. Upon validation, the 1 μg of each DNA is taken and transformed into yeast cells at $OD_{600}$ 1.2-1.5 by Frozen-EZ Yeast transformation II Kit™. EBY100-ura3Δ-4 and YVH10 are used as a host for the cell surface display of the heavy chain library and light chain library (kappa and lambda) respectively.

More specifically, Yeast cells in 5 ml YPD broth are grown overnight at 30° C. with shaking. Overnight culture is diluted up to OD600~0.2-0.3 in to 50 ml and grown until $OD_{600}$~1.2 to 1.5 and 15 ml cells were pelleted at 500 g for 4 minutes and the supernatant is discarded. 1 ml of EZ 1 solution is added to wash the pellet. The cells are re-pelleted and the supernatant is discarded. 200 μl EZ 2 solution is added to re-suspend the pellet. 200 μl of competent cells is mixed with 1 μg DNA (in less than 5 μl volume) and 500 μl EZ 3 solution is added and mixed thoroughly and incubated at 30° C. for 1.30-2.00 hr. During this incubation, mixing vigorously by flicking with finger or vortexing every 15-20 mins was carried out. 100 μl of the above transformation mixture is plated on an appropriate drop out synthetic glucose plate. The plates are incubated at 30° C. for 2-4 days to allow for growth of transformants. Both heavy chain and light chain panned library are successfully transformed in to yeast strains (EBY100-ura3Δ and YVH10) with an efficiency of ~$10^6$.

Construction of Yeast Diploid Library Through Yeast Mating

In order to display Fab format of library on the surface, mating between two grown haploid cells representing heavy chain and light chain libraries either kappa or lambda is performed by mixing equal numbers of haploid cells. The mating efficiency is calculated as the number of diploid colonies in the double-selective plates divided by the number of total colonies in the single selective plates wherein the calculated mating percentage is ~25%. Further the diploid cells are enriched in double drop out media (Ura⁻, Trp⁻) prior to any growth and expression analysis.

More specifically, EBY100-ura3Δ-4 (MATa) transformants containing HC panned library in to p414GAL1 and the YVH10 (MATα) transformants containing LC panned library (kappa and lambda) in to p416GAL1 are grown overnight at 30° C. and 220 rpm in 5 ml of the Trp⁻ drop out glucose medium and Ura⁻ drop out glucose medium respectively. Then the haploid cells are re-inoculated at the initial cell OD600≈0.3 to freshly prepared above selective medias and grown until they reach optical densities ~1.2-1.8. Mating of the two grown haploid cells is performed by mixing equal numbers of cells (1.0 OD) by vortexing, spreading them on YPD agar plate and incubating at 30° C. for overnight. Cells are collected by gentle scraping with 1 ml of the double-selective Ura⁻ Trp⁻ double drop out glucose medium and pelleted by centrifugation (2,500 g for 3 min). The cells are washed by resuspension with 1 ml of sterilized cold deionized water and centrifuged to remove remaining media components. To estimate the mating efficiency, the washed cells are re-suspended in a total volume of 1 ml of Ura⁻ Trp⁻ double drop out glucose medium, serially diluted, and spread out onto double-selective Ura⁻ Trp⁻ double drop out glucose agar, Trp drop out glucose agar and Ura⁻ drop out glucose agar plates. Plates are incubated at 30° C. for 2-3 days and the number of colonies is counted. Percentage mating efficiency is calculated as the number of diploid colonies in the double-selective plates divided by the number of total colonies in the single selective plates. To enrich diploids, cells are then inoculated to Ura⁻ Trp⁻ double drop out glucose medium at the very low cell density of OD600=0.1 and grown at 30° C. for 24 h, whenever required.

Antibody Gene Expression and Flow Sorting Analysis of Yeast Cells

*Saccharomyces cerevisiae* 2N library having plasmids expressing heavy chain pool and light Chain pool are inoculated into 20 ml of SDCAA media and grown overnight at 30° C. The $OD_{600}$ of the overnight grown culture is measured and inoculated accordingly in 20 ml SDCAA Ura⁻ Trp⁻ double drop out glucose media (uninduced culture) and 20 ml 2×SGCAA media (induced culture) such that the final OD600 nm becomes 0.4. Uninduced and induced cells are grown for different time points ranging from 24-48 hr at 20° C.

For all flow analyses, labeling Buffer, 1×PBS containing 0.5% BSA, is prepared followed by transfer of ~$10^6$ cells (induced/un-induced) into 100 μl LB. The cells are spun down at 10000 rpm for 2 min at 4° C. The supernatant is carefully removed without disturbing the cells. 25 μl of primary antibodies (Anti-His for Light Chain or Anti-c-Myc antibody for heavy chain or STREP-Alexa 633 for biotinylated Her2) with appropriate concentrations added to the samples and incubated at 4° C. for 30 minutes (All preparations of antibody dilutions to be done in labeling buffer). Another 100 μl of labeling buffer is added to the sample tubes followed by washing the cells twice with labeling buffer. 25 μl of secondary antibody conjugated with fluorophore is mixed to the sample tubes. The samples are again incubated at 4° C. for 20 minutes. The cells were washed twice as mentioned above with 100 μl labeling buffer and the cells are re-suspended in 350 μl of 1×PBS followed by analysis of the samples on a flow-cytometer.

For sorting studies, Antigen binding is monitored using biotinylated antigen (Her2) and selected and sorted based on positive events for biotinylated antigen. 10 mM Biotin solution is made by mixing 2.2 mg of Sulfo-NHS-Biotin with 500 μL of water. Antigen, Her2 solution in 1×PBS was made at a concentration of 1 mg/mL. 20 fold molar excess measuring 0.28 mM biotin solution is added to 1 mL of Her2 solution to initiate the reaction followed by an incubation for 2 hr on ice. Thermo Scientific Zeba spin desalting Column is used to desalt the excess and unbound biotin molecules from the solution. The concentration of Biotinylated Her2 is found to be 0.56 mg/mL. 500 nM of biotinylated antigen is used to perform the binding experiments.

The expression of light chain and heavy chain are observed in significant percentages. The light chain expression are probed by anti-His antibody and found to be ~0.2-0.4% (FIGS. 23A and 24A) while heavy chain which is probed with anti-c-Myc antibody is found to be ~19-22% (FIGS. 23B and 24B). Moreover, the expression analysis with biotinylated Her2 antigen is found to be 1.5-1.8% (FIGS. 23 C and 24 C). This result indicates the successful Fab formation on the yeast surface. In addition, while sorting with biotinylated Her2 are also explored and found to be positive against Her2 antigen staining with ~1.3-2% (FIG. 25). This is in accordance with the results found and shared by other researchers. This result also indicates that the dual auxotrophic marker selected diploids express light chain associated with the heavy chain.

Advantages of the Approach Employed by the Instant Disclosure
1. The synthetic library obtained by the method of the instant disclosure will harbor higher antibody diversity considering an efficient design of CDRH3 to maximize the variety of molecules and to overcome technological limitations associated with synthesis and subsequent screening steps. These are executed using a specific series of in silico analysis solely derived from a larger dataset of antibody sequences.
   a. Antibody database sieved through identification of germline sequences, removing non-redundant sequences.
   b. Identification of heavy chain CDR3 sequences followed by estimation of amino acid frequency of occurrence and length analysis.
   c. Creation of a distribution matrix of design by introduction of positional correlation factor followed by amino acid probability index determination across various positions.
   d. Introducing concept of true diversity i.e., shannon entropy based identification & selection of unique amino acid frequency distribution.
   To best of our knowledge, this approach is mentioned for the first time in antibody library space.
2. Based on the design of the synthetic library, very similar amino acid compositional diversity of heavy chain CDR3 has been achieved after synthesis.
3. The productivity of the synthetic library as judged by next generation sequencing and peer group sequencing studies ranges from 80% to 95%.
4. CDRH3 length (4 to 23 amino acids) distribution studies indicate a uniform presence of all CDRH3 lengths, confirming a significant amount of diversity present for CDRH3 lengths which are under-represented in natural repertoire, especially CDRH3 length up to 9 amino acid. Thus, an unbiased and uniform presence of diversity for CDRH3 lengths ranging from 4 to 23 amino acids is achieved.
5. The instant disclosure employs a unique combination of phage and yeast antibody surface display, which allows to screen large library size (more than $10^{11}$ clones) and facilitates better folding of antibody structure because of yeast post translational modifications.
6. The library will incorporate the antibody CDR optimization or motif grafting approaches for improved binding feature of the said antibody.
7. The library will incorporate antibody rational designing for high antibody stability, lesser antibody aggregation, lesser immunogenicity, better solubility and other antibody characteristics for improved manufacturability of said antibody.
8. The instant disclosure adopts an exclusive screening methodology wherein phage display screening is employed to remove only non-binders while subsequent yeast screening is employed to execute affinity based selection of the binders.
9. The vectors used for phage and yeast surface expression are unique.
10. The clones selected from phage library will be transferred to yeast library in different antibody formats including ScFv or Fab with or without a particular combination of heavy and light chains and thereby retaining the original diversity with improved screening process.
11. The instant disclosure also provides flexibility in accommodating multiple variants of Fab and/or ScFv sequences at display platforms and flexibility of transferring panned molecules in Fab format and/or ScFv format to yeast expression system via combinatorial and non-combinatorial approaches.

Although disclosure and exemplification has been provided by way of illustrations and examples for the purpose of clarity and understanding, it is apparent to a person skilled in the art that various changes and modifications can be practiced without departing from the spirit or scope of the disclosure. Accordingly, the foregoing descriptions and examples should not be construed as limiting the scope of the present disclosure.

The description of the embodiments of the present disclosure reveals the general nature of the embodiments that are readily suitable for modification and/or adaptation for various applications by applying the current knowledge. Such specific embodiments of the disclosure, without departing from the generic concept, and, therefore, such adaptations and modifications should and are intended to be comprehended and considered within the meaning and range of equivalents of the disclosed embodiments.

It is also to be understood that the phrases or terms employed herein are for the purpose of description and not intended to be of any limitation. Throughout the present disclosure, the word "comprise", or variations such as "comprises" or "comprising" wherever used, are to be understood to imply the inclusion of a stated element, integer or step, or group of elements, integers or steps, but not the exclusion of any other element, integer or step, or group of elements, integers or steps.

Where a numerical limit or range is stated herein, the endpoints are included. Also, values and sub-ranges within a numerical limit or range are specifically included as if explicitly written out.

With respect to the use of any plural and/or singular terms in the present disclosure, those of skill in the art can translate from the plural to the singular and/or from the singular to the plural as is considered appropriate to the context and/or application. The various singular/plural permutations may be expressly set forth herein for the sake of clarity.

Any discussion of documents, acts, materials, devices, articles and the like that has been included in this specification is solely for the purpose of providing a context for the present disclosure. It is not to be taken as an admission that any or all of these matters form a part of the prior art base or are common general knowledge in the field relevant to the present disclosure, as it existed anywhere before the priority date of this application.

The contents of all references, patents, and published patent applications cited throughout this application are incorporated herein by reference for all purposes.

SEQUENCE LISTING

```
<160> NUMBER OF SEQ ID NOS: 132

<210> SEQ ID NO 1
<211> LENGTH: 372
<212> TYPE: DNA
<213> ORGANISM: Homo sapiens
<220> FEATURE:
<221> NAME/KEY: gene
<222> LOCATION: (1)..(372)
<223> OTHER INFORMATION: ZB_H1A

<400> SEQUENCE: 1
ccatggcagg tgcaattggt gcagagcgga gccgaagtga agaaacccgg cagcagcgtg      60
aaggtgtcct gcaaggcctc cggaggcacc ttcagcagct acgccatcag ctgggtgcgc     120
caggccccag gccagggcct cgagtggatg ggcggcatca tccccatctt cggcaccgcc     180
aactacgccc agaaattcca gggcagggtg accatcaccg ccgacgagag caccagcacc     240
gcctacatga aactgagcag cctgcggagc gaggacaccg ccgtgtacta ctgtgcgcgc     300
tggggaggcg acggcttcta cgctatggac tactggggcc aaggaaccct ggtgacagtg     360
tccagctcta ga                                                         372

<210> SEQ ID NO 2
<211> LENGTH: 124
<212> TYPE: PRT
<213> ORGANISM: Homo sapiens
<220> FEATURE:
<221> NAME/KEY: PEPTIDE
<222> LOCATION: (1)..(124)
<223> OTHER INFORMATION: ZB_H1A

<400> SEQUENCE: 2

Pro Trp Gln Val Gln Leu Val Gln Ser Gly Ala Glu Val Lys Lys Pro
1               5                   10                  15

Gly Ser Ser Val Lys Val Ser Cys Lys Ala Ser Gly Gly Thr Phe Ser
            20                  25                  30

Ser Tyr Ala Ile Ser Trp Val Arg Gln Ala Pro Gly Gln Gly Leu Glu
        35                  40                  45

Trp Met Gly Gly Ile Ile Pro Ile Phe Gly Thr Ala Asn Tyr Ala Gln
    50                  55                  60

Lys Phe Gln Gly Arg Val Thr Ile Thr Ala Asp Glu Ser Thr Ser Thr
65                  70                  75                  80

Ala Tyr Met Glu Leu Ser Ser Leu Arg Ser Glu Asp Thr Ala Val Tyr
                85                  90                  95

Tyr Cys Ala Arg Trp Gly Gly Asp Gly Phe Tyr Ala Met Asp Tyr Trp
            100                 105                 110

Gly Gln Gly Thr Leu Val Thr Val Ser Ser Ser Arg
        115                 120

<210> SEQ ID NO 3
<211> LENGTH: 372
<212> TYPE: DNA
<213> ORGANISM: Homo sapiens
<220> FEATURE:
<221> NAME/KEY: gene
<222> LOCATION: (1)..(372)
<223> OTHER INFORMATION: ZB_H1B
```

```
<400> SEQUENCE: 3
ccatggcagg tgcaattggt gcagagcgga gccgaagtga agaaacccgg cgccagcgtg        60
aaggtgtcct gcaaggcctc cggatacacc ttcaccagct actacatgca ctgggtgcgc       120
caggccccag gccagggcct cgagtggatg ggctggatca accccaacag cggcggcacc       180
aactacgccc agaaattcca gggcagggtg accatgacca gagacaccag catcagcacc       240
gcctacatgg aactgagcag cctgcggagc gaggacaccg ccgtgtacta ctgtgcgcgc       300
tggggaggcg acggcttcta cgctatggac tactggggcc aaggaaccct ggtgacagtg       360
tccagctcta ga                                                           372

<210> SEQ ID NO 4
<211> LENGTH: 124
<212> TYPE: PRT
<213> ORGANISM: Homo sapiens
<220> FEATURE:
<221> NAME/KEY: PEPTIDE
<222> LOCATION: (1)..(124)
<223> OTHER INFORMATION: ZB_H1B

<400> SEQUENCE: 4

Pro Trp Gln Val Gln Leu Val Gln Ser Gly Ala Glu Val Lys Lys Pro
1               5                   10                  15

Gly Ala Ser Val Lys Val Ser Cys Lys Ala Ser Gly Tyr Thr Phe Thr
            20                  25                  30

Ser Tyr Tyr Met His Trp Val Arg Gln Ala Pro Gly Gln Gly Leu Glu
        35                  40                  45

Trp Met Gly Trp Ile Asn Pro Asn Ser Gly Gly Thr Asn Tyr Ala Gln
    50                  55                  60

Lys Phe Gln Gly Arg Val Thr Met Thr Arg Asp Thr Ser Ile Ser Thr
65                  70                  75                  80

Ala Tyr Met Glu Leu Ser Ser Leu Arg Ser Glu Asp Thr Ala Val Tyr
                85                  90                  95

Tyr Cys Ala Arg Trp Gly Gly Asp Gly Phe Tyr Ala Met Asp Tyr Trp
            100                 105                 110

Gly Gln Gly Thr Leu Val Thr Val Ser Ser Arg
        115                 120

<210> SEQ ID NO 5
<211> LENGTH: 375
<212> TYPE: DNA
<213> ORGANISM: Homo sapiens
<220> FEATURE:
<221> NAME/KEY: gene
<222> LOCATION: (1)..(375)
<223> OTHER INFORMATION: ZB_H2

<400> SEQUENCE: 5
ccatggcagg tgcaattgaa agagtccggc cctgccctgg tgaaacccac ccagaccctg        60
accctgacat gcaccttctc cggattcagc ctgagcacct ctggcgtggg cgtgggctgg       120
atcagacagc cccctggcaa ggccctcgag tggctggccc tgatcgactg ggacgacgac       180
aagtactaca gcaccagcct gaaaacccgg ctgaccatca gcaaggacac ttcgaaaaat       240
caggtggtgc tgaccatgac caacatggac cccgtggaca ccgccaccta ctactgtgcg       300
cgctggggag cgacggcttc tacgctatg gactactggg gccaaggaac cctggtgaca       360
gtgtccagct ctaga                                                        375
```

-continued

```
<210> SEQ ID NO 6
<211> LENGTH: 125
<212> TYPE: PRT
<213> ORGANISM: Homo sapiens
<220> FEATURE:
<221> NAME/KEY: PEPTIDE
<222> LOCATION: (1)..(125)
<223> OTHER INFORMATION: ZB_H2

<400> SEQUENCE: 6

Pro Trp Gln Val Gln Leu Lys Glu Ser Gly Pro Ala Leu Val Lys Pro
1               5                   10                  15

Thr Gln Thr Leu Thr Leu Thr Cys Thr Phe Ser Gly Phe Ser Leu Ser
            20                  25                  30

Thr Ser Gly Val Gly Val Gly Trp Ile Arg Gln Pro Pro Gly Lys Ala
        35                  40                  45

Leu Glu Trp Leu Ala Leu Ile Asp Trp Asp Asp Asp Lys Tyr Tyr Ser
    50                  55                  60

Thr Ser Leu Lys Thr Arg Leu Thr Ile Ser Lys Asp Thr Ser Lys Asn
65                  70                  75                  80

Gln Val Val Leu Thr Met Thr Asn Met Asp Pro Val Asp Thr Ala Thr
                85                  90                  95

Tyr Tyr Cys Ala Arg Trp Gly Gly Asp Gly Phe Tyr Ala Met Asp Tyr
            100                 105                 110

Trp Gly Gln Gly Thr Leu Val Thr Val Ser Ser Arg
        115                 120                 125

<210> SEQ ID NO 7
<211> LENGTH: 372
<212> TYPE: DNA
<213> ORGANISM: Homo sapiens
<220> FEATURE:
<221> NAME/KEY: gene
<222> LOCATION: (1)..(372)
<223> OTHER INFORMATION: ZB_H3

<400> SEQUENCE: 7
ccatgggagg tgcaattggt ggaaagcggc ggaggactgg tgcagcctgg cggcagcctg      60
agactgtctt gcgccgcctc cggattcacc ttcagcagct acgccatgag ctgggtgcgc    120
caggccccag gcaagggcct cgagtgggtg tccgccatca gcggcagcgg cggcagcacc    180
tactacgccg acagcgtgaa gggccggttc accatcagcc gggacaattc gaaaaacacc    240
ctgtacctgc agatgaacag cctgcgggcc gaggacaccg ccgtgtacta ctgtgcgcgc    300
tggggaggcg acggcttcta cgctatggac tactggggcc aaggaaccct ggtgacagtg    360
tccagctcta ga                                                        372

<210> SEQ ID NO 8
<211> LENGTH: 124
<212> TYPE: PRT
<213> ORGANISM: Homo sapiens
<220> FEATURE:
<221> NAME/KEY: PEPTIDE
<222> LOCATION: (1)..(124)
<223> OTHER INFORMATION: ZB_H3

<400> SEQUENCE: 8

Pro Trp Glu Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30
```

Ser Tyr Ala Met Ser Trp Val Arg Gln Ala Pro Gly Lys Gly Leu Glu
            35                  40                  45

Trp Val Ser Ala Ile Ser Gly Ser Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Trp Gly Gly Asp Gly Phe Tyr Ala Met Asp Tyr Trp
                100                 105                 110

Gly Gln Gly Thr Leu Val Thr Val Ser Ser Arg
            115                 120

<210> SEQ ID NO 9
<211> LENGTH: 369
<212> TYPE: DNA
<213> ORGANISM: Homo sapiens
<220> FEATURE:
<221> NAME/KEY: gene
<222> LOCATION: (1)..(369)
<223> OTHER INFORMATION: ZB_H4

<400> SEQUENCE: 9
ccatggcagg tgcaattgca ggaaagcggc cctggcctgg tgaaacccag cgagacactg      60
agcctgacct gcaccgtgtc cggaggcagc atcagcagct actactggtc ctggatcaga     120 cagcccctg gcaagggcct cgagtggatc ggctacatct actacagcgg cagcaccaac     180
tacaacccca gcctgaagtc cagggtgacc atcagcgtgg acacttcgaa aaaccagttc     240
agcctgaagc tgtccagcgt gacagccgcc gacaccgccg tgtactactg cgcgcgctgg     300
ggaggcgacg gcttctacgc tatggactac tggggccaag gaaccctggt gacagtgtcc     360
agctctaga                                                              369

<210> SEQ ID NO 10
<211> LENGTH: 123
<212> TYPE: PRT
<213> ORGANISM: Homo sapiens
<220> FEATURE:
<221> NAME/KEY: PEPTIDE
<222> LOCATION: (1)..(123)
<223> OTHER INFORMATION: ZB_H4

<400> SEQUENCE: 10

Pro Trp Gln Val Gln Leu Gln Glu Ser Gly Pro Gly Leu Val Lys Pro
1               5                   10                  15

Ser Glu Thr Leu Ser Leu Thr Cys Thr Val Ser Gly Gly Ser Ile Ser
            20                  25                  30

Ser Tyr Tyr Trp Ser Trp Ile Arg Gln Pro Pro Gly Lys Gly Leu Glu
            35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Trp Gly Gly Asp Gly Phe Tyr Ala Met Asp Tyr Trp Gly
                100                 105                 110

Gln Gly Thr Leu Val Thr Val Ser Ser Arg
            115                 120

<210> SEQ ID NO 11
<211> LENGTH: 372
<212> TYPE: DNA
<213> ORGANISM: Homo sapiens
<220> FEATURE:
<221> NAME/KEY: gene
<222> LOCATION: (1)..(372)
<223> OTHER INFORMATION: ZB_H5

<400> SEQUENCE: 11

```
ccatgggagg tgcaattggt gcagagcgga gccgaagtga agaagcccgg cgagagcctg    60
aagatcagct gcaagggctc cggatacagc ttcaccagct actggatcgg ctgggtgcgc   120
cagatgcccg gcaagggcct cgagtggatg ggcatcatct accccggcga cagcgacacc   180
cggtacagcc ccagcttcca gggccaggtg accatcagcg ccgacaagag catcagcacc   240
gcctacctgc agtggtccag cctgaaggcc agcgacaccg ccatgtacta ctgtgcgcgc   300
tggggaggcg acggcttcta cgctatggac tactggggcc aaggaaccct ggtgacagtg   360
tccagctcta ga                                                       372
```

<210> SEQ ID NO 12
<211> LENGTH: 124
<212> TYPE: PRT
<213> ORGANISM: Homo sapiens
<220> FEATURE:
<221> NAME/KEY: PEPTIDE
<222> LOCATION: (1)..(124)
<223> OTHER INFORMATION: ZB_H5

<400> SEQUENCE: 12

```
Pro Trp Glu Val Gln Leu Val Gln Ser Gly Ala Glu Val Lys Lys Pro
 1               5                  10                  15

Gly Glu Ser Leu Lys Ile Ser Cys Lys Gly Ser Gly Tyr Ser Phe Thr
            20                  25                  30

Ser Tyr Trp Ile Gly Trp Val Arg Gln Met Pro Gly Lys Gly Leu Glu
        35                  40                  45

Trp Met Gly Ile Ile Tyr Pro Gly Asp Ser Asp Thr Arg Tyr Ser Pro
    50                  55                  60

Ser Phe Gln Gly Gln Val Thr Ile Ser Ala Asp Lys Ser Ile Ser Thr
65                  70                  75                  80

Ala Tyr Leu Gln Trp Ser Ser Leu Lys Ala Ser Asp Thr Ala Met Tyr
                85                  90                  95

Tyr Cys Ala Arg Trp Gly Gly Asp Gly Phe Tyr Ala Met Asp Tyr Trp
            100                 105                 110

Gly Gln Gly Thr Leu Val Thr Val Ser Ser Ser Arg
        115                 120
```

<210> SEQ ID NO 13
<211> LENGTH: 381
<212> TYPE: DNA
<213> ORGANISM: Homo sapiens
<220> FEATURE:
<221> NAME/KEY: gene
<222> LOCATION: (1)..(381)
<223> OTHER INFORMATION: ZB_H6

<400> SEQUENCE: 13

```
ccatggcagg tgcaattgca acagtctggg cctggcctgg tgaaacccag ccagaccctg    60
agcctgacct gcgccatctc cggagacagc gtgtccagca cagcgccgc ctggaactgg   120
```

```
atcagacagt ccccggcag aggcctcgag tggctgggcc ggacctacta ccggtccaag      180
tggtacaacg actacgccgt gtccgtgaag tcccggatca ccatcaaccc cgacacttcg      240
aaaaaccagt tctccctgca actgaacagc gtgacccccg aggacaccgc cgtgtactac      300
tgtgcgcgct ggggaggcga cggcttctac gctatggact actggggcca aggaaccctg      360
gtgacagtgt ccagctctag a                                                381
```

<210> SEQ ID NO 14
<211> LENGTH: 127
<212> TYPE: PRT
<213> ORGANISM: Homo sapiens
<220> FEATURE:
<221> NAME/KEY: PEPTIDE
<222> LOCATION: (1)..(127)
<223> OTHER INFORMATION: ZB_H6

<400> SEQUENCE: 14

```
Pro Trp Gln Val Gln Leu Gln Gln Ser Gly Pro Gly Leu Val Lys Pro
1               5                   10                  15

Ser Gln Thr Leu Ser Leu Thr Cys Ala Ile Ser Gly Asp Ser Val Ser
            20                  25                  30

Ser Asn Ser Ala Ala Trp Asn Trp Ile Arg Gln Ser Pro Gly Arg Gly
        35                  40                  45

Leu Glu Trp Leu Gly Arg Thr Tyr Tyr Arg Ser Lys Trp Tyr Asn Asp
    50                  55                  60

Tyr Ala Val Ser Val Lys Ser Arg Ile Thr Ile Asn Pro Asp Thr Ser
65                  70                  75                  80

Lys Asn Gln Phe Ser Leu Gln Leu Asn Ser Val Thr Pro Glu Asp Thr
                85                  90                  95

Ala Val Tyr Tyr Cys Ala Arg Trp Gly Gly Asp Gly Phe Tyr Ala Met
            100                 105                 110

Asp Tyr Trp Gly Gln Gly Thr Leu Val Thr Val Ser Ser Arg
        115                 120                 125
```

<210> SEQ ID NO 15
<211> LENGTH: 339
<212> TYPE: DNA
<213> ORGANISM: Homo sapiens
<220> FEATURE:
<221> NAME/KEY: gene
<222> LOCATION: (1)..(339)
<223> OTHER INFORMATION: ZB_K1

<400> SEQUENCE: 15

```
aagcttgata tccagatgac ccagtccccc agcagcctga gcgccagcgt gggcgacaga      60
gtgaccatca cctgcagagc cagccagggc atcagcagct acctggcctg gtaccagcag     120
aagcccggca aggccccaa gctattaatc tacgccgcca gctctctgca aagcggcgtg     180
ccaagcagat tcagcggatc cggctccggc accgacttca ccctgaccat cagcagcctg     240
caacccgagg acttcgccac ctactactgc cagcagcact acaccacccc cccatttggc     300
cagggaacaa aggtggaaat caagcgtacg ggcgcgccg                            339
```

<210> SEQ ID NO 16
<211> LENGTH: 113
<212> TYPE: PRT
<213> ORGANISM: Homo sapiens
<220> FEATURE:
<221> NAME/KEY: PEPTIDE
<222> LOCATION: (1)..(113)
<223> OTHER INFORMATION: ZB_K1

<400> SEQUENCE: 16

| Lys | Leu | Asp | Ile | Gln | Met | Thr | Gln | Ser | Pro | Ser | Ser | Leu | Ser | Ala | Ser |
| 1 | | | | 5 | | | | | 10 | | | | | 15 | |

| Val | Gly | Asp | Arg | Val | Thr | Ile | Thr | Cys | Arg | Ala | Ser | Gln | Gly | Ile | Ser |
| | | | 20 | | | | | 25 | | | | | 30 | | |

| Ser | Tyr | Leu | Ala | Trp | Tyr | Gln | Gln | Lys | Pro | Gly | Lys | Ala | Pro | Lys | Leu |
| | | 35 | | | | | 40 | | | | | 45 | | | |

| Leu | Ile | Tyr | Ala | Ala | Ser | Ser | Leu | Gln | Ser | Gly | Val | Pro | Ser | Arg | Phe |
| | 50 | | | | | 55 | | | | | 60 | | | | |

| Ser | Gly | Ser | Gly | Ser | Gly | Thr | Asp | Phe | Thr | Leu | Thr | Ile | Ser | Ser | Leu |
| 65 | | | | | 70 | | | | | 75 | | | | | 80 |

| Gln | Pro | Glu | Asp | Phe | Ala | Thr | Tyr | Tyr | Cys | Gln | Gln | His | Tyr | Thr | Thr |
| | | | | 85 | | | | | 90 | | | | | 95 | |

| Pro | Pro | Phe | Gly | Gln | Gly | Thr | Lys | Val | Glu | Ile | Lys | Arg | Thr | Gly | Ala |
| | | | 100 | | | | | 105 | | | | | 110 | | |

Pro

<210> SEQ ID NO 17
<211> LENGTH: 366
<212> TYPE: DNA
<213> ORGANISM: Homo sapiens
<220> FEATURE:
<221> NAME/KEY: gene
<222> LOCATION: (1)..(366)
<223> OTHER INFORMATION: ZB_K2

<400> SEQUENCE: 17

```
aagcttgata tcgtgatgac ccagtccccc ctgagcctga gcctgcccgt gacacctggc      60
gagcctgcca gcatcagctg cagatccagc cagagcctgc tgcacagcaa cggctacaac     120
tacctggact ggtacctgca aaagcccggc cagtcccctc agctattaat ctacctgggc     180
agcaaccggg ccagcggcgt gccagataga ttcagcggat ccggctccgg caccgacttc     240
accctgaaga tcagccgggt ggaagccgag gacgtgggcg tgtactactg catgcagcag     300
cactacacca ccccccccatt tggccaggga accgtgaagg tggaaatcaa gcgtacgggc     360
gcgccg                                                                366
```

<210> SEQ ID NO 18
<211> LENGTH: 122
<212> TYPE: PRT
<213> ORGANISM: Homo sapiens
<220> FEATURE:
<221> NAME/KEY: PEPTIDE
<222> LOCATION: (1)..(122)
<223> OTHER INFORMATION: ZB_K2

<400> SEQUENCE: 18

| Lys | Leu | Asp | Ile | Val | Met | Thr | Gln | Ser | Pro | Leu | Ser | Leu | Ser | Leu | Pro |
| 1 | | | | 5 | | | | | 10 | | | | | 15 | |

| Val | Thr | Pro | Gly | Glu | Pro | Ala | Ser | Ile | Ser | Cys | Arg | Ser | Ser | Gln | Ser |
| | | | 20 | | | | | 25 | | | | | 30 | | |

| Leu | Leu | His | Ser | Asn | Gly | Tyr | Asn | Tyr | Leu | Asp | Trp | Tyr | Leu | Gln | Lys |
| | | 35 | | | | | 40 | | | | | 45 | | | |

| Pro | Gly | Gln | Ser | Pro | Gln | Leu | Leu | Ile | Tyr | Leu | Gly | Ser | Asn | Arg | Ala |
| | 50 | | | | | 55 | | | | | 60 | | | | |

| Ser | Gly | Val | Pro | Asp | Arg | Phe | Ser | Gly | Ser | Gly | Ser | Gly | Thr | Asp | Phe |
| 65 | | | | | 70 | | | | | 75 | | | | | 80 |

```
Thr Leu Lys Ile Ser Arg Val Glu Ala Glu Asp Val Gly Val Tyr Tyr
                85                  90                  95
Cys Met Gln Gln His Tyr Thr Thr Pro Pro Phe Gly Gly Gly Thr Val
            100                 105                 110
Lys Val Glu Ile Lys Arg Thr Gly Ala Pro
        115                 120
```

<210> SEQ ID NO 19
<211> LENGTH: 345
<212> TYPE: DNA
<213> ORGANISM: Homo sapiens
<220> FEATURE:
<221> NAME/KEY: gene
<222> LOCATION: (1)..(345)
<223> OTHER INFORMATION: ZB_K3

<400> SEQUENCE: 19

```
aagcttgata tcgtgctgac ccagtccccc ctggctaccc tgagcctgtc tcctggcgag      60
agagccaccc tgagctgcag agccagccag agcgtgtcca gcagctacct ggcctggtac     120
cagcagaagc ccggccaggc ccccagacta ttaatctacg gcgcttccag cagagccacc     180
ggcgtgccag ccagattttc tggcagcgga tccggcaccg acttcaccct gaccatcagc     240
agcctggaac ccgaggactt cgccgtgtac tactgccagc agcactacac caccccccca     300
tttggccagg gaacaaaggt ggaaatcaag cgtacgggcg cgccg                     345
```

<210> SEQ ID NO 20
<211> LENGTH: 115
<212> TYPE: PRT
<213> ORGANISM: Homo sapiens
<220> FEATURE:
<221> NAME/KEY: PEPTIDE
<222> LOCATION: (1)..(115)
<223> OTHER INFORMATION: ZB_K3

<400> SEQUENCE: 20

```
Lys Leu Asp Ile Val Leu Thr Gln Ser Pro Leu Ala Thr Leu Ser Leu
1               5                   10                  15
Ser Pro Gly Glu Arg Ala Thr Leu Ser Cys Arg Ala Ser Gln Ser Val
            20                  25                  30
Ser Ser Ser Tyr Leu Ala Trp Tyr Gln Gln Lys Pro Gly Gln Ala Pro
        35                  40                  45
Arg Leu Leu Ile Tyr Gly Ala Ser Ser Arg Ala Thr Gly Val Pro Ala
    50                  55                  60
Arg Phe Ser Gly Ser Gly Ser Gly Thr Asp Phe Thr Leu Thr Ile Ser
65                  70                  75                  80
Ser Leu Glu Pro Glu Asp Phe Ala Val Tyr Tyr Cys Gln Gln His Tyr
                85                  90                  95
Thr Thr Pro Pro Phe Gly Gln Gly Thr Lys Val Glu Ile Lys Arg Thr
            100                 105                 110
Gly Ala Pro
        115
```

<210> SEQ ID NO 21
<211> LENGTH: 357
<212> TYPE: DNA
<213> ORGANISM: Homo sapiens
<220> FEATURE:
<221> NAME/KEY: gene
<222> LOCATION: (1)..(357)
<223> OTHER INFORMATION: ZB_K4

<400> SEQUENCE: 21

```
aagcttgata tcgtgatgac ccagtccccc gacagcctgg ccgtgtctct gggcgagcgg      60
gccaccatca actgcagatc cagccagagc gtgctgtaca gctccaacaa caagaactac     120
ctggcctggt accagcagaa gcccggccag cccccaagc tattaatcta ctgggccagc      180
acccgcgaga gcggcgtgcc agatagattc agcggatccg gctccggcac cgacttcacc     240
ctgaccatca gcagcctgca agccgaggac gtggccgtgt actactgcca gcagcactac     300
accaccccc catttggcca gggaacaaag gtggaaatca agcgtacggg cgcgccg         357
```

<210> SEQ ID NO 22
<211> LENGTH: 119
<212> TYPE: PRT
<213> ORGANISM: Homo sapiens
<220> FEATURE:
<221> NAME/KEY: PEPTIDE
<222> LOCATION: (1)..(119)
<223> OTHER INFORMATION: ZB_K4

<400> SEQUENCE: 22

```
Lys Leu Asp Ile Val Met Thr Gln Ser Pro Asp Ser Leu Ala Val Ser
1               5                   10                  15

Leu Gly Glu Arg Ala Thr Ile Asn Cys Arg Ser Ser Gln Ser Val Leu
            20                  25                  30

Tyr Ser Ser Asn Asn Lys Asn Tyr Leu Ala Trp Tyr Gln Gln Lys Pro
        35                  40                  45

Gly Gln Pro Pro Lys Leu Leu Ile Tyr Trp Ala Ser Thr Arg Glu Ser
    50                  55                  60

Gly Val Pro Asp Arg Phe Ser Gly Ser Gly Ser Gly Thr Asp Phe Thr
65                  70                  75                  80

Leu Thr Ile Ser Ser Leu Gln Ala Glu Asp Val Ala Val Tyr Tyr Cys
                85                  90                  95

Gln Gln His Tyr Thr Thr Pro Pro Phe Gly Gln Gly Thr Lys Val Glu
            100                 105                 110

Ile Lys Arg Thr Gly Ala Pro
        115
```

<210> SEQ ID NO 23
<211> LENGTH: 339
<212> TYPE: DNA
<213> ORGANISM: Homo sapiens
<220> FEATURE:
<221> NAME/KEY: gene
<222> LOCATION: (1)..(339)
<223> OTHER INFORMATION: ZB_L1

<400> SEQUENCE: 23

```
aagcttgata tcgtgctgac ccagcctccc agcgtgtccg gcgcaccagg tcagagagtg      60
accatcagct gctccggcag cagcagcaac atcggcagca actacgtgtc ctggtaccag     120
cagctgcccg ggaccgcccc caagctgctg atctacgaca caaccagcg gcccagcggc      180
gtgccagacc ggtttagcgg atccaagagc ggcaccagcg ccagcctggc tatcaccggc     240
ctgcagagcg aggacgaggc cgactactac tgccagcagc actacaccac cccccattc      300
ggcggaggca ccaagttaac cgtgctgggc ggcgcgccg                            339
```

<210> SEQ ID NO 24
<211> LENGTH: 113
<212> TYPE: PRT
<213> ORGANISM: Homo sapiens

```
<220> FEATURE:
<221> NAME/KEY: PEPTIDE
<222> LOCATION: (1)..(113)
<223> OTHER INFORMATION: ZB_L1

<400> SEQUENCE: 24

Lys Leu Asp Ile Val Leu Thr Gln Pro Pro Ser Val Ser Gly Ala Pro
1               5                   10                  15

Gly Gln Arg Val Thr Ile Ser Cys Ser Gly Ser Ser Asn Ile Gly
            20                  25                  30

Ser Asn Tyr Val Ser Trp Tyr Gln Gln Leu Pro Gly Thr Ala Pro Lys
        35                  40                  45

Leu Leu Ile Tyr Asp Asn Asn Gln Arg Pro Ser Gly Val Pro Asp Arg
    50                  55                  60

Phe Ser Gly Ser Lys Ser Gly Thr Ser Ala Ser Leu Ala Ile Thr Gly
65                  70                  75                  80

Leu Gln Ser Glu Asp Glu Ala Asp Tyr Tyr Cys Gln Gln His Tyr Thr
                85                  90                  95

Thr Pro Pro Phe Gly Gly Gly Thr Lys Leu Thr Val Leu Gly Gly Ala
            100                 105                 110

Pro

<210> SEQ ID NO 25
<211> LENGTH: 342
<212> TYPE: DNA
<213> ORGANISM: Homo sapiens
<220> FEATURE:
<221> NAME/KEY: gene
<222> LOCATION: (1)..(342)
<223> OTHER INFORMATION: ZB_L2

<400> SEQUENCE: 25
aagcttgata tcgccctgac ccagcctgcc agcgtgtccg gctcaccagg tcagagcatc      60
accatcagct gcaccggcac cagcagcgac gtgggcggct acaactacgt gtcctggtac     120
cagcagcacc ccgggaaggc ccccaagctg atgatctacg acgtgtccaa ccggcccagc     180
ggcgtgtcca acagattcag cggatccaag agcggcaaca ccgccagcct gaccatcagc     240
ggactgcagg ccgaggacga ggccgactac tactgccagc agcactacac caccccccca     300
ttcggcggag gcaccaagtt aaccgtgctg ggcggcgcgc cg                        342

<210> SEQ ID NO 26
<211> LENGTH: 114
<212> TYPE: PRT
<213> ORGANISM: Homo sapiens
<220> FEATURE:
<221> NAME/KEY: PEPTIDE
<222> LOCATION: (1)..(114)
<223> OTHER INFORMATION: ZB_L2

<400> SEQUENCE: 26

Lys Leu Asp Ile Ala Leu Thr Gln Pro Ala Ser Val Ser Gly Ser Pro
1               5                   10                  15

Gly Gln Ser Ile Thr Ile Ser Cys Thr Gly Thr Ser Ser Asp Val Gly
            20                  25                  30

Gly Tyr Asn Tyr Val Ser Trp Tyr Gln Gln His Pro Gly Lys Ala Pro
        35                  40                  45

Lys Leu Met Ile Tyr Asp Val Ser Asn Arg Pro Ser Gly Val Ser Asn
    50                  55                  60

Arg Phe Ser Gly Ser Lys Ser Gly Asn Thr Ala Ser Leu Thr Ile Ser
```

```
                65                  70                  75                  80
Gly Leu Gln Ala Glu Asp Glu Ala Asp Tyr Tyr Cys Gln Gln His Tyr
                    85                  90                  95

Thr Thr Pro Pro Phe Gly Gly Gly Thr Lys Leu Thr Val Leu Gly Gly
                100                 105                 110

Ala Pro
```

<210> SEQ ID NO 27
<211> LENGTH: 330
<212> TYPE: DNA
<213> ORGANISM: Homo sapiens
<220> FEATURE:
<221> NAME/KEY: gene
<222> LOCATION: (1)..(330)
<223> OTHER INFORMATION: ZB_L3

<400> SEQUENCE: 27

```
aagcttgata tcgagctgac ccagcccccc tccgtgtctg tggcaccagg tcagaccgcc        60
agaatcagct gcggcgacgc cctgggcgat aagtacgcca gctggtacca gcagaagccc       120
gggcaggccc ccgtgctggt gatctacgac gacagcgaca gacccagcgg catccccgag       180
cggttcagcg gatccaacag cggcaatacc gccaccctga ccatcagcgg cacccaggcc       240
gaggacgagg ccgactacta ctgccagcag cactacacca ccccccccatt cggcggaggc       300
accaagttaa ccgtgctggg cggcgcgccg                                        330
```

<210> SEQ ID NO 28
<211> LENGTH: 110
<212> TYPE: PRT
<213> ORGANISM: Homo sapiens
<220> FEATURE:
<221> NAME/KEY: PEPTIDE
<222> LOCATION: (1)..(110)
<223> OTHER INFORMATION: ZB_L3

<400> SEQUENCE: 28

```
Lys Leu Asp Ile Glu Leu Thr Gln Pro Pro Ser Val Ser Val Ala Pro
1               5                   10                  15

Gly Gln Thr Ala Arg Ile Ser Cys Gly Asp Ala Leu Gly Asp Lys Tyr
                20                  25                  30

Ala Ser Trp Tyr Gln Gln Lys Pro Gly Gln Ala Pro Val Leu Val Ile
            35                  40                  45

Tyr Asp Asp Ser Asp Arg Pro Ser Gly Ile Pro Glu Arg Phe Ser Gly
        50                  55                  60

Ser Asn Ser Gly Asn Thr Ala Thr Leu Thr Ile Ser Gly Thr Gln Ala
65                  70                  75                  80

Glu Asp Glu Ala Asp Tyr Tyr Cys Gln Gln His Tyr Thr Thr Pro Pro
                85                  90                  95

Phe Gly Gly Gly Thr Lys Leu Thr Val Leu Gly Gly Ala Pro
                100                 105                 110
```

<210> SEQ ID NO 29
<211> LENGTH: 75
<212> TYPE: DNA
<213> ORGANISM: Homo sapiens
<220> FEATURE:
<221> NAME/KEY: gene
<222> LOCATION: (1)..(75)
<223> OTHER INFORMATION: ZB_H1A_FR1

<400> SEQUENCE: 29

```
caggtgcaat tggtgcagag cggagccgaa gtgaagaaac ccggcagcag cgtgaaggtg    60
tcctgcaagg cctcc                                                     75
```

<210> SEQ ID NO 30
<211> LENGTH: 42
<212> TYPE: DNA
<213> ORGANISM: Homo sapiens
<220> FEATURE:
<221> NAME/KEY: gene
<222> LOCATION: (1)..(42)
<223> OTHER INFORMATION: ZB_H1A_FR2

<400> SEQUENCE: 30

```
tgggtgcgcc aggccccagg ccagggcctc gagtggatgg gc                       42
```

<210> SEQ ID NO 31
<211> LENGTH: 96
<212> TYPE: DNA
<213> ORGANISM: Homo sapiens
<220> FEATURE:
<221> NAME/KEY: gene
<222> LOCATION: (1)..(96)
<223> OTHER INFORMATION: ZB_H1A_FR3

<400> SEQUENCE: 31

```
agggtgacca tcaccgccga cgagagcacc agcaccgcct acatggaact gagcagcctg    60
cggagcgagg acaccgccgt gtactactgt gcgcgc                              96
```

<210> SEQ ID NO 32
<211> LENGTH: 75
<212> TYPE: DNA
<213> ORGANISM: Homo sapiens
<220> FEATURE:
<221> NAME/KEY: gene
<222> LOCATION: (1)..(75)
<223> OTHER INFORMATION: ZB_H1B_FR1

<400> SEQUENCE: 32

```
caggtgcaat tggtgcagag cggagccgaa gtgaagaaac ccggcgccag cgtgaaggtg    60
tcctgcaagg cctcc                                                     75
```

<210> SEQ ID NO 33
<211> LENGTH: 42
<212> TYPE: DNA
<213> ORGANISM: Homo sapiens
<220> FEATURE:
<221> NAME/KEY: gene
<222> LOCATION: (1)..(42)
<223> OTHER INFORMATION: ZB_H1B_FR2

<400> SEQUENCE: 33

```
tgggtgcgcc aggccccagg ccagggcctc gagtggatgg gc                       42
```

<210> SEQ ID NO 34
<211> LENGTH: 96
<212> TYPE: DNA
<213> ORGANISM: Homo sapiens
<220> FEATURE:
<221> NAME/KEY: gene
<222> LOCATION: (1)..(96)
<223> OTHER INFORMATION: ZB_H1B_FR3

<400> SEQUENCE: 34

```
agggtgacca tgaccagaga caccagcatc agcaccgcct acatggaact gagcagcctg    60
cggagcgagg acaccgccgt gtactactgt gcgcgc                              96
```

<210> SEQ ID NO 35
<211> LENGTH: 75
<212> TYPE: DNA
<213> ORGANISM: Homo sapiens
<220> FEATURE:
<221> NAME/KEY: gene
<222> LOCATION: (1)..(75)
<223> OTHER INFORMATION: ZB_H2_FR1

<400> SEQUENCE: 35
caggtgcaat tgaaagagtc cggccctgcc ctggtgaaac ccacccagac cctgaccctg    60
acatgcacct tctcc                                                    75

<210> SEQ ID NO 36
<211> LENGTH: 42
<212> TYPE: DNA
<213> ORGANISM: Homo sapiens
<220> FEATURE:
<221> NAME/KEY: gene
<222> LOCATION: (1)..(42)
<223> OTHER INFORMATION: ZB_H2_FR2

<400> SEQUENCE: 36
tggatcagac agcccctgg caaggccctc gagtggctgg cc                       42

<210> SEQ ID NO 37
<211> LENGTH: 96
<212> TYPE: DNA
<213> ORGANISM: Homo sapiens
<220> FEATURE:
<221> NAME/KEY: gene
<222> LOCATION: (1)..(96)
<223> OTHER INFORMATION: ZB_H2_FR3

<400> SEQUENCE: 37
cggctgacca tcagcaagga cacttcgaaa aatcaggtgg tgctgaccat gaccaacatg    60
gaccccgtgg acaccgccac ctactactgt gcgcgc                             96

<210> SEQ ID NO 38
<211> LENGTH: 75
<212> TYPE: DNA
<213> ORGANISM: Homo sapiens
<220> FEATURE:
<221> NAME/KEY: gene
<222> LOCATION: (1)..(75)
<223> OTHER INFORMATION: ZB_H3_FR1

<400> SEQUENCE: 38
gaggtgcaat tggtggaaag cggcggagga ctggtgcagc ctggcggcag cctgagactg    60
tcttgcgccg cctcc                                                    75

<210> SEQ ID NO 39
<211> LENGTH: 42
<212> TYPE: DNA
<213> ORGANISM: Homo sapiens
<220> FEATURE:
<221> NAME/KEY: gene
<222> LOCATION: (1)..(42)
<223> OTHER INFORMATION: ZB_H3_FR2

<400> SEQUENCE: 39
tgggtgcgcc aggccccagg caagggcctc gagtgggtgt cc                      42

<210> SEQ ID NO 40

```
<211> LENGTH: 96
<212> TYPE: DNA
<213> ORGANISM: Homo sapiens
<220> FEATURE:
<221> NAME/KEY: gene
<222> LOCATION: (1)..(96)
<223> OTHER INFORMATION: ZB_H3_FR3

<400> SEQUENCE: 40
cggttcacca tcagccggga caattcgaaa aacaccctgt acctgcagat gaacagcctg      60
cgggccgagg acaccgccgt gtactactgt gcgcgc                                96

<210> SEQ ID NO 41
<211> LENGTH: 75
<212> TYPE: DNA
<213> ORGANISM: Homo sapiens
<220> FEATURE:
<221> NAME/KEY: gene
<222> LOCATION: (1)..(75)
<223> OTHER INFORMATION: ZB_H4_FR1

<400> SEQUENCE: 41
caggtgcaat tgcaggaaag cggccctggc ctggtgaaac ccagcgagac actgagcctg      60
acctgcaccg tgtcc                                                      75

<210> SEQ ID NO 42
<211> LENGTH: 42
<212> TYPE: DNA
<213> ORGANISM: Homo sapiens
<220> FEATURE:
<221> NAME/KEY: gene
<222> LOCATION: (1)..(42)
<223> OTHER INFORMATION: ZB_H4_FR2

<400> SEQUENCE: 42
tggatcagac agccccctgg caagggcctc gagtggatcg gc                         42

<210> SEQ ID NO 43
<211> LENGTH: 96
<212> TYPE: DNA
<213> ORGANISM: Homo sapiens
<220> FEATURE:
<221> NAME/KEY: gene
<222> LOCATION: (1)..(96)
<223> OTHER INFORMATION: ZB_H4_FR3

<400> SEQUENCE: 43
agggtgacca tcagcgtgga cacttcgaaa aaccagttca gcctgaagct gtccagcgtg      60
acagccgccg acaccgccgt gtactactgt gcgcgc                                96

<210> SEQ ID NO 44
<211> LENGTH: 75
<212> TYPE: DNA
<213> ORGANISM: Homo sapiens
<220> FEATURE:
<221> NAME/KEY: gene
<222> LOCATION: (1)..(75)
<223> OTHER INFORMATION: ZB_H5_FR1

<400> SEQUENCE: 44
gaggtgcaat tggtgcagag cggagccgaa gtgaagaagc ccggcgagag cctgaagatc      60
agctgcaagg gctcc                                                      75

<210> SEQ ID NO 45
<211> LENGTH: 42
```

```
<212> TYPE: DNA
<213> ORGANISM: Homo sapiens
<220> FEATURE:
<221> NAME/KEY: gene
<222> LOCATION: (1)..(42)
<223> OTHER INFORMATION: ZB_H5_FR2

<400> SEQUENCE: 45
tgggtgcgcc agatgcccgg caagggcctc gagtggatgg gc                           42

<210> SEQ ID NO 46
<211> LENGTH: 96
<212> TYPE: DNA
<213> ORGANISM: Homo sapiens
<220> FEATURE:
<221> NAME/KEY: gene
<222> LOCATION: (1)..(96)
<223> OTHER INFORMATION: ZB_H5_FR3

<400> SEQUENCE: 46
caggtgacca tcagcgccga caagagcatc agcaccgcct acctgcagtg gtccagcctg        60
aaggccagcg acaccgccat gtactactgt gcgcgc                                  96

<210> SEQ ID NO 47
<211> LENGTH: 75
<212> TYPE: DNA
<213> ORGANISM: Homo sapiens
<220> FEATURE:
<221> NAME/KEY: gene
<222> LOCATION: (1)..(75)
<223> OTHER INFORMATION: ZB_H6_FR1

<400> SEQUENCE: 47
caggtgcaat tgcaacagtc tggccctggc ctggtgaaac ccagccagac cctgagcctg        60
acctgcgcca tctcc                                                         75

<210> SEQ ID NO 48
<211> LENGTH: 42
<212> TYPE: DNA
<213> ORGANISM: Homo sapiens
<220> FEATURE:
<221> NAME/KEY: gene
<222> LOCATION: (1)..(42)
<223> OTHER INFORMATION: ZB_H6_FR2

<400> SEQUENCE: 48
tggatcagac agtcccccgg cagaggcctc gagtggctgg gc                           42

<210> SEQ ID NO 49
<211> LENGTH: 96
<212> TYPE: DNA
<213> ORGANISM: Homo sapiens
<220> FEATURE:
<221> NAME/KEY: gene
<222> LOCATION: (1)..(96)
<223> OTHER INFORMATION: ZB_H6_FR3

<400> SEQUENCE: 49
cggatcacca tcaaccccga cacttcgaaa aaccagttct ccctgcaact gaacagcgtg        60 accccccgagg acaccgccgt gtactactgt gcgcgc                                 96

<210> SEQ ID NO 50
<211> LENGTH: 30
<212> TYPE: DNA
<213> ORGANISM: Homo sapiens
<220> FEATURE:
```

<210> SEQ ID NO 50
<211> LENGTH: 30
<212> TYPE: DNA
<213> ORGANISM: Homo sapiens
<220> FEATURE:
<221> NAME/KEY: gene
<222> LOCATION: (1)..(30)
<223> OTHER INFORMATION: ZB_H1A_CDR1

<400> SEQUENCE: 50
ggaggcacct tcagcagcta cgccatcagc                                    30

<210> SEQ ID NO 51
<211> LENGTH: 51
<212> TYPE: DNA
<213> ORGANISM: Homo sapiens
<220> FEATURE:
<221> NAME/KEY: gene
<222> LOCATION: (1)..(51)
<223> OTHER INFORMATION: ZB_H1A_CDR2

<400> SEQUENCE: 51
ggcatcatcc ccatcttcgg caccgccaac tacgcccaga aattccaggg c             51

<210> SEQ ID NO 52
<211> LENGTH: 30
<212> TYPE: DNA
<213> ORGANISM: Homo sapiens
<220> FEATURE:
<221> NAME/KEY: gene
<222> LOCATION: (1)..(30)
<223> OTHER INFORMATION: ZB_H1B_CDR1

<400> SEQUENCE: 52
ggatacacct tcaccagcta ctacatgcac                                    30

<210> SEQ ID NO 53
<211> LENGTH: 51
<212> TYPE: DNA
<213> ORGANISM: Homo sapiens
<220> FEATURE:
<221> NAME/KEY: gene
<222> LOCATION: (1)..(51)
<223> OTHER INFORMATION: ZB_H1B_CDR2

<400> SEQUENCE: 53
tggatcaacc ccaacagcgg cggcaccaac tacgcccaga aattccaggg c             51

<210> SEQ ID NO 54
<211> LENGTH: 24
<212> TYPE: DNA
<213> ORGANISM: Homo sapiens
<220> FEATURE:
<221> NAME/KEY: gene
<222> LOCATION: (1)..(24)
<223> OTHER INFORMATION: ZB_H2_CDR1

<400> SEQUENCE: 54
tactacgccg acagcgtgaa gggc                                          24

<210> SEQ ID NO 55
<211> LENGTH: 48
<212> TYPE: DNA
<213> ORGANISM: Homo sapiens
<220> FEATURE:
<221> NAME/KEY: gene
<222> LOCATION: (1)..(48)
<223> OTHER INFORMATION: ZB_H2_CDR2

<400> SEQUENCE: 55
ctgatcgact gggacgacga caagtactac agcaccagcc tgaaaacc                48

```
<210> SEQ ID NO 56
<211> LENGTH: 30
<212> TYPE: DNA
<213> ORGANISM: Homo sapiens
<220> FEATURE:
<221> NAME/KEY: gene
<222> LOCATION: (1)..(30)
<223> OTHER INFORMATION: ZB_H3_CDR1

<400> SEQUENCE: 56
ggattcacct tcagcagcta cgccatgagc                                          30

<210> SEQ ID NO 57
<211> LENGTH: 51
<212> TYPE: DNA
<213> ORGANISM: Homo sapiens
<220> FEATURE:
<221> NAME/KEY: gene
<222> LOCATION: (1)..(51)
<223> OTHER INFORMATION: ZB_H3_CDR2

<400> SEQUENCE: 57
gccatcagcg gcagcggcgg cagcacctac tacgccgaca gcgtgaaggg c                  51

<210> SEQ ID NO 58
<211> LENGTH: 30
<212> TYPE: DNA
<213> ORGANISM: Homo sapiens
<220> FEATURE:
<221> NAME/KEY: gene
<222> LOCATION: (1)..(30)
<223> OTHER INFORMATION: ZB_H4_CDR1

<400> SEQUENCE: 58
ggaggcagca tcagcagcta ctactggtcc                                          30

<210> SEQ ID NO 59
<211> LENGTH: 48
<212> TYPE: DNA
<213> ORGANISM: Homo sapiens
<220> FEATURE:
<221> NAME/KEY: gene
<222> LOCATION: (1)..(48)
<223> OTHER INFORMATION: ZB_H4_CDR2

<400> SEQUENCE: 59
tacatctact acagcggcag caccaactac aaccccagcc tgaagtcc                      48

<210> SEQ ID NO 60
<211> LENGTH: 30
<212> TYPE: DNA
<213> ORGANISM: Homo sapiens
<220> FEATURE:
<221> NAME/KEY: gene
<222> LOCATION: (1)..(30)
<223> OTHER INFORMATION: ZB_H5_CDR1

<400> SEQUENCE: 60
ggatacagct tcaccagcta ctggatcggc                                          30

<210> SEQ ID NO 61
<211> LENGTH: 51
<212> TYPE: DNA
<213> ORGANISM: Homo sapiens
<220> FEATURE:
<221> NAME/KEY: gene
<222> LOCATION: (1)..(51)
<223> OTHER INFORMATION: ZB_H5_CDR2
```

<400> SEQUENCE: 61
atcatctacc ccggcgacag cgacacccgg tacagcccca gcttccaggg c    51

<210> SEQ ID NO 62
<211> LENGTH: 36
<212> TYPE: DNA
<213> ORGANISM: Homo sapiens
<220> FEATURE:
<221> NAME/KEY: gene
<222> LOCATION: (1)..(36)
<223> OTHER INFORMATION: ZB_H6_CDR1

<400> SEQUENCE: 62
ggagacagcg tgtccagcaa cagcgccgcc tggaac    36

<210> SEQ ID NO 63
<211> LENGTH: 54
<212> TYPE: DNA
<213> ORGANISM: Homo sapiens
<220> FEATURE:
<221> NAME/KEY: gene
<222> LOCATION: (1)..(54)
<223> OTHER INFORMATION: ZB_H6_CDR2

<400> SEQUENCE: 63
cggacctact accggtccaa gtggtacaac gactacgccg tgtccgtgaa gtcc    54

<210> SEQ ID NO 64
<211> LENGTH: 72
<212> TYPE: DNA
<213> ORGANISM: Homo sapiens
<220> FEATURE:
<221> NAME/KEY: gene
<222> LOCATION: (1)..(72)
<223> OTHER INFORMATION: ZB_K1_FR1

<400> SEQUENCE: 64
gatatccaga tgacccagtc ccccagcagc ctgagcgcca gcgtgggcga cagagtgacc    60
atcacctgca ga    72

<210> SEQ ID NO 65
<211> LENGTH: 45
<212> TYPE: DNA
<213> ORGANISM: Homo sapiens
<220> FEATURE:
<221> NAME/KEY: gene
<222> LOCATION: (1)..(45)
<223> OTHER INFORMATION: ZB_K1_FR2

<400> SEQUENCE: 65
taccagcaga gcccggcaa ggcccccaag ctattaatct acgcc    45

<210> SEQ ID NO 66
<211> LENGTH: 96
<212> TYPE: DNA
<213> ORGANISM: Homo sapiens
<220> FEATURE:
<221> NAME/KEY: gene
<222> LOCATION: (1)..(96)
<223> OTHER INFORMATION: ZB_K1_FR3

<400> SEQUENCE: 66
gtgccaagca gattcagcgg atccggctcc ggcaccgact caccctgac catcagcagc    60 ctgcaacccg aggacttcgc cacctactac tgccag    96

<210> SEQ ID NO 67
<211> LENGTH: 33
<212> TYPE: DNA
<213> ORGANISM: Homo sapiens
<220> FEATURE:
<221> NAME/KEY: gene
<222> LOCATION: (1)..(33)
<223> OTHER INFORMATION: ZB_K1_FR4

<400> SEQUENCE: 67
ggccagggaa caaaggtgga aatcaagcgt acg                          33

<210> SEQ ID NO 68
<211> LENGTH: 78
<212> TYPE: DNA
<213> ORGANISM: Homo sapiens
<220> FEATURE:
<221> NAME/KEY: gene
<222> LOCATION: (1)..(78)
<223> OTHER INFORMATION: ZB_K2_FR1

<400> SEQUENCE: 68
gatatcgtga tgacccagtc cccctgagc ctgagcctgc ccgtgacacc tggcgagcct    60
gccagcatca gctgcaga                                                78

<210> SEQ ID NO 69
<211> LENGTH: 45
<212> TYPE: DNA
<213> ORGANISM: Homo sapiens
<220> FEATURE:
<221> NAME/KEY: gene
<222> LOCATION: (1)..(45)
<223> OTHER INFORMATION: ZB_K2_FR2

<400> SEQUENCE: 69
tacctgcaaa agcccggcca gtcccctcag ctattaatct acctg              45

<210> SEQ ID NO 70
<211> LENGTH: 96
<212> TYPE: DNA
<213> ORGANISM: Homo sapiens
<220> FEATURE:
<221> NAME/KEY: gene
<222> LOCATION: (1)..(96)
<223> OTHER INFORMATION: ZB_K2_FR3

<400> SEQUENCE: 70
gtgccagata gattcagcgg atccggctcc ggcaccgact tcaccctgaa gatcagccgg    60
gtggaagccg aggacgtggg cgtgtactac tgcatg                             96

<210> SEQ ID NO 71
<211> LENGTH: 33
<212> TYPE: DNA
<213> ORGANISM: Homo sapiens
<220> FEATURE:
<221> NAME/KEY: gene
<222> LOCATION: (1)..(33)
<223> OTHER INFORMATION: ZB_K2_FR4

<400> SEQUENCE: 71
ggccagggaa caaaggtgga aatcaagcgt acg                          33

<210> SEQ ID NO 72
<211> LENGTH: 75
<212> TYPE: DNA
<213> ORGANISM: Homo sapiens
<220> FEATURE:

```
<221> NAME/KEY: gene
<222> LOCATION: (1)..(75)
<223> OTHER INFORMATION: ZB_K3_FR1

<400> SEQUENCE: 72
gatatcgtgc tgacccagtc ccccctggct accctgagcc tgtctcctgg cgagagagcc      60
accctgagct gcaga                                                        75

<210> SEQ ID NO 73
<211> LENGTH: 45
<212> TYPE: DNA
<213> ORGANISM: Homo sapiens
<220> FEATURE:
<221> NAME/KEY: gene
<222> LOCATION: (1)..(45)
<223> OTHER INFORMATION: ZB_K3_FR2

<400> SEQUENCE: 73
taccagcaga agcccggcca ggcccccaga ctattaatct acggc                       45

<210> SEQ ID NO 74
<211> LENGTH: 96
<212> TYPE: DNA
<213> ORGANISM: Homo sapiens
<220> FEATURE:
<221> NAME/KEY: gene
<222> LOCATION: (1)..(96)
<223> OTHER INFORMATION: ZB_K3_FR3

<400> SEQUENCE: 74
gtgccagcca gattttctgg cagcggatcc ggcaccgact tcaccctgac catcagcagc      60
ctggaacccg aggacttcgc cgtgtactac tgccag                                 96

<210> SEQ ID NO 75
<211> LENGTH: 33
<212> TYPE: DNA
<213> ORGANISM: Homo sapiens
<220> FEATURE:
<221> NAME/KEY: gene
<222> LOCATION: (1)..(33)
<223> OTHER INFORMATION: ZB_K3_FR4

<400> SEQUENCE: 75
ggccagggaa caaaggtgga aatcaagcgt acg                                    33

<210> SEQ ID NO 76
<211> LENGTH: 72
<212> TYPE: DNA
<213> ORGANISM: Homo sapiens
<220> FEATURE:
<221> NAME/KEY: gene
<222> LOCATION: (1)..(72)
<223> OTHER INFORMATION: ZB_K4_FR1

<400> SEQUENCE: 76
gatatcgtga tgacccagtc ccccgacagc ctggccgtgt ctctgggcga gcgggccacc      60
atcaactgca ga                                                           72

<210> SEQ ID NO 77
<211> LENGTH: 44
<212> TYPE: DNA
<213> ORGANISM: Homo sapiens
<220> FEATURE:
<221> NAME/KEY: gene
<222> LOCATION: (1)..(44)
<223> OTHER INFORMATION: ZB_K4_FR2
```

<400> SEQUENCE: 77
taccagcaga agcccggcca gccccccaag ctattaatct actg    44

<210> SEQ ID NO 78
<211> LENGTH: 96
<212> TYPE: DNA
<213> ORGANISM: Homo sapiens
<220> FEATURE:
<221> NAME/KEY: gene
<222> LOCATION: (1)..(96)
<223> OTHER INFORMATION: ZB_K4_FR3

<400> SEQUENCE: 78
gtgccagata gattcagcgg atccggctcc ggcaccgact tcaccctgac catcagcagc    60
ctgcaagccg aggacgtggc cgtgtactac tgccag    96

<210> SEQ ID NO 79
<211> LENGTH: 33
<212> TYPE: DNA
<213> ORGANISM: Homo sapiens
<220> FEATURE:
<221> NAME/KEY: gene
<222> LOCATION: (1)..(33)
<223> OTHER INFORMATION: ZB_K4_FR4

<400> SEQUENCE: 79
ggccagggaa caaaggtgga aatcaagcgt acg    33

<210> SEQ ID NO 80
<211> LENGTH: 33
<212> TYPE: DNA
<213> ORGANISM: Homo sapiens
<220> FEATURE:
<221> NAME/KEY: gene
<222> LOCATION: (1)..(33)
<223> OTHER INFORMATION: ZB_K1_CDR1

<400> SEQUENCE: 80
gccagccagg gcatcagcag ctacctggcc tgg    33

<210> SEQ ID NO 81
<211> LENGTH: 21
<212> TYPE: DNA
<213> ORGANISM: Homo sapiens
<220> FEATURE:
<221> NAME/KEY: gene
<222> LOCATION: (1)..(21)
<223> OTHER INFORMATION: ZB_K1_CDR2

<400> SEQUENCE: 81
gccagctctc tgcaaagcgg c    21

<210> SEQ ID NO 82
<211> LENGTH: 24
<212> TYPE: DNA
<213> ORGANISM: Homo sapiens
<220> FEATURE:
<221> NAME/KEY: gene
<222> LOCATION: (1)..(24)
<223> OTHER INFORMATION: ZB_K1_CDR3

<400> SEQUENCE: 82
cagcactaca ccaccccccc attt    24

<210> SEQ ID NO 83

```
<211> LENGTH: 48
<212> TYPE: DNA
<213> ORGANISM: Homo sapiens
<220> FEATURE:
<221> NAME/KEY: gene
<222> LOCATION: (1)..(48)
<223> OTHER INFORMATION: ZB_K2_CDR1

<400> SEQUENCE: 83
tccagccaga gcctgctgca cagcaacggc tacaactacc tggactgg            48

<210> SEQ ID NO 84
<211> LENGTH: 21
<212> TYPE: DNA
<213> ORGANISM: Homo sapiens
<220> FEATURE:
<221> NAME/KEY: gene
<222> LOCATION: (1)..(21)
<223> OTHER INFORMATION: ZB_K2_CDR2

<400> SEQUENCE: 84
ggcagcaacc gggccagcgg c                                         21

<210> SEQ ID NO 85
<211> LENGTH: 27
<212> TYPE: DNA
<213> ORGANISM: Homo sapiens
<220> FEATURE:
<221> NAME/KEY: gene
<222> LOCATION: (1)..(27)
<223> OTHER INFORMATION: ZB_K2_CDR3

<400> SEQUENCE: 85
cagcagcact acaccacccc cccattt                                   27

<210> SEQ ID NO 86
<211> LENGTH: 36
<212> TYPE: DNA
<213> ORGANISM: Homo sapiens
<220> FEATURE:
<221> NAME/KEY: gene
<222> LOCATION: (1)..(36)
<223> OTHER INFORMATION: ZB_K3_CDR1

<400> SEQUENCE: 86
gccagccaga gcgtgtccag cagctacctg gcctgg                         36

<210> SEQ ID NO 87
<211> LENGTH: 21
<212> TYPE: DNA
<213> ORGANISM: Homo sapiens
<220> FEATURE:
<221> NAME/KEY: gene
<222> LOCATION: (1)..(21)
<223> OTHER INFORMATION: ZB_K3_CDR2

<400> SEQUENCE: 87
gcttccagca gagccaccgg c                                         21

<210> SEQ ID NO 88
<211> LENGTH: 24
<212> TYPE: DNA
<213> ORGANISM: Homo sapiens
<220> FEATURE:
<221> NAME/KEY: gene
<222> LOCATION: (1)..(24)
<223> OTHER INFORMATION: ZB_K3_CDR3

<400> SEQUENCE: 88
```
cagcactaca ccaccccccc attt                                          24

<210> SEQ ID NO 89
<211> LENGTH: 51
<212> TYPE: DNA
<213> ORGANISM: Homo sapiens
<220> FEATURE:
<221> NAME/KEY: gene
<222> LOCATION: (1)..(51)
<223> OTHER INFORMATION: ZB_K4_CDR1

<400> SEQUENCE: 89
tccagccaga gcgtgctgta cagctccaac aacaagaact acctggcctg g            51

<210> SEQ ID NO 90
<211> LENGTH: 22
<212> TYPE: DNA
<213> ORGANISM: Homo sapiens
<220> FEATURE:
<221> NAME/KEY: gene
<222> LOCATION: (1)..(22)
<223> OTHER INFORMATION: ZB_K4_CDR2

<400> SEQUENCE: 90
ggccagcacc cgcgagagcg gc                                            22

<210> SEQ ID NO 91
<211> LENGTH: 24
<212> TYPE: DNA
<213> ORGANISM: Homo sapiens
<220> FEATURE:
<221> NAME/KEY: gene
<222> LOCATION: (1)..(24)
<223> OTHER INFORMATION: ZB_K4_CDR3

<400> SEQUENCE: 91
cagcactaca ccaccccccc attt                                          24

<210> SEQ ID NO 92
<211> LENGTH: 66
<212> TYPE: DNA
<213> ORGANISM: Homo sapiens
<220> FEATURE:
<221> NAME/KEY: gene
<222> LOCATION: (1)..(66)
<223> OTHER INFORMATION: ZB_L1_FR1

<400> SEQUENCE: 92
gatatcgtgc tgacccagcc tcccagcgtg tccggcgcac caggtcagag agtgaccatc   60
agctgc                                                              66

<210> SEQ ID NO 93
<211> LENGTH: 45
<212> TYPE: DNA
<213> ORGANISM: Homo sapiens
<220> FEATURE:
<221> NAME/KEY: gene
<222> LOCATION: (1)..(45)
<223> OTHER INFORMATION: ZB_L1_FR2

<400> SEQUENCE: 93
taccagcagc tgcccgggac cgcccccaag ctgctgatct acgac                   45

<210> SEQ ID NO 94
<211> LENGTH: 93
<212> TYPE: DNA

```
<213> ORGANISM: Homo sapiens
<220> FEATURE:
<221> NAME/KEY: gene
<222> LOCATION: (1)..(93)
<223> OTHER INFORMATION: ZB_L1_FR3

<400> SEQUENCE: 94
gtgccagacc ggtttagcgg atccaagagc ggcaccagcg ccagcctggc tatcaccggc    60
ctgcagagcg aggacgaggc cgactactac tgc                                 93

<210> SEQ ID NO 95
<211> LENGTH: 30
<212> TYPE: DNA
<213> ORGANISM: Homo sapiens
<220> FEATURE:
<221> NAME/KEY: gene
<222> LOCATION: (1)..(30)
<223> OTHER INFORMATION: ZB_L1_FR4

<400> SEQUENCE: 95
ggcggaggca ccaagttaac cgtgctgggc                                     30

<210> SEQ ID NO 96
<211> LENGTH: 66
<212> TYPE: DNA
<213> ORGANISM: Homo sapiens
<220> FEATURE:
<221> NAME/KEY: gene
<222> LOCATION: (1)..(66)
<223> OTHER INFORMATION: ZB_L2_FR1

<400> SEQUENCE: 96
gatatcgccc tgacccagcc tgccagcgtg tccggctcac caggtcagag catcaccatc    60
agctgc                                                               66

<210> SEQ ID NO 97
<211> LENGTH: 45
<212> TYPE: DNA
<213> ORGANISM: Homo sapiens
<220> FEATURE:
<221> NAME/KEY: gene
<222> LOCATION: (1)..(45)
<223> OTHER INFORMATION: ZB_L2_FR2

<400> SEQUENCE: 97
taccagcagc accccgggaa ggcccccaag ctgatgatct acgac                    45

<210> SEQ ID NO 98
<211> LENGTH: 93
<212> TYPE: DNA
<213> ORGANISM: Homo sapiens
<220> FEATURE:
<221> NAME/KEY: gene
<222> LOCATION: (1)..(93)
<223> OTHER INFORMATION: ZB_L2_FR3

<400> SEQUENCE: 98
gtgtccaaca gattcagcgg atccaagagc ggcaacaccg ccagcctgac catcagcgga    60
ctgcaggccg aggacgaggc cgactactac tgc                                 93

<210> SEQ ID NO 99
<211> LENGTH: 30
<212> TYPE: DNA
<213> ORGANISM: Homo sapiens
<220> FEATURE:
<221> NAME/KEY: gene
```

<222> LOCATION: (1)..(30)
<223> OTHER INFORMATION: ZB_L2_FR4

<400> SEQUENCE: 99
ggcggaggca ccaagttaac cgtgctgggc                                    30

<210> SEQ ID NO 100
<211> LENGTH: 66
<212> TYPE: DNA
<213> ORGANISM: Homo sapiens
<220> FEATURE:
<221> NAME/KEY: gene
<222> LOCATION: (1)..(66)
<223> OTHER INFORMATION: ZB_L3_FR1

<400> SEQUENCE: 100
gatatcgagc tgacccagcc cccctccgtg tctgtggcac caggtcagac cgccagaatc    60
agctgc                                                              66

<210> SEQ ID NO 101
<211> LENGTH: 45
<212> TYPE: DNA
<213> ORGANISM: Homo sapiens
<220> FEATURE:
<221> NAME/KEY: gene
<222> LOCATION: (1)..(45)
<223> OTHER INFORMATION: ZB_L3_FR2

<400> SEQUENCE: 101
taccagcaga agcccgggca ggccccgtg ctggtgatct acgac                     45

<210> SEQ ID NO 102
<211> LENGTH: 93
<212> TYPE: DNA
<213> ORGANISM: Homo sapiens
<220> FEATURE:
<221> NAME/KEY: gene
<222> LOCATION: (1)..(93)
<223> OTHER INFORMATION: ZB_L3_FR3

<400> SEQUENCE: 102
atccccgagc ggttcagcgg atccaacagc ggcaataccg ccaccctgac catcagcggc    60
acccaggccg aggacgaggc cgactactac tgc                                93

<210> SEQ ID NO 103
<211> LENGTH: 30
<212> TYPE: DNA
<213> ORGANISM: Homo sapiens
<220> FEATURE:
<221> NAME/KEY: gene
<222> LOCATION: (1)..(30)
<223> OTHER INFORMATION: ZB_L3_FR4

<400> SEQUENCE: 103
ggcggaggca ccaagttaac cgtgctgggc                                    30

<210> SEQ ID NO 104
<211> LENGTH: 42
<212> TYPE: DNA
<213> ORGANISM: Homo sapiens
<220> FEATURE:
<221> NAME/KEY: gene
<222> LOCATION: (1)..(42)
<223> OTHER INFORMATION: ZB_L1_CDR1

<400> SEQUENCE: 104

```
tccggcagca gcagcaacat cggcagcaac tacgtgtcct gg                    42

<210> SEQ ID NO 105
<211> LENGTH: 21
<212> TYPE: DNA
<213> ORGANISM: Homo sapiens
<220> FEATURE:
<221> NAME/KEY: gene
<222> LOCATION: (1)..(21)
<223> OTHER INFORMATION: ZB_L1_CDR2

<400> SEQUENCE: 105
aacaaccagc ggcccagcgg c                                           21

<210> SEQ ID NO 106
<211> LENGTH: 27
<212> TYPE: DNA
<213> ORGANISM: Homo sapiens
<220> FEATURE:
<221> NAME/KEY: gene
<222> LOCATION: (1)..(27)
<223> OTHER INFORMATION: ZB_L1_CDR3

<400> SEQUENCE: 106
cagcagcact acaccacccc cccattc                                     27

<210> SEQ ID NO 107
<211> LENGTH: 45
<212> TYPE: DNA
<213> ORGANISM: Homo sapiens
<220> FEATURE:
<221> NAME/KEY: gene
<222> LOCATION: (1)..(45)
<223> OTHER INFORMATION: ZB_L2_CDR1

<400> SEQUENCE: 107
accggcacca gcagcgacgt gggcggctac aactacgtgt cctgg                 45

<210> SEQ ID NO 108
<211> LENGTH: 21
<212> TYPE: DNA
<213> ORGANISM: Homo sapiens
<220> FEATURE:
<221> NAME/KEY: gene
<222> LOCATION: (1)..(21)
<223> OTHER INFORMATION: ZB_L2_CDR2

<400> SEQUENCE: 108
gtgtccaacc ggcccagcgg c                                           21

<210> SEQ ID NO 109
<211> LENGTH: 27
<212> TYPE: DNA
<213> ORGANISM: Homo sapiens
<220> FEATURE:
<221> NAME/KEY: gene
<222> LOCATION: (1)..(27)
<223> OTHER INFORMATION: ZB_L2_CDR3

<400> SEQUENCE: 109
cagcagcact acaccacccc cccattc                                     27

<210> SEQ ID NO 110
<211> LENGTH: 33
<212> TYPE: DNA
<213> ORGANISM: Homo sapiens
<220> FEATURE:
<221> NAME/KEY: gene
```

<222> LOCATION: (1)..(33)
<223> OTHER INFORMATION: ZB_L3_CDR1

<400> SEQUENCE: 110
ggcgacgccc tgggcgataa gtacgccagc tgg    33

<210> SEQ ID NO 111
<211> LENGTH: 21
<212> TYPE: DNA
<213> ORGANISM: Homo sapiens
<220> FEATURE:
<221> NAME/KEY: gene
<222> LOCATION: (1)..(21)
<223> OTHER INFORMATION: ZB_L3_CDR2

<400> SEQUENCE: 111
gacagcgaca gacccagcgg c    21

<210> SEQ ID NO 112
<211> LENGTH: 27
<212> TYPE: DNA
<213> ORGANISM: Homo sapiens
<220> FEATURE:
<221> NAME/KEY: gene
<222> LOCATION: (1)..(27)
<223> OTHER INFORMATION: ZB_L3_CDR3

<400> SEQUENCE: 112
cagcagcact acaccacccc cccattc    27

<210> SEQ ID NO 113
<211> LENGTH: 4
<212> TYPE: PRT
<213> ORGANISM: Artificial Sequence
<220> FEATURE:
<223> OTHER INFORMATION: CDRH3 Length 4
<220> FEATURE:
<221> NAME/KEY: MOD_RES
<222> LOCATION: (1)..(1)
<223> OTHER INFORMATION: G is 36.83%, D is 10.18%, E is 9.33%, V is
    8.80%, R is 5.38%, Y is 5.22%, A is 0.21%, C is 0.05%, F is 4.21%,
    H is 0.94%, I is 3.09%, K is 4.14%, L is 2.93%, M is 0.05%, N is
    2.42%, P is 0.05%, S is 1.15%, T is 0.07% and W is 4.90%
<220> FEATURE:
<221> NAME/KEY: MOD_RES
<222> LOCATION: (2)..(2)
<223> OTHER INFORMATION: L is 22.64%, Y is 20.29%, D is 19.97%, R is
    19.12%, T is 16.51%, A is 0.09%, F is 0.18%, G is 0.44%, I is
    0.05%, M is 0.27%, N is 0.09%, P is 0.09%, Q is 0.04%, S is 0.16%,
    and W is 0.05%
<220> FEATURE:
<221> NAME/KEY: MOD_RES
<222> LOCATION: (3)..(3)
<223> OTHER INFORMATION: A is 23.97%, E is 21.57%, R is 19.44%, Y is
    17.18%, G is 16.29%, D is 0.60%, F is 0.04%, L is 0.21%, M is
    0.05%, N is 0.04%, P is 0.05%, Q is 0.04%, S is 0.14%, T is 0.12%,
    V is 0.09%, C is 0.05% and W is 0.05%
<220> FEATURE:
<221> NAME/KEY: MOD_RES
<222> LOCATION: (4)..(4)
<223> OTHER INFORMATION: N is 24.57%, Y is 22.44%, R is 20.42%, S is
    18.19%, P is 13.24%, D is 0.07%, F is 0.11%, G is 0.25%, I is
    0.21%, L is 0.14%, V is 0.20% and W is 0.04%

<400> SEQUENCE: 113

Xaa Xaa Xaa Xaa
1

<210> SEQ ID NO 114
<211> LENGTH: 5
<212> TYPE: PRT

```
<213> ORGANISM: Artificial Sequence
<220> FEATURE:
<223> OTHER INFORMATION: CDRH3 Length 5
<220> FEATURE:
<221> NAME/KEY: MOD_RES
<222> LOCATION: (1)..(1)
<223> OTHER INFORMATION: G is 35.44%, D is 9.98%, E is 8.42%, V is
      7.44%, R is 6.81%, A is 0.39%, C is 0.08%, F is 3.55%, H is 1.60%,
      I is 3.93%, K is 4.88%, L is 4.32%, N is 2.98%, S is 1.40%, T is
      0.19%, W is 4.25% and Y is 4.29%
<220> FEATURE:
<221> NAME/KEY: MOD_RES
<222> LOCATION: (2)..(2)
<223> OTHER INFORMATION: G is 37.64%, R is 16.75%, M is 11.46%, N is
      9.28%, V is 8.83%, H is 7.30%, T is 7.02%, A is 0.31%, D is 0.18%,
      E is 0.07%, F is 0.07%, I is 0.10%, K is 0.07%, L is 0.15%, P is
      0.18%, Q is 4.00%, S is 0.18%, W is 0.10% and Y is 0.26%
<220> FEATURE:
<221> NAME/KEY: MOD_RES
<222> LOCATION: (3)..(3)
<223> OTHER INFORMATION: M is 24.29%, G is 22.40%, F is 18.08%, E is
      10.74%, L is 8.38%, W is 7.62%, S is 7.30%, A is 0.08%, C is
      0.07%, D is 0.11%, H is 0.07%, I is 0.19%, Q is 0.04%, R is 0.18%,
      T is 0.04%, V is 0.17% and Y is 0.19%
<220> FEATURE:
<221> NAME/KEY: MOD_RES
<222> LOCATION: (4)..(4)
<223> OTHER INFORMATION: D is 41.08%, A is 34.90%, L is 15.65%, V is
      6.99%,  C is 0.04%, E is 0.17%, F is 0.08%, G is 0.33%, H is
      0.07%, M is 0.08%, P is 0.06%, Q is 0.06%, R is 0.10%, S is 0.17%,
      T is 0.04%, and Y is 0.11%
<220> FEATURE:
<221> NAME/KEY: MOD_RES
<222> LOCATION: (5)..(5)
<223> OTHER INFORMATION: Y is 65.74%, N is 15.00%, I is 9.60%, L is
      6.56%, V is 6.22%, F is 5.91%,  C is 0.12%, D is 0.12%, G is
      0.15%, M is 0.04%, P is 0.11%,  R is 0.07%, S is 0.12% and T is
      4.94%

<400> SEQUENCE: 114

Xaa Xaa Xaa Xaa Xaa
1               5

<210> SEQ ID NO 115
<211> LENGTH: 6
<212> TYPE: PRT
<213> ORGANISM: Artificial Sequence
<220> FEATURE:
<223> OTHER INFORMATION: CDRH3 Length 6
<220> FEATURE:
<221> NAME/KEY: MOD_RES
<222> LOCATION: (1)..(1)
<223> OTHER INFORMATION: G is 32.77%, D is 9.78%, E is 9.04%, V is
      7.72%, R is 7.15%, K is 5.11%,  Y is 4.53%, W is 4.34%, I is
      4.33%, L is 4.20%, N is 3.43%, F is 3.40%, S is 1.76%, H is 1.54%,
      A is 0.37%, T is 0.31%, C is 0.09%, P is 0.05%, Q is 0.05% and M
      is 0.03%
<220> FEATURE:
<221> NAME/KEY: MOD_RES
<222> LOCATION: (2)..(2)
<223> OTHER INFORMATION: A is 17.54%, Y is 23.01%, G is 11.00%, S is
      9.44%, P is 7.78%, N is 5.61%, K is 5.44%,  V is 4.53%, L is
      4.02%, T is 3.85%, R is 2.06%, D is 2.00%, W is 1.62%, H is 1.36%,
      F is 0.15%, E is 0.14%, I is 0.14%, M is 0.14%, and Q is 0.14%
<220> FEATURE:
<221> NAME/KEY: MOD_RES
<222> LOCATION: (3)..(3)
<223> OTHER INFORMATION: G is 34.05%, Y is 12.12%, A is 9.75%, S is
      8.13%, P is 7.48%, V is 6.92%, E is 6.36%,  D is 4.77%, K is
      2.25%, F is 1.93%, R is 1.57%, L is 1.56%, H is 1.43%, T is 0.95%,
      I is 0.14%, M is 0.14%, C is 0.11%, W is 0.11%, N is 0.09% and Q
      is 0.08%
<220> FEATURE:
<221> NAME/KEY: MOD_RES
<222> LOCATION: (4)..(4)
<223> OTHER INFORMATION: F is 23.18%, G is 12.64%, M is 9.18%, S is
      8.93%, E is 7.42%, D is 7.25%, L is 6.75%, V is 5.28%,  P is
```

```
       4.37%, Y is 2.77%, H is 2.71%, I is 2.71%, A is 2.53%, W is 1.71%,
       T is 1.28%, Q is 0.92%, R is 0.14%, K is 0.08%, N is 0.06% and C
       is 0.05%
<220> FEATURE:
<221> NAME/KEY: MOD_RES
<222> LOCATION: (5)..(5)
<223> OTHER INFORMATION: D is 59.06%, A is 10.04%, G is 7.96%, N is
       7.79%, P is 4.53%, I is 2.19%, M is 2.05%, R is 1.60%, V is
       1.39%, H is 1.36%, T is 0.95%, Y is 0.28%, S is 0.26%, L is 0.17%,
       E is 0.11%, F is 0.09%, K is 0.09%, Q is 0.03%, and W is 0.03%
<220> FEATURE:
<221> NAME/KEY: MOD_RES
<222> LOCATION: (6)..(6)
<223> OTHER INFORMATION: Y is 63.36%, C is 7.85%, V is 7.76%, G is
       3.94%, L is 3.73%, D is 3.45%, F is 3.39%, P is 1.77%, R is 1.51%,
       S is 1.43%, H is 0.95%, I is 0.46%, N is 0.08%, A is 0.05%, Q is
       0.05%, K is 0.03%, and M is 0.03%

<400> SEQUENCE: 115

Xaa Xaa Xaa Xaa Xaa Xaa
1               5

<210> SEQ ID NO 116
<211> LENGTH: 7
<212> TYPE: PRT
<213> ORGANISM: Artificial Sequence
<220> FEATURE:
<223> OTHER INFORMATION: CDRH3 Length 7
<220> FEATURE:
<221> NAME/KEY: MOD_RES
<222> LOCATION: (1)..(1)
<223> OTHER INFORMATION: G is 31.73%, D is 10.11%, E is 8.67%, V is
       7.43%, R is 6.98%, K is 5.49%, Y is 4.88%, L is 4.30%, W is
       4.06%, I is 4.01%, F is 3.65%, N is 3.33%, S is 1.87%, H is 1.69%,
       A is 0.85%, T is 0.58%, Q is 0.14%, P is 0.09%, C is 0.08% and M
       is 0.08%
<220> FEATURE:
<221> NAME/KEY: MOD_RES
<222> LOCATION: (2)..(2)
<223> OTHER INFORMATION: R is 15.99%, G is 12.37%, A is 9.55%, Y is
       9.41%, N is 7.19%, D is 6.98%, S is 5.72%, H is 4.93%, P is
       4.68%, E is 3.97%, I is 3.86%, V is 3.85%, L is 3.39%, Q is 2.81%,
       T is 2.52%, K is 1.34%, W is 1.08%, F is 0.18%, M is 0.12% and C
       is 0.06%
<220> FEATURE:
<221> NAME/KEY: MOD_RES
<222> LOCATION: (3)..(3)
<223> OTHER INFORMATION: G is 21.33%, D is 14.56%, Y is 13.01%, N is
       12.74%, S is 7.39%, A is 6.55%, L is 5.93%, W is 4.67%, T is
       4.07%, R is 3.98%, E is 1.40%, K is 1.32%, V is 1.09%, H is 1.06%,
       I is 0.23%, P is 0.23%, Q is 0.12%, C is 0.11%, M is 0.11% and F
       is 0.08%
<220> FEATURE:
<221> NAME/KEY: MOD_RES
<222> LOCATION: (4)..(4)
<223> OTHER INFORMATION: G is 37.46%, A is 13.29%, Y is 10.44%, W is
       6.05%, D is 5.29%, E is 5.15%, R is 4.13%, S is 3.16%, F is
       3.09%, P is 2.74%, H is 2.30%, T is 1.72%, L is 1.25%, M is 1.17%,
       N is 1.11%, V is 1.08%, K is 0.20%, I is 0.18%, C is 0.09% and Q
       is 0.08%
<220> FEATURE:
<221> NAME/KEY: MOD_RES
<222> LOCATION: (5)..(5)
<223> OTHER INFORMATION: F is 43.63%, M is 18.58%, L is 8.83%, G is
       6.34%, P is 3.95%, I is 3.39%, W is 2.48%, S is 2.34%, V is
       2.23%, Q is 1.58%, Y is 1.49%, A is 1.26%, R is 1.00%, C is 0.99%,
       H is 0.62%, T is 0.62%, D is 0.24%, N is 0.21%, E is 0.15% and K
       is 0.03%
<220> FEATURE:
<221> NAME/KEY: MOD_RES
<222> LOCATION: (6)..(6)
<223> OTHER INFORMATION: D is 77.08%, G is 5.05%, A is 3.75%, K is
       3.07%, Y is 2.84%, S is 2.40%, T is 1.32%, R is 1.16%, E is 1.12%,
       V is 0.94%, L is 0.59%, F is 0.15%, H is 0.14%, N is 0.09%, M is
       0.08%, P is 0.06%, I is 0.05%, C is 0.03% and Q is 0.03%
<220> FEATURE:
<221> NAME/KEY: MOD_RES
```

```
<222> LOCATION: (7)..(7)
<223> OTHER INFORMATION: Y is 49.26%, V is 20.01%, I is 8.62%, S is
      3.92%, P is 3.53%, N is 3.34%, F is 3.01%, L is 2.98%, G is 1.84%,
      D is 1.28%, R is 0.67%, H is 0.55%, T is 0.55%, A is 0.12%, K is
      0.08%, M is 0.08%, C is 0.06% and W is 0.05%

<400> SEQUENCE: 116

Xaa Xaa Xaa Xaa Xaa Xaa Xaa
1               5

<210> SEQ ID NO 117
<211> LENGTH: 8
<212> TYPE: PRT
<213> ORGANISM: Artificial Sequence
<220> FEATURE:
<223> OTHER INFORMATION: CDRH3 Length 8
<220> FEATURE:
<221> NAME/KEY: MOD_RES
<222> LOCATION: (1)..(1)
<223> OTHER INFORMATION: G is 33.76%, D is 10.40%, E is 9.17%, V is
      8.12%, R is 6.24%,  Y is 4.95%, K is 4.73%, F is 4.56%, I is
      3.98%, W is 3.93%, L is 3.54%, N is 3.17%, H is 1.54%, S is 1.29%,
      A is 0.18%, C is 0.13%, T is 0.11%, P is 0.05% and M is 0.04%
<220> FEATURE:
<221> NAME/KEY: MOD_RES
<222> LOCATION: (2)..(2)
<223> OTHER INFORMATION: G is 18.07%, L is 10.46%, S is 7.48%, T is
      6.21%, P is 6.05%, F is 6.02%, R is 5.58%, Y is 5.51%, D is 5.22%,
      E is 4.27%, A is 3.90%, I is 3.51%, N is 3.28%, W is 3.27%, V is
      2.77%, M is 2.62%, K is 2.25%, H is 2.00%, Q is 1.46% and C is
      0.05%
<220> FEATURE:
<221> NAME/KEY: MOD_RES
<222> LOCATION: (3)..(3)
<223> OTHER INFORMATION: G is 14.48%, S is 9.89%, R is 8.88%, Y is
      7.85%, L is 7.23%, H is 6.09%, I is 5.98%,  A is 4.41%, D is
      3.99%, P is 3.76%, E is 3.72%, Q is 3.56%, W is 3.46%, N is 3.30%,
      T is 2.82%, M is 2.71%, F is 2.69%, V is 2.15%, C is 1.73% and K
      is 1.28%
<220> FEATURE:
<221> NAME/KEY: MOD_RES
<222> LOCATION: (4)..(4)
<223> OTHER INFORMATION: G is 28.59%, S is 8.39%, R is 8.36%, W is
      7.71%, A is 6.07%, V is 6.04%, N is 5.44%,  D is 4.55%, F is
      4.00%, Y is 3.53%, K is 2.65%, T is 2.63%, H is 2.22%, Q is 2.20%,
      L is 1.93%, M is 1.60%, E is 1.52%, I is 1.39%, P is 1.04% and C
      is 0.13%
<220> FEATURE:
<221> NAME/KEY: MOD_RES
<222> LOCATION: (5)..(5)
<223> OTHER INFORMATION: A is 18.48%, G is 17.93%, S is 9.53%, Y is
      8.37%, L is 6.58%, R is 5.24%, D is 4.89%, P is 3.79%, V is
      3.72%, T is 3.20%, M is 2.73%, H is 2.61%, W is 2.57%, E is 2.43%,
      N is 2.19%, F is 1.82%, C is 1.60%, Q is 1.12%, I is 1.08% and K
      is 0.09%
<220> FEATURE:
<221> NAME/KEY: MOD_RES
<222> LOCATION: (6)..(6)
<223> OTHER INFORMATION: F is 35.24%, L is 12.91%, A is 9.55%, I is
      7.50%,  G is 4.40%, Y is 4.38%, V is 3.54%, S is 3.48%, D is
      3.13%, N is 2.99%, H is 2.91%, W is 2.28%, E is 2.27%, M is 1.58%,
      P is 1.47%, C is 0.78%, Q is 0.75%, T is 0.68%, R is 0.10% and K
      is 0.06%
<220> FEATURE:
<221> NAME/KEY: MOD_RES
<222> LOCATION: (7)..(7)
<223> OTHER INFORMATION: D is 78.56%, G is 4.18%, E is 2.32%, A is
      1.94%, H is 1.84%, S is 1.39%, V is 1.34%, K is 1.04%, Y is 1.03%,
      F is 0.98%, L is 0.94%, N is 0.93%, R is 0.88%, C is 0.76%, P is
      0.68%, Q is 0.56%, T is 0.56% and I is 0.06%
<220> FEATURE:
<221> NAME/KEY: MOD_RES
<222> LOCATION: (8)..(8)
<223> OTHER INFORMATION: Y is 53.04%, G is 11.28%, S is 5.38%,  N is
      4.74%, P is 4.64%, D is 3.78%, V is 3.23%, R is 3.18%, I is 3.03%,
      F is 2.61%, K is 1.02%, L is 1.01%, H is 0.90%, A is 0.89%, W is
      0.58%, T is 0.53% and C is 0.06%
```

<400> SEQUENCE: 117

Xaa Xaa Xaa Xaa Xaa Xaa Xaa Xaa
1               5

<210> SEQ ID NO 118
<211> LENGTH: 9
<212> TYPE: PRT
<213> ORGANISM: Artificial Sequence
<220> FEATURE:
<223> OTHER INFORMATION: CDRH3 Length 9
<220> FEATURE:
<221> NAME/KEY: MOD_RES
<222> LOCATION: (1)..(1)
<223> OTHER INFORMATION: G is 43.79%, D is 20.00%, S is 5.55%, E is
      5.28%, R is 4.93%, L is 3.53%, V is 3.44%, K is 2.25%, H is
      1.92%, I is 1.78%, Q is 1.51%, M is 1.29%, P is 0.98%, F is 0.96%,
      W is 0.93%, N is 0.68%, A is 0.55%, Y is 0.37%, T is 0.20% and C
      is 0.03%
<220> FEATURE:
<221> NAME/KEY: MOD_RES
<222> LOCATION: (2)..(2)
<223> OTHER INFORMATION: G is 17.08%, S is 9.50%, R is 9.19%, Y is
      7.46%, L is 6.35%, H is 5.60%, I is 5.54%, A is 4.66%, E is
      4.51%, D is 4.20%, Q is 3.63%, P is 3.49%, W is 3.49%, T is 2.87%,
      N is 2.83%, V is 2.52%, M is 2.41%, F is 1.92%, C is 1.69% and K
      is 1.04%
<220> FEATURE:
<221> NAME/KEY: MOD_RES
<222> LOCATION: (3)..(3)
<223> OTHER INFORMATION: G is 14.76%, S is 10.20%, R is 9.45%, Y is
      7.77%, L is 6.64%, I is 6.01%, H is 5.34%, A is 4.14%, D is
      3.96%, Q is 3.93%, E is 3.89%, W is 3.73%, P is 3.57%, N is 3.24%,
      M is 2.88%, T is 2.88%, F is 2.31%, V is 2.18%, C is 1.92% and K
      is 1.19%
<220> FEATURE:
<221> NAME/KEY: MOD_RES
<222> LOCATION: (4)..(4)
<223> OTHER INFORMATION: G is 15.10%, S is 9.89%, R is 9.10%, Y is
      8.27%, L is 6.55%, I is 6.14%, H is 5.83%, D is 4.32%, E is 4.04%,
      P is 3.96%, A is 3.89%, Q is 3.66%, N is 3.36%, W is 3.21%, M is
      2.72%, T is 2.54%, V is 2.15%, F is 2.13%, C is 2.04% and K is
      1.06%
<220> FEATURE:
<221> NAME/KEY: MOD_RES
<222> LOCATION: (5)..(5)
<223> OTHER INFORMATION: G is 15.44%, S is 9.76%, R is 9.50%, Y is
      8.03%, L is 6.30%, I is 5.78%, H is 5.55%, D is 4.27%, A is
      4.14%, E is 3.79%, P is 3.79%, Q is 3.75%, N is 3.13%, W is 3.05%,
      M is 2.82%, T is 2.75%, V is 2.52%, F is 2.36%, C is 2.13% and K
      is 1.07%
<220> FEATURE:
<221> NAME/KEY: MOD_RES
<222> LOCATION: (6)..(6)
<223> OTHER INFORMATION: A is 24.67%, G is 12.08%, P is 9.19%, Y is
      9.02%, S is 7.51%, W is 4.71%, D is 4.17%, N is 3.94%, L is
      3.84%, H is 3.44%, R is 3.21%, T is 2.51%, F is 2.05%, E is 1.94%,
      V is 1.78%, I is 1.53%, M is 1.45%, K is 1.09%, C is 1.01% and Q
      is 0.85%
<220> FEATURE:
<221> NAME/KEY: MOD_RES
<222> LOCATION: (7)..(7)
<223> OTHER INFORMATION: F is 44.15%, L is 11.63%, Y is 8.50%, I is
      6.87%, S is 5.49%, M is 4.61%, P is 3.71%, V is 3.11%, A is
      2.65%, G is 2.13%, H is 1.55%, Q is 1.55%, N is 1.12%, D is 0.99%,
      W is 0.85%, T is 0.80%, E is 0.15%, R is 0.07% and C is 0.03%
<220> FEATURE:
<221> NAME/KEY: MOD_RES
<222> LOCATION: (8)..(8)
<223> OTHER INFORMATION: D is 76.27%, G is 4.51%, E is 2.20%, H is
      2.12%, A is 1.94%, S is 1.82%, V is 1.66%, L is 1.12%, Y is 1.07%,
      K is 1.06%, P is 1.06%, C is 0.96%, N is 0.93%, F is 0.86%, R is
      0.83%, Q is 0.77%, T is 0.75% and I is 0.05%
<220> FEATURE:
<221> NAME/KEY: MOD_RES
<222> LOCATION: (9)..(9)
<223> OTHER INFORMATION: Y is 50.77%, G is 10.94%, S is 5.41%, P is 5.26%, N is 4.74%, D is 4.10%, R is 3.97%, V is 3.83%, I is 3.11%, F is 2.59%, L is 1.17%, H is 1.04%, K is 0.94%, A is 0.88%, W is 0.55%, T is 0.44%, C is 0.10%, M is 0.03% and Q is 0.03%

<400> SEQUENCE: 118

Xaa Xaa Xaa Xaa Xaa Xaa Xaa Xaa Xaa
1               5

<210> SEQ ID NO 119
<211> LENGTH: 10
<212> TYPE: PRT
<213> ORGANISM: Artificial Sequence
<220> FEATURE:
<223> OTHER INFORMATION: CDRH3 Length 10
<220> FEATURE:
<221> NAME/KEY: MOD_RES
<222> LOCATION: (1)..(1)
<223> OTHER INFORMATION: G is 27.45%, D is 23.76%, E is 14.63%, V is 7.40%, R is 5.28%, Y is 3.59%, S is 2.96%, L is 2.25%, H is 1.88%, M is 1.81%, K is 1.68%, Q is 1.61%, W is 1.51%, P is 1.42%, I is 0.91%, A is 0.69%, N is 0.66%, T is 0.34%, F is 0.12% and C is 0.05%
<220> FEATURE:
<221> NAME/KEY: MOD_RES
<222> LOCATION: (2)..(2)
<223> OTHER INFORMATION: G is 16.66%, S is 9.67%, R is 9.13%, Y is 7.84%, L is 6.40%, I is 5.96%, D is 5.13%, H is 4.91%, E is 4.59%, A is 4.11%, Q is 3.45%, W is 3.40%, P is 3.12%, N is 2.95%, M is 2.78%, T is 2.74%, F is 2.44%, V is 1.93%, C is 1.79% and K is 0.97%
<220> FEATURE:
<221> NAME/KEY: MOD_RES
<222> LOCATION: (3)..(3)
<223> OTHER INFORMATION: G is 16.34%, S is 10.57%, R is 9.97%, Y is 7.87%, L is 6.01%, H is 5.52%, I is 5.08%, D is 3.98%, E is 3.86%, A is 3.71%, Q is 3.71%, P is 3.57%, W is 3.44%, N is 3.25%, T is 2.86%, M is 2.79%, V is 2.47%, F is 2.27%, C is 1.51% and K is 1.20%
<220> FEATURE:
<221> NAME/KEY: MOD_RES
<222> LOCATION: (4)..(4)
<223> OTHER INFORMATION: G is 16.80%, S is 10.43%, R is 9.70%, Y is 8.04%, I is 5.94%, L is 5.38%, H is 5.16%, D is 4.33%, E is 4.18%, A is 3.88%, W is 3.79%, Q is 3.52%, N is 3.15%, P is 2.78%, F is 2.49%, M is 2.42%, T is 2.40%, V is 2.35%, C is 1.76% and K is 1.44%
<220> FEATURE:
<221> NAME/KEY: MOD_RES
<222> LOCATION: (5)..(5)
<223> OTHER INFORMATION: G is 14.66%, S is 10.29%, R is 10.04%, Y is 8.36%, L is 5.79%, H is 5.28%, I is 5.20%, E is 4.61%, D is 4.15%, W is 4.01%, A is 4.00%, Q is 3.93%, M is 3.22%, N is 3.22%, P is 3.00%, T is 2.54%, V is 2.40%, F is 2.18%, C is 1.86% and K is 1.19%
<220> FEATURE:
<221> NAME/KEY: MOD_RES
<222> LOCATION: (6)..(6)
<223> OTHER INFORMATION: G is 15.31%, S is 10.45%, R is 9.91%, Y is 9.13%, I is 5.44%, H is 5.35%, L is 4.72%, D is 4.71%, A is 4.20%, E is 4.18%, W is 3.40%, Q is 3.20%, M is 3.18%, N is 3.10%, P is 2.81%, F is 2.78%, V is 2.62%, T is 2.56%, C is 1.73% and K is 1.22%
<220> FEATURE:
<221> NAME/KEY: MOD_RES
<222> LOCATION: (7)..(7)
<223> OTHER INFORMATION: A is 26.92%, G is 16.10%, Y is 11.80%, D is 5.98%, W is 5.79%, S is 4.45%, R is 4.20%, P is 4.00%, L is 3.42%, H is 2.79%, F is 2.64%, E is 2.62%, I is 2.57%, V is 2.17%, T is 1.98%, N is 1.22%, Q is 1.02%, K is 0.10%, M is 0.10% and C is 0.07%
<220> FEATURE:
<221> NAME/KEY: MOD_RES
<222> LOCATION: (8)..(8)
<223> OTHER INFORMATION: F is 55.93%, L is 8.74%, M is 5.33%, Y is 5.15%, G is 5.11%, I is 5.05%, S is 3.78%, E is 2.30%, V is 1.78%, N is 1.35%, P is 1.22%, C is 1.15%, W is 1.15%, H is 0.91%, T is 0.54%, D is 0.22%, A is 0.17%, R is 0.07% and Q is 0.03%

```
<220> FEATURE:
<221> NAME/KEY: MOD_RES
<222> LOCATION: (9)..(9)
<223> OTHER INFORMATION: D is 79.00%,  G is 3.86%, E is 2.13%, H is
      1.98%, A is 1.74%, S is 1.54%, K is 1.32%, R is 1.12%, V is 1.10%,
      Y is 1.08%, N is 0.91%, L is 0.90%, C is 0.85%, P is 0.78%, Q is
      0.66%, F is 0.56%, T is 0.37%, I is 0.05% and M is 0.03%
<220> FEATURE:
<221> NAME/KEY: MOD_RES
<222> LOCATION: (10)..(10)
<223> OTHER INFORMATION: Y is 50.54%, G is 12.58%, S is 6.42%,  N is
      4.76%, P is 4.08%, D is 4.05%, R is 3.81%, V is 3.61%, I is 3.03%,
      F is 2.32%, K is 1.02%, A is 0.98%, H is 0.85%, W is 0.81%, L is
      0.61%, T is 0.44% and C is 0.03%

<400> SEQUENCE: 119

Xaa Xaa Xaa Xaa Xaa Xaa Xaa Xaa Xaa Xaa
1               5                   10

<210> SEQ ID NO 120
<211> LENGTH: 11
<212> TYPE: PRT
<213> ORGANISM: Artificial Sequence
<220> FEATURE:
<223> OTHER INFORMATION: CDRH3 Length 11
<220> FEATURE:
<221> NAME/KEY: MOD_RES
<222> LOCATION: (1)..(1)
<223> OTHER INFORMATION: G is 26.14%, D is 24.10%, E is 13.67%, V is
      7.72%, R is 5.62%,  A is 0.58%, C is 0.16%, F is 0.10%, H is
      2.04%, I is 0.80%, K is 1.93%, L is 2.37%, M is 1.83%, N is 0.68%,
      P is 1.61%, Q is 1.96%, S is 2.53%, T is 0.29%, W is 1.67% and Y
      is 4.10%
<220> FEATURE:
<221> NAME/KEY: MOD_RES
<222> LOCATION: (2)..(2)
<223> OTHER INFORMATION: G is 15.23%, S is 9.80%, R is 9.57%, Y is
      7.08%, L is 6.77%, I is 6.30%, H is 5.17%,  A is 4.53%, C is
      1.60%, D is 4.03%, E is 4.79%, F is 2.30%, K is 1.30%, M is 2.55%,
      N is 2.74%, P is 3.72%, Q is 3.79%, T is 2.66%, V is 2.51% and W
      is 3.56%
<220> FEATURE:
<221> NAME/KEY: MOD_RES
<222> LOCATION: (3)..(3)
<223> OTHER INFORMATION: G is 14.63%, S is 10.56%, R is 10.06%, Y is
      7.37%, L is 6.21%, I is 6.13%, H is 5.15%,   A is 4.34%, C is
      2.06%, D is 4.01%, E is 4.08%, F is 2.51%, K is 1.21%, M is 3.01%,
      N is 2.98%, P is 2.90%, Q is 3.70%, T is 3.25%, V is 2.16% and W
      is 3.66%
<220> FEATURE:
<221> NAME/KEY: MOD_RES
<222> LOCATION: (4)..(4)
<223> OTHER INFORMATION: G is 15.29%, R is 10.35%, S is 9.76%, Y is
      8.99%, L is 5.56%, I is 5.49%, H is 5.15%,  A is 4.01%, C is
      1.61%, D is 4.05%, E is 4.47%, F is 2.24%, K is 1.03%, M is 2.82%,
      N is 3.40%, P is 3.27%, Q is 3.85%, T is 2.82%, V is 2.24% and W
      is 3.54%
<220> FEATURE:
<221> NAME/KEY: MOD_RES
<222> LOCATION: (5)..(5)
<223> OTHER INFORMATION: G is 14.88%, S is 11.42%, R is 9.61%, Y is
      8.34%, L is 6.05%, I is 5.41%, H is 5.14%,  A is 4.53%, C is
      1.54%, D is 4.53%, E is 3.93%, F is 2.47%, K is 1.44%, M is 2.74%,
      N is 2.98%, P is 3.07%, Q is 3.81%, T is 2.49%, V is 2.26% and W
      is 3.37%
<220> FEATURE:
<221> NAME/KEY: MOD_RES
<222> LOCATION: (6)..(6)
<223> OTHER INFORMATION: G is 16.13%,  S is 10.60%, R is 9.14%, Y is
      8.52%, I is 5.84%, H is 5.31%, L is 5.27%,  A is 3.66%, C is
      1.81%, D is 4.28%, E is 4.45%, F is 2.43%, K is 1.23%, M is 2.82%,
      N is 3.33%, P is 2.90%, Q is 3.38%, T is 2.70%, V is 2.14% and W
      is 4.01%
<220> FEATURE:
<221> NAME/KEY: MOD_RES
<222> LOCATION: (7)..(7)
<223> OTHER INFORMATION: G is 14.84%, S is 10.37%, R is 10.00%, Y is
```

```
            8.87%, I is 5.89%, H is 5.21%, L is 5.21%, A is 4.32%, C is
            1.63%, D is 4.98%, E is 4.30%, F is 2.24%, K is 1.19%, M is 3.07%,
            N is 3.54%, P is 2.98%, Q is 3.29%, T is 2.43%, V is 2.41% and W
            is 3.17%
<220> FEATURE:
<221> NAME/KEY: MOD_RES
<222> LOCATION: (8)..(8)
<223> OTHER INFORMATION: A is 20.31%, Y is 19.12%, G is 14.26%, S is
            6.17%, P is 5.78%,  C is 1.07%, D is 4.90%, E is 1.21%, F is
            2.10%, H is 1.52%, I is 2.22%, K is 1.52%, L is 2.74%, M is 0.06%,
            N is 4.20%, Q is 0.95%, R is 2.18%, T is 3.85%, V is 1.07% and W
            is 4.77%
<220> FEATURE:
<221> NAME/KEY: MOD_RES
<222> LOCATION: (9)..(9)
<223> OTHER INFORMATION: F is 54.27%, M is 12.12%, L is 11.52%,  A is
            0.04%, C is 0.91%, D is 1.09%, E is 1.17%, G is 2.61%, H is 0.10%,
            I is 4.34%, N is 0.97%, P is 3.05%, Q is 0.78%, S is 1.13%, T is
            0.54%, V is 2.63%, W is 0.93% and Y is 1.77%
<220> FEATURE:
<221> NAME/KEY: MOD_RES
<222> LOCATION: (10)..(10)
<223> OTHER INFORMATION: D is 77.57%,  A is 1.65%, C is 0.54%, E is
            2.04%, F is 0.58%, G is 3.93%, H is 2.28%, K is 1.21%, L is 1.09%,
            N is 1.26%, P is 0.99%, Q is 0.66%, R is 1.11%, S is 1.95%, T is
            0.62%, V is 1.34%, and Y is 1.11%
<220> FEATURE:
<221> NAME/KEY: MOD_RES
<222> LOCATION: (11)..(11)
<223> OTHER INFORMATION: Y is 49.60%, G is 11.15%, S is 6.21%, A is
            0.82%, C is 0.04%, D is 4.49%, F is 2.76%, H is 0.78%, I is 3.42%,
            K is 1.34%, L is 0.70%, M is 0.08%, N is 4.40%, P is 4.22%, R is
            4.14%, T is 0.47%, V is 4.71% and W is 0.62%

<400> SEQUENCE: 120

Xaa Xaa Xaa Xaa Xaa Xaa Xaa Xaa Xaa Xaa Xaa
1               5                   10

<210> SEQ ID NO 121
<211> LENGTH: 12
<212> TYPE: PRT
<213> ORGANISM: Artificial Sequence
<220> FEATURE:
<223> OTHER INFORMATION: CDRH3 Length 12
<220> FEATURE:
<221> NAME/KEY: MOD_RES
<222> LOCATION: (1)..(1)
<223> OTHER INFORMATION: G is 26.20%, D is 24.18%, E is 14.76%, V is
            7.81%, R is 5.18%,  Y is 3.56%, S is 2.82%, L is 2.21%, H is
            2.11%, M is 1.96%, Q is 1.83%, P is 1.62%, W is 1.58%, K is 1.47%,
            I is 0.95%, A is 0.72%, N is 0.59%, T is 0.23%, C is 0.13% and F
            is 0.06%
<220> FEATURE:
<221> NAME/KEY: MOD_RES
<222> LOCATION: (2)..(2)
<223> OTHER INFORMATION: G is 16.11%, R is 10.28%, S is 10.09%, Y is
            7.31%, L is 5.96%, I is 5.73%, H is 5.31%,  E is 4.74%, D is
            4.51%, Q is 3.98%, A is 3.60%, P is 3.52%, N is 3.31%, W is 2.82%,
            M is 2.67%, T is 2.63%, F is 2.42%, V is 2.09%, C is 1.71% and K
            is 1.16%
<220> FEATURE:
<221> NAME/KEY: MOD_RES
<222> LOCATION: (3)..(3)
<223> OTHER INFORMATION: G is 15.16%, S is 10.21%, R is 10.15%, Y is
            8.19%, L is 6.55%, I is 6.19%, H is 5.69%,  E is 4.17%, Q is
            4.02%, D is 3.77%, N is 3.58%, P is 3.50%, A is 3.43%, W is 3.18%,
            T is 2.65%, M is 2.51%, F is 2.08%, V is 2.04%, C is 1.90% and K
            is 1.01%
<220> FEATURE:
<221> NAME/KEY: MOD_RES
<222> LOCATION: (4)..(4)
<223> OTHER INFORMATION: G is 16.07%, R is 10.64%, S is 9.77%, Y is
            7.25%, L is 6.13%, I is 5.92%,  H is 4.59%, E is 4.57%, D is
            4.09%, A is 4.04%, W is 3.62%, P is 3.43%, Q is 3.43%, N is 3.12%,
            M is 2.99%, T is 2.91%, F is 2.44%, V is 2.04%, C is 1.77% and K
            is 1.10%
<220> FEATURE:
```

```
<221> NAME/KEY: MOD_RES
<222> LOCATION: (5)..(5)
<223> OTHER INFORMATION: G is 15.00%, S is 10.43%, R is 10.28%, Y is
      8.13%, L is 5.79%, H is 5.48%, I is 5.37%, Q is 4.36%, E is
      4.25%, D is 4.23%, A is 3.96%, W is 3.67%, P is 3.64%, N is 3.24%,
      M is 2.68%, T is 2.23%, V is 2.21%, F is 1.88%, C is 1.79% and K
      is 1.33%
<220> FEATURE:
<221> NAME/KEY: MOD_RES
<222> LOCATION: (6)..(6)
<223> OTHER INFORMATION: G is 15.16%, S is 10.47%, R is 10.11%, Y is
      7.79%, I is 6.55%, L is 5.69%, H is 5.20%, E is 4.53%, D is
      4.49%, A is 4.17%, W is 3.66%, Q is 3.37%, N is 3.27%, M is 2.78%,
      P is 2.72%, F is 2.46%, T is 2.38%, V is 2.19%, C is 1.66% and K
      is 1.35%
<220> FEATURE:
<221> NAME/KEY: MOD_RES
<222> LOCATION: (7)..(7)
<223> OTHER INFORMATION: G is 14.95%, R is 10.11%, S is 10.03%, Y is
      8.57%, H is 6.68%, I is 5.60%, L is 5.35%, D is 4.07%, A is
      3.96%, E is 3.96%, N is 3.62%, P is 3.35%, W is 3.16%, Q is 3.03%,
      M is 2.97%, F is 2.59%, T is 2.55%, V is 2.32%, C is 1.81% and K
      is 1.28%
<220> FEATURE:
<221> NAME/KEY: MOD_RES
<222> LOCATION: (8)..(8)
<223> OTHER INFORMATION: G is 18.74%, Y is 18.39%, D is 13.25%, N is
      6.42%, S is 5.69%, R is 5.52%, P is 4.82%, H is 3.26%, E is
      2.74%, T is 2.68%, V is 2.59%, A is 2.51%, I is 2.36%, F is 2.34%,
      C is 1.87%, W is 1.47%, K is 1.45%, L is 1.41%, Q is 1.22% and M
      is 1.14%
<220> FEATURE:
<221> NAME/KEY: MOD_RES
<222> LOCATION: (9)..(9)
<223> OTHER INFORMATION: G is 20.39%, A is 18.34%, Y is 17.65%, W is
      9.03%, P is 6.23%, S is 4.34%, R is 2.88%, L is 2.74%, C is 2.48%,
      T is 2.38%, F is 2.17%, H is 2.02%, M is 1.81%, D is 1.58%, V is
      1.37%, N is 1.28%, I is 1.16%, E is 1.09%, Q is 0.80% and K is
      0.15%
<220> FEATURE:
<221> NAME/KEY: MOD_RES
<222> LOCATION: (10)..(10)
<223> OTHER INFORMATION: F is 52.70%, L is 12.64%, M is 11.69%, I is
      4.76%, P is 3.16%, G is 3.03%, V is 2.44%, Y is 1.73%, S is 1.31%,
      E is 1.16%, D is 1.10%, W is 0.93%, N is 0.89%, Q is 0.86%, T is
      0.74%, C is 0.65% and A is 0.15%
<220> FEATURE:
<221> NAME/KEY: MOD_RES
<222> LOCATION: (11)..(11)
<223> OTHER INFORMATION: D is 78.03%, G is 4.09%, E is 2.06%, A is
      1.87%, H is 1.87%, S is 1.58%, K is 1.43%, V is 1.41%, N is 1.14%,
      L is 1.01%, Y is 0.99%, T is 0.88%, P is 0.82%, R is 0.80%, Q is
      0.67%, F is 0.65%, C is 0.57%, I is 0.06% and M is 0.04%
<220> FEATURE:
<221> NAME/KEY: MOD_RES
<222> LOCATION: (12)..(12)
<223> OTHER INFORMATION: Y is 49.52%, G is 11.90%, S is 6.26%, N is
      4.65%, D is 4.36%, V is 4.27%, P is 3.96%, I is 3.60%, R is 3.50%,
      F is 2.49%, K is 1.20%, A is 0.95%, W is 0.88%, L is 0.86%, H is
      0.84%, T is 0.48%, M is 0.11%, C is 0.06% and E is 0.04%

<400> SEQUENCE: 121

Xaa Xaa Xaa Xaa Xaa Xaa Xaa Xaa Xaa Xaa Xaa Xaa
1               5                   10

<210> SEQ ID NO 122
<211> LENGTH: 13
<212> TYPE: PRT
<213> ORGANISM: Artificial Sequence
<220> FEATURE:
<223> OTHER INFORMATION: CDRH3 Length 13
<220> FEATURE:
<221> NAME/KEY: MOD_RES
<222> LOCATION: (1)..(1)
<223> OTHER INFORMATION: G is 25.88%, D is 22.97%, E is 14.18%, V is
      7.62%, R is 5.85%, A is 0.73%, C is 0.10%, F is 0.02%, H is
      2.15%, I is 0.79%, K is 2.03%, L is 2.46%, M is 2.09%, N is 0.61%,
```

P is 1.86%, Q is 1.80%, S is 3.49%, T is 0.31%, W is 1.65% and Y
  is 3.34%
<220> FEATURE:
<221> NAME/KEY: MOD_RES
<222> LOCATION: (2)..(2)
<223> OTHER INFORMATION: G is 16.85%, S is 10.07%, R is 9.77%, Y is
  7.60%, L is 5.83%, H is 5.41%, I is 5.24%, A is 4.72%, C is 1.92%,
  D is 4.39%, E is 4.43%, F is 2.09%, K is 1.04%, M is 2.46%, N is
  3.28%, P is 3.70%, Q is 3.05%, T is 2.69%, V is 2.13% and W is
  3.24%
<220> FEATURE:
<221> NAME/KEY: MOD_RES
<222> LOCATION: (3)..(3)
<223> OTHER INFORMATION: G is 15.48%, S is 10.67%, R is 9.46%, Y is
  7.41%, I is 6.52%, L is 6.45%, H is 5.03%, A is 4.39%, C is
  1.86%, D is 4.03%, E is 3.78%, F is 2.13%, K is 1.42%, M is 2.78%,
  N is 3.34%, P is 3.49%, Q is 3.53%, T is 2.92%, V is 2.07% and W
  is 3.20%
<220> FEATURE:
<221> NAME/KEY: MOD_RES
<222> LOCATION: (4)..(4)
<223> OTHER INFORMATION: G is 15.20%, S is 10.44%, R is 9.38%, Y is
  7.54%, L is 6.10%, H is 5.91%, I is 5.51%, A is 4.18%, C is
  1.71%, D is 4.51%, E is 4.26%, F is 2.28%, K is 1.25%, M is 2.90%,
  N is 3.07%, P is 3.53%, Q is 3.43%, T is 2.74%, V is 2.51% and W
  is 3.45%
<220> FEATURE:
<221> NAME/KEY: MOD_RES
<222> LOCATION: (5)..(5)
<223> OTHER INFORMATION: G is 16.10%, S is 10.23%, R is 9.86%, Y is
  7.58%, L is 5.64%, H is 5.53%, I is 5.24%, A is 4.43%, C is
  1.84%, D is 4.62%, E is 4.22%, F is 2.44%, K is 1.50%, M is 2.57%,
  N is 3.47%, P is 3.07%, Q is 3.82%, T is 2.46%, V is 2.28% and W
  is 3.03%
<220> FEATURE:
<221> NAME/KEY: MOD_RES
<222> LOCATION: (6)..(6)
<223> OTHER INFORMATION: G is 15.39%, S is 10.36%, R is 9.94%, Y is
  7.81%, I is 6.58%, H is 5.60%, L is 5.33%, A is 3.47%, C is
  1.75%, D is 4.47%, E is 4.55%, F is 2.32%, K is 1.34%, M is 2.59%,
  N is 3.22%, P is 3.07%, Q is 3.72%, T is 2.84%, V is 2.28% and W
  is 3.38%
<220> FEATURE:
<221> NAME/KEY: MOD_RES
<222> LOCATION: (7)..(7)
<223> OTHER INFORMATION: G is 15.12%, S is 10.36%, R is 9.90%, Y is
  8.67%, L is 6.24%, I is 5.45%, H is 5.05%, A is 3.76%, C is 1.78%,
  D is 4.72%, E is 4.62%, F is 2.49%, K is 1.27%, M is 2.53%, N is
  3.32%, P is 3.24%, Q is 3.51%, T is 2.59%, V is 1.86% and W is
  3.51%
<220> FEATURE:
<221> NAME/KEY: MOD_RES
<222> LOCATION: (8)..(8)
<223> OTHER INFORMATION: G is 13.99%, S is 10.32%, R is 9.54%, Y is
  9.31%, L is 6.12%, I is 5.68%, H is 5.30%, A is 4.09%, C is
  1.73%, D is 4.80%, E is 3.97%, F is 2.40%, K is 1.67%, M is 2.88%,
  N is 3.34%, P is 3.24%, Q is 3.22%, T is 2.49%, V is 2.23% and W
  is 3.63%
<220> FEATURE:
<221> NAME/KEY: MOD_RES
<222> LOCATION: (9)..(9)
<223> OTHER INFORMATION: Y is 18.73%, G is 17.44%, D is 10.42%, N is
  9.54%, S is 7.31%, R is 5.14%, A is 2.67%, C is 1.78%, E is
  3.84%, F is 4.51%, H is 3.40%, I is 1.61%, K is 2.72%, L is 2.38%,
  M is 0.06%, P is 1.98%, Q is 0.81%, T is 2.36%, V is 2.42 and W is
  0.86%
<220> FEATURE:
<221> NAME/KEY: MOD_RES
<222> LOCATION: (10)..(10)
<223> OTHER INFORMATION: A is 21.07%, Y is 19.84%, G is 18.30%, W is
  6.83%, C is 2.17%, D is 2.32%, E is at 1.59%, F is 4.85%, H is
  1.46%, I is 2.11%, K is 1.52%, L is 2.07%, M is 1.44%, N is 2.13%,
  P is 4.26%, Q is 0.08%, R is 1.34%, S is 3.72%, T is 1.02% and V
  is 1.86%
<220> FEATURE:
<221> NAME/KEY: MOD_RES
<222> LOCATION: (11)..(11)
<223> OTHER INFORMATION: F is 54.39%, L is 12.43%, M is 11.51%, C is
  0.81%, D is 1.21%, E is 1.11%, G is 2.74%, H is 0.06%, I is 4.34%, N is 0.94%, P is 2.61%, Q is 0.94%, S is 0.98%, T is 0.48%, V is
2.23%, W is 1.00% and Y is 2.13%
<220> FEATURE:
<221> NAME/KEY: MOD_RES
<222> LOCATION: (12)..(12)
<223> OTHER INFORMATION: D is 77.80, A is 1.92%, C is 0.50%, E is
2.19%, F is 0.86%, G is 4.03%, H is 1.84%, I is 0.10%, K is 1.27%,
L is 1.11%, N is 1.11%, P is 0.75%, Q is 0.69%, R is 0.81%, S is
1.98%, T is 0.69%, V is 1.44%, and Y is 0.81%
<220> FEATURE:
<221> NAME/KEY: MOD_RES
<222> LOCATION: (13)..(13)
<223> OTHER INFORMATION: Y is 51.23%, G is 11.28%, S is 5.43%, V is
5.43%, A is 0.81%, C is 0.02%, D is 4.39%, F is 2.65%, H is 1.11%,
I is 3.86%, K is 0.86%, L is 0.96%, M is 0.04%, N is 4.16%, P is
3.38%, Q is 0.04%, R is 3.13%, T is 0.52% and W is 0.56%

<400> SEQUENCE: 122

Xaa Xaa Xaa Xaa Xaa Xaa Xaa Xaa Xaa Xaa Xaa Xaa Xaa
1               5                   10

<210> SEQ ID NO 123
<211> LENGTH: 14
<212> TYPE: PRT
<213> ORGANISM: Artificial Sequence
<220> FEATURE:
<223> OTHER INFORMATION: CDRH3 Length 14
<220> FEATURE:
<221> NAME/KEY: MOD_RES
<222> LOCATION: (1)..(1)
<223> OTHER INFORMATION: G is 24.96%, D is 23.95%, E is 15.20%, V is
6.94%, R is 5.78%, Y is 3.32%, S is 3.08%, L is 2.72%, M is
2.26%, H is 2.22%, Q is 2.17%, P is 1.82%, W is 1.63%, K is 1.49%,
A is 0.81%, I is 0.70%, N is 0.46%, T is 0.35% and C is 0.07%
<220> FEATURE:
<221> NAME/KEY: MOD_RES
<222> LOCATION: (2)..(2)
<223> OTHER INFORMATION: G is 17.46%, R is 9.69%, S is 9.42%, Y is
7.05%, L is 5.76%, I is 5.47%, E is 4.68%, D is 4.66%, H is
4.66%, A is 4.46%, P is 3.58%, N is 3.49%, W is 3.25%, Q is 2.99%,
M is 2.77%, T is 2.64%, F is 2.48%, V is 2.37%, C is 1.80% and K
is 1.30%
<220> FEATURE:
<221> NAME/KEY: MOD_RES
<222> LOCATION: (3)..(3)
<223> OTHER INFORMATION: G is 16.37%, S is 10.22%, R is 8.94%, Y is
7.10%, L is 6.85%, I is 6.24%, H is 5.16%, E is 4.15%, D is
3.91%, W is 3.80%, Q is 3.65%, A is 3.58%, N is 3.56%, P is 3.41%,
M is 3.12%, F is 2.33%, T is 2.26%, C is 2.02%, V is 1.89% and K
is 1.41%
<220> FEATURE:
<221> NAME/KEY: MOD_RES
<222> LOCATION: (4)..(4)
<223> OTHER INFORMATION: G is 14.54%, S is 10.61%, R is 9.53%, Y is
7.54%, I is 6.41%, L is 6.26%, H is 5.43%, D is 4.35%, E is
4.04%, A is 3.62%, N is 3.41%, Q is 3.41%, T is 3.25%, M is 3.16%,
P is 3.10%, W is 2.94%, V is 2.55%, F is 2.42%, C is 2.00% and K
is 1.43%
<220> FEATURE:
<221> NAME/KEY: MOD_RES
<222> LOCATION: (5)..(5)
<223> OTHER INFORMATION: G is 15.69%, S is 10.76%, R is 10.04%, Y is
7.89%, L is 5.89%, I is 5.78%, H is 5.40%, D is 4.96%, E is
4.28%, A is 4.26%, Q is 3.30%, N is 3.23%, W is 3.01%, P is 2.86%,
M is 2.70%, F is 2.37%, T is 2.33%, V is 2.17%, C is 1.58% and K
is 1.45%
<220> FEATURE:
<221> NAME/KEY: MOD_RES
<222> LOCATION: (6)..(6)
<223> OTHER INFORMATION: G is 15.03%, S is 10.35%, R is 9.89%, Y is
7.86%, L is 5.82%, I is 5.76%, H is 5.27%, D is 4.59%, E is
4.15%, A is 4.02%, N is 3.58%, P is 3.45%, Q is 3.45%, W is 3.41%,
F is 3.01%, T is 2.64%, M is 2.59%, V is 2.17%, C is 1.49% and K
is 1.38%
<220> FEATURE:
<221> NAME/KEY: MOD_RES
<222> LOCATION: (7)..(7)

```
<223> OTHER INFORMATION: G is 14.63%, S is 11.47%, R is 9.82%, Y is
      7.91%, I is 6.37%, L is 5.62%, H is 5.16%, E is 4.75%, D is
      4.42%, A is 4.20%, Q is 3.32%, W is 3.32%, N is 3.27%, M is 2.75%,
      P is 2.50%, T is 2.50%, F is 2.42%, V is 2.24%, C is 1.87% and K
      is 1.36%
<220> FEATURE:
<221> NAME/KEY: MOD_RES
<222> LOCATION: (8)..(8)
<223> OTHER INFORMATION: G is 14.78%, S is 11.07%, R is 10.26%, Y is
      8.72%, I is 5.60%, L is 5.40%, H is 5.03%, D is 4.81%, E is
      4.81%, A is 4.11%, W is 3.38%, N is 3.25%, P is 3.05%, Q is 2.88%,
      M is 2.83%, V is 2.42%, T is 2.37%, F is 2.22%, C is 1.49% and K
      is 1.47%
<220> FEATURE:
<221> NAME/KEY: MOD_RES
<222> LOCATION: (9)..(9)
<223> OTHER INFORMATION: G is 14.10%, S is 11.16%, R is 10.22%, Y is
      8.72%, I is 5.56%, H is 5.43%, L is 5.14%, D is 4.92%, E is
      4.92%, A is 3.76%, Q is 3.49%, N is 3.19%, W is 3.08%, M is
      2.86%, F is 2.79%, P is 2.53%, T is 2.17%, V is 2.17%, C is 2.09%
      and K is 1.60%
<220> FEATURE:
<221> NAME/KEY: MOD_RES
<222> LOCATION: (10)..(10)
<223> OTHER INFORMATION: Y is 15.55%, R is 10.26%, G is 8.88%, P is
      7.32%, D is 6.57%, I is 5.93%, E is 5.78%, A is 5.16%, S is
      4.75%, V is 4.57%, L is 4.22%, F is 4.02%, Q is 3.98%, T is 3.03%,
      W is 2.11%, N is 2.04%, C is 1.93%, M is 1.41%, K is 1.27% and H
      is 1.16%
<220> FEATURE:
<221> NAME/KEY: MOD_RES
<222> LOCATION: (11)..(11)
<223> OTHER INFORMATION: A is 20.45%, G is 19.46%, Y is 16.61%, W is
      9.47%, P is 5.36%, F is 4.09%, S is 3.30%, L is 3.19%, H is
      2.77%, T is 2.57%, V is 2.57%, N is 2.37%, C is 2.17%, R is 1.82%,
      K is 1.58%, D is 1.19%, I is 0.70%, E is 0.15% and Q is 0.09%
<220> FEATURE:
<221> NAME/KEY: MOD_RES
<222> LOCATION: (12)..(12)
<223> OTHER INFORMATION: F is 54.77%, L is 11.97%, M is 10.79%, I is
      4.88%, G is 3.12%, P is 3.05%, V is 2.33%, Y is 1.78%, D is 1.23%,
      E is 1.05%, N is 0.92%, S is 0.90%, W is 0.88%, C is 0.83%, Q is
      0.77%, T is 0.59% and A is 0.09%
<220> FEATURE:
<221> NAME/KEY: MOD_RES
<222> LOCATION: (13)..(13)
<223> OTHER INFORMATION: D is 77.07%, G is 4.37%, E is 2.11%, H is
      1.98%, A is 1.93%, S is 1.85%, N is 1.54%, V is 1.45%, K is 1.05%,
      L is 1.05%, Q is 0.90%, R is 0.90%, Y is 0.86%, C is 0.81%, P is
      0.81%, F is 0.70%, T is 0.57% and I is 0.04%
<220> FEATURE:
<221> NAME/KEY: MOD_RES
<222> LOCATION: (14)..(14)
<223> OTHER INFORMATION: Y is 46.09%, V is 17.38%, I is 16.17%, S is
      4.88%, H is 3.21%, N is 2.94%, D is 2.66%, F is 1.96%, A is 1.16%,
      R is 1.14%, L is 0.83%, T is 0.75%, G is 0.26%, P is 0.26% and M
      is 0.13%

<400> SEQUENCE: 123

Xaa Xaa Xaa Xaa Xaa Xaa Xaa Xaa Xaa Xaa Xaa Xaa Xaa Xaa
1               5                   10

<210> SEQ ID NO 124
<211> LENGTH: 15
<212> TYPE: PRT
<213> ORGANISM: Artificial Sequence
<220> FEATURE:
<223> OTHER INFORMATION: CDRH3 Length 15
<220> FEATURE:
<221> NAME/KEY: MOD_RES
<222> LOCATION: (1)..(1)
<223> OTHER INFORMATION: G is 24.51%, D is 24.03%, E is 14.58%, V is
      7.89%, R is 5.96%, Y is 2.98%, S is 2.91%, L is 2.82%, Q is
      2.43%, H is 2.18%, M is 2.13%, P is 1.65%, K is 1.63%, W is 1.22%,
      A is 0.92%, N is 0.80%, I is 0.78%, T is 0.37%, C is 0.07%, F is
      0.07%
<220> FEATURE:
```

```
<221> NAME/KEY: MOD_RES
<222> LOCATION: (2)..(2)
<223> OTHER INFORMATION: G is 17.63%, S is 10.41%, R is 10.13%, Y is
      7.06%, L is 6.19%, I is 5.89%, H is 4.75%, D is 4.03%, A is 4.01%,
      E is 3.85%, P is 3.44%, W is 3.42%, N is 3.32%, Q is 3.23%, M is
      2.89%, T is 2.75%, F is 2.02%, V is 1.97%, C is 1.63% and K is
      1.35%
<220> FEATURE:
<221> NAME/KEY: MOD_RES
<222> LOCATION: (3)..(3)
<223> OTHER INFORMATION: G is 15.77%, S is 9.74%, R is 9.26%, Y is
      7.75%, L is 6.05%, I is 5.73%, H is 5.64%, E is 4.79%, D is 4.49%,
      A is 4.45%, P is 3.62%, Q is 3.62%, W is 3.44%, M is 3.03%, N is
      2.91%, T is 2.45%, F is 2.25%, C is 1.88%, V is 1.74% and K is
      1.28%
<220> FEATURE:
<221> NAME/KEY: MOD_RES
<222> LOCATION: (4)..(4)
<223> OTHER INFORMATION: G is 15.41%, S is 11.03%, R is 9.58%, Y is
      7.82%, L is 6.21%, I is 5.46%, H is 5.14%, D is 4.03%, Q is 4.01%,
      A is 3.92%, E is 3.76%, P is 3.58%, W is 3.48%, N is 2.98%, M is
      2.93%, T is 2.66%, V is 2.48%, F is 2.29%, C is 1.99% and K is
      1.17%
<220> FEATURE:
<221> NAME/KEY: MOD_RES
<222> LOCATION: (5)..(5)
<223> OTHER INFORMATION: G is 15.06%, S is 10.84%, R is 10.32%, Y is
      7.40%, I is 5.75%, L is 5.43%, H is 4.75%, D is 4.49%, E is 4.42%,
      A is 3.99%, N is 3.42%, Q is 3.42%, W is 3.42%, P is 3.09%, F is
      2.82%, M is 2.75%, T is 2.73%, V is 2.29%, C is 2.02% and K is
      1.56%
<220> FEATURE:
<221> NAME/KEY: MOD_RES
<222> LOCATION: (6)..(6)
<223> OTHER INFORMATION: G is 15.15%, S is 10.80%, R is 10.09%, Y is
      7.15%, L is 6.12%, I is 5.96%, H is 5.59%, E is 4.26%, D is 4.15%,
      A is 4.10%, W is 3.69%, N is 3.46%, P is 3.12%, Q is 3.00%, M is
      2.98%, T is 2.45%, F is 2.43%, V is 2.20%, C is 2.04% and K is
      1.19%
<220> FEATURE:
<221> NAME/KEY: MOD_RES
<222> LOCATION: (7)..(7)
<223> OTHER INFORMATION: G is 15.77%, S is 11.33%, R is 9.01%, Y is
      7.91%, I is 6.28%, L is 5.82%, H is 4.86%, A is 4.68%, E is 4.29%,
      D is 4.24%, W is 3.65%, Q is 3.23%, M is 3.14%, N is 2.89%, P is
      2.66%, F is 2.38%, V is 2.18%, C is 2.13%, T is 1.97% and K is
      1.54%
<220> FEATURE:
<221> NAME/KEY: MOD_RES
<222> LOCATION: (8)..(8)
<223> OTHER INFORMATION: G is 14.51%, S is 11.65%, R is 9.67%, Y is
      7.29%, I is 5.91%, H is 5.82%, L is 4.91%, D is 4.68%, E is 4.49%,
      A is 4.36%, W is 4.15%, N is 3.44%, Q is 3.14%, T is 3.03%, M is
      2.73%, P is 2.61%, F is 2.32%, V is 2.32%, K is 1.54% and C is
      1.38%
<220> FEATURE:
<221> NAME/KEY: MOD_RES
<222> LOCATION: (9)..(9)
<223> OTHER INFORMATION: Y is 14.24%, R is 11.10%, G is 9.67%, P is
      7.66%, D is 6.17%, E is 5.50%, A is 5.48%, I is 5.34%, S is 5.20%,
      V is 4.86%, L is 4.70%, Q is 4.15%, F is 3.74%, T is 3.12%, N is
      1.93%, C is 1.79%, W is 1.77%, M is 1.35%, K is 1.17%, H is 1.01%
<220> FEATURE:
<221> NAME/KEY: MOD_RES
<222> LOCATION: (10)..(10)
<223> OTHER INFORMATION: Y is 15.13%, R is 10.45%, G is 9.31%, P is
      6.92%, D is 6.79%, E is 5.66%, I is 5.32%, S is 5.18%, L is 4.86%,
      A is 4.84%, Q is 4.72%, V is 4.72%, F is 3.23%, T is 2.84%, N is
      2.34%, W is 1.77%, C is 1.70%, M is 1.54%, H is 1.33% and K is
      1.31%
<220> FEATURE:
<221> NAME/KEY: MOD_RES
<222> LOCATION: (11)..(11)
<223> OTHER INFORMATION: Y is 16.25%, R is 9.67%, G is 8.78%, P is
      7.40%, D is 6.63%, I is 5.64%, A is 5.14%, E is 5.02%, V is 4.97%,
      S is 4.91%, L is 4.47%, Q is 4.10%, F is 4.03%, T is 2.82%, N is
      2.73%, C is 2.06%, W is 1.51%, M is 1.44%, K is 1.33% and H is
      0.92%
<220> FEATURE:
```

```
<221> NAME/KEY: MOD_RES
<222> LOCATION: (12)..(12)
<223> OTHER INFORMATION: G is 28.40%, A is 22.01%, Y is 13.78%, W is
      6.12%, S is 5.11%, F is 4.38%, R is 3.42%, P is 3.12%, N is 2.77%,
      L is 2.75%, I is 1.90%, V is 1.83%, D is 1.77%, T is 1.10%, Q is
      0.99%, C is 0.21%, E is 0.18%, H is 0.09% and K is 0.05%
<220> FEATURE:
<221> NAME/KEY: MOD_RES
<222> LOCATION: (13)..(13)
<223> OTHER INFORMATION: F is 54.81%, M is 12.10%, L is 11.23%, I is
      4.42%, G is 3.21%, V is 2.80%, P is 2.43%, Y is 1.74%, E is 1.22%,
      D is 1.05%, S is 1.01%, W is 0.94%, C is 0.87%, Q is 0.83%, N is
      0.78%, T is 0.48% and A is 0.05%
<220> FEATURE:
<221> NAME/KEY: MOD_RES
<222> LOCATION: (14)..(14)
<223> OTHER INFORMATION: D is 77.42%, G is 4.08%, S is 2.04%, E is
      2.02%, H is 2.02%, A is 1.65%, V is 1.44%, K is 1.38%, N is 1.33%,
      Q is 1.03%, C is 0.94%, L is 0.87%, R is 0.83%, F is 0.80%, Y is
      0.80%, P is 0.69%, T is 0.57% and I is 0.07%
<220> FEATURE:
<221> NAME/KEY: MOD_RES
<222> LOCATION: (15)..(15)
<223> OTHER INFORMATION: Y is 45.62%, I is 17.08%, V is 16.46%, S is
      5.23%, H is 2.98%, D is 2.96%, N is 2.54%, F is 2.29%, L is 1.44%,
      T is 1.01%, A is 0.99%, R is 0.85%, P is 0.23%, M is 0.09%, G is
      0.07% and C is 0.05%

<400> SEQUENCE: 124

Xaa Xaa Xaa Xaa Xaa Xaa Xaa Xaa Xaa Xaa Xaa Xaa Xaa Xaa Xaa
1               5                   10                  15

<210> SEQ ID NO 125
<211> LENGTH: 16
<212> TYPE: PRT
<213> ORGANISM: Artificial Sequence
<220> FEATURE:
<223> OTHER INFORMATION: CDRH3 Length 16
<220> FEATURE:
<221> NAME/KEY: MOD_RES
<222> LOCATION: (1)..(1)
<223> OTHER INFORMATION: G is 23.28%, D is 21.54%, E is 12.51%, R is
      6.40%, V is 6.34%, S is 3.90%, H is 3.49%, Q is 3.26%, Y is 3.20%,
      L is 3.03%, A is 2.44%, P is 2.44%, M is 2.39%, K is 1.86%, W is
      1.11%, I is 0.93%, N is 0.87%, T is 0.70%, C is 0.12% and F is
      0.12%
<220> FEATURE:
<221> NAME/KEY: MOD_RES
<222> LOCATION: (2)..(2)
<223> OTHER INFORMATION: G is 19.85%, P is 16.94%, R is 9.72%, Y is
      6.40%, S is 6.17%, L is 5.70%, A is 4.71%, K is 4.48%, Q is 3.90%,
      V is 3.84%, I is 3.26%, E is 2.50%, D is 2.33%, N is 2.33%, T is
      2.10%, M is 1.75%, F is 1.57%, H is 1.28%, W is 0.81% and C is
      0.35%
<220> FEATURE:
<221> NAME/KEY: MOD_RES
<222> LOCATION: (3)..(3)
<223> OTHER INFORMATION: G is 13.85%, S is 10.48%, R is 8.91%, Y is
      8.91%, L is 6.58%, H is 6.29%, I is 5.94%, A is 4.71%, E is 4.54%,
      D is 4.42%, Q is 4.13%, P is 3.61%, N is 3.03%, T is 2.97%, W is
      2.56%, C is 2.39%, V is 2.04%, M is 1.92%, F is 1.75% and K is
      0.99%
<220> FEATURE:
<221> NAME/KEY: MOD_RES
<222> LOCATION: (4)..(4)
<223> OTHER INFORMATION: G is 13.85%, R is 9.84%, Y is 9.66%, S is
      9.02%, L is 7.92%, P is 6.00%, I is 5.41%, H is 5.18%, Q is 4.31%,
      D is 4.19%, E is 3.20%, A is 3.08%, W is 3.03%, N is 2.85%, T is
      2.74%, F is 2.62%, M is 2.39%, V is 1.86%, C is 1.69% and K is
      1.11%
<220> FEATURE:
<221> NAME/KEY: MOD_RES
<222> LOCATION: (5)..(5)
<223> OTHER INFORMATION: G is 12.86%, R is 10.01%, Y is 9.84%, S is
      9.78%, L is 7.68%, A is 4.95%, H is 4.89%, I is 4.89%, Q is 3.90%,
      E is 3.78%, D is 3.73%, N is 3.67%, P is 3.61%, W is 3.61%, T is
      3.08%, F is 2.85%, M is 2.04%, C is 1.98%, V is 1.63% and K is
```

```
                                       1.16%
<220> FEATURE:
<221> NAME/KEY: MOD_RES
<222> LOCATION: (6)..(6)
<223> OTHER INFORMATION: G is 12.92%, S is 11.29%, R is 9.14%, Y is
      8.79%, I is 7.33%, H is 5.88%, L is 5.76%, W is 4.19%, A is 4.13%,
      D is 4.07%, Q is 3.78%, E is 3.61%, P is 3.61%, M is 2.79%, N is
      2.56%, F is 2.50%, T is 2.27%, V is 2.21%, C is 1.92% and K is
      1.22%
<220> FEATURE:
<221> NAME/KEY: MOD_RES
<222> LOCATION: (7)..(7)
<223> OTHER INFORMATION: G is 13.80%, S is 10.54%, R is 9.66%, Y is
      7.97%, H is 6.69%, I is 5.88%, L is 5.76%, E is 4.95%, D is 4.42%,
      A is 3.78%, P is 3.73%, Q is 3.43%, N is 3.32%, F is 2.85%, W is
      2.85%, T is 2.74%, M is 2.10%, V is 2.10%, C is 2.04% and K is
      1.28%
<220> FEATURE:
<221> NAME/KEY: MOD_RES
<222> LOCATION: (8)..(8)
<223> OTHER INFORMATION: G is 13.39%, S is 10.36%, R is 9.49%, Y is
      7.80%, L is 6.75%, I is 5.94%, H is 5.59% D is 4.95%, A is 4.77%,
      T is 3.96%, M is 3.73%, Q is 3.73%, E is 3.67%, P is 3.38%, W is
      2.79%, N is 2.74%, F is 2.21%, V is 2.10%, C is 1.51% and K is
      1.16%
<220> FEATURE:
<221> NAME/KEY: MOD_RES
<222> LOCATION: (9)..(9)
<223> OTHER INFORMATION: Y is 15.83%, G is 8.91%, R is 8.21%, P is
      7.51%, A is 6.46%, L is 5.94%, D is 5.82%, I is 5.59%, V is 4.89%,
      S is 4.77%, E is 4.37%, Q  is 4.13%, T is 3.96%, F is 2.97%, N is
      2.68%, C is 2.39%, M is 1.63%, W is 1.40%, H is 1.28% and K is
      1.28%
<220> FEATURE:
<221> NAME/KEY: MOD_RES
<222> LOCATION: (10)..(10)
<223> OTHER INFORMATION: Y is 16.94%, P is 10.30%, R is 9.60%, G is
      7.16%, Q is 6.11%, D is 5.59%, I is 5.41%, S is 5.06%, A is 4.95%,
      V is 4.66%, L is 4.07%, T is 4.02%, E is 3.73%, F is 2.74%, W is
      2.15%, N is 1.98%, C is 1.80%, H is 1.34%, M is 1.16% and K is
      1.11%
<220> FEATURE:
<221> NAME/KEY: MOD_RES
<222> LOCATION: (11)..(11)
<223> OTHER INFORMATION: Y is 15.77%, P is 11.76%, R is 8.15%, G is
      7.22%, L is 6.46%, I is 6.00%, S is 5.18%, D is 5.12%, E is 4.77%,
      V is 4.66%, A is 4.60%, Q is 3.96%, F is 3.38%, T is 3.14%, N is
      2.39%, C is 1.75%, K is 1.63%, H is 1.40%, W is 1.40% and M is
      1.22%
<220> FEATURE:
<221> NAME/KEY: MOD_RES
<222> LOCATION: (12)..(12)
<223> OTHER INFORMATION: Y is 16.41%, R is 8.96%, P is 8.21%, G is
      7.74%, I is 5.70%, L is 5.70%, A is 5.47%, D is 5.47%, S is 5.24%,
      V is 5.24%, E is 4.77%, Q is 4.42%, T is 3.55%, F is 3.38%, N is
      2.27%, W is 2.04%, C is 1.98%, H is 1.46%, K is 0.93% and M is
      0.87%
<220> FEATURE:
<221> NAME/KEY: MOD_RES
<222> LOCATION: (13)..(13)
<223> OTHER INFORMATION: G is 34.52%, A is 20.20%, Y is 13.10%, W is
      8.15%, P is 4.95%, V is 3.14%, D is 2.62%, F is 2.39%, H is 2.39%,
      L is 1.92%, S is 1.69%, T is 1.69%, E is 0.99%, C is 0.87%, R is
      0.58%, I is 0.47%, N is 0.17% and Q is 0.06%
<220> FEATURE:
<221> NAME/KEY: MOD_RES
<222> LOCATION: (14)..(14)
<223> OTHER INFORMATION: F is 50.47%, M is 16.01%, L is 12.69%, I is
      4.66%, V is 2.62%, P is 2.56%, Y is 2.04%, G is 1.92%, D is 1.57%,
      Q is 0.93%, E is 0.81%, C is 0.76%, T is 0.70%, W is 0.70%, N is
      0.64%, S is 0.47%, A is 0.29%, and H is 0.17%
<220> FEATURE:
<221> NAME/KEY: MOD_RES
<222> LOCATION: (15)..(15)
<223> OTHER INFORMATION: D is 76.37%, G is 4.19%, H is 2.27%, A is
      2.21%, S is 1.69%, Y is 1.63%, V is 1.51%, E is 1.40%, R is 1.34%,
      K is 1.28%, F is 1.22%, T is 0.87%, N is 0.81%, P is 0.81%, C is
      0.64%, L is 0.64%, Q is 0.52%, I is 0.29% and M is 0.29%
<220> FEATURE:
```

```
<221> NAME/KEY: MOD_RES
<222> LOCATION: (16)..(16)
<223> OTHER INFORMATION: Y is 40.28%, V is 21.42%, I is 15.48%, S is
      5.18%, H is 3.73%, F is 2.91%, N is 2.79%, D is 2.21%, L is 1.57%,
      P is 1.34%, R is 0.99%, T is 0.99%, A is 0.64%, M is 0.17%, C is
      0.06%, G is 0.06%, and K is 0.06%

<400> SEQUENCE: 125

Xaa Xaa Xaa Xaa Xaa Xaa Xaa Xaa Xaa Xaa Xaa Xaa Xaa Xaa Xaa Xaa
1               5                   10                  15

<210> SEQ ID NO 126
<211> LENGTH: 17
<212> TYPE: PRT
<213> ORGANISM: Artificial Sequence
<220> FEATURE:
<223> OTHER INFORMATION: CDRH3 Length 17
<220> FEATURE:
<221> NAME/KEY: MOD_RES
<222> LOCATION: (1)..(1)
<223> OTHER INFORMATION: D is 23.68%, G is 22.67%, E is 14.15%, V is
      7.09%, R is 5.81%, Y is 3.46%, S is 3.40%, Q is 2.91%, P is 2.79%,
      H is 2.67%, L is 2.64%, M is 2.03%, K is 1.60%, A is 1.57%, W is
      1.57%, T is 0.67%, N is 0.64%, I is 0.46%, C is 0.09%  and F is
      0.06%
<220> FEATURE:
<221> NAME/KEY: MOD_RES
<222> LOCATION: (2)..(2)
<223> OTHER INFORMATION: R is 14.44%, L is 12.06%, G is 11.30%, P is
      7.29%, A is 6.25%, Y is 6.16%, I is 5.87%, H is 4.88%, N is 4.56%,
      T is 4.48%, V is 4.10%, Q is 3.55%, K is 3.28%, S is 2.73%, E is
      2.15%, D is 1.89%, W is 1.54%, F is 1.37%, M is 1.31% and C is
      0.67%
<220> FEATURE:
<221> NAME/KEY: MOD_RES
<222> LOCATION: (3)..(3)
<223> OTHER INFORMATION: G is 14.50%, S is 10.96%, R is 9.97%, Y is
      7.47%, L is 6.77%, I is 6.66%, H is 5.90%, D is 4.48%, A is 3.89%,
      E is 3.49%, Q is 3.49%, P is 3.31%, T is 3.17%, N is 3.14%, W is
      2.91%, M is 2.56%, F is 2.47%, C is 2.01%, V is 1.60% and K is
      1.28%
<220> FEATURE:
<221> NAME/KEY: MOD_RES
<222> LOCATION: (4)..(4)
<223> OTHER INFORMATION: Y is 14.71%, P is 10.52%, G is 9.01%, R is
      8.95%, I is 6.66%, L is 5.58%, D is 5.55%, S is 5.26%, A is 5.17%,
      E is 4.45%, V is 4.30%, Q is 4.01%, T is 3.49%, F is 2.96%, N is
      2.47%, W is 1.71%, M is 1.63%, C is 1.37%, H is 1.08% and K is
      1.02%
<220> FEATURE:
<221> NAME/KEY: MOD_RES
<222> LOCATION: (5)..(5)
<223> OTHER INFORMATION: G is 17.44%, Y is 11.10%, R is 8.78%, S is
      8.02%, I is 4.85%, L is 4.80%, A is 4.33%, E is 4.33%, W is 4.18%,
      D is 4.04%, H is 3.69%, N is 3.69%, T is 3.08%, M is 2.96%, F is
      2.91%, V is 2.70%, Q is 2.64%, P is 2.44%, C is 2.41% and K is
      1.48%
<220> FEATURE:
<221> NAME/KEY: MOD_RES
<222> LOCATION: (6)..(6)
<223> OTHER INFORMATION: G is 14.41%, R is 9.47%, S is 8.57%, Y is
      8.31%, L is 7.67%, H is 6.48%, I is 5.38%, P is 4.50%, A is 4.04%,
      E is 3.89%, Q is 3.87%, W is 3.60%, N is 3.25%, D is 3.23%, T is
      3.11%, M is 2.94%, V is 2.18%, C is 2.01%, F is 2.01% and K is
      1.02%
<220> FEATURE:
<221> NAME/KEY: MOD_RES
<222> LOCATION: (7)..(7)
<223> OTHER INFORMATION: G is 15.00%, S is 8.92%, R is 8.37%, Y is
      8.34%, H is 6.89%, L is 6.86%, I is 5.03%, A is 4.24%, C is 2.47%,
      D is 2.79%, E is 4.53%, F is 2.85%, K is 1.60%, M is 2.76%, N is
      3.11%, P is 3.89%, Q is 4.27%, T is 2.67%, V is 1.66% and W is
      3.69%
<220> FEATURE:
<221> NAME/KEY: MOD_RES
<222> LOCATION: (8)..(8)
<223> OTHER INFORMATION: G is 13.34%, R is 9.47%, Y is 8.08%, S is
```

8.05%, L is 7.47%, H is 6.19%, I is 5.09%, A is 4.88%, C is 1.83%,
D is 3.37%, E is 4.18%, F is 2.44%, K is 1.13%, M is 2.67%, N is
3.84%, P is 4.53%, Q is 3.95%, T is 3.63%, V is 2.32%, W is 3.43%
<220> FEATURE:
<221> NAME/KEY: MOD_RES
<222> LOCATION: (9)..(9)
<223> OTHER INFORMATION: G is 14.94%, R is 9.33%, Y is 9.13%, S is
7.15%, L is 6.77%, H is 6.07%, I is 5.14%, A is 4.45%, C is 2.15%,
D is 3.34%, E is 3.57%, F is 3.05%, K is 1.25%, M is 2.73%, N is
3.55%, P is 3.95%, Q is 3.57%, T is 3.46%, V is 3.02% and W is
3.37%
<220> FEATURE:
<221> NAME/KEY: MOD_RES
<222> LOCATION: (10)..(10)
<223> OTHER INFORMATION: Y is 14.82%, R is 9.82%, P is 9.79%, G is
8.25%, D is 6.19%, I is 6.07%, Q is 5.55%, L is 5.32%, A is 4.85%,
C is 2.15%, E is 4.53%, F is 2.59%, H is 1.51%, K is 0.93%, M is
1.22%, N is 2.27%, S is 4.68%, T is 3.72%, V is 4.21% and W is
1.45%
<220> FEATURE:
<221> NAME/KEY: MOD_RES
<222> LOCATION: (11)..(11)
<223> OTHER INFORMATION: Y is 14.68%, R is 10.29%, P is 9.82%, G is
7.73%, L is 6.25%, I is 5.70%, S is 5.49%, D is 5.32%, A is 5.26%,
Q is 5.03%, C is 1.92%, E is 4.33%, F is 3.31%, H is 1.31%, K is
1.13%, M is 1.16%, N is 1.95%, T is 3.81%, V is 4.10% and W is
1.39%
<220> FEATURE:
<221> NAME/KEY: MOD_RES
<222> LOCATION: (12)..(12)
<223> OTHER INFORMATION: Y is 15.02%, P is 10.20%, R is 9.76%, G is
7.79%, I is 5.73%, A is 5.38%, S is 5.32%, D is 5.14%, C is 1.71%,
E is 4.88%, F is 3.37%, H is 1.31%, K is 1.51%, L is 4.97%, M is
1.19%, N is 1.74%, Q is 4.91%, T is 3.95%, V is 4.33% and W is
1.71%
<220> FEATURE:
<221> NAME/KEY: MOD_RES
<222> LOCATION: (13)..(13)
<223> OTHER INFORMATION: Y is 16.54%, P is 10.32%, R is 9.85%, G is
8.49%, D is 5.90%, I is 5.78%, L is 5.26%, S is 5.06%, A is 5.00%,
C is 1.54%, E is 4.27%, F is 2.59%, H is 1.08%, K is 1.28%, M is
1.39%, N is 2.35%, Q is 3.78%, T is 3.63%, V is 4.18% and W is
1.63%
<220> FEATURE:
<221> NAME/KEY: MOD_RES
<222> LOCATION: (14)..(14)
<223> OTHER INFORMATION: G is 35.89%, A is 24.38%, Y is 12.67%, W is
7.70%, C is 0.17%, D is 2.41%, E is 1.28%, F is 0.64%, H is 0.15%,
I is 1.39%, L is 2.35%, N is 1.71%, P is 2.32%, Q is 0.44%, R is
1.31%, S is 1.08%, T is 2.12% and V is 1.89%
<220> FEATURE:
<221> NAME/KEY: MOD_RES
<222> LOCATION: (15)..(15)
<223> OTHER INFORMATION: M is 41.88%, F is 37.93%, L is 9.68%, D is
0.06%, E is 0.06%, G is 1.19%, H is 0.81%, I is 1.83%, P is 1.63%,
S is 0.70%, T is 0.55%, V is 1.86%, W is 0.70% and Y is 1.08%
<220> FEATURE:
<221> NAME/KEY: MOD_RES
<222> LOCATION: (16)..(16)
<223> OTHER INFORMATION: D is 76.23%, A is 1.80%, C is 0.67%, E is
2.03%, F is 0.70%, G is 4.36%, H is 2.01%, K is 1.45%, L is 1.16%,
N is 1.28%, P is 1.25%, Q is 0.93%, R is 1.16%, S is 1.92%, T is
0.90%, V is 1.05%, and Y is 1.05%
<220> FEATURE:
<221> NAME/KEY: MOD_RES
<222> LOCATION: (17)..(17)
<223> OTHER INFORMATION: V is 33.97%, Y is 22.03%, I is 17.67%, P is
7.90%, A is 1.28%, C is 0.09%, D is 0.32%, F is 3.31%, G is
0.15%, H is 2.06%, L is 1.69%, M is 2.62%, N is 1.39%, Q is 0.81%,
R is 1.02%, S is 3.55% and T is 0.09%

<400> SEQUENCE: 126

Xaa Xaa Xaa Xaa Xaa Xaa Xaa Xaa Xaa Xaa Xaa Xaa Xaa Xaa Xaa Xaa
1               5                   10                  15

Xaa

```
<210> SEQ ID NO 127
<211> LENGTH: 18
<212> TYPE: PRT
<213> ORGANISM: Artificial Sequence
<220> FEATURE:
<223> OTHER INFORMATION: CDRH3 Length 18
<220> FEATURE:
<221> NAME/KEY: MOD_RES
<222> LOCATION: (1)..(1)
<223> OTHER INFORMATION: D is 23.99%, G is 22.77%, E is 14.07%, V is
      6.83%, R is 5.97%, S is 4.00%, L is 2.83%, H is 2.68%, Y is 2.63%,
      Q is 2.38%, A is 2.13%, P is 2.02%, M is 1.92%, K is 1.72%, W is
      1.42%, T is 1.06%, I is 0.76%, N is 0.66%, C is 0.05% and F is
      0.05%
<220> FEATURE:
<221> NAME/KEY: MOD_RES
<222> LOCATION: (2)..(2)
<223> OTHER INFORMATION: G is 16.75%, S is 11.54%, R is 9.77%, Y is
      7.84%, L is 6.22%, I is 6.02%, H is 5.82%, P is 4.35%, E is 4.10%,
      D is 4.00%, Q is 3.64%, A is 3.09%, N is 2.78%, W is 2.53%, M is
      2.38%, T is 2.38%, V is 2.33%, C is 1.77%, F is 1.37% and K is
      1.32%
<220> FEATURE:
<221> NAME/KEY: MOD_RES
<222> LOCATION: (3)..(3)
<223> OTHER INFORMATION: G is 14.57%, S is 10.22%, R is 9.01%, Y is
      8.30%, L is 6.48%, I is 6.43%, H is 6.02%, Q is 4.15%, A is 4.05%,
      T is 4.00%, D is 3.90%, P is 3.64%, E is 3.54%, W is 3.09%, N is
      2.83%, V is 2.53%, M is 2.28%, F is 2.07%, C is 1.62% and K is
      1.21%
<220> FEATURE:
<221> NAME/KEY: MOD_RES
<222> LOCATION: (4)..(4)
<223> OTHER INFORMATION: Y is 12.55%, P is 11.69%, G is 10.12%, R is
      9.56%, L is 6.38%, I is 6.02%, D is 5.72%, S is 5.31%, Q is 5.01%,
      E is 4.71%, A is 4.30%, V is 3.90%, T is 3.69%, F is 2.43%, W is
      2.07%, N is 1.52%, H is 1.47%, M is 1.32%, C is 1.16% and K is
      1.06%
<220> FEATURE:
<221> NAME/KEY: MOD_RES
<222> LOCATION: (5)..(5)
<223> OTHER INFORMATION: Y is 14.93%, P is 11.03%, R is 8.50%, G is
      7.24%, I is 6.22%, L is 5.92%, A is 5.26%, Q is 5.16%, S is 4.76%,
      E is 4.55%, D is 4.25%, V is 4.25%, T is 3.54%, F is 3.39%, C is
      2.53%, N is 2.33%, M is 1.87%, W is 1.82%, K is 1.42% and H is
      0.96%
<220> FEATURE:
<221> NAME/KEY: MOD_RES
<222> LOCATION: (6)..(6)
<223> OTHER INFORMATION: G is 15.08%, Y is 9.46%, S is 9.11%, R is
      8.96%, L is 6.12%, H is 5.41%, I is 5.41%, A is 4.35%, E is 4.25%,
      Q is 4.05%, D is 3.85%, N is 3.64%, T is 3.44%, P is 3.29%, M is
      2.63%, W is 2.53%, V is 2.43%, C is 2.38%, F is 2.28% and K is
      1.32%
<220> FEATURE:
<221> NAME/KEY: MOD_RES
<222> LOCATION: (7)..(7)
<223> OTHER INFORMATION: G is 14.32%, R is 9.36%, Y is 8.40%, S is
      8.00%, L is 7.79%, H is 5.52%, P is 4.61%, A is 4.45%, I is 4.15%,
      Q is 3.95%, T is 3.95%, N is 3.90%, W is 3.69%, D is 3.44%, E is
      3.34%, V is 2.94%, F is 2.73%, M is 2.63%, C is 1.62% and K is
      1.16%
<220> FEATURE:
<221> NAME/KEY: MOD_RES
<222> LOCATION: (8)..(8)
<223> OTHER INFORMATION: G is 13.92%, Y is 9.16%, R is 9.11%, S is
      8.65%, L is 7.79%, H is 5.41%, I is 5.21%, A is 4.96%, E is 4.35%,
      Q is 4.35%, W is 3.74%, P is 3.54%, F is 3.39%, T is 3.04%, M is
      2.99%, D is 2.78%, N is 2.73%, V is 2.13%, C is 1.82% and K is
      0.91%
<220> FEATURE:
<221> NAME/KEY: MOD_RES
<222> LOCATION: (9)..(9)
<223> OTHER INFORMATION: G is 14.78%, R is 10.98%, Y is 8.50%, S is
      8.10%, L is 6.53%, H is 6.17%, P is 5.31%, I is 4.55%, A is 4.15%,
      D is 3.80%, T is 3.74%, N is 3.64%, W is 3.49%, E is 3.44%, Q is
      3.19%, F is 2.83%, M is 2.33%, V is 1.77%, C is 1.57% and K is
      1.11%
<220> FEATURE:
```

```
<221> NAME/KEY: MOD_RES
<222> LOCATION: (10)..(10)
<223> OTHER INFORMATION: G is 14.12%, R is 9.46%, Y is 8.91%, L is
      7.74%, S is 7.59%, H is 6.33%, A is 4.76%, I is 4.71%, P is 4.55%,
      N is 4.25%, Q is 3.85%, E is 3.64%, D is 3.29%, W is 3.29%, T is
      3.24%, F is 2.53%, V is 2.48%, M is 2.43%, C is 1.82% and K is
      1.01%
<220> FEATURE:
<221> NAME/KEY: MOD_RES
<222> LOCATION: (11)..(11)
<223> OTHER INFORMATION: Y is 13.87%, P is 11.39%, R is 10.58%, G is
      7.89%, A is 6.12%, D is 5.62%, I is 5.16%, V is 5.11%, E is 4.81%,
      S is 4.61%, L is 4.45%, Q is 4.10%, T is 3.95%, F is 3.59%, N is
      2.02%, C is 1.97%, M is 1.42%, H is 1.21%, W is 1.06% and K is
      1.01%
<220> FEATURE:
<221> NAME/KEY: MOD_RES
<222> LOCATION: (12)..(12)
<223> OTHER INFORMATION: Y is 15.94%, R is 8.96%, P is 8.76%, G is
      8.60%, L is 5.92%, D is 5.82%, Q is 5.52%, I is 4.91%, S is 4.71%,
      A is 4.66%, E is 4.35%, V is 4.10%, T is 3.59%, F is 3.19%, N is
      2.53%, W is 2.53%, C is 1.92%, K is 1.42%, M is 1.42% and H is
      1.06%
<220> FEATURE:
<221> NAME/KEY: MOD_RES
<222> LOCATION: (13)..(13)
<223> OTHER INFORMATION: Y is 16.95%, P is 10.17%, R is 9.36%, G is
      7.34%, D is 5.47%, A is 5.41%, L is 5.16%, I is 4.81%, Q is 4.81%,
      V is 4.76%, E is 4.25%, S is 4.05%, T is 3.59%, F is 3.14%, N is
      2.63%, C is 1.92%, W is 1.67%, H is 1.62%, M is 1.57% and K is
      1.27%
<220> FEATURE:
<221> NAME/KEY: MOD_RES
<222> LOCATION: (14)..(14)
<223> OTHER INFORMATION: Y is 18.37%, G is 9.01%, P is 8.76%, R is
      8.25%, I is 6.02%, D is 5.57%, A is 5.47%, L is 4.71%, E is 4.55%,
      V is 4.50%, S is 4.25%, Q is 3.74%, T is 3.39%, F is 3.14%, N is
      2.94%, W is 2.02%, M is 1.62%, C is 1.37%, H is 1.37% and K is
      0.91%
<220> FEATURE:
<221> NAME/KEY: MOD_RES
<222> LOCATION: (15)..(15)
<223> OTHER INFORMATION: G is 30.57%, A is 20.70%, W is 12.80%, Y is
      10.32%, P is 5.11%, S is 5.01%, T is 3.54%, V is 2.58%, D is
      2.28%, R is 2.23%, L is 1.27%, K is 0.91%, I is 0.71%, F is 0.56%,
      N is 0.51%, C is 0.30%, M is 0.20%, E is 0.15%, H is 0.15% and Q
      is 0.05%
<220> FEATURE:
<221> NAME/KEY: MOD_RES
<222> LOCATION: (16)..(16)
<223> OTHER INFORMATION: M is 40.59%, F is 37.96%, L is 9.16%, I is
      2.58%, P is 2.13%, V is 2.02%, G is 1.47%, H is 1.01%, Y is 1.01%,
      W is 0.81%, S is 0.51%, A is 0.20%, D is 0.20%, T is 0.20%, C is
      0.05%, N is 0.05% and R is 0.05%
<220> FEATURE:
<221> NAME/KEY: MOD_RES
<222> LOCATION: (17)..(17)
<223> OTHER INFORMATION: D is 76.62%, G is 4.35%, E is 2.13%, S is
      1.97%, A is 1.92%, H is 1.77%, V is 1.42%, K is 1.37%, N is 1.32%,
      F is 1.11%, L is 1.06%, P is 0.91%, Q is 0.86%, Y is 0.81%, R is
      0.76%, T is 0.76%, C is 0.51%, M is 0.25% and I is 0.05%
<220> FEATURE:
<221> NAME/KEY: MOD_RES
<222> LOCATION: (18)..(18)
<223> OTHER INFORMATION: V is 32.59%, Y is 20.65%, I is 18.12%, P is
      9.67%, S is 4.50%, F is 3.39%, M is 2.38%, L is 2.18%, H is 1.62%,
      N is 1.42%, A is 1.01%, Q is 0.86%, R is 0.86%, D is at 0.66% and
      G is 0.05%

<400> SEQUENCE: 127

Xaa Xaa Xaa Xaa Xaa Xaa Xaa Xaa Xaa Xaa Xaa Xaa Xaa Xaa Xaa Xaa
1               5                   10                  15

Xaa Xaa

<210> SEQ ID NO 128
<211> LENGTH: 19
```

```
<212> TYPE: PRT
<213> ORGANISM: Artificial Sequence
<220> FEATURE:
<223> OTHER INFORMATION: CDRH3 Length 19
<220> FEATURE:
<221> NAME/KEY: MOD_RES
<222> LOCATION: (1)..(1)
<223> OTHER INFORMATION: D is 23.33%, G is 22.55%, E is 13.92%, V is
      6.81%, R is 5.38%, A is 2.44%, C is 0.24%, F is 0.17%, H is 3.28%,
      I is 0.85%, K is 2.27%, L is 2.30%, M is 2.24%, N is 0.98%, P is
      2.54%, Q is 2.57%, S is 3.79%, T is 0.37%, W is 1.05% and Y is
      2.88%
<220> FEATURE:
<221> NAME/KEY: MOD_RES
<222> LOCATION: (2)..(2)
<223> OTHER INFORMATION: G is 19.67%, R is 12.09%, D is 11.48%, P is
      10.26%, I is 8.74%, S is 6.16%, L is 5.89%, A is 5.79%, E is
      5.08%, C is 0.88%, F is 0.81%, H is 2.40%, K is 0.27%, M is 0.14%,
      N is 1.69%, Q is 2.24%, T is 2.51%, V is 0.24%, W is 1.66% and Y
      is 2.00%
<220> FEATURE:
<221> NAME/KEY: MOD_RES
<222> LOCATION: (3)..(3)
<223> OTHER INFORMATION: G is 14.05%, S is 10.43%, R is 7.92%, Y is
      7.69%, L is 7.55%, I is 6.30%, H is 5.62%, A is 3.76%, C is 2.30%,
      D is 4.47%, E is 4.00%, F is 2.20%, K is 1.22%, M is 2.71%, N is
      2.88%, P is 3.66%, Q is 4.54%, T is 3.25%, V is 2.20% and W is
      3.18%
<220> FEATURE:
<221> NAME/KEY: MOD_RES
<222> LOCATION: (4)..(4)
<223> OTHER INFORMATION: Y is 12.83%, P is 11.62%, R is 9.04%, G is
      8.50%, L is 6.30%, I is 5.66%, A is 5.55%, D is 5.49%, S is 5.49%,
      C is 1.59%, E is 4.67%, F is 3.08%, H is 1.42%, K is 1.25%, M is
      1.46%, N is 2.84%, Q is 3.79%, T is 3.79%, V is 4.13% and W is
      1.49%
<220> FEATURE:
<221> NAME/KEY: MOD_RES
<222> LOCATION: (5)..(5)
<223> OTHER INFORMATION: Y is 14.02%, P is 9.82%, R is 9.21%, G is
      7.48%, L is 6.23%, E is 5.69%, I is 5.69%, D is 5.35%, S is 5.05%,
      A is 4.88%, C is 1.59%, F is 2.84%, H is 1.42%, K is 0.85%, M is
      1.52%, N is 2.64%, Q is 4.91%, T is 4.20%, V is 4.81% and W is
      1.76%
<220> FEATURE:
<221> NAME/KEY: MOD_RES
<222> LOCATION: (6)..(6)
<223> OTHER INFORMATION: Y is 14.39%, P is 9.92%, G is 9.01%, R is
      8.53%, S is 6.06%, I is 5.99%, D is 5.93%, A is 5.11%, E is 5.01%,
      C is 1.63%, F is 3.28%, H is 1.02%, K is 0.91%, L is 4.64%, M is
      1.52%, N is 1.76%, Q is 4.44%, T is 4.44%, V is 4.37% and W is
      1.93%
<220> FEATURE:
<221> NAME/KEY: MOD_RES
<222> LOCATION: (7)..(7)
<223> OTHER INFORMATION: Y is 14.26%, S is 12.26%, V is 10.13%, D is
      9.89%, G is 9.08%, I is 7.75%, F is 6.30%, E is 5.86%, A is 4.61%,
      C is 1.86%, H is 0.37%, K is 0.27%, L is 1.63%, M is 1.59%, N is
      4.03%, P is 0.44%, Q is 0.78%, R is 0.61%, T is 4.20% and W is
      4.00%
<220> FEATURE:
<221> NAME/KEY: MOD_RES
<222> LOCATION: (8)..(8)
<223> OTHER INFORMATION: G is 14.39%, W is 10.36%, S is 9.14%, F is
      8.97%, V is 8.03%, I is 7.38%, H is 6.64%, T is 6.50%, D is 5.32%,
      A is 5.28%, C is 1.73%, E is 2.61%, K is 0.10%, L is 0.95%, M is
      0.27%, N is 2.57%, P is 4.03%, Q is 0.37%, R is 1.76% and Y is
      3.56%
<220> FEATURE:
<221> NAME/KEY: MOD_RES
<222> LOCATION: (9)..(9)
<223> OTHER INFORMATION: G is 14.32%, R is 9.18%, S is 8.09%, Y is
      8.09%, L is 7.04%, H is 6.23%, I is 5.25%, A is 4.37%, C is 2.07%,
      D is 3.66%, E is 4.44%, F is 2.40%, K is 1.32%, M is 2.40%, N is
      4.30%, P is 4.27%, Q is 3.83%, T is 2.78%, V is 2.44% and W is
      3.42%
<220> FEATURE:
<221> NAME/KEY: MOD_RES
<222> LOCATION: (10)..(10)
```

```
<223> OTHER INFORMATION: G is 13.92%, R is 8.91%, Y is 8.20%, S is
      8.16%, L is 7.38%, H is 5.99%, P is 5.25%, I is 5.15%, A is 4.54%,
      C is 1.86%, D is 3.28%, E is 3.73%, F is 3.08%, K is 1.15%, M is
      2.91%, N is 3.12%, Q is 3.93%, T is 3.15%, V is 2.47% and W is
      3.79%
<220> FEATURE:
<221> NAME/KEY: MOD_RES
<222> LOCATION: (11)..(11)
<223> OTHER INFORMATION: Y is 13.65%, R is 10.19%, P is 9.85%, G is
      7.65%, D is 5.76%, Q is 5.69%, E is 5.35%, I is 5.32%, L is 5.18%,
      A is 4.88%, C is 1.90%, F is 3.39%, H is 1.25%, K is 0.95%, M is
      0.98%, N is 2.47%, S is 4.88%, T is 3.93%, V is 4.74% and W is
      1.96%
<220> FEATURE:
<221> NAME/KEY: MOD_RES
<222> LOCATION: (12)..(12)
<223> OTHER INFORMATION: Y is 14.22%, P is 9.99%, R is 8.77%, G is
      8.16%, D is 6.13%, I is 5.82%, S is 5.72%, L is 5.49%, A is 5.05%,
      Q is 5.05%, C is 1.69%, E is 4.84%, F is 3.73%, H is 1.39%, K is
      0.95%, M is 1.56%, N is 2.10%, T is 3.45%, V is 4.00% and W is
      1.83%
<220> FEATURE:
<221> NAME/KEY: MOD_RES
<222> LOCATION: (13)..(13)
<223> OTHER INFORMATION: Y is 16.59%, R is 9.11%, P is 8.84%, G is
      8.70%, D is 5.89%, I is 5.76%, S is 5.05%, A is 4.94%, C is 2.00%,
      E is 4.57%, F is 3.45%, H is 1.15%, K is 1.29%, L is 4.61%, M is
      1.69%, N is 2.64%, Q is 4.17%, T is 3.73%, V is 4.17% and W is
      1.52%
<220> FEATURE:
<221> NAME/KEY: MOD_RES
<222> LOCATION: (14)..(14)
<223> OTHER INFORMATION: Y is 41.62%, N is 11.45%, G is 10.02%, A is
      4.17%, C is 0.24%, D is 1.56%, E is 1.25%, F is 1.19%, H is 4.17%,
      I is 2.84%, K is 1.19%, L is 4.57%, M is 0.10%, P is 2.44%, Q is
      0.24%, R is 3.93%, S is 4.17%, T is 1.56%, V is 1.86% and W is
      1.35%
<220> FEATURE:
<221> NAME/KEY: MOD_RES
<222> LOCATION: (15)..(15)
<223> OTHER INFORMATION: Y is 49.44%, D is 14.63%, G is 8.57%, N is
      7.31%, A is 0.30%, C is 0.14%, E is 0.17%, F is 4.20%, H is 1.02%,
      I is 0.34%, K is 0.03%, L is 0.24%, M is 0.03%, P is 3.05%, Q is
      0.81%, R is 0.54%, S is 3.83%, T is 2.81%, V is 1.66% and W is
      0.81%
<220> FEATURE:
<221> NAME/KEY: MOD_RES
<222> LOCATION: (16)..(16)
<223> OTHER INFORMATION: G is 45.38%, A is 20.72%, Y is 13.27%, C is
      0.85%, D is 1.19%, E is 0.07%, F is 0.44%, H is 1.22%, I is 1.49%,
      K is 0.07%, L is 0.95%, N is 0.03%, P is 2.78%, R is 1.08%, S is
      1.63%, T is 0.88%, V is 4.00% and W is 3.96%
<220> FEATURE:
<221> NAME/KEY: MOD_RES
<222> LOCATION: (17)..(17)
<223> OTHER INFORMATION: F is 40.09%, M is 39.45%, L is 8.57%, A is
      0.07%, D is 0.07%, G is 1.05%, H is 1.02%, I is 2.37%, P is 1.42%,
      S is 0.85%, T is 0.68%, V is 2.17%, W is 0.91% and Y is 1.29%
<220> FEATURE:
<221> NAME/KEY: MOD_RES
<222> LOCATION: (18)..(18)
<223> OTHER INFORMATION: D is 75.72%, A is 1.83%, C is 0.91%, E is
      2.20%, F is 1.02%, G is 4.81%, H is 1.93%, K is 1.22%, L is 1.19%,
      M is 0.20%, N is 1.46%, P is 0.81%, Q is 0.85%, R is 0.95%, S is
      1.83%, T is 0.71%, V is 1.35%, and Y is 0.98%
<220> FEATURE:
<221> NAME/KEY: MOD_RES
<222> LOCATION: (19)..(19)
<223> OTHER INFORMATION: V is 33.12%, I is 20.01%, Y is 19.13%, P is
      9.72%, A is 1.22%, C is 0.03%, D is 0.37%, E is 0.03%, F is 3.49%,
      G is 0.03%, H is 1.90%, L is 1.56%, M is 2.71%, N is 1.19%, Q is
      0.47%, R is 1.05%, S is 3.89% and T is 0.03%

<400> SEQUENCE: 128

Xaa Xaa Xaa Xaa Xaa Xaa Xaa Xaa Xaa Xaa Xaa Xaa Xaa Xaa Xaa Xaa
1               5                   10                  15

Xaa Xaa Xaa
```

<210> SEQ ID NO 129
<211> LENGTH: 20
<212> TYPE: PRT
<213> ORGANISM: Artificial Sequence
<220> FEATURE:
<223> OTHER INFORMATION: CDRH3 Length 20
<220> FEATURE:
<221> NAME/KEY: MOD_RES
<222> LOCATION: (1)..(1)
<223> OTHER INFORMATION: D is 24.17%, G is 22.63%, E is 15.56%, V is
     7.04%, R is 5.41%, S is 3.27%, H is 2.99%, Y is 2.80%, L is 2.58%,
     P is 2.39%, Q is 2.33%, K is 1.89%, M is 1.76%, A is 1.67%, W is
     1.16%, I is 0.88%, N is 0.66%, T is 0.63%, C is 0.09% and F is
     0.09%
<220> FEATURE:
<221> NAME/KEY: MOD_RES
<222> LOCATION: (2)..(2)
<223> OTHER INFORMATION: G is 15.46%, S is 11.53%, R is 8.67%, Y is
     7.79%, L is 6.19%, H is 5.85%, I is 5.78%, D is 4.68%, E is
     4.65%, A is 3.77%, Q is 3.52%, P is 3.49%, T is 3.11%, M is 2.95%,
     W is 2.70%, N is 2.67%, F is 2.36%, V is 1.82%, C is 1.73% and K
     is 1.23%
<220> FEATURE:
<221> NAME/KEY: MOD_RES
<222> LOCATION: (3)..(3)
<223> OTHER INFORMATION: G is 13.70%, S is 10.40%, R is 9.71%, Y is
     7.64%, L is 6.63%, I is 6.00%, H is 5.15%, D is 4.49%, A is 4.40%,
     Q is 4.18%, E is 3.96%, P is 3.61%, W is 3.33%, N is 3.17%, T is
     3.14%, M is 2.70%, V is 2.39%, F is 2.14%, C is 1.82% and K is
     1.41%
<220> FEATURE:
<221> NAME/KEY: MOD_RES
<222> LOCATION: (4)..(4)
<223> OTHER INFORMATION: L is 11.00%, I is 9.49%, G is 8.89%, Y is
     8.42%, S is 8.08%, E is 7.86%, D is 7.13%, A is 6.95%, F is
     6.73%, V is 5.28%, R is 4.87%, P is 3.11%, T is 2.70%, W is 2.36%,
     M is 2.11%, C is 1.89%, K is 1.16%, N is 1.13%, Q is 0.41% and H
     is 0.38%
<220> FEATURE:
<221> NAME/KEY: MOD_RES
<222> LOCATION: (5)..(5)
<223> OTHER INFORMATION: Y is 13.70%, P is 11.44%, R is 9.37%, G is
     8.36%, I is 5.72%, D is 5.63%, Q is 5.31%, S is 5.28%, L is 5.12%,
     E is 4.75%, A is 4.62%, V is 4.56%, T is 3.55%, F is 2.73%, N is
     2.01%, C is 1.98%, W is 1.73%, H is 1.41%, M is 1.35% and K is
     1.29%
<220> FEATURE:
<221> NAME/KEY: MOD_RES
<222> LOCATION: (6)..(6)
<223> OTHER INFORMATION: D is 16.25%, Y is 13.89%, I is 11.35%, S is
     10.03%, G is 8.80%, V is 5.81%, L is 5.59%, F is 5.50%, T is
     5.22%, C is 3.99%, A is 3.21%, W is 2.55%, E is 2.14%, R is 1.98%,
     P is 1.76%, Q is 1.04%, M is 0.35%, N is 0.31%, H is 0.19% and K
     is 0.06%
<220> FEATURE:
<221> NAME/KEY: MOD_RES
<222> LOCATION: (7)..(7)
<223> OTHER INFORMATION: Y is 17.38%, S is 16.59%, F is 14.11%, G is
     9.49%, D is 7.01%, I is 4.53%, K is 4.15%, T is 4.09%, C is 4.05%,
     V is 3.58%, N is 3.52%, R is 3.49%, L is 2.33%, A is 1.54%, P is
     1.38%, H is 1.10%, E is 0.82%, M is 0.35%, W is 0.28% and Q is
     0.09%
<220> FEATURE:
<221> NAME/KEY: MOD_RES
<222> LOCATION: (8)..(8)
<223> OTHER INFORMATION: G is 15.24%, R is 8.74%, L is 7.95%, S is
     7.89%, Y is 7.35%, H is 6.16%, I is 4.75%, A is 4.40%, P is 4.37%,
     D is 4.21%, E is 3.96%, Q is 3.96%, N is 3.49%, W is 3.39%, T is
     3.08%, V is 3.05%, M is 2.58%, C is 2.17%, F is 1.95% and K is
     1.29%
<220> FEATURE:
<221> NAME/KEY: MOD_RES
<222> LOCATION: (9)..(9)
<223> OTHER INFORMATION: G is 14.24%, R is 9.21%, S is 8.45%, Y is
     8.33%, L is 7.83%, I is 5.34%, H is 5.28%, E is 4.59%, A is 4.56%,
     P is 3.71%, T is 3.68%, Q is 3.49%, W is 3.46%, N is 3.36%, D is
     3.05%, M is 2.92%, F is 2.73%, V is 2.42%, C is 1.89% and K is -continued

```
      1.45%
<220> FEATURE:
<221> NAME/KEY: MOD_RES
<222> LOCATION: (10)..(10)
<223> OTHER INFORMATION: G is 13.92%, R is 8.89%, Y is 8.89%, S is
      7.86%, L is 7.54%, H is 6.79%, I is 5.06%, P is 5.00%, A is 4.78%,
      E is 3.99%, Q is 3.71%, D is 3.33%, N is 3.21%, T is 3.14%, W is
      3.11%, F is 2.92%, V is 2.48%, M is 2.33%, C is 1.89% and K is
      1.13%
<220> FEATURE:
<221> NAME/KEY: MOD_RES
<222> LOCATION: (11)..(11)
<223> OTHER INFORMATION: Y is 12.82%, P is 10.09%, R is 8.96%, G is
      8.11%, D is 5.85%, I is 5.59%, L is 5.31%, E is 5.19%, A is
      5.15%, S is 5.09%, V is 4.71%, Q is 4.68%, T is 4.53%, F is 3.87%,
      W is 2.39%, N is 2.36%, C is 1.79%, H is 1.51%, M is 1.23% and K
      is 0.79%
<220> FEATURE:
<221> NAME/KEY: MOD_RES
<222> LOCATION: (12)..(12)
<223> OTHER INFORMATION: Y is 13.26%, P is 9.90%, R is 9.87%, G is
      7.54%, L is 5.78%, A is 5.66%, I is 5.41%, S is 5.37%, D is 5.03%,
      V is 4.93%, Q is 4.87%, E is 4.71%, T is 3.68%, F is 3.33%, N is
      2.64%, W is 2.11%, C is 1.57%, M is 1.54%, K is 1.45% and H is
      1.32%
<220> FEATURE:
<221> NAME/KEY: MOD_RES
<222> LOCATION: (13)..(13)
<223> OTHER INFORMATION: Y is 15.71%, R is 10.47%, P is 9.90%, G is
      7.54%, L is 5.50%, S is 5.47%, D is 5.44%, E is 5.03%, I is 4.84%,
      A is 4.65%, V is 4.65%, Q is 4.62%, T is 3.52%, F is 2.99%, N is
      2.42%, C is 1.92%, W is 1.70%, M is 1.35%, H is 1.13% and K is
      1.13%
<220> FEATURE:
<221> NAME/KEY: MOD_RES
<222> LOCATION: (14)..(14)
<223> OTHER INFORMATION: Y is 48.52%, G is 9.62%, P is 6.38%, S is
      5.94%, R is 4.43%, N is 4.34%, D is 3.74%, I is 3.71%, V is 2.99%,
      F is 2.48%, K is 1.48%, A is 1.35%, H is 1.23%, L is 1.10%, T is
      0.94%, W is 0.94%, E is 0.31%, Q is 0.25%, C is 0.09% and M is
      0.06%
<220> FEATURE:
<221> NAME/KEY: MOD_RES
<222> LOCATION: (15)..(15)
<223> OTHER INFORMATION: Y is 46.48%, S is 7.73%, P is 4.87%, V is
      4.27%, H is 4.18%, N is 4.09%, E is 3.99%, I is 3.36%, A is 3.33%,
      G is 3.30%, W is 3.21%, T is 2.45%, C is 2.29%, D is 1.89%, R is
      1.67%, M is 0.97%, L is 0.94%, F is 0.41%, K is 0.35% and Q is
      0.16%
<220> FEATURE:
<221> NAME/KEY: MOD_RES
<222> LOCATION: (16)..(16)
<223> OTHER INFORMATION: Y is 47.49%, G is 10.78%, P is 6.44%, S is
      6.07%, R is 4.09%, D is 4.02%, N is 3.96%, I is 3.68%, V is 3.36%,
      F is 3.08%, H is 1.41%, A is 1.23%, W is 1.07%, K is 1.01%, L is
      1.01%, T is 0.85%, C is 0.06%, E is 0.06%, Q is 0.06% and M is
      0.03%
<220> FEATURE:
<221> NAME/KEY: MOD_RES
<222> LOCATION: (17)..(17)
<223> OTHER INFORMATION: G is 43.84%, A is 17.38%, Y is 10.78%, W is
      8.64%, T is 3.90%, R is 2.83%, S is 2.80%, F is 2.51%, V is 2.36%,
      D is 1.60%, K is 1.41%, N is 1.16%, P is 0.31%, I is 0.19%, L is
      0.09%, E is 0.06%, H is 0.06% and M is 0.06%
<220> FEATURE:
<221> NAME/KEY: MOD_RES
<222> LOCATION: (18)..(18)
<223> OTHER INFORMATION: M is 40.19%, F is 39.79%, L is 7.35%, V is
      2.77%, I is 2.20%, Y is 1.35%, P is 1.19%, G is 1.13%, H is 1.13%,
      W is 0.91%, S is 0.82%, T is 0.72%, D is 0.19%, C is 0.13%, N is
      0.09% and A is 0.03%
<220> FEATURE:
<221> NAME/KEY: MOD_RES
<222> LOCATION: (19)..(19)
<223> OTHER INFORMATION: D is 74.67%, G is 4.31%, E is 2.39%, A is
      2.23%, H is 2.23%, S is 1.89%, V is 1.51%, N is 1.45%, K is 1.32%,
      Q is 1.19%, Y is 1.19%, F is 1.10%, L is 1.04%, R is 0.97%, P is
      0.91%, T is 0.66%, C is 0.63%, M is 0.19% and W is 0.06%
<220> FEATURE:
```

```
<221> NAME/KEY: MOD_RES
<222> LOCATION: (20)..(20)
<223> OTHER INFORMATION: V is 34.51%, Y is 20.05%, I is 18.48%, P is
      9.55%, S is 3.68%, F is 3.05%, M is 2.42%, H is 1.76%, L is 1.57%,
      R is 1.26%, N is 1.07%, Q is 1.01%, A is 0.94%, D is 0.41%, G is
      0.13%, C is 0.03% and T is 0.03%

<400> SEQUENCE: 129

Xaa Xaa Xaa Xaa Xaa Xaa Xaa Xaa Xaa Xaa Xaa Xaa Xaa Xaa Xaa Xaa
 1               5                   10                  15

Xaa Xaa Xaa Xaa
        20

<210> SEQ ID NO 130
<211> LENGTH: 21
<212> TYPE: PRT
<213> ORGANISM: Artificial Sequence
<220> FEATURE:
<223> OTHER INFORMATION: CDRH3 Length 21
<220> FEATURE:
<221> NAME/KEY: MOD_RES
<222> LOCATION: (1)..(1)
<223> OTHER INFORMATION: D is 24.63%, E is 14.85%, G is 21.67%, V is
      7.17%, R is 5.99%, I is 0.86%, K is 1.62%, L is 2.34%, M is 1.86%,
      N is 0.65%, P is 2.20%, Q is 2.65%, S is 2.72%, T is 0.65%, W is
      1.62%, Y is 2.79%, C is 0.07%, H is 3.10% and A is 2.48%
<220> FEATURE:
<221> NAME/KEY: MOD_RES
<222> LOCATION: (2)..(2)
<223> OTHER INFORMATION: G is 25.32%, S is 20.22%, P is 9.06%, Y is
      8.72%, K is 6.92%, A is 6.27%, L is 5.20%, C is 0.24%, D is 3.79%,
      E is 0.62%, F is 2.07%, H is 0.41%, I is 2.34%, M is 0.55%, N is
      0.14%, Q is 0.28%, R is 3.82%, T is 0.28%, V is 1.86% and W is
      1.86%
<220> FEATURE:
<221> NAME/KEY: MOD_RES
<222> LOCATION: (3)..(3)
<223> OTHER INFORMATION: A is 11.78%, S is 10.54%, R is 8.96%, Y is
      8.75%, G is 8.47%, L is 8.10%, E is 7.13%, I is 7.13%, D is 5.82%,
      V is 5.75%, C is 3.31%, F is 0.28%, H is 0.38%, K is 2.82%, M is
      0.14%, N is 4.17%, P is 4.48%, Q is 0.28%, T is 1.45% and W is
      0.14%
<220> FEATURE:
<221> NAME/KEY: MOD_RES
<222> LOCATION: (4)..(4)
<223> OTHER INFORMATION: G is 14.50%, S is 10.02%, R is 9.20%, Y is
      7.68%, L is 6.10%, I is 5.58%, E is 5.37%, H is 5.03%, A is 3.79%,
      C is 2.10%, D is 3.79%, F is 2.93%, K is 1.31%, M is 3.20%, N is
      2.79%, P is 4.24%, Q is 3.07%, T is 3.34%, V is 2.34% and W is
      3.58%
<220> FEATURE:
<221> NAME/KEY: MOD_RES
<222> LOCATION: (5)..(5)
<223> OTHER INFORMATION: G is 13.26%, R is 9.20%, S is 8.89%, Y is
      7.51%, H is 6.72%, L is 6.41%, D is 5.96%, I is 5.96%, A is 3.96%,
      C is 1.76%, E is 3.55%, F is 2.31%, K is 1.31%, M is 2.41%, N is
      3.44%, P is 4.13%, Q is 4.00%, T is 3.41%, V is 2.65% and W is
      3.10%
<220> FEATURE:
<221> NAME/KEY: MOD_RES
<222> LOCATION: (6)..(6)
<223> OTHER INFORMATION: I is 10.54%, L is 10.47%, Y is 8.85%, A is
      8.51%, S is 8.47%, G is 8.34%, D is 8.23%, E is 6.72%, V is 5.99%,
      F is 5.82%, C is 2.10%, H is 0.34%, K is 0.83%, M is 1.58%, N is
      1.52%, P is 2.86%, Q is 0.24%, R is 4.27%, T is 1.65% and W is
      2.58%
<220> FEATURE:
<221> NAME/KEY: MOD_RES
<222> LOCATION: (7)..(7)
<223> OTHER INFORMATION: L is 11.26%, I is 10.99%, G is 9.09%, S is
      7.99%, Y is 7.68%, A is 7.58%, E is 7.51%, D is 7.44%, F is 6.92%,
      V is 5.79%, C is 1.48%, K is 1.62%, M is 1.65%, N is 1.31%, P is
      2.55%, Q is 0.17%, R is 4.13%, T is 2.45% and W is 2.27%
<220> FEATURE:
<221> NAME/KEY: MOD_RES
<222> LOCATION: (8)..(8)
```

-continued

```
<223> OTHER INFORMATION: L is 10.78%, I is 9.75%, G is 8.75%, Y is
      8.34%, D is 8.30%, E is 8.06%, A is 7.75%, S is 7.68%, F is 7.44%,
      V is 5.72%, C is 2.03%, H is 0.14%, K is 1.10%, M is 1.79%, N is
      0.93%, P is 2.24%, Q is 0.10%, R is 4.68%, T is 2.10% and W is
      2.20%
<220> FEATURE:
<221> NAME/KEY: MOD_RES
<222> LOCATION: (9)..(9)
<223> OTHER INFORMATION: L is 10.68%, I is 9.75%, A is 8.47%, G is
      8.13%, Y is 7.82%, D is 7.65%, E is 7.65%, S is 7.41%, F is 7.10%,
      V is 5.27%, C is 1.76%, H is 0.24%, K is 1.76%, M is 1.72%, N is
      1.17%, P is 3.10%, Q is 0.07%, R is 4.99%, T is 2.27% and W is
      2.93%
<220> FEATURE:
<221> NAME/KEY: MOD_RES
<222> LOCATION: (10)..(10)
<223> OTHER INFORMATION: L is 11.75%, I is 9.85%, D is 8.34%, Y is
      7.99%, A is 7.85%, E is 7.48%, G is 7.48%, S is 7.17%, F is 7.13%,
      V is 5.03%, C is 1.89%, H is 0.41%, K is 1.45%, M is 1.31%, N is
      1.38%, P is 3.38%, Q is 0.55%, R is 4.62%, T is 2.55% and W is
      2.41%
<220> FEATURE:
<221> NAME/KEY: MOD_RES
<222> LOCATION: (11)..(11)
<223> OTHER INFORMATION: L is 11.23%, I is 10.02%, G is 8.99%, Y is
      8.37%, A is 7.58%, D is 7.37%, F is 7.20%, E is 6.96%, S is 6.85%,
      V is 5.34%, C is 2.00%, H is 0.28%, K is 1.21%, M is 2.03%, N is
      1.76%, P is 3.31%, Q is 0.38%, R is 4.00%, T is 2.62% and W is
      2.48%
<220> FEATURE:
<221> NAME/KEY: MOD_RES
<222> LOCATION: (12)..(12)
<223> OTHER INFORMATION: P is 18.05%, G is 14.88%, S is 12.09%, F is
      11.47%, R is 10.27%, H is 9.37%, A is 0.59%, C is 0.24%, D is
      2.51%, E is 0.62%, I is 1.21%, K is 0.03%, L is 2.62%, M is 0.14%,
      N is 2.89%, Q is 2.79%, T is 3.07%, V is 2.24%, W is 0.28% and Y
      is 4.65%
<220> FEATURE:
<221> NAME/KEY: MOD_RES
<222> LOCATION: (13)..(13)
<223> OTHER INFORMATION: G is 17.57%, Y is 13.02%, D is 12.19%, T is
      8.89%, S is 7.51%, N is 6.48%, P is 6.44%, R is 6.30%, L is 5.34%,
      A is 2.24%, C is 0.34%, E is 2.48%, F is 0.59%, H is 0.10%, I is
      3.17%, K is 2.79%, M is 3.10%, Q is 0.31%, V is 0.83% and W is
      0.31%
<220> FEATURE:
<221> NAME/KEY: MOD_RES
<222> LOCATION: (14)..(14)
<223> OTHER INFORMATION: Y is 35.62%, S is 13.64%, R is 9.68%, P is
      8.54%, V is 6.41%, A is 0.90%, C is 2.14%, D is 0.79%, E is 2.51%,
      F is 0.65%, G is 3.89%, H is 3.55%, I is 0.59%, K is 2.58%, L is
      4.31%, M is 0.14%, N is 0.41%, Q is 0.28%, T is 1.65% and W is
      1.62%
<220> FEATURE:
<221> NAME/KEY: MOD_RES
<222> LOCATION: (15)..(15)
<223> OTHER INFORMATION: Y is 50.43%, A is 9.65%, R is 5.99%, C is
      1.89%, D is 2.79%, E is 2.17%, F is 4.34%, G is 1.96%, H is 0.17%,
      I is 2.89%, K is 2.27%, L is 0.48%, N is 4.20%, P is 2.79%, Q is
      0.17%, S is 2.20%, T is 2.89%, V is 0.17% and W is 2.38%
<220> FEATURE:
<221> NAME/KEY: MOD_RES
<222> LOCATION: (16)..(16)
<223> OTHER INFORMATION: Y is 54.98%, G is 10.71%, F is 6.17%, S is
      5.65%, A is 0.31%, C is 0.07%, D is 4.44%, E is 0.31%, H is 3.03%,
      I is 2.38%, K is 0.21%, L is 2.20%, M is 2.34%, N is 0.24%, P is
      2.89%, Q is 1.03%, R is 1.79%, T is 0.45%, V is 0.45% and W is
      0.21%
<220> FEATURE:
<221> NAME/KEY: MOD_RES
<222> LOCATION: (17)..(17)
<223> OTHER INFORMATION: Y is 48.33%, G is 10.27%, P is 8.27%, S is
      5.20%, A is 1.24%, C is 0.14%, D is 3.93%, E is 0.14%, F is 2.20%,
      H is 1.45%, I is 3.41%, K is 1.38%, L is 1.27%, N is 4.51%, Q is
      0.10%, R is 3.41%, T is 0.83%, V is 3.13% and W is 0.79%
<220> FEATURE:
<221> NAME/KEY: MOD_RES
<222> LOCATION: (18)..(18)
<223> OTHER INFORMATION: G is 43.82%, Y is 19.57%, A is 11.44%, C is
```

1.69%, D is 4.86%, E is 0.03%, F is 0.17%, H is 0.24%, I is 2.14%, K is 0.07%, L is 4.06%, M is 0.07%, N is 0.34%, P is 1.10%, Q is 0.03%, R is 1.72%, S is 0.14%, T is 0.83%, V is 0.21% and W is 7.41%
<220> FEATURE:
<221> NAME/KEY: MOD_RES
<222> LOCATION: (19)..(19)
<223> OTHER INFORMATION: M is 39.03%, F is 35.45%, L is 10.16%, A is 0.21%, C is 0.07%, D is 0.24%, G is 2.93%, H is 1.14%, I is 2.07%, K is 0.03%, P is 1.83%, Q is 0.03%, R is 0.24%, S is 0.86%, T is 0.38%, V is 2.96%, W is 1.17% and Y is 1.21%
<220> FEATURE:
<221> NAME/KEY: MOD_RES
<222> LOCATION: (20)..(20)
<223> OTHER INFORMATION: D is 71.96%, A is 2.03%, C is 0.69%, E is 1.38%, F is 2.17%, G is 4.79%, H is 2.79%, I is 0.03%, K is 0.86%, L is 1.38%, M is 1.62%, N is 1.03%, P is 1.55%, Q is 1.03%, R is 1.00%, S is 1.58%, T is 1.10%, V is 2.00% and Y is 1.00%
<220> FEATURE:
<221> NAME/KEY: MOD_RES
<222> LOCATION: (21)..(21)
<223> OTHER INFORMATION: V is 53.57%, Y is 8.44%, H is 8.37%, P is 8.23%, A is 0.07%, D is 4.72%, E is 0.03%, F is 2.58%, G is 0.24%, I is 3.17%, K is 0.03%, L is 0.03%, M is 2.27%, N is 2.17%, Q is 2.69%, R is 0.03% and S is 3.31%

<400> SEQUENCE: 130

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa
            20

<210> SEQ ID NO 131
<211> LENGTH: 22
<212> TYPE: PRT
<213> ORGANISM: Artificial Sequence
<220> FEATURE:
<223> OTHER INFORMATION: CDRH3 Length 22
<220> FEATURE:
<221> NAME/KEY: MOD_RES
<222> LOCATION: (1)..(1)
<223> OTHER INFORMATION: D is 23.37%, E is 14.91%, G is 21.75%, V is 8.46%, R is 5.83%, A is 3.13%, C is 0.04%, F is 0.04%, H is 2.74%, I is 0.70%, K is 1.89%, L is 2.51%, M is 1.97%, N is 0.50%, P is 2.74%, Q is 2.05%, S is 2.94%, T is 0.46%, W is 1.04% and Y is 2.94%
<220> FEATURE:
<221> NAME/KEY: MOD_RES
<222> LOCATION: (2)..(2)
<223> OTHER INFORMATION: F is 5.37%, G is 17.19%, L is 18.89%, P is 7.96%, R is 17.50%, S is 7.34%, A is 3.79%, C is 0.04%, D is 0.54%, E is 4.87%, H is 0.27%, I is 4.06%, K is 0.35%, M is 4.94%, Q is 0.58%, T is 2.28%, V is 0.58%, W is 2.97% and Y is 0.46%
<220> FEATURE:
<221> NAME/KEY: MOD_RES
<222> LOCATION: (3)..(3)
<223> OTHER INFORMATION: A is 16.22%, G is 8.30%, K is 8.85%, L is 8.96%, R is 8.42%, S is 7.26%, Y is 8.03%, C is 3.59%, D is 3.17%, E is 4.52%, F is 3.13%, H is 0.08%, I is 4.44%, M is 0.08%, N is 4.21%, P is 4.75%, Q is 0.23%, T is 3.21%, V is 2.39% and W is 0.12%
<220> FEATURE:
<221> NAME/KEY: MOD_RES
<222> LOCATION: (4)..(4)
<223> OTHER INFORMATION: E is 12.98%, F is 6.33%, G is 11.09%, I is 9.81%, P is 18.23%, R is 5.06%, S is 15.22%, T is 5.60%, Y is 5.37%, A is 0.42%, C is 0.19%, D is 3.79%, H is 0.08%, K is 0.19%, L is 3.94%, M is 0.46%, N is 0.19%, Q is 0.35%, V is 0.39% and W is 0.31%
<220> FEATURE:
<221> NAME/KEY: MOD_RES
<222> LOCATION: (5)..(5)
<223> OTHER INFORMATION: D is 17.77%, H is 6.22%, P is 8.50%, S is 7.88%, T is 5.99%, Y is 14.41%, A is 4.98%, C is 3.82%, E is 0.50%, F is 3.67%, G is 4.40%, I is 0.42%, K is 4.94%, L is 0.46%, M is 0.35%, N is 4.17%, Q is 0.12%, R is 4.52%, V is 3.86% and W

```
                   is 2.94%
<220> FEATURE:
<221> NAME/KEY: MOD_RES
<222> LOCATION: (6)..(6)
<223> OTHER INFORMATION: D is 16.11%, G is 17.15%, M is 5.10%, V is
      9.69%, Y is 13.13%, C is 3.36%, A is 0.70%, E is 4.48%, F is
      0.27%, H is 4.79%, I is 1.16%, K is 0.19%, L is 0.42%, N is 4.21%,
      P is 3.59%, Q is 0.04%, R is 4.79%, S is 4.75%, T is 0.39% and W
      is 5.68%
<220> FEATURE:
<221> NAME/KEY: MOD_RES
<222> LOCATION: (7)..(7)
<223> OTHER INFORMATION: A is 7.57%, D is 6.80%, E is 9.19%, F is 6.95%,
      G is 9.46%, I is 10.04%, L is 11.16%, S is 7.11%, V is 5.79%, W is
      1.89%, C is 2.01%, H is 0.27%, K is 1.16%, M is 1.78%, N is 1.04%,
      P is 2.47%, Q is 0.23%, R is 4.91%, T is 2.24% and Y is 7.80%
<220> FEATURE:
<221> NAME/KEY: MOD_RES
<222> LOCATION: (8)..(8)
<223> OTHER INFORMATION: A is 9.31%, D is 6.80%, E is 7.57%, I is
      10.20%, F is 6.49%, G is 7.07%, L is 11.94%, S is 8.07%, V is
      5.21%, Y is 8.96%, C is 1.58%, K is 1.08%, M is 1.93%, N is 1.43%,
      P is 2.94%, H is 0.08%, Q is 0.08%, R is 4.48%, T is 2.05% and W
      is 2.70%
<220> FEATURE:
<221> NAME/KEY: MOD_RES
<222> LOCATION: (9)..(9)
<223> OTHER INFORMATION: A is 8.19%, D is 6.53%, E is 7.61%, F is 7.34%,
      G is 8.07%, I is 10.81%, L is 10.27%, S is 7.49%, V is 5.25%, Y is
      8.96%, C is 1.89%, H is 0.12%, K is 1.51%, M is 1.85%, N is 1.51%,
      P is 2.74%, Q is 0.08%, R is 4.60%, T is 2.51% and W is 2.67%
<220> FEATURE:
<221> NAME/KEY: MOD_RES
<222> LOCATION: (10)..(10)
<223> OTHER INFORMATION: Y is 13.02%, P is 10.31%, R is 9.39%, G is
      9.31%, L is 6.30%, I is 6.10%, D is 5.33%, A is 4.87%, S is 4.87%,
      V is 4.67%, Q is 4.56%, E is 4.29%, T is 4.09%, F is 3.79%, N is
      1.85%, C is 1.78%, W is 1.74%, H is 1.39%, M is 1.27% and K is
      1.00%
<220> FEATURE:
<221> NAME/KEY: MOD_RES
<222> LOCATION: (11)..(11)
<223> OTHER INFORMATION: Y is 13.44%, P is 10.35%, G is 8.65%, R is
      8.42%, L is 6.49%, I is 5.52%, D is 5.29%, E is 5.29%, S is 4.91%,
      T is 4.87%, A is 4.75%, V is 4.75%, Q is 3.86%, F is 3.28%, N is
      2.90%, W is 1.82%, C is 1.78%, H is 1.39%, K is 1.12% and M is
      1.08%
<220> FEATURE:
<221> NAME/KEY: MOD_RES
<222> LOCATION: (12)..(12)
<223> OTHER INFORMATION: Y is 13.75%, P is 9.62%, G is 9.04%, R is
      8.57%, I is 7.72%, L is 6.10%, Q is 5.21%, S is 5.10%, A is 5.06%,
      D is 4.52%, E is 4.48%, F is 3.79%, V is 3.67%, T is 3.51%, N is
      2.01%, W is 1.85%, H is 1.74%, C is 1.66%, M is 1.51% and K is
      1.04%
<220> FEATURE:
<221> NAME/KEY: MOD_RES
<222> LOCATION: (13)..(13)
<223> OTHER INFORMATION: L is 12.55%, I is 9.62%, S is 8.38%, Y is
      8.27%, G is 7.84%, E is 7.61%, A is 7.45%, D is 7.26%, V is 6.06%,
      F is 5.99%, R is 4.36%, P is 3.13%, T is 2.82%, W is 2.36%, C is
      1.78%, M is 1.66%, K is 1.27%, N is 1.27%, Q is 0.15% and H is
      0.12%
<220> FEATURE:
<221> NAME/KEY: MOD_RES
<222> LOCATION: (14)..(14)
<223> OTHER INFORMATION: L is 11.36%, I is 10.54%, Y is 8.38%, E is
      8.15%, G is 8.07%, S is 8.00%, A is 7.84%, F is 7.34%, D is 7.26%,
      V is 5.21%, R is 4.44%, P is 3.05%, T is 2.36%, W is 2.09%, C is
      2.01%, K is 1.43%, M is 1.31%, N is 1.08% and H is 0.08%
<220> FEATURE:
<221> NAME/KEY: MOD_RES
<222> LOCATION: (15)..(15)
<223> OTHER INFORMATION: Y is 55.62%, P is 13.90%, T is 4.98%, S is
      4.13%, D is 4.09%, E is 4.06%, L is 3.86%, G is 3.82%, Q is 3.24%,
      R is 0.58%, N is 0.39%, I is 0.35%, F is 0.19%, V is 0.19%, C is
      0.15%, K is 0.15%, A is 0.12%, W is 0.08% and H is 0.04%
<220> FEATURE:
<221> NAME/KEY: MOD_RES
```

```
<222> LOCATION: (16)..(16)
<223> OTHER INFORMATION: Y is 60.22%, G is 6.33%, T is 5.48%, K is
      4.60%, L is 3.82%, V is 3.79%, E is 3.67%, R is 3.59%, S is 2.90%,
      W is 2.43%, I is 0.73%, A is 0.50%, D is 0.50%, F is 0.27%, N is
      0.27%, P is 0.27%, Q is 0.19%, C is 0.15%, H is 0.04% and M is
      0.04%
<220> FEATURE:
<221> NAME/KEY: MOD_RES
<222> LOCATION: (17)..(17)
<223> OTHER INFORMATION: Y is 62.50, R is 6.06%, P is 5.37%, K is
      5.25%, H is 4.21%, D is 4.02%, S is 3.82%, G is 3.67%, T is 3.28%,
      L is 0.62%, F is 0.19%, V is 0.19%, C is 0.12%, M is 0.12%, N is
      0.12%, A is 0.08%, I is 0.08% and Q is 0.08%
<220> FEATURE:
<221> NAME/KEY: MOD_RES
<222> LOCATION: (18)..(18)
<223> OTHER INFORMATION: Y is 69.83%, N is 7.61%, G is 5.52%, D is
      3.98%, A is 3.90%, H is 3.71%, E is 2.94%, S is 0.50%, F is 0.31%,
      K is 0.27%, C is 0.23%, P is 0.23%, R is 0.23%, L is 0.15%, W is
      0.15%, V is 0.12%, I is 0.08%, Q is 0.04% and T is 0.04%
<220> FEATURE:
<221> NAME/KEY: MOD_RES
<222> LOCATION: (19)..(19)
<223> OTHER INFORMATION: G is 57.44%, A is 10.12%, Y is 9.19%, R is
      6.30%, D is 4.79%, W is 4.17%, H is 3.32%, F is 3.24%, P is 0.31%,
      I is 0.19%, M is 0.19%, C is 0.12%, E is 0.12%, L is 0.12%, N is
      0.12%, S is 0.12%, T is 0.12% and K is 0.04%
<220> FEATURE:
<221> NAME/KEY: MOD_RES
<222> LOCATION: (20)..(20)
<223> OTHER INFORMATION: M is 41.10%, F is 36.27%, L is 9.81%, I is
      2.74%, V is 2.59%, P is 1.78%, G is 1.27%, H is 1.20%, Y is 1.08%,
      W is 0.89%, S is 0.54%, T is 0.46%, A is 0.08%, D is 0.08%, N is
      0.08% and R is 0.04%
<220> FEATURE:
<221> NAME/KEY: MOD_RES
<222> LOCATION: (21)..(21)
<223> OTHER INFORMATION: D is 74.55%, M is 0.23%, F is 0.85%, L is
      1.27%, V is 1.16%, P is 1.39%, G is 4.25%, H is 2.16%, Y is 1.12%,
      S is 1.97%, T is 1.16%, A is 2.39%, N is 1.47%, R is 0.77%, C is
      1.00%, E is 2.12%, K is 1.08% and Q is 1.04%
<220> FEATURE:
<221> NAME/KEY: MOD_RES
<222> LOCATION: (22)..(22)
<223> OTHER INFORMATION: V is 67.59%, Y is 10.97%, F is 9.35%, I is
      8.42%, P is 2.47%, H is 0.42%, D is 0.35%, C is 0.12%, S is 0.12%,
      Q is 0.08%, A is 0.04%, L is 0.04% and T is 0.04%

<400> SEQUENCE: 131

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 132
<211> LENGTH: 23
<212> TYPE: PRT
<213> ORGANISM: Artificial Sequence
<220> FEATURE:
<223> OTHER INFORMATION: CDRH3 Length 23
<220> FEATURE:
<221> NAME/KEY: MOD_RES
<222> LOCATION: (1)..(1)
<223> OTHER INFORMATION: D is 46.36%, E is 9.86%, G is 22.89%, H is
      8.78%, V is 7.32%, I is 0.10%, K is 0.10%, L is 0.24%, M is 0.05%,
      N is 0.24%, P is 0.24%, Q is 0.10%, R is 0.44%, S is 0.34%, A is
      1.81%, W is 0.05%, Y is 0.20% and T is 0.88%
<220> FEATURE:
<221> NAME/KEY: MOD_RES
<222> LOCATION: (2)..(2)
<223> OTHER INFORMATION: A is 5.32%, E is 6.54%, D is 11.91%, H is
      10.05%, L is 12.01%, Q is 8.64%, V is 10.44%, P is 9.91%, G is
      14.79%, F is 0.29%, I is 0.34%, K is 0.20%, M is 0.39%, N is
      0.05%, R is 4.39%, S is 4.15%, T is 0.10%, W is 0.29% and Y is
      0.15%
<220> FEATURE:
```

```
<221> NAME/KEY: MOD_RES
<222> LOCATION: (3)..(3)
<223> OTHER INFORMATION: A is 15.57%, G is 11.13%, I is 15.32%, L is
      12.84%, R is 8.69%, S is 17.33%, C is 0.29%, D is 0.34%, E is
      0.29%, F is 0.15%, H is 0.10%, K is 4.59%, M is 0.05%, N is 0.15%,
      P is 3.71%, Q is 2.83%, T is 0.24%, V is 2.64%, and Y is 3.71%
<220> FEATURE:
<221> NAME/KEY: MOD_RES
<222> LOCATION: (4)..(4)
<223> OTHER INFORMATION: G is 15.71%, M is 10.98%, R is 22.40%, S is
      6.54%, T is 6.39%, Y is 9.32%, A is 0.29%, C is 0.10%, D is 4.78%,
      E is 0.98%, F is 0.49%, H is 0.05%, I is 4.93%, K is 4.25%, L is
      0.39%, N is 0.15%, P is 3.61%, Q is 2.88%, V is 2.88% and W is
      2.83%
<220> FEATURE:
<221> NAME/KEY: MOD_RES
<222> LOCATION: (5)..(5)
<223> OTHER INFORMATION: A is 10.69%, D is 17.33%, F is 8.00%, P is
      5.32%, R is 7.76%, T is 5.91%, V is 5.91%, Y is 10.40%, C is
      0.20%, E is 4.29%, G is 4.83%, H is 0.44%, I is 0.24%, K is 0.24%,
      L is 4.59%, M is 4.39%, N is 4.69%, Q is 0.05%, S is 4.54% and W
      is 0.15%
<220> FEATURE:
<221> NAME/KEY: MOD_RES
<222> LOCATION: (6)..(6)
<223> OTHER INFORMATION: Y is 10.49%, S is 21.33%, N is 5.32%, I is
      15.18%, G is 5.12%, D is 5.08%, T is 7.61%, A is 3.42%, C is
      0.49%, E is 0.34%, F is 3.07%, H is 3.51%, L is 3.51%, M is 4.05%,
      P is 2.73%, Q is 0.05%, R is 4.49%, V is 3.76% and W is 0.39%
<220> FEATURE:
<221> NAME/KEY: MOD_RES
<222> LOCATION: (7)..(7)
<223> OTHER INFORMATION: E is 19.72%, G is 13.52%, I is 5.12%, K is
      5.37%, M is 5.17%, S is 6.88%, Y is 10.00%, A is 4.39%, C is
      2.93%, D is 0.78%, F is 3.76%, H is 4.78%, L is 0.49%, N is 0.10%,
      P is 3.61%, Q is 2.54%, R is 4.05%, T is 3.22%, V is 3.22% and W
      is 0.34%
<220> FEATURE:
<221> NAME/KEY: MOD_RES
<222> LOCATION: (8)..(8)
<223> OTHER INFORMATION: A is 10.30%, D is 9.52%, G is 11.22%, I is
      11.71%, L is 14.98%, V is 11.47%, C is 0.05%, E is 3.86%, F is
      0.59%, H is 3.76%, K is 0.05%, N is 0.15%, P is 3.81%, Q is 0.10%,
      R is 3.42%, S is 4.73%, T is 3.22%, W is 2.98% and Y is 4.10%
<220> FEATURE:
<221> NAME/KEY: MOD_RES
<222> LOCATION: (9)..(9)
<223> OTHER INFORMATION: A is 11.22%, E is 5.32%, F is 9.03%, I is
      5.76%, N is 14.84%, P is 7.42%, S is 11.03%, V is 11.22%, C is
      0.15%, D is 4.20%, G is 0.44%, H is 0.05%, K is 0.15%, L is 4.83%,
      M is 0.05%, Q is 2.34%, R is 0.78%, T is 2.78%, W is 3.56% and Y
      is 4.83%
<220> FEATURE:
<221> NAME/KEY: MOD_RES
<222> LOCATION: (10)..(10)
<223> OTHER INFORMATION: G is 24.79%, I is 14.40%, R is 9.13%, S is
      7.91%, W is 10.83%, Y is 14.30%, A is 4.59%, C is 0.34%, D is
      0.24%, E is 0.88%, F is 3.90%, K is 0.10%, L is 0.73%, M is 0.15%,
      N is 0.20%, P is 2.10%, Q is 0.20%, T is 0.44% and V is 4.78%
<220> FEATURE:
<221> NAME/KEY: MOD_RES
<222> LOCATION: (11)..(11)
<223> OTHER INFORMATION: G is 9.86%, K is 5.61%, P is 6.69%, R is
      10.35%, S is 8.59%, T is 9.37%, V is 16.40%, Y is 6.78%, A is
      0.34%, C is 0.15%, D is 4.88%, E is 0.34%, F is 4.25%, H is 3.42%,
      I is 0.59%, L is 4.00%, M is 0.10%, N is 4.49%, Q is 0.34%, and W
      is 3.42%
<220> FEATURE:
<221> NAME/KEY: MOD_RES
<222> LOCATION: (12)..(12)
<223> OTHER INFORMATION: F is 9.42%, G is 12.10%, I is 14.25%, S is
      15.96%, T is 6.69%, Y is 12.10%, A is 0.29%, C is 4.05%, D is
      0.15%, E is 0.24%, H is 0.29%, K is 0.15%, L is 4.83%, M is 0.10%,
      N is 4.64%, P is 4.34%, Q is 2.68%, R is 3.66%, V is 3.90% and W
      is 0.10%
<220> FEATURE:
<221> NAME/KEY: MOD_RES
<222> LOCATION: (13)..(13)
<223> OTHER INFORMATION: A is 9.03%, G is 12.15%, I is 19.52%, L is
```

```
        6.98%, R is 11.52%, Y is 21.28%, C is 0.15%, D is 0.68%, E is
        0.20%, F is 0.44%, H is 0.15%, K is 0.10%, M is 0.15%, N is 4.25%,
        P is 2.93%, Q is 0.15%, S is 3.17%, T is 0.20%, V is 3.56% and W
        is 3.27%
<220> FEATURE:
<221> NAME/KEY: MOD_RES
<222> LOCATION: (14)..(14)
<223> OTHER INFORMATION: A is 5.12%, G is 8.44%, I is 5.51%, N is 5.42%,
        P is 8.39%, S is 22.65%, T is 10.35%, V is 11.57%, Y is 5.71%, C
        is 0.24%, D is 3.76%, E is 0.20%, F is 3.90%, H is 0.29%, K is
        0.20%, L is 0.68%, Q is 0.10%, R is 3.95% and W is 3.47%
<220> FEATURE:
<221> NAME/KEY: MOD_RES
<222> LOCATION: (15)..(15)
<223> OTHER INFORMATION: I is 19.18%, L is 10.15%, P is 11.27%, Y is
        25.48%, G is 14.20%, A is 0.29%, C is 0.10%, D is 4.34%, E is
        0.39%, F is 0.34%, K is 4.34%, M is 0.05%, N is 0.10%, Q is 0.10%,
        R is 0.29%, S is 4.05%, T is 2.20%, V is 2.83%, and W is 0.29%
<220> FEATURE:
<221> NAME/KEY: MOD_RES
<222> LOCATION: (16)..(16)
<223> OTHER INFORMATION: E is 16.35%, N is 8.30%, R is 8.25%, Y is
        45.63%, C is 0.05%, D is 4.15%, F is 3.32%, G is 2.88%, H is
        0.15%, I is 0.20%, K is 0.20%, L is 0.24%, M is 0.05%, P is 3.17%,
        Q is 0.34%, S is 3.47%, T is 0.39%, V is 2.64% and W is 0.05%
<220> FEATURE:
<221> NAME/KEY: MOD_RES
<222> LOCATION: (17)..(17)
<223> OTHER INFORMATION: D is 8.00%, G is 6.34%, I is 8.49%, Y is
        56.66%, A is 0.10%, C is 0.10%, E is 0.34%, F is 3.51%, H is
        0.10%, K is 3.42%, L is 4.93%, N is 0.05%, P is 0.20%, Q is 3.32%,
        R is 0.20%, S is 0.29%, T is 3.66%, V is 0.10% and W is 0.10%
<220> FEATURE:
<221> NAME/KEY: MOD_RES
<222> LOCATION: (18)..(18)
<223> OTHER INFORMATION: G is 7.81%, K is 9.18%, L is 8.39%, S is
        19.67%, Y is 37.73%, A is 0.05%, C is 0.05%, D is 2.59%, E is
        0.10%, F is 0.10%, H is 4.20%, I is 0.15%, M is 0.10%, N is 0.10%,
        P is 0.24%, Q is 0.05%, R is 6.69%, T is 0.24%, V is 2.54% and W
        is 0.05%
<220> FEATURE:
<221> NAME/KEY: MOD_RES
<222> LOCATION: (19)..(19)
<223> OTHER INFORMATION: D is 15.52%, G is 8.10%, Y is 59.64%, A is
        0.44%, C is 0.15%, E is 0.34%, F is 3.90%, H is 0.29%, I is 0.15%,
        K is 0.10%, L is 0.10%, N is 4.69%, P is 0.34%, R is 0.20%, S is
        2.59%, T is 0.10%, V is 0.29% and W is 2.98%
<220> FEATURE:
<221> NAME/KEY: MOD_RES
<222> LOCATION: (20)..(20)
<223> OTHER INFORMATION: A is 25.72%, G is 52.71%, W is 10.59%, D is
        4.34%, E is 0.05%, F is 0.39%, H is 0.10%, L is 0.24%, P is 4.05%,
        R is 0.44%, S is 0.05%, T is 0.15%, V is 0.20% and Y is 0.93%
<220> FEATURE:
<221> NAME/KEY: MOD_RES
<222> LOCATION: (21)..(21)
<223> OTHER INFORMATION: F is 43.24%, L is 7.61%, M is 37.48%, A is
        0.05%, C is 0.05%, D is 0.05%, G is 1.07%, H is 1.27%, I is 2.24%,
        P is 0.88%, S is 0.98%, T is 0.93%, V is 2.39%, W is 0.93% and Y
        is 0.83%
<220> FEATURE:
<221> NAME/KEY: MOD_RES
<222> LOCATION: (22)..(22)
<223> OTHER INFORMATION: D is 74.18%, A is 2.59%, C is 0.63%, E is
        1.90%, F is 0.83%, G is 4.93%, H is 2.05%, I is 0.10%, K is 1.61%,
        L is 0.88%, M is 0.05%, N is 1.12%, P is 1.22%, Q is 0.63%, R is
        1.95%, S is 1.90%, T is 1.12%, V is 1.12%, and Y is 1.17%
<220> FEATURE:
<221> NAME/KEY: MOD_RES
<222> LOCATION: (23)..(23)
<223> OTHER INFORMATION: V is 59.15%, I is 25.33%, D is 0.05%, F is
        4.73%, H is 0.15%, L is 0.05%, M is 0.05%, P is 9.22%, Q is 0.05%,
        R is 0.05%, S is 0.15%, T is 0.05% and Y is 0.98%

<400> SEQUENCE: 132

Xaa Xaa Xaa Xaa Xaa Xaa Xaa Xaa Xaa Xaa Xaa Xaa Xaa Xaa Xaa Xaa
1               5                   10                  15
```

Xaa Xaa Xaa Xaa Xaa Xaa Xaa
20

We claim:

1. A synthetic gene expression library encoding first fusion proteins, wherein each first fusion protein comprises a fusion of a display peptide, a human antibody, and an expression tag, the synthetic gene expression library comprising:
- a repertoire of $10^{10}$ to $10^{11}$ unique synthetic nucleic acid sequences encoding first fusion proteins,
- wherein each of the encoded first fusion proteins comprises:
- a human antibody variable heavy chain with a polypeptide sequence selected from the group consisting of SEQ ID NOs. 2, 4, 6, 8, 10, 12 and 14 encoded by corresponding nucleic acid sequence selected from SEQ ID NOs. 1, 3, 5, 7, 9, 11 or 13;
- a display peptide derived from a nucleotide sequence encoded in a display vector; and
- at least one expression tag peptide selected from the group consisting of FLAG, c-Myc, (His)6-tag and V5-tag;
- wherein within each of the variable heavy chains, the CDR3 region of the heavy chain (CDRH3) has been modified from the respective SEQ ID NO;
- wherein the synthetic gene expression library encodes modified CDRH3s with lengths of 4, 5, 6, 7, 8, 9, 10, 11, 12, 13, 14, 15, 16, 17, 18, 19, 20, 21, 22 and 23 amino acid residues, wherein:

when the length of the modified CDRH3 is 4 amino acid residues, the amino acid sequence is $X_1X_2X_3X_4$ (SEQ ID NO. 113),
- wherein $X_1$ encodes such that G is 36.83%, D is 10.18%, E is 9.33%, V is 8.80%, R is 5.38%, Y is 5.22%, A is 0.21%, C is 0.05%, F is 4.21%, H is 0.94%, I is 3.09%, K is 4.14%, L is 2.93%, M is 0.05%, N is 2.42%, P is 0.05%, S is 1.15%, T is 0.07% and W is 4.90%,
- wherein $X_2$ encodes such that L is 22.64%, Y is 20.29%, D is 19.97%, R is 19.12%, T is 16.51%, A is 0.09%, F is 0.18%, G is 0.44%, I is 0.05%, M is 0.27%, N is 0.09%, P is 0.09%, Q is 0.04%, S is 0.16%, and W is 0.05%,
- wherein $X_3$ encodes such that A is 23.97%, E is 21.57%, R is 19.44%, Y is 17.18%, G is 16.29%, D is 0.60%, F is 0.04%, L is 0.21%, M is 0.05%, N is 0.04%, P is 0.05%, Q is 0.04%, S is 0.14%, T is 0.12%, V is 0.09%, C is 0.05% and W is 0.05%, and
- wherein $X_4$ encodes such that N is 24.57%, Y is 22.44%, R is 20.42%, S is 18.19%, P is 13.24%, D is 0.07%, F is 0.11%, G is 0.25%, I is 0.21%, L is 0.14%, V is 0.20% and W is 0.04%;

when the length of the modified CDRH3 is 5 amino acid residues, the amino acid sequence is $X_1X_2X_3X_4X_5$ (SEQ ID NO. 114),
- wherein $X_1$ encodes such that G is 35.44%, D is 9.98%, E is 8.42%, V is 7.44%, R is 6.81%, A is 0.39%, C is 0.08%, F is 3.55%, H is 1.60%, I is 3.93%, K is 4.88%, L is 4.32%, N is 2.98%, S is 1.40%, T is 0.19%, W is 4.25% and Y is 4.29%,
- wherein $X_2$ encodes such that G is 37.64%, R is 16.75%, M is 11.46%, N is 9.28%, V is 8.83%, H is 7.30%, T is 7.02%, A is 0.31%, D is 0.18%, E is 0.07%, F is 0.07%, I is 0.10%, K is 0.07%, L is 0.15%, P is 0.18%, Q is 4.00%, S is 0.18%, W is 0.10% and Y is 0.26%,
- wherein $X_3$ encodes such that M is 24.29%, G is 22.40%, F is 18.08%, E is 10.74%, L is 8.38%, W is 7.62%, S is 7.30%, A is 0.08%, C is 0.07%, D is 0.11%, H is 0.07%, I is 0.19%, Q is 0.04%, R is 0.18%, T is 0.04%, V is 0.17% and Y is 0.19%,
- wherein $X_4$ encodes such that D is 41.08%, A is 34.90%, L is 15.65%, V is 6.99%, C is 0.04%, E is 0.17%, F is 0.08%, G is 0.33%, H is 0.07%, M is 0.08%, P is 0.06%, Q is 0.06%, R is 0.10%, S is 0.17%, T is 0.04%, and Y is 0.11%, and
- wherein $X_5$ encodes such that Y is 65.74%, N is 15.00%, I is 9.60%, L is 6.56%, V is 6.22%, F is 5.91%, C is 0.12%, D is 0.12%, G is 0.15%, M is 0.04%, P is 0.11%, R is 0.07%, S is 0.12% and T is 4.94%;

when the length of the modified CDRH3 is 6 amino acid residues, the amino acid sequence is $X_1X_2X_3X_4X_5X_6$ (SEQ ID NO. 115),
- wherein $X_1$ encodes such that G is 32.77%, D is 9.78%, E is 9.04%, V is 7.72%, R is 7.15%, K is 5.11%, Y is 4.53%, W is 4.34%, I is 4.33%, L is 4.20%, N is 3.43%, F is 3.40%, S is 1.76%, H is 1.54%, A is 0.37%, T is 0.31%, C is 0.09%, P is 0.05%, Q is 0.05% and M is 0.03%,
- wherein $X_2$ encodes such that A is 17.54%, Y is 23.01%, G is 11.00%, S is 9.44%, P is 7.78%, N is 5.61%, K is 5.44%, V is 4.53%, L is 4.02%, T is 3.85%, R is 2.06%, D is 2.00%, W is 1.62%, H is 1.36%, F is 0.15%, E is 0.14%, I is 0.14%, M is 0.14%, and Q is 0.14%,
- wherein $X_3$ encodes such that G is 34.05%, Y is 12.12%, A is 9.75%, S is 8.13%, P is 7.48%, V is 6.92%, E is 6.36%, D is 4.77%, K is 2.25%, F is 1.93%, R is 1.57%, L is 1.56%, H is 1.43%, T is 0.95%, I is 0.14%, M is 0.14%, C is 0.11%, W is 0.11%, N is 0.09% and Q is 0.08%,
- wherein $X_4$ encodes such that F is 23.18%, G is 12.64%, M is 9.18%, S is 8.93%, E is 7.42%, D is 7.25%, L is 6.75%, V is 5.28%, P is 4.37%, Y is 2.77%, H is 2.71%, I is 2.71%, A is 2.53%, W is 1.71%, T is 1.28%, Q is 0.92%, R is 0.14%, K is 0.08%, N is 0.06% and C is 0.05%,
- wherein $X_5$ encodes such that D is 59.06%, A is 10.04%, G is 7.96%, N is 7.79%, P is 4.53%, I is 2.19%, M is 2.05%, R is 1.60%, V is 1.39%, H is 1.36%, T is 0.95%, Y is 0.28%, S is 0.26%, L is 0.17%, E is 0.11%, F is 0.09%, K is 0.09%, Q is 0.03%, and W is 0.03%, and
- wherein $X_6$ encodes such that Y is 63.36%, C is 7.85%, V is 7.76%, G is 3.94%, L is 3.73%, D is 3.45%, F is 3.39%, P is 1.77%, R is 1.51%, S is 1.43%, H is 0.95%, I is 0.46%, N is 0.08%, A is 0.05%, Q is 0.05%, K is 0.03%, and M is 0.03%;

when the length of the modified CDRH3 is 7 amino acid residues, the amino acid sequence is $X_1X_2X_3X_4X_5X_6X_7$ (SEQ ID NO. 116),
- wherein $X_1$ encodes such that G is 31.73%, D is 10.11%, E is 8.67%, V is 7.43%, R is 6.98%, K is 5.49%, Y is 4.88%, L is 4.30%, W is 4.06%, I is 4.01%, F is 3.65%, N is 3.33%, S is 1.87%, H is 1.69%, A is 0.85%, T is 0.58%, Q is 0.14%, P is 0.09%, C is 0.08% and M is 0.08%, wherein $X_2$ encodes such that R is 15.99%, G is 12.37%, A is 9.55%, Y is 9.41%, N is 7.19%, D is 6.98%, S is 5.72%, H is 4.93%, P is 4.68%, E is 3.97%, I is 3.86%, V is 3.85%, L is 3.39%, Q is 2.81%, T is 2.52%, K is 1.34%, W is 1.08%, F is 0.18%, M is 0.12% and C is 0.06%, wherein $X_3$ encodes such that G is 21.33%, D is 14.56%, Y is 13.01%, N is 12.74%, S is 7.39%, A is 6.55%, L is 5.93%, W is 4.67%, T is 4.07%, R is 3.98%, E is 1.40%, K is 1.32%, V is 1.09%, H is 1.06%, I is 0.23%, P is 0.23%, Q is 0.12%, C is 0.11%, M is 0.11% and F is 0.08%, wherein $X_4$ encodes such that G is 37.46%, A is 13.29%, Y is 10.44%, W is 6.05%, D is 5.29%, E is 5.15%, R is 4.13%, S is 3.16%, F is 3.09%, P is 2.74%, H is 2.30%, T is 1.72%, L is 1.25%, M is 1.17%, N is 1.11%, V is 1.08%, K is 0.20%, I is 0.18%, C is 0.09% and Q is 0.08%, wherein $X_5$ encodes such that F is 43.63%, M is 18.58%, L is 8.83%, G is 6.34%, P is 3.95%, I is 3.39%, W is 2.48%, S is 2.34%, V is 2.23%, Q is 1.58%, Y is 1.49%, A is 1.26%, R is 1.00%, C is 0.99%, H is 0.62%, T is 0.62%, D is 0.24%, N is 0.21%, E is 0.15% and K is 0.03%, wherein $X_6$ encodes such that D is 77.08%, G is 5.05%, A is 3.75%, K is 3.07%, Y is 2.84%, S is 2.40%, T is 1.32%, R is 1.16%, E is 1.12%, V is 0.94%, L is 0.59%, F is 0.15%, H is 0.14%, N is 0.09%, M is 0.08%, P is 0.06%, I is 0.05%, C is 0.03% and Q is 0.03%, and wherein $X_7$ encodes such that Y is 49.26%, V is 20.01%, I is 8.62%, S is 3.92%, P is 3.53%, N is 3.34%, F is 3.01%, L is 2.98%, G is 1.84%, D is 1.28%, R is 0.67%, H is 0.55%, T is 0.55%, A is 0.12%, K is 0.08%, M is 0.08%, C is 0.06% and W is 0.05%;

when the length of the modified CDRH3 is 8 amino acid residues, the amino acid sequence is $X_1X_2X_3X_4X_5X_6X_7X_8$ (SEQ ID NO. 117), wherein $X_1$ encodes such that G is 33.76%, D is 10.40%, E is 9.17%, V is 8.12%, R is 6.24%, Y is 4.95%, K is 4.73%, F is 4.56%, I is 3.98%, W is 3.93%, L is 3.54%, N is 3.17%, H is 1.54%, S is 1.29%, A is 0.18%, C is 0.13%, T is 0.11%, P is 0.05% and M is 0.04%, wherein $X_2$ encodes such that G is 18.07%, L is 10.46%, S is 7.48%, T is 6.21%, P is 6.05%, F is 6.02%, R is 5.58%, Y is 5.51%, D is 5.22%, E is 4.27%, A is 3.90%, I is 3.51%, N is 3.28%, W is 3.27%, V is 2.77%, M is 2.62%, K is 2.25%, H is 2.00%, Q is 1.46% and C is 0.05%, wherein $X_3$ encodes such that G is 14.48%, S is 9.89%, R is 8.88%, Y is 7.85%, L is 7.23%, H is 6.09%, I is 5.98%, A is 4.41%, D is 3.99%, P is 3.76%, E is 3.72%, Q is 3.56%, W is 3.46%, N is 3.30%, T is 2.82%, M is 2.71%, F is 2.69%, V is 2.15%, C is 1.73% and K is 1.28%, wherein $X_4$ encodes such that G is 28.59%, S is 8.39%, R is 8.36%, W is 7.71%, A is 6.07%, V is 6.04%, N is 5.44%, D is 4.55%, F is 4.00%, Y is 3.53%, K is 2.65%, T is 2.63%, H is 2.22%, Q is 2.20%, L is 1.93%, M is 1.60%, E is 1.52%, I is 1.39%, P is 1.04% and C is 0.13%, wherein $X_5$ encodes such that A is 18.48%, G is 17.93%, S is 9.53%, Y is 8.37%, L is 6.58%, R is 5.24%, D is 4.89%, P is 3.79%, V is 3.72%, T is 3.20%, M is 2.73%, H is 2.61%, W is 2.57%, E is 2.43%, N is 2.19%, F is 1.82%, C is 1.60%, Q is 1.12%, I is 1.08% and K is 0.09%, wherein $X_6$ encodes such that F is 35.24%, L is 12.91%, A is 9.55%, I is 7.50%, G is 4.40%, Y is 4.38%, V is 3.54%, S is 3.48%, D is 3.13%, N is 2.99%, H is 2.91%, W is 2.28%, E is 2.27%, M is 1.58%, P is 1.47%, C is 0.78%, Q is 0.75%, T is 0.68%, R is 0.10% and K is 0.06%, wherein $X_7$ encodes such that D is 78.56%, G is 4.18%, E is 2.32%, A is 1.94%, H is 1.84%, S is 1.39%, V is 1.34%, K is 1.04%, Y is 1.03%, F is 0.98%, L is 0.94%, N is 0.93%, R is 0.88%, C is 0.76%, P is 0.68%, Q is 0.56%, T is 0.56% and I is 0.06%, and wherein $X_8$ encodes such that Y is 53.04%, G is 11.28%, S is 5.38%, N is 4.74%, P is 4.64%, D is 3.78%, V is 3.23%, R is 3.18%, I is 3.03%, F is 2.61%, K is 1.02%, L is 1.01%, H is 0.90%, A is 0.89%, W is 0.58%, T is 0.53% and C is 0.06%;

when the length of the modified CDRH3 is 9 amino acid residues, the amino acid sequence is $X_1X_2X_3X_4X_5X_6X_7X_8X_9$ (SEQ ID NO. 118), wherein $X_1$ encodes such that G is 43.79%, D is 20.00%, S is 5.55%, E is 5.28%, R is 4.93%, L is 3.53%, V is 3.44%, K is 2.25%, H is 1.92%, I is 1.78%, Q is 1.51%, M is 1.29%, P is 0.98%, F is 0.96%, W is 0.93%, N is 0.68%, A is 0.55%, Y is 0.37%, T is 0.20% and C is 0.03%, wherein $X_2$ encodes such that G is 17.08%, S is 9.50%, R is 9.19%, Y is 7.46%, L is 6.35%, H is 5.60%, I is 5.54%, A is 4.66%, E is 4.51%, D is 4.20%, Q is 3.63%, P is 3.49%, W is 3.49%, T is 2.87%, N is 2.83%, V is 2.52%, M is 2.41%, F is 1.92%, C is 1.69% and K is 1.04%, wherein $X_3$ encodes such that G is 14.76%, S is 10.20%, R is 9.45%, Y is 7.77%, L is 6.64%, I is 6.01%, H is 5.34%, A is 4.14%, D is 3.96%, Q is 3.93%, E is 3.89%, W is 3.73%, P is 3.57%, N is 3.24%, M is 2.88%, T is 2.88%, F is 2.31%, V is 2.18%, C is 1.92% and K is 1.19%, wherein $X_4$ encodes such that G is 15.10%, S is 9.89%, R is 9.10%, Y is 8.27%, L is 6.55%, I is 6.14%, H is 5.83%, D is 4.32%, E is 4.04%, P is 3.96%, A is 3.89%, Q is 3.66%, N is 3.36%, W is 3.21%, M is 2.72%, T is 2.54%, V is 2.15%, F is 2.13%, C is 2.04% and K is 1.06%, wherein $X_5$ encodes such that G is 15.44%, S is 9.76%, R is 9.50%, Y is 8.03%, L is 6.30%, I is 5.78%, H is 5.55%, D is 4.27%, A is 4.14%, E is 3.79%, P is 3.79%, Q is 3.75%, N is 3.13%, W is 3.05%, M is 2.82%, T is 2.75%, V is 2.52%, F is 2.36%, C is 2.13% and K is 1.07%, wherein $X_6$ encodes such that A is 24.67%, G is 12.08%, P is 9.19%, Y is 9.02%, S is 7.51%, W is 4.71%, D is 4.17%, N is 3.94%, L is 3.84%, H is 3.44%, R is 3.21%, T is 2.51%, F is 2.05%, E is 1.94%, V is 1.78%, I is 1.53%, M is 1.45%, K is 1.09%, C is 1.01% and Q is 0.85%, wherein $X_7$ encodes such that F is 44.15%, L is 11.63%, Y is 8.50%, I is 6.87%, S is 5.49%, M is 4.61%, P is 3.71%, V is 3.11%, A is 2.65%, G is 2.13%, H is 1.55%, Q is 1.55%, N is 1.12%, D is 0.99%, W is 0.85%, T is 0.80%, E is 0.15%, R is 0.07% and C is 0.03%, wherein $X_8$ encodes such that D is 76.27%, G is 4.51%, E is 2.20%, H is 2.12%, A is 1.94%, S is 1.82%, V is 1.66%, L is 1.12%, Y is 1.07%, K is 1.06%, P is 1.06%, C is 0.96%, N is 0.93%, F is 0.86%, R is 0.83%, Q is 0.77%, T is 0.75% and I is 0.05%, and wherein $X_9$ encodes such that Y is 50.77%, G is 10.94%, S is 5.41%, P is 5.26%, N is 4.74%, D is 4.10%, R is 3.97%, V is 3.83%, I is 3.11%, F is 2.59%, L is 1.17%, H is 1.04%, K is 0.94%, A is 0.88%, W is 0.55%, T is 0.44%, C is 0.10%, M is 0.03% and Q is 0.03%;

when the length of the modified CDRH3 is 10 amino acid residues, the amino acid sequence is $X_1X_2X_3X_4X_5X_6X_7X_8X_9X_{10}$ (SEQ ID NO. 119), wherein $X_1$ encodes such that G is 27.45%, D is 23.76%, E is 14.63%, V is 7.40%, R is 5.28%, Y is 3.59%, S is 2.96%, L is 2.25%, H is 1.88%, M is 1.81%, K is 1.68%, Q is 1.61%, W is 1.51%, P is 1.42%, I is 0.91%, A is 0.69%, N is 0.66%, T is 0.34%, F is 0.12% and C is 0.05%, wherein $X_2$ encodes such that G is 16.66%, S is 9.67%, R is 9.13%, Y is 7.84%, L is 6.40%, I is 5.96%, D is 5.13%, H is 4.91%, E is 4.59%, A is 4.11%, Q is 3.45%, W is 3.40%, P is 3.12%, N is 2.95%, M is 2.78%, T is 2.74%, F is 2.44%, V is 1.93%, C is 1.79% and K is 0.97%, wherein $X_3$ encodes such that G is 16.34%, S is 10.57%, R is 9.97%, Y is 7.87%, L is 6.01%, H is 5.52%, I is 5.08%, D is 3.98%, E is 3.86%, A is 3.71%, Q is 3.71%, P is 3.57%, W is 3.44%, N is 3.25%, T is 2.86%, M is 2.79%, V is 2.47%, F is 2.27%, C is 1.51% and K is 1.20%, wherein $X_4$ encodes such that G is 16.80%, S is 10.43%, R is 9.70%, Y is 8.04%, I is 5.94%, L is 5.38%, H is 5.16%, D is 4.33%, E is 4.18%, A is 3.88%, W is 3.79%, Q is 3.52%, N is 3.15%, P is 2.78%, F is 2.49%, M is 2.42%, T is 2.40%, V is 2.35%, C is 1.76% and K is 1.44%, wherein $X_5$ encodes such that G is 14.66%, S is 10.29%, R is 10.04%, Y is 8.36%, L is 5.79%, H is 5.28%, I is 5.20%, E is 4.61%, D is 4.15%, W is 4.01%, A is 4.00%, Q is 3.93%, M is 3.22%, N is 3.22%, P is 3.00%, T is 2.54%, V is 2.40%, F is 2.18%, C is 1.86% and K is 1.19%, wherein $X_6$ encodes such that G is 15.31%, S is 10.45%, R is 9.91%, Y is 9.13%, I is 5.44%, H is 5.35%, L is 4.72%, D is 4.71%, A is 4.20%, E is 4.18%, W is 3.40%, Q is 3.20%, M is 3.18%, N is 3.10%, P is 2.81%, F is 2.78%, V is 2.62%, T is 2.56%, C is 1.73% and K is 1.22%, wherein $X_7$ encodes such that A is 26.92%, G is 16.10%, Y is 11.80%, D is 5.98%, W is 5.79%, S is 4.45%, R is 4.20%, P is 4.00%, L is 3.42%, H is 2.79%, F is 2.64%, E is 2.62%, I is 2.57%, V is 2.17%, T is 1.98%, N is 1.22%, Q is 1.02%, K is 0.10%, M is 0.10% and C is 0.07%, wherein $X_8$ encodes such that F is 55.93%, L is 8.74%, M is 5.33%, Y is 5.15%, G is 5.11%, I is 5.05%, S is 3.78%, E is 2.30%, V is 1.78%, N is 1.35%, P is 1.22%, C is 1.15%, W is 1.15%, H is 0.91%, T is 0.54%, D is 0.22%, A is 0.17%, R is 0.07% and Q is 0.03% wherein $X_9$ encodes such that D is 79.00%, G is 3.86%, E is 2.13%, H is 1.98%, A is 1.74%, S is 1.54%, K is 1.32%, R is 1.12%, V is 1.10%, Y is 1.08%, N is 0.91%, L is 0.90%, C is 0.85%, P is 0.78%, Q is 0.66%, F is 0.56%, T is 0.37%, I is 0.05% and M is 0.03%, and wherein $X_{10}$ encodes such that Y is 50.54%, G is 12.58%, S is 6.42%, N is 4.76%, P is 4.08%, D is 4.05%, R is 3.81%, V is 3.61%, I is 3.03%, F is 2.32%, K is 1.02%, A is 0.98%, H is 0.85%, W is 0.81%, L is 0.61%, T is 0.44% and C is 0.03%;

when the length of the modified CDRH3 is 11 amino acid residues, the amino acid sequence is $X_1X_2X_3X_4X_5X_6X_7X_8X_9X_{10}X_{11}$ (SEQ ID NO. 120), wherein $X_1$ encodes such that G is 26.14%, D is 24.10%, E is 13.67%, V is 7.72%, R is 5.62%, A is 0.58%, C is 0.16%, F is 0.10%, H is 2.04%, I is 0.80%, K is 1.93%, L is 2.37%, M is 1.83%, N is 0.68%, P is 1.61%, Q is 1.96%, S is 2.53%, T is 0.29%, W is 1.67% and Y is 4.10%, wherein $X_2$ encodes such that G is 15.23%, S is 9.80%, R is 9.57%, Y is 7.08%, L is 6.77%, I is 6.30%, H is 5.17%, A is 4.53%, C is 1.60%, D is 4.03%, E is 4.79%, F is 2.30%, K is 1.30%, M is 2.55%, N is 2.74%, P is 3.72%, Q is 3.79%, T is 2.66%, V is 2.51% and W is 3.56%, wherein $X_3$ encodes such that G is 14.63%, S is 10.56%, R is 10.06%, Y is 7.37%, L is 6.21%, I is 6.13%, H is 5.15%, A is 4.34%, C is 2.06%, D is 4.01%, E is 4.08%, F is 2.51%, K is 1.21%, M is 3.01%, N is 2.98%, P is 2.90%, Q is 3.70%, T is 3.25%, V is 2.16% and W is 3.66%, wherein $X_4$ encodes such that G is 15.29%, R is 10.35%, S is 9.76%, Y is 8.99%, L is 5.56%, I is 5.49%, H is 5.15%, A is 4.01%, C is 1.61%, D is 4.05%, E is 4.47%, F is 2.24%, K is 1.03%, M is 2.82%, N is 3.40%, P is 3.27%, Q is 3.85%, T is 2.82%, V is 2.24% and W is 3.54%, wherein $X_5$ encodes such that G is 14.88%, S is 11.42%, R is 9.61%, Y is 8.34%, L is 6.05%, I is 5.41%, H is 5.14%, A is 4.53%, C is 1.54%, D is 4.53%, E is 3.93%, F is 2.47%, K is 1.44%, M is 2.74%, N is 2.98%, P is 3.07%, Q is 3.81%, T is 2.49%, V is 2.26% and W is 3.37%, wherein $X_6$ encodes such that G is 16.13%, S is 10.60%, R is 9.14%, Y is 8.52%, I is 5.84%, H is 5.31%, L is 5.27%, A is 3.66%, C is 1.81%, D is 4.28%, E is 4.45%, F is 2.43%, K is 1.23%, M is 2.82%, N is 3.33%, P is 2.90%, Q is 3.38%, T is 2.70%, V is 2.14% and W is 4.01%, wherein $X_7$ encodes such that G is 14.84%, S is 10.37%, R is 10.00%, Y is 8.87%, I is 5.89%, H is 5.21%, L is 5.21%, A is 4.32%, C is 1.63%, D is 4.98%, E is 4.30%, F is 2.24%, K is 1.19%, M is 3.07%, N is 3.54%, P is 2.98%, Q is 3.29%, T is 2.43%, V is 2.41% and W is 3.17%, wherein $X_8$ encodes such that A is 20.31%, Y is 19.12%, G is 14.26%, S is 6.17%, P is 5.78%, C is 1.07%, D is 4.90%, E is 1.21%, F is 2.10%, H is 1.52%, I is 2.22%, K is 1.52%, L is 2.74%, M is 0.06%, N is 4.20%, Q is 0.95%, R is 2.18%, T is 3.85%, V is 1.07% and W is 4.77%, wherein $X_9$ encodes such that F is 54.27%, M is 12.12%, L is 11.52%, A is 0.04%, C is 0.91%, D is 1.09%, E is 1.17%, G is 2.61%, H is 0.10%, I is 4.34%, N is 0.97%, P is 3.05%, Q is 0.78%, S is 1.13%, T is 0.54%, V is 2.63%, W is 0.93% and Y is 1.77%, wherein $X_{10}$ encodes such that D is 77.57%, A is 1.65%, C is 0.54%, E is 2.04%, F is 0.58%, G is 3.93%, H is 2.28%, K is 1.21%, L is 1.09%, N is 1.26%, P is 0.99%, Q is 0.66%, R is 1.11%, S is 1.95%, T is 0.62%, V is 1.34%, and Y is 1.11%, and wherein $X_{11}$ encodes such that Y is 49.60%, G is 11.15%, S is 6.21%, A is 0.82%, C is 0.04%, D is 4.49%, F is 2.76%, H is 0.78%, I is 3.42%, K is 1.34%, L is 0.70%, M is 0.08%, N is 4.40%, P is 4.22%, R is 4.14%, T is 0.47%, V is 4.71% and W is 0.62%;

when the length of the modified CDRH3 is 12 amino acid residues, the amino acid sequence is $X_1X_2X_3X_4X_5X_6X_7X_8X_9X_{10}X_{11}X_{12}$ (SEQ ID NO. 121), wherein $X_1$ encodes such that G is 26.20%, D is 24.18%, E is 14.76%, V is 7.81%, R is 5.18%, Y is 3.56%, S is 2.82%, L is 2.21%, H is 2.11%, M is 1.96%, Q is 1.83%, P is 1.62%, W is 1.58%, K is 1.47%, I is 0.95%, A is 0.72%, N is 0.59%, T is 0.23%, C is 0.13% and F is 0.06%, wherein $X_2$ encodes such that G is 16.11%, R is 10.28%, S is 10.09%, Y is 7.31%, L is 5.96%, I is 5.73%, H is 5.31%, E is 4.74%, D is 4.51%, Q is 3.98%, A is 3.60%, P is 3.52%, N is 3.31%, W is 2.82%, M is 2.67%, T is 2.63%, F is 2.42%, V is 2.09%, C is 1.71% and K is 1.16%, wherein $X_3$ encodes such that G is 15.16%, S is 10.21%, R is 10.15%, Y is 8.19%, L is 6.55%, I is 6.19%, H is 5.69%, E is 4.17%, Q is 4.02%, D is 3.77%, N is 3.58%, P is 3.50%, A is 3.43%, W is 3.18%, T is 2.65%, M is 2.51%, F is 2.08%, V is 2.04%, C is 1.90% and K is 1.01%, wherein $X_4$ encodes such that G is 16.07%, R is 10.64%, S is 9.77%, Y is 7.25%, L is 6.13%, I is 5.92%, H is 4.59%, E is 4.57%, D is 4.09%, A is 4.04%, W is 3.62%, P is 3.43%, Q is 3.43%, N is 3.12%, M is 2.99%, T is 2.91%, F is 2.44%, V is 2.04%, C is 1.77% and K is 1.10%, wherein $X_5$ encodes such that G is 15.00%, S is 10.43%, R is 10.28%, Y is 8.13%, L is 5.79%, H is 5.48%, I is 5.37%, Q is 4.36%, E is 4.25%, D is 4.23%, A is 3.96%, W is 3.67%, P is 3.64%, N is 3.24%, M is 2.68%, T is 2.23%, V is 2.21%, F is 1.88%, C is 1.79% and K is 1.33%, wherein $X_6$ encodes such that G is 15.16%, S is 10.47%, R is 10.11%, Y is 7.79%, I is 6.55%, L is 5.69%, H is 5.20%, E is 4.53%, D is 4.49%, A is 4.17%, W is 3.66%, Q is 3.37%, N is 3.27%, M is 2.78%, P is 2.72%, F is 2.46%, T is 2.38%, V is 2.19%, C is 1.66% and K is 1.35%, wherein $X_7$ encodes such that G is 14.95%, R is 10.11%, S is 10.03%, Y is 8.57%, H is 6.68%, I is 5.60%, L is 5.35%, D is 4.07%, A is 3.96%, E is 3.96%, N is 3.62%, P is 3.35%, W is 3.16%, Q is 3.03%, M is 2.97%, F is 2.59%, T is 2.55%, V is 2.32%, C is 1.81% and K is 1.28%, wherein $X_8$ encodes such that G is 18.74%, Y is 18.39%, D is 13.25%, N is 6.42%, S is 5.69%, R is 5.52%, P is 4.82%, H is 3.26%, E is 2.74%, T is 2.68%, V is 2.59%, A is 2.51%, I is 2.36%, F is 2.34%, C is 1.87%, W is 1.47%, K is 1.45%, L is 1.41%, Q is 1.22% and M is 1.14%, wherein $X_9$ encodes such that G is 20.39%, A is 18.34%, Y is 17.65%, W is 9.03%, P is 6.23%, S is 4.34%, R is 2.88%, L is 2.74%, C is 2.48%, T is 2.38%, F is 2.17%, H is 2.02%, M is 1.81%, D is 1.58%, V is 1.37%, N is 1.28%, I is 1.16%, E is 1.09%, Q is 0.80% and K is 0.15%, wherein $X_{10}$ encodes such that F is 52.70%, L is 12.64%, M is 11.69%, I is 4.76%, P is 3.16%, G is 3.03%, V is 2.44%, Y is 1.73%, S is 1.31%, E is 1.16%, D is 1.10%, W is 0.93%, N is 0.89%, Q is 0.86%, T is 0.74%, C is 0.65% and A is 0.15%, wherein $X_{11}$ encodes such that D is 78.03%, G is 4.09%, E is 2.06%, A is 1.87%, H is 1.87%, S is 1.58%, K is 1.43%, V is 1.41%, N is 1.14%, L is 1.01%, Y is 0.99%, T is 0.88%, P is 0.82%, R is 0.80%, Q is 0.67%, F is 0.65%, C is 0.57%, I is 0.06% and M is 0.04%, and wherein $X_{12}$ encodes such that Y is 49.52%, G is 11.90%, S is 6.26%, N is 4.65%, D is 4.36%, V is 4.27%, P is 3.96%, I is 3.60%, R is 3.50%, F is 2.49%, K is 1.20%, A is 0.95%, W is 0.88%, L is 0.86%, H is 0.84%, T is 0.48%, M is 0.11%, C is 0.06% and E is 0.04%;

when the length of the modified CDRH3 is 13 amino acid residues, the amino acid sequence is $X_1X_2X_3X_4X_5X_6X_7X_8X_9X_{10}X_{11}X_{12}X_{13}$ (SEQ ID NO. 122), wherein $X_1$ encodes such that G is 25.88%, D is 22.97%, E is 14.18%, V is 7.62%, R is 5.85%, A is 0.73%, C is 0.10%, F is 0.02%, H is 2.15%, I is 0.79%, K is 2.03%, L is 2.46%, M is 2.09%, N is 0.61%, P is 1.86%, Q is 1.80%, S is 3.49%, T is 0.31%, W is 1.65% and Y is 3.34%, wherein $X_2$ encodes such that G is 16.85%, S is 10.07%, R is 9.77%, Y is 7.60%, L is 5.83%, H is 5.41%, I is 5.24%, A is 4.72%, C is 1.92%, D is 4.39%, E is 4.43%, F is 2.09%, K is 1.04%, M is 2.46%, N is 3.28%, P is 3.70%, Q is 3.05%, T is 2.69%, V is 2.13% and W is 3.24%, wherein $X_3$ encodes such that G is 15.48%, S is 10.67%, R is 9.46%, Y is 7.41%, I is 6.52%, L is 6.45%, H is 5.03%, A is 4.39%, C is 1.86%, D is 4.03%, E is 3.78%, F is 2.13%, K is 1.42%, M is 2.78%, N is 3.34%, P is 3.49%, Q is 3.53%, T is 2.92%, V is 2.07% and W is 3.20%, wherein $X_4$ encodes such that G is 15.20%, S is 10.44%, R is 9.38%, Y is 7.54%, L is 6.10%, H is 5.91%, I is 5.51%, A is 4.18%, C is 1.71%, D is 4.51%, E is 4.26%, F is 2.28%, K is 1.25%, M is 2.90%, N is 3.07%, P is 3.53%, Q is 3.43%, T is 2.74%, V is 2.51% and W is 3.45%, wherein $X_5$ encodes such that G is 16.10%, S is 10.23%, R is 9.86%, Y is 7.58%, L is 5.64%, H is 5.53%, I is 5.24%, A is 4.43%, C is 1.84%, D is 4.62%, E is 4.22%, F is 2.44%, K is 1.50%, M is 2.57%, N is 3.47%, P is 3.07%, Q is 3.82%, T is 2.46%, V is 2.28% and W is 3.03%, wherein $X_6$ encodes such that G is 15.39%, S is 10.36%, R is 9.94%, Y is 7.81%, I is 6.58%, H is 5.60%, L is 5.33%, A is 3.47%, C is 1.75%, D is 4.47%, E is 4.55%, F is 2.32%, K is 1.34%, M is 2.59%, N is 3.22%, P is 3.07%, Q is 3.72%, T is 2.84%, V is 2.28% and W is 3.38%, wherein $X_7$ encodes such that G is 15.12%, S is 10.36%, R is 9.90%, Y is 8.67%, L is 6.24%, I is 5.45%, H is 5.05%, A is 3.76%, C is 1.78%, D is 4.72%, E is 4.62%, F is 2.49%, K is 1.27%, M is 2.53%, N is 3.32%, P is 3.24%, Q is 3.51%, T is 2.59%, V is 1.86% and W is 3.51%, wherein $X_8$ encodes such that G is 13.99%, S is 10.32%, R is 9.54%, Y is 9.31%, L is 6.12%, I is 5.68%, H is 5.30%, A is 4.09%, C is 1.73%, D is 4.80%, E is 3.97%, F is 2.40%, K is 1.67%, M is 2.88%, N is 3.34%, P is 3.24%, Q is 3.22%, T is 2.49%, V is 2.23% and W is 3.63%, wherein $X_9$ encodes such that Y is 18.73%, G is 17.44%, D is 10.42%, N is 9.54%, S is 7.31%, R is 5.14%, A is 2.67%, C is 1.78%, E is 3.84%, F is 4.51%, H is 3.40%, I is 1.61%, K is 2.72%, L is 2.38%, M is 0.06%, P is 1.98%, Q is 0.81%, T is 2.36%, V is 2.42 and W is 0.86%, wherein $X_{10}$ encodes such that A is 21.07%, Y is 19.84%, G is 18.30%, W is 6.83%, C is 2.17%, D is 2.32%, E is at 1.59%, F is 4.85%, H is 1.46%, I is 2.11%, K is 1.52%, L is 2.07%, M is 1.44%, N is 2.13%, P is 4.26%, Q is 0.08%, R is 1.34%, S is 3.72%, T is 1.02% and V is 1.86%, wherein $X_{11}$ encodes such that F is 54.39%, L is 12.43%, M is 11.51%, C is 0.81%, D is 1.21%, E is 1.11%, G is 2.74%, H is 0.06%, I is 4.34%, N is 0.94%, P is 2.61%, Q is 0.94%, S is 0.98%, T is 0.48%, V is 2.23%, W is 1.00% and Y is 2.13%, wherein $X_{12}$ encodes such that D is 77.80%, A is 1.92%, C is 0.50%, E is 2.19%, F is 0.86%, G is 4.03%, H is 1.84%, I is 0.10%, K is 1.27%, L is 1.11%, N is 1.11%, P is 0.75%, Q is 0.69%, R is 0.81%, S is 1.98%, T is 0.69%, V is 1.44%, and Y is 0.81%, and wherein $X_{13}$ encodes such that Y is 51.23%, G is 11.28%, S is 5.43%, V is 5.43%, A is 0.81%, C is 0.02%, D is 4.39%, F is 2.65%, H is 1.11%, I is 3.86%, K is 0.86%, L is 0.96%, M is 0.04%, N is 4.16%, P is 3.38%, Q is 0.04%, R is 3.13%, T is 0.52% and W is 0.56%:

when the length of the modified CDRH3 is 14 amino acid residues, the amino acid sequence is $X_1X_2X_3X_4X_5X_6X_7X_8X_9X_{10}X_{11}X_{12}X_{13}X_{14}$ (SEQ ID NO. 123), wherein $X_1$ encodes such that G is 24.96%, D is 23.95%, E is 15.20%, V is 6.94%, R is 5.78%, Y is 3.32%, S is 3.08%, L is 2.72%, M is 2.26%, H is 2.22%, Q is 2.17%, P is 1.82%, W is 1.63%, K is 1.49%, A is 0.81%, I is 0.70%, N is 0.46%, T is 0.35% and C is 0.07%, wherein $X_2$ encodes such that G is 17.46%, R is 9.69%, S is 9.42%, Y is 7.05%, L is 5.76%, I is 5.47%, E is 4.68%, D is 4.66%, H is 4.66%, A is 4.46%, P is 3.58%, N is 3.49%, W is 3.25%, Q is 2.99%, M is 2.77%, T is 2.64%, F is 2.48%, V is 2.37%, C is 1.80% and K is 1.30%, wherein $X_3$ encodes such that G is 16.37%, S is 10.22%, R is 8.94%, Y is 7.10%, L is 6.85%, I is 6.24%, H is 5.16%, E is 4.15%, D is 3.91%, W is 3.80%, Q is 3.65%, A is 3.58%, N is 3.56%, P is 3.41%, M is 3.12%, F is 2.33%, T is 2.26%, C is 2.02%, V is 1.89% and K is 1.41%, wherein $X_4$ encodes such that G is 14.54%, S is 10.61%, R is 9.53%, Y is 7.54%, I is 6.41%, L is 6.26%, H is 5.43%, D is 4.35%, E is 4.04%, A is 3.62%, N is 3.41%, Q is 3.41%, T is 3.25%, M is 3.16%, P is 3.10%, W is 2.94%, V is 2.55%, F is 2.42%, C is 2.00% and K is 1.43%, wherein $X_5$ encodes such that G is 15.69%, S is 10.76%, R is 10.04%, Y is 7.89%, L is 5.89%, I is 5.78%, H is 5.40%, D is 4.96%, E is 4.28%, A is 4.26%, Q is 3.30%, N is 3.23%, W is 3.01%, P is 2.86%, M is 2.70%, F is 2.37%, T is 2.33%, V is 2.17%, C is 1.58% and K is 1.45%, wherein $X_6$ encodes such that G is 15.03%, S is 10.35%, R is 9.89%, Y is 7.86%, L is 5.82%, I is 5.76%, H is 5.27%, D is 4.59%, E is 4.15%, A is 4.02%, N is 3.58%, P is 3.45%, Q is 3.45%, W is 3.41%, F is 3.01%, T is 2.64%, M is 2.59%, V is 2.17%, C is 1.49% and K is 1.38%, wherein $X_7$ encodes such that G is 14.63%, S is 11.47%, R is 9.82%, Y is 7.91%, I is 6.37%, L is 5.62%, H is 5.16%, E is 4.75%, D is 4.42%, A is 4.20%, Q is 3.32%, W is 3.32%, N is 3.27%, M is 2.75%, P is 2.50%, T is 2.50%, F is 2.42%, V is 2.24%, C is 1.87% and K is 1.36%, wherein $X_8$ encodes such that G is 14.78%, S is 11.07%, R is 10.26%, Y is 8.72%, I is 5.60%, L is 5.40%, H is 5.03%, D is 4.81%, E is 4.81%, A is 4.11%, W is 3.38%, N is 3.25%, P is 3.05%, Q is 2.88%, M is 2.83%, V is 2.42%, T is 2.37%, F is 2.22%, C is 1.49% and K is 1.47%, wherein $X_9$ encodes such that G is 14.10%, S is 11.16%, R is 10.22%, Y is 8.72%, I is 5.56%, H is 5.43%, L is 5.14%, D is 4.92%, E is 4.92%, A is 3.76%, Q is 3.49%, N is 3.19%, W is 3.08%, M is 2.86%, F is 2.79%, P is 2.53%, T is 2.17%, V is 2.17%, C is 2.09% and K is 1.60%, wherein $X_{10}$ encodes such that Y is 15.55%, R is 10.26%, G is 8.88%, P is 7.32%, D is 6.57%, I is 5.93%, E is 5.78%, A is 5.16%, S is 4.75%, V is 4.57%, L is 4.22%, F is 4.02%, Q is 3.98%, T is 3.03%, W is 2.11%, N is 2.04%, C is 1.93%, M is 1.41%, K is 1.27% and H is 1.16%, wherein $X_{11}$ encodes such that A is 20.45%, G is 19.46%, Y is 16.61%, W is 9.47%, P is 5.36%, F is 4.09%, S is 3.30%, L is 3.19%, H is 2.77%, T is 2.57%, V is 2.57%, N is 2.37%, C is 2.17%, R is 1.82%, K is 1.58%, D is 1.19%, I is 0.70%, E is 0.15% and Q is 0.09%, wherein $X_{12}$ encodes such that F is 54.77%, L is 11.97%, M is 10.79%, I is 4.88%, G is 3.12%, P is 3.05%, V is 2.33%, Y is 1.78%, D is 1.23%, E is 1.05%, N is 0.92%, S is 0.90%, W is 0.88%, C is 0.83%, Q is 0.77%, T is 0.59% and A is 0.09%, wherein $X_{13}$ encodes such that D is 77.07%, G is 4.37%, E is 2.11%, H is 1.98%, A is 1.93%, S is 1.85%, N is 1.54%, V is 1.45%, K is 1.05%, L is 1.05%, Q is 0.90%, R is 0.90%, Y is 0.86%, C is 0.81%, P is 0.81%, F is 0.70%, T is 0.57% and I is 0.04%, and wherein $X_{14}$ encodes such that Y is 46.09%, V is 17.38%, I is 16.17%, S is 4.88%, H is 3.21%, N is 2.94%, D is 2.66%, F is 1.96%, A is 1.16%, R is 1.14%, L is 0.83%, T is 0.75%, G is 0.26%, P is 0.26% and M is 0.13%;

when the length of the modified CDRH3 is 15 amino acid residues, the amino acid sequence is $X_1X_2X_3X_4X_5X_6X_7X_8X_9X_{10}X_{11}X_{12}X_{13}X_{14}X_{15}$ (SEQ ID NO. 124), wherein $X_1$ encodes such that G is 24.51%, D is 24.03%, E is 14.58%, V is 7.89%, R is 5.96%, Y is 2.98%, S is 2.91%, L is 2.82%, Q is 2.43%, H is 2.18%, M is 2.13%, P is 1.65%, K is 1.63%, W is 1.22%, A is 0.92%, N is 0.80%, I is 0.78%, T is 0.37%, C is 0.07%, F is 0.07%, wherein $X_2$ encodes such that G is 17.63%, S is 10.41%, R is 10.13%, Y is 7.06%, L is 6.19%, I is 5.89%, H is 4.75%, D is 4.03%, A is 4.01%, E is 3.85%, P is 3.44%, W is 3.42%, N is 3.32%, Q is 3.23%, M is 2.89%, T is 2.75%, F is 2.02%, V is 1.97%, C is 1.63% and K is 1.35%, wherein $X_3$ encodes such that G is 15.77%, S is 9.74%, R is 9.26%, Y is 7.75%, L is 6.05%, I is 5.73%, H is 5.64%, E is 4.79%, D is 4.49%, A is 4.45%, P is 3.62%, Q is 3.62%, W is 3.44%, M is 3.03%, N is 2.91%, T is 2.45%, F is 2.25%, C is 1.88%, V is 1.74% and K is 1.28%, wherein $X_4$ encodes such that G is 15.41%, S is 11.03%, R is 9.58%, Y is 7.82%, L is 6.21%, I is 5.46%, H is 5.14%, D is 4.03%, Q is 4.01%, A is 3.92%, E is 3.76%, P is 3.58%, W is 3.48%, N is 2.98%, M is 2.93%, T is 2.66%, V is 2.48%, F is 2.29%, C is 1.99% and K is 1.17%, wherein $X_5$ encodes such that G is 15.06%, S is 10.84%, R is 10.32%, Y is 7.40%, I is 5.75%, L is 5.43%, H is 4.75%, D is 4.49%, E is 4.42%, A is 3.99%, N is 3.42%, Q is 3.42%, W is 3.42%, P is 3.09%, F is 2.82%, M is 2.75%, T is 2.73%, V is 2.29%, C is 2.02% and K is 1.56%, wherein $X_6$ encodes such that G is 15.15%, S is 10.80%, R is 10.09%, Y is 7.15%, L is 6.12%, I is 5.96%, H is 5.59%, E is 4.26%, D is 4.15%, A is 4.10%, W is 3.69%, N is 3.46%, P is 3.12%, Q is 3.00%, M is 2.98%, T is 2.45%, F is 2.43%, V is 2.20%, C is 2.04% and K is 1.19%, wherein $X_7$ encodes such that G is 15.77%, S is 11.33%, R is 9.01%, Y is 7.91%, I is 6.28%, L is 5.82%, H is 4.86, A is 4.68%, E is 4.29%, D is 4.24%, W is 3.65%, Q is 3.23%, M is 3.14%, N is 2.89%, P is 2.66%, F is 2.38%, V is 2.18%, C is 2.13%, T is 1.97% and K is 1.54%, wherein $X_8$ encodes such that G is 14.51%, S is 11.65%, R is 9.67%, Y is 7.29%, I is 5.91%, H is 5.82%, L is 4.91%, D is 4.68%, E is 4.49%, A is 4.36%, W is 4.15%, N is 3.44%, Q is 3.14%, T is 3.03%, M is 2.73%, P is 2.61%, F is 2.32%, V is 2.32%, K is 1.54% and C is 1.38%, wherein $X_9$ encodes such that Y is 14.24%, R is 11.10%, G is 9.67%, P is 7.66%, D is 6.17%, E is 5.50%, A is 5.48%, I is 5.34%, S is 5.20%, V is 4.86%, L is 4.70%, Q is 4.15%, F is 3.74%, T is 3.12%, N is 1.93%, C is 1.79%, W is 1.77%, M is 1.35%, K is 1.17%, H is 1.01%, wherein $X_{10}$ encodes such that Y is 15.13%, R is 10.45%, G is 9.31%, P is 6.92%, D is 6.79%, E is 5.66%, I is 5.32%, S is 5.18%, L is 4.86%, A is 4.84%, Q is 4.72%, V is 4.72%, F is 3.23%, T is 2.84%, N is 2.34%, W is 1.77%, C is 1.70%, M is 1.54%, H is 1.33% and K is 1.31%, wherein $X_{11}$ encodes such that Y is 16.25%, R is 9.67%, G is 8.78%, P is 7.40%, D is 6.63%, I is 5.64%, A is 5.14%, E is 5.02%, V is 4.97%, S is 4.91%, L is 4.47%, Q is 4.10%, F is 4.03%, T is 2.82%, N is 2.73%, C is 2.06%, W is 1.51%, M is 1.44%, K is 1.33% and H is 0.92%, wherein $X_{12}$ encodes such that G is 28.40%, A is 22.01%, Y is 13.78%, W is 6.12%, S is 5.11%, F is 4.38%, R is 3.42%, P is 3.12%, N is 2.77%, M is 2.75%, I is 1.90%, V is 1.83%, D is 1.77%, T is 1.10%, Q is 0.99%, C is 0.21%, E is 0.18%, H is 0.09% and K is 0.05% wherein $X_{13}$ encodes such that F is 54.81%, M is 12.10%, L is 11.23%, I is 4.42%, G is 3.21%, V is 2.80%, P is 2.43%, Y is 1.74%, E is 1.22%, D is 1.05%, S is 1.01%, W is 0.94%, C is 0.87%, Q is 0.83%, N is 0.78%, T is 0.48% and A is 0.05%, wherein $X_{14}$ encodes such that D is 77.42%, G is 4.08%, S is 2.04%, E is 2.02%, H is 2.02%, A is 1.65%, V is 1.44%, K is 1.38%, N is 1.33%, Q is 1.03%, C is 0.94%, L is 0.87%, R is 0.83%, F is 0.80%, Y is 0.80%, P is 0.69%, T is 0.57% and I is 0.07%, and wherein $X_{15}$ encodes such that Y is 45.62%, I is 17.08%, V is 16.46%, S is 5.23%, H is 2.98%, D is 2.96%, N is 2.54%, F is 2.29%, L is 1.44%, T is 1.01%, A is 0.99%, R is 0.85%, P is 0.23%, M is 0.09%, G is 0.07% and C is 0.05%;

when the length of the modified CDRH3 is 16 amino acid residues, the amino acid sequence is $X_1X_2X_3X_4X_5X_6X_7X_8X_9X_{10}X_{11}X_{12}X_{13}X_{14}X_{15}X_{16}$ (SEQ ID NO. 125), wherein $X_1$ encodes such that G is 23.28%, D is 21.54%, E is 12.51%, R is 6.40%, V is 6.34%, S is 3.90%, H is 3.49%, Q is 3.26%, Y is 3.20%, L is 3.03%, A is 2.44%, P is 2.44%, M is 2.39%, K is 1.86%, W is 1.11%, I is 0.93%, N is 0.87%, T is 0.70%, C is 0.12% and F is 0.12%, wherein $X_2$ encodes such that G is 19.85%, P is 16.94%, R is 9.72%, Y is 6.40%, S is 6.17%, L is 5.70%, A is 4.71%, K is 4.48%, Q is 3.90%, V is 3.84%, I is 3.26%, E is 2.50%, D is 2.33%, N is 2.33%, T is 2.10%, M is 1.75%, F is 1.57%, H is 1.28%, W is 0.81% and C is 0.35%, wherein $X_3$ encodes such that G is 13.85%, S is 10.48%, R is 8.91%, Y is 8.91%, L is 6.58%, H is 6.29%, I is 5.94%, A is 4.71%, E is 4.54%, D is 4.42%, Q is 4.13%, P is 3.61%, N is 3.03%, T is 2.97%, W is 2.56%, C is 2.39%, V is 2.04%, M is 1.92%, F is 1.75% and K is 0.99%, wherein $X_4$ encodes such that G is 13.85%, R is 9.84%, Y is 9.66%, S is 9.02%, L is 7.92%, P is 6.00%, I is 5.41%, H is 5.18%, Q is 4.31%, D is 4.19%, E is 3.20%, A is 3.08%, W is 3.03%, N is 2.85%, T is 2.74%, F is 2.62%, M is 2.39%, V is 1.86%, C is 1.69% and K is 1.11%, wherein $X_5$ encodes such that G is 12.86%, R is 10.01%, Y is 9.84%, S is 9.78%, L is 7.68%, A is 4.95%, H is 4.89%, I is 4.89%, Q is 3.90%, E is 3.78%, D is 3.73%, N is 3.67%, P is 3.61%, W is 3.61%, T is 3.08%, F is 2.85%, M is 2.04%, C is 1.98%, V is 1.63% and K is 1.16%, wherein $X_6$ encodes such that G is 12.92%, S is 11.29%, R is 9.14%, Y is 8.79%, I is 7.33%, H is 5.88%, L is 5.76%, W is 4.19%, A is 4.13%, D is 4.07%, Q is 3.78%, E is 3.61%, P is 3.61%, M is 2.79%, N is 2.56%, F is 2.50%, T is 2.27%, V is 2.21%, C is 1.92% and K is 1.22%, wherein $X_7$ encodes such that G is 13.80%, S is 10.54%, R is 9.66%, Y is 7.97%, H is 6.69%, I is 5.88%, L is 5.76%, E is 4.95%, D is 4.42%, A is 3.78%, P is 3.73%, Q is 3.43%, N is 3.32%, F is 2.85%, W is 2.85%, T is 2.74%, M is 2.10%, V is 2.10%, C is 2.04% and K is 1.28%, wherein $X_8$ encodes such that G is 13.39%, S is 10.36%, R is 9.49%, Y is 7.80%, L is 6.75%, I is 5.94%, H is 5.59% D is 4.95%, A is 4.77%, T is 3.96%, M is 3.73%, Q is 3.73%, E is 3.67%, P is 3.38%, W is 2.79%, N is 2.74%, F is 2.21%, V is 2.10%, C is 1.51% and K is 1.16%, wherein $X_9$ encodes such that Y is 15.83%, G is 8.91%, R is 8.21%, P is 7.51%, A is 6.46%, L is 5.94%, D is 5.82%, I is 5.59%, V is 4.89%, S is 4.77%, E is 4.37%, Q is 4.13%, T is 3.96%, F is 2.97%, N is 2.68%, C is 2.39%, M is 1.63%, W is 1.40%, H is 1.28% and K is 1.28%, wherein $X_{10}$ encodes such that Y is 16.94%, P is 10.30%, R is 9.60%, G is 7.16%, Q is 6.11%, D is 5.59%, I is 5.41%, S is 5.06%, A is 4.95%, V is 4.66%, L is 4.07%, T is 4.02%, E is 3.73%, F is 2.74%, W is 2.15%, N is 1.98%, C is 1.80%, H is 1.34%, M is 1.16% and K is 1.11%, wherein $X_{11}$ encodes such that Y is 15.77%, P is 11.76%, R is 8.15%, G is 7.22%, L is 6.46%, I is 6.00%, S is 5.18%, D is 5.12%, E is 4.77%, V is 4.66%, A is 4.60%, Q is 3.96%, F is 3.38%, T is 3.14%, N is 2.39%, C is 1.75%, K is 1.63%, H is 1.40%, W is 1.40% and M is 1.22%, wherein $X_{12}$ encodes such that Y is 16.41%, R is 8.96%, P is 8.21%, G is 7.74%, I is 5.70%, L is 5.70%, A is 5.47%, D is 5.47%, S is 5.24%, V is 5.24%, E is 4.77%, Q is 4.42%, T is 3.55%, F is 3.38%, N is 2.27%, W is 2.04%, C is 1.98%, H is 1.46%, K is 0.93% and M is 0.87%, wherein $X_{13}$ encodes such that G is 34.52%, A is 20.20%, Y is 13.10%, W is 8.15%, P is 4.95%, V is 3.14%, D is 2.62%, F is 2.39%, H is 2.39%, L is 1.92%, S is 1.69%, T is 1.69%, E is 0.99%, C is 0.87%, R is 0.58%, I is 0.47%, N is 0.17% and Q is 0.06%, wherein $X_{14}$ encodes such that F is 50.47%, M is 16.01%, L is 12.69%, I is 4.66%, V is 2.62%, P is 2.56%, Y is 2.04%, G is 1.92%, D is 1.57%, Q is 0.93%, E is 0.81%, C is 0.76%, T is 0.70%, W is 0.70%, N is 0.64%, S is 0.47%, A is 0.29%, and H is 0.17%, wherein $X_{15}$ encodes such that D is 76.37%, G is 4.19%, H is 2.27%, A is 2.21%, S is 1.69%, Y is 1.63%, V is 1.51%, E is 1.40%, R is 1.34%, K is 1.28%, F is 1.22%, T is 0.87%, N is 0.81%, P is 0.81%, C is 0.64%, L is 0.64%, Q is 0.52%, I is 0.29% and M is 0.29%, and wherein $X_{16}$ encodes such that Y is 40.28%, V is 21.42%, I is 15.48%, S is 5.18%, H is 3.73%, F is 2.91%, N is 2.79%, D is 2.21%, L is 1.57%, P is 1.34%, R is 0.99%, T is 0.99%, A is 0.64%, M is 0.17%, C is 0.06%, G is 0.06%, and K is 0.06%;

when the length of the modified CDRH3 is 17 amino acid residues, the amino acid sequence is $X_1X_2X_3X_4X_5X_6X_7X_8X_9X_{10}X_{11}X_{12}X_{13}X_{14}X_{15}X_{16}X_{17}$ (SEQ ID NO. 126), wherein $X_1$ encodes such that D is 23.68%, G is 22.67%, E is 14.15%, V is 7.09%, R is 5.81%, Y is 3.46%, S is 3.40%, Q is 2.91%, P is 2.79%, H is 2.67%, L is 2.64%, M is 2.03%, K is 1.60%, A is 1.57%, W is 1.57%, T is 0.67%, N is 0.64%, I is 0.46%, C is 0.09% and F is 0.06%, wherein $X_2$ encodes such that R is 14.44%, L is 12.06%, G is 11.30%, P is 7.29%, A is 6.25%, Y is 6.16%, I is 5.87%, H is 4.88%, N is 4.56%, T is 4.48%, V is 4.10%, Q is 3.55%, K is 3.28%, S is 2.73%, E is 2.15%, D is 1.89%, W is 1.54%, F is 1.37%, M is 1.31% and C is 0.67%, wherein $X_3$ encodes such that G is 14.50%, S is 10.96%, R is 9.97%, Y is 7.47%, L is 6.77%, I is 6.66%, H is 5.90%, D is 4.48%, A is 3.89%, E is 3.49%, Q is 3.49%, P is 3.31%, T is 3.17%, N is 3.14%, W is 2.91%, M is 2.56%, F is 2.47%, C is 2.01%, V is 1.60% and K is 1.28%, wherein $X_4$ encodes such that Y is 14.71%, P is 10.52%, G is 9.01%, R is 8.95%, I is 6.66%, L is 5.58%, D is 5.55%, S is 5.26%, A is 5.17%, E is 4.45%, V is 4.30%, Q is 4.01%, T is 3.49%, F is 2.96%, N is 2.47%, W is 1.71%, M is 1.63%, C is 1.37%, H is 1.08% and K is 1.02%, wherein $X_5$ encodes such that G is 17.44%, Y is 11.10%, R is 8.78%, S is 8.02%, I is 4.85%, L is 4.80%, A is 4.33%, E is 4.33%, W is 4.18%, D is 4.04%, H is 3.69%, N is 3.69%, T is 3.08%, M is 2.96%, F is 2.91%, V is 2.70%, Q is 2.64%, P is 2.44%, C is 2.41% and K is 1.48%, wherein $X_6$ encodes such that G is 14.41%, R is 9.47%, S is 8.57%, Y is 8.31%, L is 7.67%, H is 6.48%, I is 5.38%, P is 4.50%, A is 4.04%, E is 3.89%, Q is 3.87%, W is 3.60%, N is 3.25%, D is 3.23%, T is 3.11%, M is 2.94%, V is 2.18%, C is 2.01%, F is 2.01% and K is 1.02%, wherein $X_7$ encodes such that G is 15.00%, S is 8.92%, R is 8.37%, Y is 8.34%, H is 6.89%, L is 6.86%, I is 5.03%, A is 4.24%, C is 2.47%, D is 2.79%, E is 4.53%, F is 2.85%, K is 1.60%, M is 2.76%, N is 3.11%, P is 3.89%, Q is 4.27%, T is 2.67%, V is 1.66% and W is 3.69%, wherein $X_8$ encodes such that G is 13.34%, R is 9.47%, Y is 8.08%, S is 8.05%, L is 7.47%, H is 6.19%, I is 5.09%, A is 4.88%, C is 1.83%, D is 3.37%, E is 4.18%, F is 2.44%, K is 1.13%, M is 2.67%, N is 3.84%, P is 4.53%, Q is 3.95%, T is 3.63%, V is 2.32%, W is 3.43%, wherein $X_9$ encodes such that G is 14.94%, R is 9.33%, Y is 9.13%, S is 7.15%, L is 6.77%, H is 6.07%, I is 5.14%, A is 4.45%, C is 2.15%, D is 3.34%, E is 3.57%, F is 3.05%, K is 1.25%, M is 2.73%, N is 3.55%, P is 3.95%, Q is 3.57%, T is 3.46%, V is 3.02% and W is 3.37%, wherein $X_{10}$ encodes such that Y is 14.82%, R is 9.82%, P is 9.79%, G is 8.25%, D is 6.19%, I is 6.07%, Q is 5.55%, L is 5.32%, A is 4.85%, C is 2.15%, E is 4.53%, F is 2.59%, H is 1.51%, K is 0.93%, M is 1.22%, N is 2.27%, S is 4.68%, T is 3.72%, V is 4.21% and W is 1.45%, wherein $X_{11}$ encodes such that Y is 14.68%, R is 10.29%, P is 9.82%, G is 7.73%, L is 6.25%, I is 5.70%, S is 5.49%, D is 5.32%, A is 5.26%, Q is 5.03%, C is 1.92%, E is 4.33%, F is 3.31%, H is 1.31%, K is 1.13%, M is 1.16%, N is 1.95%, T is 3.81%, V is 4.10% and W is 1.39%, wherein $X_{12}$ encodes such that Y is 15.02%, P is 10.20%, R is 9.76%, G is 7.79%, I is 5.73%, A is 5.38%, S is 5.32%, D is 5.14%, C is 1.71%, E is 4.88%, F is 3.37%, H is 1.31%, K is 1.51%, L is 4.97%, M is 1.19%, N is 1.74%, Q is 4.91%, T is 3.95%, V is 4.33% and W is 1.71%, wherein $X_{13}$ encodes such that Y is 16.54%, P is 10.32%, R is 9.85%, G is 8.49%, D is 5.90%, I is 5.78%, L is 5.26%, S is 5.06%, A is 5.00%, C is 1.54%, E is 4.27%, F is 2.59%, H is 1.08%, K is 1.28%, M is 1.39%, N is 2.35%, Q is 3.78%, T is 3.63%, V is 4.18% and W is 1.63%, wherein $X_{14}$ encodes such that G is 35.89%, A is 24.38%, Y is 12.67%, W is 7.70%, C is 0.17%, D is 2.41%, E is 1.28%, F is 0.64%, H is 0.15%, I is 1.39%, L is 2.35%, N is 1.71%, P is 2.32%, Q is 0.44%, R is 1.31%, S is 1.08%, T is 2.12% and V is 1.89%, wherein $X_{15}$ encodes such that M is 41.88%, F is 37.93%, L is 9.68%, D is 0.06%, E is 0.06%, G is 1.19%, H is 0.81%, I is 1.83%, P is 1.63%, S is 0.70%, T is 0.55%, V is 1.86%, W is 0.70% and Y is 1.08%, wherein $X_{16}$ encodes such that D is 76.23%, A is 1.80%, C is 0.67%, E is 2.03%, F is 0.70%, G is 4.36%, H is 2.01%, K is 1.45%, L is 1.16%, N is 1.28%, P is 1.25%, Q is 0.93%, R is 1.16%, S is 1.92%, T is 0.90%, V is 1.05%, and Y is 1.05%, and wherein $X_{17}$ encodes such that V is 33.97%, Y is 22.03%, I is 17.67%, P is 7.90%, A is 1.28%, C is 0.09%, D is 0.32%, F is 3.31%, G is 0.15%, H is 2.06%, L is 1.69%, M is 2.62%, N is 1.39%, Q is 0.81%, R is 1.02%, S is 3.55% and T is 0.09%;

when the length of the modified CDRH3 is 18 amino acid residues, the amino acid sequence is $X_1X_2X_3X_4X_5X_6X_7X_8X_9X_{10}X_{11}X_{12}X_{13}X_{14}X_{15}X_{16}X_{17}X_{18}$ (SEQ ID NO. 127), wherein $X_1$ encodes such that D is 23.99%, G is 22.77%, E is 14.07%, V is 6.83%, R is 5.97%, S is 4.00%, L is 2.83%, H is 2.68%, Y is 2.63%, Q is 2.38%, A is 2.13%, P is 2.02%, M is 1.92%, K is 1.72%, W is 1.42%, T is 1.06%, I is 0.76%, N is 0.66%, C is 0.05% and F is 0.05%, wherein $X_2$ encodes such that G is 16.75%, S is 11.54%, R is 9.77%, Y is 7.84%, L is 6.22%, I is 6.02%, H is 5.82%, P is 4.35%, E is 4.10%, D is 4.00%, Q is 3.64%, A is 3.09%, N is 2.78%, W is 2.53%, M is 2.38%, T is 2.38%, V is 2.33%, C is 1.77%, F is 1.37% and K is 1.32%, wherein $X_3$ encodes such that G is 14.57%, S is 10.22%, R is 9.01%, Y is 8.30%, L is 6.48%, I is 6.43%, H is 6.02%, Q is 4.15%, A is 4.05%, T is 4.00%, D is 3.90%, P is 3.64%, E is 3.54%, W is 3.09%, N is 2.83%, V is 2.53%, M is 2.28%, F is 2.07%, C is 1.62% and K is 1.21%, wherein $X_4$ encodes such that Y is 12.55%, P is 11.69%, G is 10.12%, R is 9.56%, L is 6.38%, I is 6.02%, D is 5.72%, S is 5.31%, Q is 5.01%, E is 4.71%, A is 4.30%, V is 3.90%, T is 3.69%, F is 2.43%, W is 2.07%, N is 1.52%, H is 1.47%, M is 1.32%, C is 1.16% and K is 1.06%, wherein $X_5$ encodes such that Y is 14.93%, P is 11.03%, R is 8.50%, G is 7.24%, I is 6.22%, L is 5.92%, A is 5.26%, Q is 5.16%, S is 4.76%, E is 4.55%, D is 4.25%, V is 4.25%, T is 3.54%, F is 3.39%, C is 2.53%, N is 2.33%, M is 1.87%, W is 1.82%, K is 1.42% and H is 0.96%, wherein $X_6$ encodes such that G is 15.08%, Y is 9.46%, S is 9.11%, R is 8.96%, L is 6.12%, H is 5.41%, I is 5.41%, A is 4.35%, E is 4.25%, Q is 4.05%, D is 3.85%, N is 3.64%, T is 3.44%, P is 3.29%, M is 2.63%, W is 2.53%, V is 2.43%, C is 2.38%, F is 2.28% and K is 1.32%, wherein $X_7$ encodes such that G is 14.32%, R is 9.36%, Y is 8.40%, S is 8.00%, L is 7.79%, H is 5.52%, P is 4.61%, A is 4.45%, I is 4.15%, Q is 3.95%, T is 3.95%, N is 3.90%, W is 3.69%, D is 3.44%, E is 3.34%, V is 2.94%, F is 2.73%, M is 2.63%, C is 1.62% and K is 1.16%, wherein $X_8$ encodes such that G is 13.92%, Y is 9.16%, R is 9.11%, S is 8.65%, L is 7.79%, H is 5.41%, I is 5.21%, A is 4.96%, E is 4.35%, Q is 4.35%, W is 3.74%, P is 3.54%, F is 3.39%, T is 3.04%, M is 2.99%, D is 2.78%, N is 2.73%, V is 2.13%, C is 1.82% and K is 0.91%, wherein $X_9$ encodes such that G is 14.78%, R is 10.98%, Y is 8.50%, S is 8.10%, L is 6.53%, H is 6.17%, P is 5.31%, I is 4.55%, A is 4.15%, D is 3.80%, T is 3.74%, N is 3.64%, W is 3.49%, E is 3.44%, Q is 3.19%, F is 2.83%, M is 2.33%, V is 1.77%, C is 1.57% and K is 1.11%, wherein $X_{10}$ encodes such that G is 14.12%, R is 9.46%, Y is 8.91%, L is 7.74%, S is 7.59%, H is 6.33%, A is 4.76%, I is 4.71%, P is 4.55%, N is 4.25%, Q is 3.85%, E is 3.64%, D is 3.29%, W is 3.29%, T is 3.24%, F is 2.53%, V is 2.48%, M is 2.43%, C is 1.82% and K is 1.01%, wherein $X_{11}$ encodes such that Y is 13.87%, P is 11.39%, R is 10.58%, G is 7.89%, A is 6.12%, D is 5.62%, I is 5.16%, V is 5.11%, E is 4.81%, S is 4.61%, L is 4.45%, Q is 4.10%, T is 3.95%, F is 3.59%, N is 2.02%, C is 1.97%, M is 1.42%, H is 1.21%, W is 1.06% and K is 1.01%, wherein $X_{12}$ encodes such that Y is 15.94%, R is 8.96%, P is 8.76%, G is 8.60%, L is 5.92%, D is 5.82%, Q is 5.52%, I is 4.91%, S is 4.71%, A is 4.66%, E is 4.35%, V is 4.10%, T is 3.59%, F is 3.19%, N is 2.53%, W is 2.53%, C is 1.92%, K is 1.42%, M is 1.42% and H is 1.06%, wherein $X_{13}$ encodes such that Y is 16.95%, P is 10.17%, R is 9.36%, G is 7.34%, D is 5.47%, A is 5.41%, L is 5.16%, I is 4.81%, Q is 4.81%, V is 4.76%, E is 4.25%, S is 4.05%, T is 3.59%, F is 3.14%, N is 2.63%, C is 1.92%, W is 1.67%, H is 1.62%, M is 1.57% and K is 1.27%, wherein $X_{14}$ encodes such that Y is 18.37%, G is 9.01%, P is 8.76%, R is 8.25%, I is 6.02%, D is 5.57%, A is 5.47%, L is 4.71%, E is 4.55%, V is 4.50%, S is 4.25%, Q is 3.74%, T is 3.39%, F is 3.14%, N is 2.94%, W is 2.02%, M is 1.62%, C is 1.37%, H is 1.37% and K is 0.91%, wherein $X_{15}$ encodes such that G is 30.57%, A is 20.70%, W is 12.80%, Y is 10.32%, P is 5.11%, S is 5.01%, T is 3.54%, V is 2.58%, D is 2.28%, R is 2.23%, L is 1.27%, K is 0.91%, I is 0.71%, F is 0.56%, N is 0.51%, C is 0.30%, M is 0.20%, E is 0.15%, H is 0.15% and Q is 0.05%, wherein $X_{16}$ encodes such that M is 40.59%, F is 37.96%, L is 9.16%, I is 2.58%, P is 2.13%, V is 2.02%, G is 1.47%, H is 1.01%, Y is 1.01%, W is 0.81%, S is 0.51%, A is 0.20%, D is 0.20%, T is 0.20%, C is 0.05%, N is 0.05% and R is 0.05%, wherein $X_{17}$ encodes such that D is 76.62%, G is 4.35%, E is 2.13%, S is 1.97%, A is 1.92%, H is 1.77%, V is 1.42%, K is 1.37%, N is 1.32%, F is 1.11%, L is 1.06%, P is 0.91%, Q is 0.86%, Y is 0.81%, R is 0.76%, T is 0.76%, C is 0.51%, M is 0.25% and I is 0.05%, and wherein $X_{18}$ encodes such that V is 32.59%, Y is 20.65%, I is 18.12%, P is 9.67%, S is 4.50%, F is 3.39%, M is 2.38%, L is 2.18%, H is 1.62%, N is 1.42%, A is 1.01%, Q is 0.86%, R is 0.86%, D is at 0.66% and G is 0.05%;

when the length of the modified CDRH3 is 19 amino acid residues, the amino acid sequence is $X_1X_2X_3X_4X_5X_6X_7X_8X_9X_{10}X_{11}X_{12}X_{13}X_{14}X_{15}X_{16}X_{17}X_{18}X_{19}$ (SEQ ID NO. 128), wherein $X_1$ encodes such that D is 23.33%, G is 22.55%, E is 13.92%, V is 6.81%, R is 5.38%, A is 2.44%, C is 0.24%, F is 0.17%, H is 3.28%, I is 0.85%, K is 2.27%, L is 2.30%, M is 2.24%, N is 0.98%, P is 2.54%, Q is 2.57%, S is 3.79%, T is 0.37%, W is 1.05% and Y is 2.88%, wherein $X_2$ encodes such that G is 19.67%, R is 12.09%, D is 11.48%, P is 10.26%, I is 8.74%, S is 6.16%, L is 5.89%, A is 5.79%, E is 5.08%, C is 0.88%, F is 0.81%, H is 2.40%, K is 0.27%, M is 0.14%, N is 1.69%, Q is 2.24%, T is 2.51%, V is 0.24%, W is 1.66% and Y is 2.00%, wherein $X_3$ encodes such that G is 14.05%, S is 10.43%, R is 7.92%, Y is 7.69%, L is 7.55%, I is 6.30%, H is 5.62%, A is 3.76%, C is 2.30%, D is 4.47%, E is 4.00%, F is 2.20%, K is 1.22%, M is 2.71%, N is 2.88%, P is 3.66%, Q is 4.54%, T is 3.25%, V is 2.20% and W is 3.18%, wherein $X_4$ encodes such that Y is 12.83%, P is 11.62%, R is 9.04%, G is 8.50%, L is 6.30%, I is 5.66%, A is 5.55%, D is 5.49%, S is 5.49%, C is 1.59%, E is 4.67%, F is 3.08%, H is 1.42%, K is 1.25%, M is 1.46%, N is 2.84%, Q is 3.79%, T is 3.79%, V is 4.13% and W is 1.49%, wherein $X_5$ encodes such that Y is 14.02%, P is 9.82%, R is 9.21%, G is 7.48%, L is 6.23%, E is 5.69%, I is 5.69%, D is 5.35%, S is 5.05%, A is 4.88%, C is 1.59%, F is 2.84%, H is 1.42%, K is 0.85%, M is 1.52%, N is 2.64%, Q is 4.91%, T is 4.20%, V is 4.81% and W is 1.76%, wherein $X_6$ encodes such that Y is 14.39%, P is 9.92%, G is 9.01%, R is 8.53%, S is 6.06%, I is 5.99%, D is 5.93%, A is 5.11%, E is 5.01%, C is 1.63%, F is 3.28%, H is 1.02%, K is 0.91%, L is 4.64%, M is 1.52%, N is 1.76%, Q is 4.44%, T is 4.44%, V is 4.37% and W is 1.93%, wherein $X_7$ encodes such that Y is 14.26%, S is 12.26%, V is 10.13%, D is 9.89%, G is 9.08%, I is 7.75%, F is 6.30%, E is 5.86%, A is 4.61%, C is 1.86%, H is 0.37%, K is 0.27%, L is 1.63%, M is 1.59%, N is 4.03%, P is 0.44%, Q is 0.78%, R is 0.61%, T is 4.20% and W is 4.00%, wherein $X_8$ encodes such that G is 14.39%, W is 10.36%, S is 9.14%, F is 8.97%, V is 8.03%, I is 7.38%, H is 6.64%, T is 6.50%, D is 5.32%, A is 5.28%, C is 1.73%, E is 2.61%, K is 0.10%, L is 0.95%, M is 0.27%, N is 2.57%, P is 4.03%, Q is 0.37%, R is 1.76% and Y is 3.56%, wherein $X_9$ encodes such that G is 14.32%, R is 9.18%, S is 8.09%, Y is 8.09%, L is 7.04%, H is 6.23%, I is 5.25%, A is 4.37%, C is 2.07%, D is 3.66%, E is 4.44%, F is 2.40%, K is 1.32%, M is 2.40%, N is 4.30%, P is 4.27%, Q is 3.83%, T is 2.78%, V is 2.44% and W is 3.42%, wherein $X_{10}$ encodes such that G is 13.92%, R is 8.91%, Y is 8.20%, S is 8.16%, L is 7.38%, H is 5.99%, P is 5.25%, I is 5.15%, A is 4.54%, C is 1.86%, D is 3.28%, E is 3.73%, F is 3.08%, K is 1.15%, M is 2.91%, N is 3.12%, Q is 3.93%, T is 3.15%, V is 2.47% and W is 3.79%, wherein $X_{11}$ encodes such that Y is 13.65%, R is 10.19%, P is 9.85%, G is 7.65%, D is 5.76%, Q is 5.69%, E is 5.35%, I is 5.32%, L is 5.18%, A is 4.88%, C is 1.90%, F is 3.39%, H is 1.25%, K is 0.95%, M is 0.98%, N is 2.47%, S is 4.88%, T is 3.93%, V is 4.74% and W is 1.96%, wherein $X_{12}$ encodes such that Y is 14.22%, P is 9.99%, R is 8.77%, G is 8.16%, D is 6.13%, I is 5.82%, S is 5.72%, L is 5.49%, A is 5.05%, Q is 5.05%, C is 1.69%, E is 4.84%, F is 3.73%, H is 1.39%, K is 0.95%, M is 1.56%, N is 2.10%, T is 3.45%, V is 4.00% and W is 1.83%, wherein $X_{13}$ encodes such that Y is 16.59%, R is 9.11%, P is 8.84%, G is 8.70%, D is 5.89%, I is 5.76%, S is 5.05%, A is 4.94%, C is 2.00%, E is 4.57%, F is 3.45%, H is 1.15%, K is 1.29%, L is 4.61%, M is 1.69%, N is 2.64%, Q is 4.17%, T is 3.73%, V is 4.17% and W is 1.52%, wherein $X_{14}$ encodes such that Y is 41.62%, N is 11.45%, G is 10.02%, A is 4.17%, C is 0.24%, D is 1.56%, E is 1.25%, F is 1.19%, H is 4.17%, I is 2.84%, K is 1.19%, L is 4.57%, M is 0.10%, P is 2.44%, Q is 0.24%, R is 3.93%, S is 4.17%, T is 1.56%, V is 1.86% and W is 1.35%, wherein $X_{15}$ encodes such that Y is 49.44%, D is 14.63%, G is 8.57%, N is 7.31%, A is 0.30%, C is 0.14%, E is 0.17%, F is 4.20%, H is 1.02%, I is 0.34%, K is 0.03%, L is 0.24%, M is 0.03%, P is 3.05%, Q is 0.81%, R is 0.54%, S is 3.83%, T is 2.81%, V is 1.66% and W is 0.81%, wherein $X_{16}$ encodes such that G is 45.38%, A is 20.72%, Y is 13.27%, C is 0.85%, D is 1.19%, E is 0.07%, F is 0.44%, H is 1.22%, I is 1.49%, K is 0.07%, L is 0.95%, N is 0.03%, P is 2.78%, R is 1.08%, S is 1.63%, T is 0.88%, V is 4.00% and W is 3.96%, wherein $X_{17}$ encodes such that F is 40.09%, M is 39.45%, L is 8.57%, A is 0.07%, D is 0.07%, G is 1.05%, H is 1.02%, I is 2.37%, P is 1.42%, S is 0.85%, T is 0.68%, V is 2.17%, W is 0.91% and Y is 1.29%, wherein $X_{18}$ encodes such that D is 75.72%, A is 1.83%, C is 0.91%, E is 2.20%, F is 1.02%, G is 4.81%, H is 1.93%, K is 1.22%, L is 1.19%, M is 0.20%, N is 1.46%, P is 0.81%, Q is 0.85%, R is 0.95%, S is 1.83%, T is 0.71%, V is 1.35%, and Y is 0.98%, and wherein $X_{19}$ encodes such that V is 33.12%, I is 20.01%, Y is 19.13%, P is 9.72%, A is 1.22%, C is 0.03%, D is 0.37%, E is 0.03%, F is 3.49%, G is 0.03%, H is 1.90%, L is 1.56%, M is 2.71%, N is 1.19%, Q is 0.47%, R is 1.05%, S is 3.89% and T is 0.03%;

when the length of the modified CDRH3 is 20 amino acid residues, the amino acid sequence is $X_1X_2X_3X_4X_5X_6X_7X_8X_9X_{10}X_{11}X_{12}X_{13}X_{14}X_{15}X_{16}X_{17}X_{18}X_{19}X_{20}$ (SEQ ID NO. 129), wherein $X_1$ encodes such that D is 24.17%, G is 22.63%, E is 15.56%, V is 7.04%, R is 5.41%, S is 3.27%, H is 2.99%, Y is 2.80%, L is 2.58%, P is 2.39%, Q is 2.33%, K is 1.89%, M is 1.76%, A is 1.67%, W is 1.16%, I is 0.88%, N is 0.66%, T is 0.63%, C is 0.09% and F is 0.09%, wherein $X_2$ encodes such that G is 15.46%, S is 11.53%, R is 8.67%, Y is 7.79%, L is 6.19%, H is 5.85%, I is 5.78%, D is 4.68%, E is 4.65%, A is 3.77%, Q is 3.52%, P is 3.49%, T is 3.11%, M is 2.95%, W is 2.70%, N is 2.67%, F is 2.36%, V is 1.82%, C is 1.73% and K is 1.23%, wherein $X_3$ encodes such that G is 13.70%, S is 10.40%, R is 9.71%, Y is 7.64%, L is 6.63%, I is 6.00%, H is 5.15%, D is 4.49%, A is 4.40%, Q is 4.18%, E is 3.96%, P is 3.61%, W is 3.33%, N is 3.17%, T is 3.14%, M is 2.70%, V is 2.39%, F is 2.14%, C is 1.82% and K is 1.41%, wherein $X_4$ encodes such that L is 11.00%, I is 9.49%, G is 8.89%, Y is 8.42%, S is 8.08%, E is 7.86%, D is 7.13%, A is 6.95%, F is 6.73%, V is 5.28%, R is 4.87%, P is 3.11%, T is 2.70%, W is 2.36%, M is 2.11%, C is 1.89%, K is 1.16%, N is 1.13%, Q is 0.41% and H is 0.38%, wherein $X_5$ encodes such that Y is 13.70%, P is 11.44%, R is 9.37%, G is 8.36%, I is 5.72%, D is 5.63%, Q is 5.31%, S is 5.28%, L is 5.12%, E is 4.75%, A is 4.62%, V is 4.56%, T is 3.55%, F is 2.73%, N is 2.01%, C is 1.98%, W is 1.73%, H is 1.41%, M is 1.35% and K is 1.29%, wherein $X_6$ encodes such that D is 16.25%, Y is 13.89%, I is 11.35%, S is 10.03%, G is 8.80%, V is 5.81%, L is 5.59%, F is 5.50%, T is 5.22%, C is 3.99%, A is 3.21%, W is 2.55%, E is 2.14%, R is 1.98%, P is 1.76%, Q is 1.04%, M is 0.35%, N is 0.31%, H is 0.19% and K is 0.06%, wherein $X_7$ encodes such that Y is 17.38%, S is 16.59%, F is 14.11%, G is 9.49%, D is 7.01%, I is 4.53%, K is 4.15%, T is 4.09%, C is 4.05%, V is 3.58%, N is 3.52%, R is 3.49%, L is 2.33%, A is 1.54%, P is 1.38%, H is 1.10%, E is 0.82%, M is 0.35%, W is 0.28% and Q is 0.09%, wherein $X_8$ encodes such that G is 15.24%, R is 8.74%, L is 7.95%, S is 7.89%, Y is 7.35%, H is 6.16%, I is 4.75%, A is 4.40%, P is 4.37%, D is 4.21%, E is 3.96%, Q is 3.96%, N is 3.49%, W is 3.39%, T is 3.08%, V is 3.05%, M is 2.58%, C is 2.17%, F is 1.95% and K is 1.29%, wherein $X_9$ encodes such that G is 14.24%, R is 9.21%, S is 8.45%, Y is 8.33%, L is 7.83%, I is 5.34%, H is 5.28%, E is 4.59%, A is 4.56%, P is 3.71%, T is 3.68%, Q is 3.49%, W is 3.46%, N is 3.36%, D is 3.05%, M is 2.92%, F is 2.73%, V is 2.42%, C is 1.89% and K is 1.45%, wherein $X_{10}$ encodes such that G is 13.92%, R is 8.89%, Y is 8.89%, S is 7.86%, L is 7.54%, H is 6.79%, I is 5.06%, P is 5.00%, A is 4.78%, E is 3.99%, Q is 3.71%, D is 3.33%, N is 3.21%, T is 3.14%, W is 3.11%, F is 2.92%, V is 2.48%, M is 2.33%, C is 1.89% and K is 1.13%, wherein $X_{11}$ encodes such that Y is 12.82%, P is 10.09%, R is 8.96%, G is 8.11%, D is 5.85%, I is 5.59%, L is 5.31%, E is 5.19%, A is 5.15%, S is 5.09%, V is 4.71%, Q is 4.68%, T is 4.53%, F is 3.87%, W is 2.39%, N is 2.36%, C is 1.79%, H is 1.51%, M is 1.23% and K is 0.79%, wherein $X_{12}$ encodes such that Y is 13.26%, P is 9.90%, R is 9.87%, G is 7.54%, L is 5.78%, A is 5.66%, I is 5.41%, S is 5.37%, D is 5.03%, V is 4.93%, Q is 4.87%, E is 4.71%, T is 3.68%, F is 3.33%, N is 2.64%, W is 2.11%, C is 1.57%, M is 1.54%, K is 1.45% and H is 1.32%, wherein $X_{13}$ encodes such that Y is 15.71%, R is 10.47%, P is 9.90%, G is 7.54%, L is 5.50%, S is 5.47%, D is 5.44%, E is 5.03%, I is 4.84%, A is 4.65%, V is 4.65%, Q is 4.62%, T is 3.52%, F is 2.99%, N is 2.42%, C is 1.92%, W is 1.70%, M is 1.35%, H is 1.13% and K is 1.13%, wherein $X_{14}$ encodes such that Y is 48.52%, G is 9.62%, P is 6.38%, S is 5.94%, R is 4.43%, N is 4.34%, D is 3.74%, I is 3.71%, V is 2.99%, F is 2.48%, K is 1.48%, A is 1.35%, H is 1.23%, L is 1.10%, T is 0.94%, W is 0.94%, E is 0.31%, Q is 0.25%, C is 0.09% and M is 0.06%, wherein $X_{15}$ encodes such that Y is 46.48%, S is 7.73%, P is 4.87%, V is 4.27%, H is 4.18%, N is 4.09%, E is 3.99%, I is 3.36%, A is 3.33%, G is 3.30%, W is 3.21%, T is 2.45%, C is 2.29%, D is 1.89%, R is 1.67%, M is 0.97%, L is 0.94%, F is 0.41%, K is 0.35% and Q is 0.16%, wherein $X_{16}$ encodes such that Y is 47.49%, G is 10.78%, P is 6.44%, S is 6.07%, R is 4.09%, D is 4.02%, N is 3.96%, I is 3.68%, V is 3.36%, F is 3.08%, H is 1.41%, A is 1.23%, W is 1.07%, K is 1.01%, L is 1.01%, T is 0.85%, C is 0.06%, E is 0.06%, Q is 0.06% and M is 0.03%, wherein $X_{17}$ encodes such that G is 43.84%, A is 17.38%, Y is 10.78%, W is 8.64%, T is 3.90%, R is 2.83%, S is 2.80%, F is 2.51%, V is 2.36%, D is 1.60%, K is 1.41%, N is 1.16%, P is 0.31%, I is 0.19%, L is 0.09%, E is 0.06%, H is 0.06% and M is 0.06%, wherein $X_{18}$ encodes such that M is 40.19%, F is 39.79%, L is 7.35%, V is 2.77%, I is 2.20%, Y is 1.35%, P is 1.19%, G is 1.13%, H is 1.13%, W is 0.91%, S is 0.82%, T is 0.72%, D is 0.19%, C is 0.13%, N is 0.09% and A is 0.03%, wherein $X_{19}$ encodes such that D is 74.67%, G is 4.31%, E is 2.39%, A is 2.23%, H is 2.23%, S is 1.89%, V is 1.51%, N is 1.45%, K is 1.32%, Q is 1.19%, Y is 1.19%, F is 1.10%, L is 1.04%, R is 0.97%, P is 0.91%, T is 0.66%, C is 0.63%, M is 0.19% and W is 0.06%, and wherein $X_{20}$ encodes such that V is 34.51%, Y is 20.05%, I is 18.48%, P is 9.55%, S is 3.68%, F is 3.05%, M is 2.42%, H is 1.76%, L is 1.57%, R is 1.26%, N is 1.07%, Q is 1.01%, A is 0.94%, D is 0.41%, G is 0.13%, C is 0.03% and T is 0.03%;

when the length of the modified CDRH3 is 21 amino acid residues, the amino acid sequence is $X_1X_2X_3X_4X_5X_6X_7X_8X_9X_{10}X_{11}X_{12}X_{13}X_{14}X_{15}X_{16}X_{17}X_{18}X_{19}X_{20}X_{21}$ (SEQ ID NO. 130), wherein $X_1$ encodes such that D is 24.63%, E is 14.85%, G is 21.67%, V is 7.17%, R is 5.99%, I is 0.86%, K is 1.62%, L is 2.34%, M is 1.86%, N is 0.65%, P is 2.20%, Q is 2.65%, S is 2.72%, T is 0.65%, W is 1.62%, Y is 2.79%, C is 0.07%, H is 3.10% and A is 2.48%, wherein $X_2$ encodes such that G is 25.32%, S is 20.22%, P is 9.06%, Y is 8.72%, K is 6.92%, A is 6.27%, L is 5.20%, C is 0.24%, D is 3.79%, E is 0.62%, F is 2.07%, H is 0.41%, I is 2.34%, M is 0.55%, N is 0.14%, Q is 0.28%, R is 3.82%, T is 0.28%, V is 1.86% and W is 1.86%, wherein $X_3$ encodes such that A is 11.78%, S is 10.54%, R is 8.96%, Y is 8.75%, G is 8.47%, L is 8.10%, E is 7.13%, I is 7.13%, D is 5.82%, V is 5.75%, C is 3.31%, F is 0.28%, H is 0.38%, K is 2.82%, M is 0.14%, N is 4.17%, P is 4.48%, Q is 0.28%, T is 1.45% and W is 0.14%, wherein $X_4$ encodes such that G is 14.50%, S is 10.02%, R is 9.20%, Y is 7.68%, L is 6.10%, I is 5.58%, E is 5.37%, H is 5.03%, A is 3.79%, C is 2.10%, D is 3.79%, F is 2.93%, K is 1.31%, M is 3.20%, N is 2.79%, P is 4.24%, Q is 3.07%, T is 3.34%, V is 2.34% and W is 3.58%, wherein $X_5$ encodes such that G is 13.26%, R is 9.20%, S is 8.89%, Y is 7.51%, H is 6.72%, L is 6.41%, D is 5.96%, I is 5.96%, A is 3.96%, C is 1.76%, E is 3.55%, F is 2.31%, K is 1.31%, M is 2.41%, N is 3.44%, P is 4.13%, Q is 4.00%, T is 3.41%, V is 2.65% and W is 3.10%, wherein $X_6$ encodes such that I is 10.54%, L is 10.47%, Y is 8.85%, A is 8.51%, S is 8.47%, G is 8.34%, D is is 8.23%, E is 6.72%, V is 5.99%, F is 5.82%, C is 2.10%, H is 0.34%, K is 0.83%, M is 1.58%, N is 1.52%, P is 2.86%, Q is 0.24%, R is 4.27%, T is 1.65% and W is 2.58%, wherein $X_7$ encodes such that L is 11.26%, I is 10.99%, G is 9.09%, S is 7.99%, Y is 7.68%, A is 7.58%, E is 7.51%, D is 7.44%, F is 6.92%, V is 5.79%, C is 1.48%, K is 1.62%, M is 1.65%, N is 1.31%, P is 2.55%, Q is 0.17%, R is 4.13%, T is 2.45% and W is 2.27%, wherein $X_8$ encodes such that L is 10.78%, I is 9.75%, G is 8.75%, Y is 8.34%, D is 8.30%, E is 8.06%, A is 7.75%, S is 7.68%, F is 7.44%, V is 5.72%, C is 2.03%, H is 0.14%, K is 1.10%, M is 1.79%, N is 0.93%, P is 2.24%, Q is 0.10%, R is 4.68%, T is 2.10% and W is 2.20%, wherein $X_9$ encodes such that L is 10.68%, I is 9.75%, A is 8.47%, G is 8.13%, Y is 7.82%, D is 7.65%, E is 7.65%, S is 7.41%, F is 7.10%, V is 5.27%, C is 1.76%, H is 0.24%, K is 1.76%, M is 1.72%, N is 1.17%, P is 3.10%, Q is 0.07%, R is 4.99%, T is 2.27% and W is 2.93%, wherein $X_{10}$ encodes such that L is 11.75%, I is 9.85%, D is 8.34%, Y is 7.99%, A is 7.85%, E is 7.48%, G is 7.48%, S is 7.17%, F is 7.13%, V is 5.03%, C is 1.89%, H is 0.41%, K is 1.45%, M is 1.31%, N is 1.38%, P is 3.38%, Q is 0.55%, R is 4.62%, T is 2.55% and W is 2.41%, wherein $X_{11}$ encodes such that L is 11.23%, I is 10.02%, G is 8.99%, Y is 8.37%, A is 7.58%, D is 7.37%, F is 7.20%, E is 6.96%, S is 6.85%, V is 5.34%, C is 2.00%, H is 0.28%, K is 1.21%, M is 2.03%, N is 1.76%, P is 3.31%, Q is 0.38%, R is 4.00%, T is 2.62% and W is 2.48%, wherein $X_{12}$ encodes such that P is 18.05%, G is 14.88%, S is 12.09%, F is 11.47%, R is 10.27%, H is 9.37%, A is 0.59%, C is 0.24%, D is 2.51%, E is 0.62%, I is 1.21%, K is 0.03%, L is 2.62%, M is 0.14%, N is 2.89%, Q is 2.79%, T is 3.07%, V is 2.24%, W is 0.28% and Y is 4.65%, wherein $X_{13}$ encodes such that G is 17.57%, Y is 13.02%, D is 12.19%, T is 8.89%, S is 7.51%, N is 6.48%, P is 6.44%, R is 6.30%, L is 5.34%, A is 2.24%, C is 0.34%, E is 2.48%, F is 0.59%, H is 0.10%, I is 3.17%, K is 2.79%, M is 3.10%, Q is 0.31%, V is 0.83% and W is 0.31%, wherein $X_{14}$ encodes such that Y is 35.62%, S is 13.64%, R is 9.68%, P is 8.54%, V is 6.41%, A is 0.90%, C is 2.14%, D is 0.79%, E is 2.51%, F is 0.65%, G is 3.89%, H is 3.55%, I is 0.59%, K is 2.58%, L is 4.31%, M is 0.14%, N is 0.41%, Q is 0.28%, T is 1.65% and W is 1.62%, wherein $X_{15}$ encodes such that Y is 50.43%, A is 9.65%, R is 5.99%, C is 1.89%, D is 2.79%, E is 2.17%, F is 4.34%, G is 1.96%, H is 0.17%, I is 2.89%, K is 2.27%, L is 0.48%, N is 4.20%, P is 2.79%, Q is 0.17%, S is 2.20%, T is 2.89%, V is 0.17% and W is 2.38%, wherein $X_{16}$ encodes such that Y is 54.98%, G is 10.71%, F is 6.17%, S is 5.65%, A is 0.31%, C is 0.07%, D is 4.44%, E is 0.31%, H is 3.03%, I is 2.38%, K is 0.21%, L is 2.20%, M is 2.34%, N is 0.24%, P is 2.89%, Q is 1.03%, R is 1.79%, T is 0.45%, V is 0.45% and W is 0.21%, wherein $X_{17}$ encodes such that Y is 48.33%, G is 10.27%, P is 8.27%, S is 5.20%, A is 1.24%, C is 0.14%, D is 3.93%, E is 0.14%, F is 2.20%, H is 1.45%, I is 3.41%, K is 1.38%, L is 1.27%, N is 4.51%, Q is 0.10%, R is 3.41%, T is 0.83%, V is 3.13% and W is 0.79%, wherein $X_{18}$ encodes such that G is 43.82%, Y is 19.57%, A is 11.44%, C is 1.69%, D is 4.86%, E is 0.03%, F is 0.17%, H is 0.24%, I is 2.14%, K is 0.07%, L is 4.06%, M is 0.07%, N is 0.34%, P is 1.10%, Q is 0.03%, R is 1.72%, S is 0.14%, T is 0.83%, V is 0.21% and W is 7.41%, wherein $X_{19}$ encodes such that M is 39.03%, F is 35.45%, L is 10.16%, A is 0.21%, C is 0.07%, D is 0.24%, G is 2.93%, H is 1.14%, I is 2.07%, K is 0.03%, P is 1.83%, Q is 0.03%, R is 0.24%, S is 0.86%, T is 0.38%, V is 2.96%, W is 1.17% and Y is 1.21%, wherein $X_{20}$ encodes such that D is 71.96%, A is 2.03%, C is 0.69%, E is 1.38%, F is 2.17%, G is 4.79%, H is 2.79%, I is 0.03%, K is 0.86%, L is 1.38%, M is 1.62%, N is 1.03%, P is 1.55%, Q is 1.03%, R is 1.00%, S is 1.58%, T is 1.10%, V is 2.00% and Y is 1.00%, and wherein $X_{21}$ encodes such that V is 53.57%, Y is 8.44%, H is 8.37%, P is 8.23%, A is 0.07%, D is 4.72%, E is 0.03%, F is 2.58%, G is 0.24%, I is 3.17%, K is 0.03%, L is 0.03%, M is 2.27%, N is 2.17%, Q is 2.69%, R is 0.03% and S is 3.31%;

when the length of the modified CDRH3 is 22 amino acid residues, the amino acid sequence is $X_1X_2X_3X_4X_5X_6X_7X_8X_9X_{10}X_{11}X_{12}X_{13}X_{14}X_{15}X_{16}X_{17}X_{18}X_{19}X_{20}X_{21}X_{22}$ (SEQ ID NO. 131), wherein $X_1$ encodes such that D is 23.37%, E is 14.91%, G is 21.75%, V is 8.46%, R is 5.83%, A is 3.13%, C is 0.04%, F is 0.04%, H is 2.74%, I is 0.70%, K is 1.89%, L is 2.51%, M is 1.97%, N is 0.50%, P is 2.74%, Q is 2.05%, S is 2.94%, T is 0.46%, W is 1.04% and Y is 2.94%, wherein $X_2$ encodes such that F is 5.37%, G is 17.19%, L is 18.89%, P is 7.96%, R is 17.50%, S is 7.34%, A is 3.79%, C is 0.04%, D is 0.54%, E is 4.87%, H is 0.27%, I is 4.06%, K is 0.35%, M is 4.94%, Q is 0.58%, T is 2.28%, V is 0.58%, W is 2.97% and Y is 0.46%, wherein $X_3$ encodes such that A is 16.22%, G is 8.30%, K is 8.85%, L is 8.96%, R is 8.42%, S is 7.26%, Y is 8.03%, C is 3.59%, D is 3.17%, E is 4.52%, F is 3.13%, H is 0.08%, I is 4.44%, M is 0.08%, N is 4.21%, P is 4.75%, Q is 0.23%, T is 3.21%, V is 2.39% and W is 0.12%, wherein $X_4$ encodes such that E is 12.98%, F is 6.33%, G is 11.09%, I is 9.81%, P is 18.23%, R is 5.06%, S is 15.22%, T is 5.60%, Y is 5.37%, A is 0.42%, C is 0.19%, D is 3.79%, H is 0.08%, K is 0.19%, L is 3.94%, M is 0.46%, N is 0.19%, Q is 0.35%, V is 0.39% and W is 0.31%, wherein $X_5$ encodes such that D is 17.77%, H is 6.22%, P is 8.50%, S is 7.88%, T is 5.99%, Y is 14.41%, A is 4.98%, C is 3.82%, E is 0.50%, F is 3.67%, G is 4.40%, I is 0.42%, K is 4.94%, L is 0.46%, M is 0.35%, N is 4.17%, Q is 0.12%, R is 4.52%, V is 3.86% and W is 2.94%, wherein $X_6$ encodes such that D is 16.11%, G is 17.15%, M is 5.10%, V is 9.69%, Y is 13.13%, C is 3.36%, A is 0.70%, E is 4.48%, F is 0.27%, H is 4.79%, I is 1.16%, K is 0.19%, L is 0.42%, N is 4.21%, P is 3.59%, Q is 0.04%, R is 4.79%, S is 4.75%, T is 0.39% and W is 5.68%, wherein $X_7$ encodes such that A is 7.57%, D is 6.80%, E is 9.19%, F is 6.95%, G is 9.46%, I is 10.04%, L is 11.16%, S is 7.11%, V is 5.79%, W is 1.89%, C is 2.01%, H is 0.27%, K is 1.16%, M is 1.78%, N is 1.04%, P is 2.47%, Q is 0.23%, R is 4.91%, T is 2.24% and Y is 7.80%, wherein $X_8$ encodes such that A is 9.31%, D is 6.80%, E is 7.57%, I is 10.20%, F is 6.49%, G is 7.07%, L is 11.94%, S is 8.07%, V is 5.21%, Y is 8.96%, C is 1.58%, K is 1.08%, M is 1.93%, N is 1.43%, P is 2.94%, H is 0.08%, Q is 0.08%, R is 4.48%, T is 2.05% and W is 2.70%, wherein $X_9$ encodes such that A is 8.19%, D is 6.53%, E is 7.61%, F is 7.34%, G is 8.07%, I is 10.81%, L is 10.27%, S is 7.49%, V is 5.25%, Y is 8.96%, C is 1.89%, H is 0.12%, K is 1.51%, M is 1.85%, N is 1.51%, P is 2.74%, Q is 0.08%, R is 4.60%, T is 2.51% and W is 2.67%, wherein $X_{10}$ encodes such that Y is 13.02%, P is 10.31%, R is 9.39%, G is 9.31%, L is 6.30%, I is 6.10%, D is 5.33%, A is 4.87%, S is 4.87%, V is 4.67%, Q is 4.56%, E is 4.29%, T is 4.09%, F is 3.79%, N is 1.85%, C is 1.78%, W is 1.74%, H is 1.39%, M is 1.27% and K is 1.00%, wherein $X_{11}$ encodes such that Y is 13.44%, P is 10.35%, G is 8.65%, R is 8.42%, L is 6.49%, I is 5.52%, D is 5.29%, E is 5.29%, S is 4.91%, T is 4.87%, A is 4.75%, V is 4.75%, Q is 3.86%, F is 3.28%, N is 2.90%, W is 1.82%, C is 1.78%, H is 1.39%, K is 1.12% and M is 1.08%, wherein $X_{12}$ encodes such that Y is 13.75%, P is 9.62%, G is 9.04%, R is 8.57%, I is 7.72%, L is 6.10%, Q is 5.21%, S is 5.10%, A is 5.06%, D is 4.52%, E is 4.48%, F is 3.79%, V is 3.67%, T is 3.51%, N is 2.01%, W is 1.85%, H is 1.74%, C is 1.66%, M is 1.51% and K is 1.04%, wherein $X_{13}$ encodes such that L is 12.55%, I is 9.62%, S is 8.38%, Y is 8.27%, G is 7.84%, E is 7.61%, A is 7.45%, D is 7.26%, V is 6.06%, F is 5.99%, R is 4.36%, P is 3.13%, T is 2.82%, W is 2.36%, C is 1.78%, M is 1.66%, K is 1.27%, N is 1.27%, Q is 0.15% and H is 0.12%, wherein $X_{14}$ encodes such that L is 11.36%, I is 10.54%, Y is 8.38%, E is 8.15%, G is 8.07%, S is 8.00%, A is 7.84%, F is 7.34%, D is 7.26%, V is 5.21%, R is 4.44%, P is 3.05%, T is 2.36%, W is 2.09%, C is 2.01%, K is 1.43%, M is 1.31%, N is 1.08% and H is 0.08%, wherein $X_{15}$ encodes such that Y is 55.62%, P is 13.90%, T is 4.98%, S is 4.13%, D is 4.09%, E is 4.06%, L is 3.86%, G is 3.82%, Q is 3.24%, R is 0.58%, N is 0.39%, I is 0.35%, F is 0.19%, V is 0.19%, C is 0.15%, K is 0.15%, A is 0.12%, W is 0.08% and H is 0.04%, wherein $X_{16}$ encodes such that Y is 60.22%, G is 6.33%, T is 5.48%, K is 4.60%, L is 3.82%, V is 3.79%, E is 3.67%, R is 3.59%, S is 2.90%, W is 2.43%, I is 0.73%, A is 0.50%, D is 0.50%, F is 0.27%, N is 0.27%, P is 0.27%, Q is 0.19%, C is 0.15%, H is 0.04% and M is 0.04%, wherein $X_{17}$ encodes such that Y is 62.50%, R is 6.06%, P is 5.37%, K is 5.25%, H is 4.21%, D is 4.02%, S is 3.82%, G is 3.67%, T is 3.28%, L is 0.62%, F is 0.19%, V is 0.19%, C is 0.12%, M is 0.12%, N is 0.12%, A is 0.08%, I is 0.08% and Q is 0.08%, wherein $X_{18}$ encodes such that Y is 69.83%, N is 7.61%, G is 5.52%, D is 3.98%, A is 3.90%, H is 3.71%, E is 2.94%, S is 0.50%, F is 0.31%, K is 0.27%, C is 0.23%, P is 0.23%, R is 0.23%, L is 0.15%, W is 0.15%, V is 0.12%, I is 0.08%, Q is 0.04% and T is 0.04%, wherein $X_{19}$ encodes such that G is 57.44%, A is 10.12%, Y is 9.19%, R is 6.30%, D is 4.79%, W is 4.17%, H is 3.32%, F is 3.24%, P is 0.31%, I is 0.19%, M is 0.19%, C is 0.12%, E is 0.12%, L is 0.12%, N is 0.12%, S is 0.12%, T is 0.12% and K is 0.04%, wherein $X_{20}$ encodes such that M is 41.10%, F is 36.27%, L is 9.81%, I is 2.74%, V is 2.59%, P is 1.78%, G is 1.27%, H is 1.20%, Y is 1.08%, W is 0.89%, S is 0.54%, T is 0.46%, A is 0.08%, D is 0.08%, N is 0.08% and R is 0.04%, wherein $X_{21}$ encodes such that D is 74.55%, M is 0.23%, F is 0.85%, L is 1.27%, V is 1.16%, P is 1.39%, G is 4.25%, H is 2.16%, Y is 1.12%, S is 1.97%, T is 1.16%, A is 2.39%, N is 1.47%, R is 0.77%, C is 1.00%, E is 2.12%, K is 1.08% and Q is 1.04%, and wherein $X_{22}$ encodes such that V is 67.59%, Y is 10.97%, F is 9.35%, I is 8.42%, P is 2.47%, H is 0.42%, D is 0.35%, C is 0.12%, S is 0.12%, Q is 0.08%, A is 0.04%, L is 0.04% and T is 0.04%; and when the length of the modified CDRH3 is 23 amino acid residues, the amino acid sequence is $X_1X_2X_3X_4X_5X_6X_7X_8X_9X_{10}X_{11}X_{12}X_{13}X_{14}X_{15}X_{16}X_{17}X_{18}X_{19}X_{20}X_{21}X_{22}X_{23}$ (SEQ ID NO. 132), wherein $X_1$ encodes such that D is 46.36%, E is 9.86%, G is 22.89%, H is 8.78%, V is 7.32%, I is 0.10%, K is 0.10%, L is 0.24%, M is 0.05%, N is 0.24%, P is 0.24%, Q is 0.10%, R is 0.44%, S is 0.34%, A is 1.81%, W is 0.05%, Y is 0.20% and T is 0.88%, wherein $X_2$ encodes such that A is 5.32%, E is 6.54%, D is 11.91%, H is 10.05%, L is 12.01%, Q is 8.64%, V is 10.44%, P is 9.91%, G is 14.79%, F is 0.29%, I is 0.34%, K is 0.20%, M is 0.39%, N is 0.05%, R is 4.39%, S is 4.15%, T is 0.10%, W is 0.29% and Y is 0.15%, wherein $X_3$ encodes such that A is 15.57%, G is 11.13%, I is 15.32%, L is 12.84%, R is 8.69%, S is 17.33%, C is 0.29%, D is 0.34%, E is 0.29%, F is 0.15%, H is 0.10%, K is 4.59%, M is 0.05%, N is 0.15%, P is 3.71%, Q is 2.83%, T is 0.24%, V is 2.64%, and Y is 3.71%, wherein $X_4$ encodes such that G is 15.71%, M is 10.98%, R is 22.40%, S is 6.54%, T is 6.39%, Y is 9.32%, A is 0.29%, C is 0.10%, D is 4.78%, E is 0.98%, F is 0.49%, H is 0.05%, I is 4.93%, K is 4.25%, L is 0.39%, N is 0.15%, P is 3.61%, Q is 2.88%, V is 2.88% and W is 2.83%, wherein $X_5$ encodes such that A is 10.69%, D is 17.33%, F is 8.00%, P is 5.32%, R is 7.76%, T is 5.91%, V is 5.91%, Y is 10.40%, C is 0.20%, E is 4.29%, G is 4.83%, H is 0.44%, I is 0.24%, K is 0.24%, L is 4.59%, M is 4.39%, N is 4.69%, Q is 0.05%, S is 4.54% and W is 0.15%, wherein $X_6$ encodes such that Y is 10.49%, S is 21.33%, N is 5.32%, I is 15.18%, G is 5.12%, D is 5.08%, T is 7.61%, A is 3.42%, C is 0.49%, E is 0.34%, F is 3.07%, H is 3.51%, L is 3.51%, M is 4.05%, P is 2.73%, Q is 0.05%, R is 4.49%, V is 3.76% and W is 0.39%, wherein $X_7$ encodes such that E is 19.72%, G is 13.52%, I is 5.12%, K is 5.37%, M is 5.17%, S is 6.88%, Y is 10.00%, A is 4.39%, C is 2.93%, D is 0.78%, F is 3.76%, H is 4.78%, L is 0.49%, N is 0.10%, P is 3.61%, Q is 2.54%, R is 4.05%, T is 3.22%, V is 3.22% and W is 0.34%, wherein $X_8$ encodes such that A is 10.30%, D is 9.52%, G is 11.22%, I is 11.71%, L is 14.98%, V is 11.47%, C is 0.05%, E is 3.86%, F is 0.59%, H is 3.76%, K is 0.05%, N is 0.15%, P is 3.81%, Q is 0.10%, R is 3.42%, S is 4.73%, T is 3.22%, W is 2.98% and Y is 4.10%, wherein $X_9$ encodes such that A is 11.22%, E is 5.32%, F is 9.03%, I is 5.76%, N is 14.84%, P is 7.42%, S is 11.03%, V is 11.22%, C is 0.15%, D is 4.20%, G is 0.44%, H is 0.05%, K is 0.15%, L is 4.83%, M is 0.05%, Q is 2.34%, R is 0.78%, T is 2.78%, W is 3.56% and Y is 4.83%, wherein $X_{10}$ encodes such that G is 24.79%, I is 14.40%, R is 9.13%, S is 7.91%, W is 10.83%, Y is 14.30%, A is 4.59%, C is 0.34%, D is 0.24%, E is 0.88%, F is 3.90%, K is 0.10%, L is 0.73%, M is 0.15%, N is 0.20%, P is 2.10%, Q is 0.20%, T is 0.44% and V is 4.78%, wherein $X_{11}$ encodes such that G is 9.86%, K is 5.61%, P is 6.69%, R is 10.35%, S is 8.59%, T is 9.37%, V is 16.40%, Y is 6.78%, A is 0.34%, C is 0.15%, D is 4.88%, E is 0.34%, F is 4.25%, H is 3.42%, I is 0.59%, L is 4.00%, M is 0.10%, N is 4.49%, Q is 0.34%, and W is 3.42%, wherein $X_{12}$ encodes such that F is 9.42%, G is 12.10%, I is 14.25%, S is 15.96%, T is 6.69%, Y is 12.10%, A is 0.29%, C is 4.05%, D is 0.15%, E is 0.24%, H is 0.29%, K is 0.15%, L is 4.83%, M is 0.10%, N is 4.64%, P is 4.34%, Q is 2.68%, R is 3.66%, V is 3.90% and W is 0.10%, wherein $X_{13}$ encodes such that A is 9.03%, G is 12.15%, I is 19.52%, L is 6.98%, R is 11.52%, Y is 21.28%, C is 0.15%, D is 0.68%, E is 0.20%, F is 0.44%, H is 0.15%, K is 0.10%, M is 0.15%, N is 4.25%, P is 2.93%, Q is 0.15%, S is 3.17%, T is 0.20%, V is 3.56% and W is 3.27%, wherein $X_{14}$ encodes such that A is 5.12%, G is 8.44%, I is 5.51%, N is 5.42%, P is 8.39%, S is 22.65%, T is 10.35%, V is 11.57%, Y is 5.71%, C is 0.24%, D is 3.76%, E is 0.20%, F is 3.90%, H is 0.29%, K is 0.20%, L is 0.68%, Q is 0.10%, R is 3.95% and W is 3.47%, wherein $X_{15}$ encodes such that I is 19.18%, L is 10.15%, P is 11.27%, Y is 25.48%, G is 14.20%, A is 0.29%, C is 0.10%, D is 4.34%, E is 0.39%, F is 0.34%, K is 4.34%, M is 0.05%, N is 0.10%, Q is 0.10%, R is 0.29%, S is 4.05%, T is 2.20%, V is 2.83%, and W is 0.29%, wherein $X_{16}$ encodes such that E is 16.35%, N is 8.30%, R is 8.25%, Y is 45.63%, C is 0.05%, D is 4.15%, F is 3.32%, G is 2.88%, H is 0.15%, I is 0.20%, K is 0.20%, L is 0.24%, M is 0.05%, P is 3.17%, Q is 0.34%, S is 3.47%, T is 0.39%, V is 2.64% and W is 0.05%, wherein $X_{17}$ encodes such that D is 8.00%, G is 6.34%, I is 8.49%, Y is 56.66%, A is 0.10%, C is 0.10%, E is 0.34%, F is 3.51%, H is 0.10%, K is 3.42%, L is 4.93%, N is 0.05%, P is 0.20%, Q is 3.32%, R is 0.20%, S is 0.29%, T is 3.66%, V is 0.10% and W is 0.10%, wherein $X_{18}$ encodes such that G is 7.81%, K is 9.18%, L is 8.39%, S is 19.67%, Y is 37.73%, A is 0.05%, C is 0.05%, D is 2.59%, E is 0.10%, F is 0.10%, H is 4.20%, I is 0.15%, M is 0.10%, N is 0.10%, P is 0.24%, Q is 0.05%, R is 6.69%, T is 0.24%, V is 2.54% and W is 0.05%, wherein $X_{19}$ encodes such that D is 15.52%, G is 8.10%, Y is 59.64%, A is 0.44%, C is 0.15%, E is 0.34%, F is 3.90%, H is 0.29%, I is 0.15%, K is 0.10%, L is 0.10%, N is 4.69%, P is 0.34%, R is 0.20%, S is 2.59%, T is 0.10%, V is 0.29% and W is 2.98%, wherein $X_{20}$ encodes such that A is 25.72%, G is 52.71%, W is 10.59%, D is 4.34%, E is 0.05%, F is 0.39%, H is 0.10%, L is 0.24%, P is 4.05%, R is 0.44%, S is 0.05%, T is 0.15%, V is 0.20% and Y is 0.93%, wherein $X_{21}$ encodes such that F is 43.24%, L is 7.61%, M is 37.48%, A is 0.05%, C is 0.05%, D is 0.05%, G is 1.07%, H is 1.27%, I is 2.24%, P is 0.88%, S is 0.98%, T is 0.93%, V is 2.39%, W is 0.93% and Y is 0.83%, wherein $X_{22}$ encodes such that D is 74.18%, A is 2.59%, C is 0.63%, E is 1.90%, F is 0.83%, G is 4.93%, H is 2.05%, I is 0.10%, K is 1.61%, L is 0.88%, M is 0.05%, N is 1.12%, P is 1.22%, Q is 0.63%, R is 1.95%, S is 1.90%, T is 1.12%, V is 1.12%, and Y is 1.17%, and wherein $X_{23}$ encodes such that V is 59.15%, I is 25.33%, D is 0.05%, F is 4.73%, H is 0.15%, L is 0.05%, M is 0.05%, P is 9.22%, Q is 0.05%, R is 0.05%, S is 0.15%, T is 0.05% and Y is 0.98%.

2. The synthetic gene expression library of claim 1, wherein the synthetic gene expression library encoding first fusion proteins further comprises second fusion proteins, wherein each second fusion protein comprises a human antibody light chain, wherein the human antibody light chain is either a human kappa or lambda light chain;

wherein the light chain (kappa) of the antibody comprises consensus amino acid sequence selected from SEQ ID Nos. 16, 18, 20, or 22 encoded by corresponding nucleic acid sequence selected from SEQ ID Nos. 15, 17, 19, or 21; or wherein the light chain (lambda) of the antibody comprises consensus amino acid sequence selected from SEQ ID Nos. 24, 26, or 28 encoded by corresponding nucleic acid sequence selected from SEQ ID Nos. 23, 25, or 27;

CDR 1 and 2 of the heavy chain comprises amino acid sequence encoded by consensus nucleic acid sequence selected from SEQ ID Nos. 50-63;

CDR 1, 2 and 3 of the light chain (kappa) comprises amino acid sequence encoded by consensus nucleic acid sequence selected from SEQ ID Nos. 80-91; and CDR 1, 2 and 3 of the light chain (lambda) comprises amino acid sequence encoded by consensus nucleic acid sequence selected from SEQ ID Nos. 104-112.

3. A method of making the synthetic gene expression library of claim 1, comprising:

a) screening published germline and rearranged antibody sequences, and identifying antibody molecules having at least one predetermined characteristic(s), wherein the predetermined characteristic(s) is selected from a group comprising annotation level, species, configuration type, rearranged gene type and functionality, or any combination thereof, b) analysing the identified molecules on the basis of length distribution analysis of CDR3 heavy chain (CDRH3) and frequency of occurrence of amino acids within said CDRH3 to determine optimal chain length and amino acid ratio, c) estimating probability index of amino acids having determined chain length and amino acid frequency using positional correlation analysis, d) calculating the probabilities between different positions at different CDRH3 lengths followed by adding probability differences for 20 individual amino acids to generate one number per two positions, and comparing with another pair of positions covering all CDRH3 lengths from 4 amino acids to 23 amino acids, e) introducing true diversity based on the parameters of richness and abundance of the amino acids by shannon entropy, wherein the richness parameter defines varieties of amino acids and the abundance parameter defines probability of occurrence of each amino acid, f) designing altered antibodies comprising consensus sequences of human immunoglobulin variable heavy chain regions and variable light chain regions followed by subjecting the molecule(s) to codon replacement technology on the basis of said optimal chain length and amino acid frequency as defined in claim 1, to obtain antibodies with the modified CDRH3, and g) cloning said antibodies to form the synthetic gene expression library.

4. The method of claim 3, wherein the screening involves analysing antibody gene sequences from available online database (IMGT database) for removal of redundancy.

5. The method of claim 3, wherein the designing comprises synthesizing the antibody comprising heavy chain amino acid sequence selected from SEQ ID Nos. 2, 4, 6, 8, 10, 12 or 14, and light chain amino acid sequence selected from SEQ ID Nos. 16, 18, 20, 22, 24, 26 or 28; and framework regions and CDRs having one or more amino acid sequence encoded by nucleic acid sequence selected from SEQ ID Nos. 29-112.

6. The method of claim 3, wherein the cloned antibodies with the modified CDRH3 are displayed individually by phage vector or sequentially by phage vector followed by yeast vector.

7. The method of claim 6, wherein the display of the antibodies by a phage or yeast vector, involves:

cloning of corresponding antibody genes into the phage to obtain phage gene expression library followed by screening of displayed molecule(s) against antigen(s) to obtain panned phage gene expression library, transferring the panned phage gene expression library into yeast for display of said antibodies on surface of the yeast followed by screening the yeast displayed antibodies against antigen(s) to obtain yeast screened gene expression library, and selecting the phage or the yeast displayed antibodies with desired functional properties to form the synthetic gene expression library or isolating selected antibodies with desired functional properties from the phage gene expression library or the yeast gene expression library to generate screened synthetic gene expression library.

8. The method of claim 6, wherein the antibodies are in Fab or Scfv format for cloning into phage or yeast vector; and wherein transformation efficiency into the phage vector is in the range of about $10^9$ to about $10^{10}$; and transformation efficiency into the yeast vector is in the range of about $10^6$ to about $10^8$.

9. The method of claim 7, wherein the screening to obtain phage library involves panning with antigens coated on magnetic beads to isolate antibody of interest; and wherein said phage display screening/panning is employed to remove antibody non-binders.

10. The method of claim 7, wherein the screening to obtain yeast library by the surface display is carried out by employing competing antigenic epitopes, antibody paratope conformation, sequences and sequence motifs or any combination thereof to isolate Fab or ScFv molecule using protease cleavage sites selected from a group comprising Tobacco Etch Virus (TEV), Enterokinase, Thrombin, Factor X a, HRV 3C protease and similar protease cleavage proteins or any combination thereof.

11. The method of claim 7, wherein the synthetic gene expression library is a collection of the antibodies expressed on surface of the phage or the yeast, or is a collection of the antibodies isolated from the phage or the yeast or a combination thereof.

12. A method of isolating one or more phage or yeast cells expressing one or more antibody molecules of the synthetic gene expression library of claim 1, the method comprising expressing and screening the synthetic library of antibody molecules sequentially in phage followed by yeast cells to isolate the one or more phage or yeast cells, and wherein said expression and screening comprises:

(i) cloning the antibody of the synthetically prepared antibody gene expression library into phagemid vectors;

(ii) expressing the antibody genes followed by screening the phage clones against specific antigen target(s), and selecting or isolating phage clones, (iii) transferring and expressing the antibody molecules of the selected or isolated phage clones in yeast cells and screening by contacting the yeast cells against specific antigen target(s); and (iv) separating or isolating one or more yeast cells displaying antibodies that bind to the specific antigen target(s).

13. The method of claim 12, further comprising the step of isolating one or more nucleic acid sequences encoding one or more antibodies from the one or more phage or yeast cells.

14. The synthetic gene expression library according to claim 1, wherein in the CDRH3 region, an occurrence of each encoded CDRH3 that comprises one of the amino acid length from 4 to 10 is larger than an occurrence of each corresponding CDRH3 in nature.

* * * * *